(12) United States Patent
Nishi et al.

(10) Patent No.: US 7,365,067 B2
(45) Date of Patent: Apr. 29, 2008

(54) INDANOL DERIVATIVE

(75) Inventors: Takahide Nishi, Tokyo (JP); Toshiyasu Takemoto, Tokyo (JP); Takuya Ikeda, Kawasaki (JP); Kiyoshi Morimoto, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/590,305

(22) PCT Filed: Feb. 24, 2005

(86) PCT No.: PCT/JP2005/003545

§ 371 (c)(1),
(2), (4) Date: Oct. 12, 2006

(87) PCT Pub. No.: WO2005/080385

PCT Pub. Date: Sep. 1, 2005

(65) Prior Publication Data

US 2007/0197570 A1    Aug. 23, 2007

(30) Foreign Application Priority Data

Feb. 25, 2004    (JP) .............................. 2004-049255

(51) Int. Cl.
*A61K 31/5377*    (2006.01)
*C07D 413/14*    (2006.01)
(52) U.S. Cl. .................. 514/232.2; 544/82; 544/78; 544/114; 544/124; 546/17; 514/231.5; 514/231.8; 514/232.8
(58) Field of Classification Search ............. 514/231.8, 514/278, 232.8, 231.5, 232.2; 544/82, 78, 544/114, 124; 546/17
See application file for complete search history.

(56) References Cited

U.S. PATENT DOCUMENTS

| | | | |
|---|---|---|---|
| 5,869,496 A | 2/1999 | Hale et al. | |
| 6,420,376 B1 | 7/2002 | Tata et al. | |
| 6,511,975 B1 | 1/2003 | Nishi et al. | |

FOREIGN PATENT DOCUMENTS

| | | |
|---|---|---|
| JP | 2000-34288 A | 2/2000 |
| JP | 2001-31570 A | 2/2001 |
| JP | 2001-187790 A | 7/2001 |
| JP | 2002-316987 A | 10/2002 |
| WO | WO 94/17045 A1 | 8/1994 |
| WO | WO 01/04119 A1 | 1/2001 |

OTHER PUBLICATIONS

English translation of International Preliminary Examination Report Form PCT/ISA/237 of International Application No. PCT/JP2005/003545.

*Primary Examiner*—Charanjit S. Aulakh
(74) *Attorney, Agent, or Firm*—Frishauf, Holtz, Goodman & Chick, P.C.

(57) ABSTRACT

The present invention provides a compound having the following general formula (I) which is useful as a neurokinin receptor antagonist:

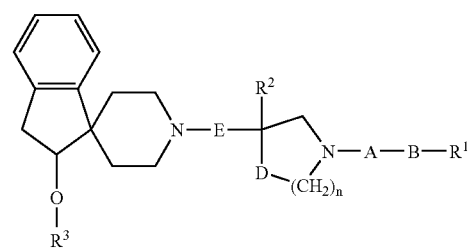

(I)

(wherein,
$R^1$, $R^2$: optionally substituted (hetero)aryl,
$R^3$: —CO—$R^4$, —CO—O—$R^4$, etc.,
$R^4$: alkyl, cycloalkyl, etc.,
A: $CH_2$, CO, $SO_2$,
B: a single bond, etc.,
D: oxygen, $CH_2$,
E: alkylene, alkenylene,
n: 1 to 3).

37 Claims, No Drawings

INDANOL DERIVATIVE

This application is a 371 of PCT/JP05/03545 filed Feb. 24, 2005 which claims priority to Japan 2004-049255 filed Feb. 25, 2004.

TECHNICAL FIELD

The present invention relates to novel indanol derivatives having antagonistic activity against tachykinin receptors ($NK_1$, $NK_2$ and $NK_3$).

BACKGROUND ART

U.S. Pat. No. 6,511,975 discloses indanol derivatives having antagonistic activity against $NK_1$ receptors, $NK_2$ receptors and $NK_3$ receptors.

The present invention differs from the compounds of the prior art in that the hydroxyl group of indanol is substituted, and there is no known prior art that motivates introduction of this substituent (the group corresponding to $R^3$ in the general formula (I) to be described later) into a compound disclosed in U.S. Pat. No. 6,511,975.

DISCLOSURE OF THE INVENTION

As a result of conducting extensive studies over the course of many years on neurokinin receptor antagonists, the inventors of the present invention found compounds which have antagonistic activity against all of the $NK_1$, $NK_2$ and $NK_3$ receptors and demonstrate continuous pharmacological effects, thereby leading to completion of the present invention.

Moreover, another object of the present invention is to provide a novel pharmaceutical having the aforementioned compound as an active ingredient thereof, and examples of diseases to which this pharmaceutical can be applied include central nervous system diseases including anxiety, depression, mental illness and schizophrenia; neurodegenerative diseases including AIDS-associated dementia, Alzheimer-type senile dementia, Alzheimer's disease, Down's syndrome, demyelinating disease, amyotrophic lateral sclerosis, neuropathy, peripheral neuropathy and neuralgia; respiratory diseases including chronic obstructive lung disease, bronchitis, pneumonia, bronchial constriction, asthma and cough; inflammatory diseases including inflammatory bowel disease (IBD), psoriasis, fibrositis, osteoarthritis, degenerative arthritis and rheumatoid arthritis; eczema; allergic diseases including rhinitis; hypersensitivity diseases including diseases of hypersensitivity to vine plants; ophthalmological diseases including conjunctivitis, vernal conjunctivitis, vernal catarrh, destruction of the blood-aqueous humor barrier accompanying various inflammatory eye diseases, increased intraocular pressure and miosis; skin diseases including contact dermatitis, atopic dermatitis, urticaria and other eczema-like dermatitis; addictions including alcoholism; stress-induced somatic diseases; sympathetic reflex dystrophy including shoulder-hand syndrome; dysthymia; diseases related to undesirable immune reactions including transplant rejections and immunoenhancement or immunosuppression including systemic lupus erythematosus; digestive organ diseases including diseases caused by abnormalities in nerves regulating internal organs, colitis, ulcerative colitis, irritable bowel syndrome and Crohn's disease; emesis including that induced by X-ray irradiation and chemotherapeutic agents, poisons, toxins, pregnancy, vestibular disorders, post-operative illnesses, gastrointestinal obstruction, gastrointestinal dysmotility, visceralgia, migraine headache, increased intracranial pressure, decreased intracranial pressure or adverse side effects accompanying administration of various pharmaceuticals; urinary bladder function diseases including cystitis and urinary incontinence; eosinophilia caused by collagen diseases, scleroderma or Fasciola hepatica infection; diseases caused by blood stream abnormalities due to vascular dilation or constriction including angina pectoris, migraine headache and Raynaud's disease; pain associated with reception of pain penetration including migraine headache, headache and toothache; and, sleep apnea syndrome. A novel pharmaceutical of the present invention can be used as a prophylactic or therapeutic for respiratory diseases such as asthma, bronchitis and chronic obstructive lung disease; allergic diseases such as rhinitis; and/or urinary incontinence in particular.

The present invention relates to:
(1) a compound represented by the general formula (I):

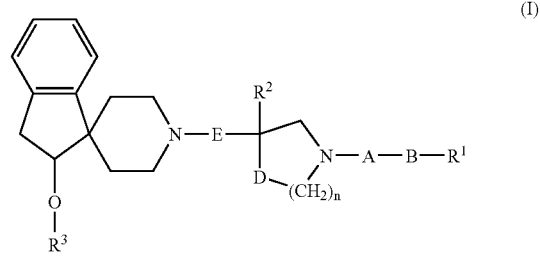

(wherein,
$R^1$ and $R^2$ may be the same or different and each represents an aryl group, heteroaryl group, aryl group substituted with 1 to 3 groups selected from Substituent group α, or heteroaryl group substituted with 1 to 3 groups selected from Substituent group α;

$R^3$ represents any one of the following groups:
—CO—$R^4$,
—CO—O—$R^4$,
—CO—NH—$R^4$,
—CO—$CH_2$—N($R^a$)$R^b$,
—($CH_2$)$_m$—CO—$R^5$,
—($CH_2$)$_m$—$R^5$,
—CO—NH—CO—N($R^a$)$R^b$,
—CO—NH—$SO_2$—N($R^a$)$R^b$,
—CO—NH—CO—($CH_2$)$_m$—N($R^a$)$R^b$, and
—CO—$NH_2$;

$R^4$ represents a lower alkyl group, cycloalkyl group, cycloalkyl group substituted with 1 to 3 groups selected from Substituent group α, lower alkenyl group, lower alkynyl group, halogeno lower alkyl group, hydroxy lower alkyl group, lower alkoxyalkyl group, lower aliphatic acyloxyalkyl group or lower alkoxycarbonylalkyl group;

$R^5$ represents a hydroxyl group, a group —O$R^4$, or a group —N($R^a$)$R^b$;

$R^a$ and $R^b$ may be the same or different and each represents a hydrogen atom, hydroxyl group, lower alkoxy group, hydroxy lower alkoxy group, hydroxy lower alkoxyalkyl group, lower alkoxy lower alkoxyalkyl group, cyano lower alkyl group, cyano lower alkoxyalkyl group, carboxy lower alkyl group, carboxy lower alkoxyalkyl group, lower alkoxycarbonyl lower alkoxyalkyl group, carbamoyl lower alkyl group, carbamoyl lower alkoxyalkyl group, lower aliphatic acylamino lower alkyl group, lower aliphatic acylamino lower alkoxyalkyl group, lower alkylsulfonylamino lower alkyl group, lower alkylsulfonylamino lower alkoxyalkyl group, (N-hydroxy-N-methylcarbamoyl) lower alkyl group, (N-hydroxy-N-methylcarbamoyl) lower alkoxyalkyl group, (N-lower alkoxy-N-methylcarbamoyl) lower alkyl group, (N-lower alkoxy-N-methylcarbamoyl) lower alkoxyalkyl group or $R^4$, or together, including the nitrogen atom to which they are attached, represent a nitrogen-containing heterocyclic group or nitrogen-containing heterocyclic group substituted with 1 to 3 groups selected from Substituent group α;

m represents an integer of 1 to 6;

A represents a methylene group, carbonyl group or sulfonyl group;

B represents a single bond, $C_1$-$C_4$ alkylene group or $C_2$-$C_4$ alkenylene group;

D represents an oxygen atom or methylene group;

E represents a $C_1$-$C_4$ alkylene group or $C_2$-$C_4$ alkenylene group;

n represents an integer of 1 to 3; and,

Substituent group α represents a group of substituents consisting of halogen atoms, lower alkyl groups, hydroxy lower alkyl groups, halogeno lower alkyl groups, carboxy lower alkyl groups, lower alkoxy groups, hydroxy lower alkoxy groups, hydroxy lower alkoxyalkyl groups, lower alkoxy carbonyl groups, carboxyl groups, hydroxyl groups, lower aliphatic acyl groups, lower aliphatic acylamino groups, (N-hydroxy-N-methylcarbamoyl) lower alkyl groups, (N-lower alkoxy-N-methylcarbamoyl) lower alkyl groups, hydroxy lower aliphatic acylamino groups, amino groups, carbamoyl groups and cyano groups), or a pharmacologically acceptable salt thereof.

Preferred compounds among the aforementioned compounds include:

(2) a compound, wherein $R^1$ is an aryl group or an aryl group substituted with 1 to 3 groups selected from Substituent group α, (3) a compound, wherein $R^1$ is phenyl or phenyl substituted with 1 to 3 groups selected from Substituent group α, (4) a compound, wherein $R^1$ is phenyl or phenyl substituted with 1 to 3 groups selected from the group consisting of halogeno lower alkyl groups, lower alkoxy groups and hydroxyl groups, (5) a compound, wherein $R^1$ is phenyl substituted with 1 to 3 groups selected from the group consisting of halogeno lower alkyl groups and lower alkoxy groups, (6) a compound, wherein $R^1$ is 3,5-bis(trifluoromethyl) phenyl or 3,4,5-trimethoxyphenyl, (7) a compound, wherein $R^2$ is an aryl group substituted with 1 to 3 groups selected from Substituent group α, (8) a compound, wherein $R^2$ is a phenyl group substituted with 1 or 2 halogen atoms, (9) a compound, wherein $R^2$ is 3,4-difluorophenyl or 3,4-dichlorophenyl,

(10) a compound, wherein A is a methylene group or carbonyl group,

(11) a compound, wherein A is a carbonyl group,

(12) a compound, wherein B is a single bond or $C_1$-$C_4$ alkylene group,

(13) a compound, wherein B is a single bond,

(14) a compound, wherein D is an oxygen atom or methylene group,

(15) a compound, wherein E is a $C_1$-$C_4$ alkylene group,

(16) a compound, wherein E is ethylene or trimethylene,

(17) a compound, wherein n is 1 or 2,

(18) a compound, wherein n is 2,

(19) a compound, wherein $R^3$ is —$(CH_2)_m$—CO—$R^5$,

(20) a compound, wherein $R^3$ is —$CH_2$—CO—N($R^a$)$R^b$,

(21) a compound, wherein one of $R^a$ and $R^b$ represents a hydrogen atom, lower alkyl group, hydroxyl group or lower alkoxy group and the other represents a hydroxy lower alkyl group, hydroxy lower alkoxyalkyl group, carboxy lower alkyl group, carboxy lower alkoxyalkyl group, lower alkoxy carbonyl lower alkyl group or lower alkoxycarbonyl lower alkoxyalkyl group, or $R^a$ and $R^b$ together, including the nitrogen atom to which they are attached, form a nitrogen-containing heterocyclic group or nitrogen-containing heterocyclic group substituted with 1 to 3 groups selected from Substituent group α, and

(22) a compound, wherein —N($R^a$)$R^b$ is N-(3-hydroxypropyl)-N-methylamino, N-(4-hydroxybutyl)-N-methylamino, N-(5-hydroxypentyl)-N-methylamino, N-(6-hydroxyhexyl)-N-methylamino, N-[2-(2-hydroxyethoxy)ethyl]-N-methylamino, N-(2-hydroxyethyl)-N-methoxyamino, N-(3-carboxypropyl)-N-methylamino, 2-(3-hydroxypropyl)pyrrolidino, 4-hydroxymethylpiperidino, 4-(2-hydroxyethyl)piperidino, 4-(3-hydroxypropyl)piperidino, 4-(2-hydroxyethoxy)piperidino, 4-(hydroxyacetamido)piperidino, 4-(2-hydroxyethoxymethyl) piperidino or 4-(2-hydroxyethyl)piperazino, or a pharmacologically acceptable salt thereof.

The present invention further relates to a pharmaceutical composition containing, as an active ingredient thereof, a compound or pharmacologically acceptable salt thereof as described in any of the aforementioned (1) to (22) (and particularly a pharmaceutical composition for the treatment or prophylaxis of diseases mediated by $NK_1$, $NK_2$ and/or $NK_3$ receptors; a pharmaceutical composition for the prophylaxis or treatment of respiratory diseases, allergic diseases and/or urinary incontinence; and, a pharmaceutical composition for the prophylaxis or treatment of asthma, bronchitis, chronic obstructive lung disease, rhinitis and/or urinary incontinence), and particularly to a pharmaceutical composition containing, as an active ingredient thereof, a compound or pharmacologically acceptable salt thereof as described in any of the aforementioned (1) to (22) for pulmonary administration for the prophylaxis or treatment of respiratory diseases (particularly, asthma, bronchitis and/or chronic obstructive lung disease).

Moreover, the present invention further relates to the use, as an active ingredient, of a compound or pharmacologically acceptable salt thereof as described in any of the aforementioned (1) to (22) for producing a pharmaceutical composition (particularly, a pharmaceutical composition for the treatment or prophylaxis of diseases mediated by $NK_1$, $NK_2$ and/or $NK_3$ receptors; a pharmaceutical composition for the prophylaxis or treatment of respiratory diseases, allergic diseases and/or urinary incontinence; and, a pharmaceutical composition for the prophylaxis or treatment of asthma, bronchitis, chronic obstructive lung disease, rhinitis and/or urinary incontinence), and particularly to the use, as an active ingredient, of a compound or pharmacologically acceptable salt thereof as described in any of the aforementioned (1) to (22) for producing a pharmaceutical composition for pulmonary administration for the prophylaxis or treatment of respiratory diseases (particularly, asthma, bronchitis and/or chronic obstructive lung disease).

Moreover, the present invention further relates to a method for preventing or treating diseases mediated by $NK_1$, $NK_2$ and/or $NK_3$ receptors (particularly respiratory diseases, allergic diseases and/or urinary incontinence; and, asthma, bronchitis, chronic obstructive lung disease, rhinitis and/or urinary incontinence) by administering an effective amount of a compound or pharmacologically acceptable salt thereof as described in any of the aforementioned (1) to (22) to mammals (particularly humans), and particularly to a method for preventing or treating respiratory diseases (particularly asthma, bronchitis and/or chronic obstructive lung disease) by administering an effective amount of a compound or pharmacologically acceptable salt thereof described in any of the aforementioned (1) to (22) to mammals (particularly humans).

In the aforementioned general formula (I), the "aryl group" and the aryl group of the "aryl group substituted with 1 to 3 groups selected from Substituent group α" in the definitions of $R^1$ and $R^2$ mean a $C_6$-$C_{10}$ aryl group, and are preferably phenyl, 1-naphthyl or 2-naphthyl, and particularly preferably phenyl.

Furthermore, the aforementioned "$C_6$-$C_{10}$ aryl group" may be fused with a $C_3$-$C_{10}$ cycloalkyl group (preferably a $C_5$-$C_6$ cycloalkyl group).

In the case where $R^1$ is an "aryl group substituted with 1 to 3 groups selected from Substituent group α", it is preferably a phenyl group substituted with 1 to 3 groups selected from hydroxyl, methyl, ethyl, methoxy, ethoxy, difluoromethyl and trifluoromethyl groups, more preferably a phenyl group substituted with 1 to 3 groups selected from hydroxyl, methoxy and trifluoromethyl groups, and particularly preferably 3,4,5-trimethoxyphenyl or 3,5-bis(trifluoromethyl)phenyl.

In the case where $R^2$ is an "aryl group substituted with 1 to 3 groups selected from Substituent group α", it is preferably a phenyl group substituted with 1 to 3 groups selected from fluorine, chlorine, bromine and iodine atoms, more preferably phenyl group substituted with 1 or 2 groups selected from fluorine and chlorine atoms, still more preferably 3,4-difluorophenyl or 3,4-dichlorophenyl, and particularly preferably 3,4-dichlorophenyl.

The "heteroaryl group" and the heteroaryl group of the "heteroaryl group substituted with 1 to 3 groups selected from Substituent group α" in the definitions of $R^1$ and $R^2$ mean a 5- to 7-membered heteroaryl group containing 1 to 3 sulfur atoms, oxygen atoms and/or nitrogen atoms, examples of which include furyl, thienyl, pyrrolyl, pyrazolyl, imidazolyl, oxazolyl, isoxazolyl, thiazolyl, isothiazolyl, triazolyl, thiadiazolyl, pyridyl, pyridazinyl, pyrimidinyl, pyrazinyl and azepinyl groups, preferably a 5- to 6-membered heteroaryl group containing 1 or 2 sulfur atoms, oxygen atoms and/or nitrogen atoms such as a furyl, thienyl, pyrrolyl, pyrazolyl, imidazolyl, oxazolyl, isoxazolyl, thiazolyl, isothiazolyl, pyridyl, pyridazinyl, pyrimidinyl or pyrazinyl group, and more preferably a pyridyl or pyrimidinyl group.

Furthermore, the aforementioned "heteroaryl group" may be fused with another cyclic group [such as a $C_6$-$C_{10}$ aryl (preferably phenyl) or $C_3$-$C_{10}$ cycloalkyl (preferably $C_5$-$C_6$ cycloalkyl) group], and examples of such groups include indolyl, benzofuranyl, benzothienyl, quinolyl, isoquinolyl, quinazolinyl, tetrahydroquinolyl and tetrahydroisoquinolyl groups.

The "lower alkyl group" in the definitions of $R^4$ and Substituent group α mean a linear or branched $C_1$-$C_6$ alkyl group such as methyl, ethyl, propyl, isopropyl, butyl, isobutyl, sec-butyl, tert-butyl, pentyl, isopentyl, 2-methylbutyl, neopentyl, 1,1-dimethylpropyl, 1-ethylpropyl, hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl, preferably methyl, ethyl, propyl, isopropyl, butyl, isobutyl, pentyl, isopentyl, neopentyl, hexyl, isohexyl or 3,3-dimethylbutyl, and more preferably methyl, ethyl, propyl or isopropyl.

The "cycloalkyl group" and the cycloalkyl group of "cycloalkyl group substituted with 1 to 3 groups selected from Substituent group α" in the definition of $R^4$ mean a $C_3$-$C_8$ cycloalkyl group such as cyclopropyl, cyclobutyl, cyclopentyl, cyclohexyl, cycloheptyl or cyclooctyl, preferably a $C_5$-$C_6$ cycloalkyl group, and more preferably cyclopentyl or cyclohexyl.

The "lower alkenyl group" in the definition of $R^4$ means a linear or branched $C_2$-$C_6$ alkenyl group, and is preferably vinyl or allyl.

The "lower alkynyl group" in the definition of $R^4$ means a linear or branched $C_2$-$C_6$ alkynyl group, and is preferably acetylenyl or propalgyl.

The "halogeno lower alkyl group" in the definitions of $R^4$ and Substituent group α means a group in which the aforementioned "lower alkyl group" is substituted with a halogen atom, examples of which include trifluoromethyl, trichloromethyl, difluoromethyl, dichloromethyl, dibromomethyl, fluoromethyl, 2-fluoroethyl, 2-chloroethyl, 2-bromoethyl, 2,2,2-trifluoroethyl, 2,2,2-trichloroethyl, 3-chloropropyl, 4-fluorobutyl, 6-iodohexyl and 2-dibromoethyl. It is more preferably 2-fluoromethyl, 2-chloroethyl or 2-bromoethyl for $R^4$. It is particularly preferably trifluoromethyl for Substituent group α.

The "hydroxy lower alkyl group" in the definitions of $R^4$ and Substituent group α means a group in which the aforementioned "lower alkyl group" is substituted with a hydroxyl group, examples of which include hydroxymethyl, 2-hydroxyethyl, 2,3-dihydroxypropyl, 3-hydroxypropyl, 3,4-dihydroxybutyl and 4-hydroxybutyl, preferably hydroxymethyl, 2-hydroxyethyl, 3-hydroxypropyl or 4-hydroxybutyl, and more preferably hydroxymethyl or 2-hydroxyethyl.

The "lower alkoxy group" in the definitions of $R^a$, $R^b$ and Substituent group α; the lower alkoxy portion of the "lower alkoxyalkyl group" and "lower alkoxycarbonylalkyl group" in the definition of $R^4$; and the lower alkoxy portion of the "lower alkoxycarbonyl group" in the definition of Substituent group α mean a group in which the aforementioned "lower alkyl group" is bonded to an oxygen atom, examples of which include a $C_1$-$C_6$ alkoxy group such as a methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy group, preferably a $C_1$-$C_6$ alkoxy group, and more preferably methoxy or ethoxy group.

The "lower alkoxyalkyl group" in the definition of $R^4$ means a group in which the aforementioned "lower alkyl group" is substituted with the aforementioned "lower alkoxy group", and is preferably a $C_1$-$C_4$ alkoxyalkyl group such as methoxymethyl, 2-methoxyethyl, 3-methoxypropyl, ethoxymethyl, 2-ethoxyethyl or propoxymethyl, more preferably methoxymethyl, 2-methoxyethyl, ethoxymethyl or 2-ethoxyethyl, and still more preferably methoxymethyl, 2-methoxyethyl or 2-ethoxyethyl.

The "lower aliphatic acyl group" in the definition of Substituent group α; the lower aliphatic acyl portion of the "lower aliphatic acyloxyalkyl group" in the definition of $R^4$; the lower aliphatic acyl portion of the "lower aliphatic acylamino lower alkyl group" and the "lower aliphatic acylamino lower alkoxyalkyl group" in the definitions of $R^a$ and $R^b$, and the lower aliphatic acyl portion of the "lower aliphatic acylamino group" in the definition of Substituent group α mean a $C_1$-$C_6$ aliphatic acyl group, examples of which include formyl, acetyl, propionyl, butyryl, isobutyryl, pentanoyl, pivaloyl, valeryl and isovaleryl, preferably formyl, acetyl or propionyl, and particularly preferably acetyl.

The "lower aliphatic acyloxyalkyl group" in the definition of $R^4$ means a group in which the aforementioned "lower alkyl group" is substituted with $C_1$-$C_6$ aliphatic acyloxy (such as formyloxy, acetyloxy, propionyloxy, butyryloxy, isobutyryloxy, pentanoyloxy, pivaloyloxy, valeryloxy or isovaleryloxy), preferably it is a $C_2$-$C_6$ aliphatic acyloxyalkyl group, more preferably formyloxymethyl, 2-formyloxyethyl, acetyloxymethyl, 2-acetyloxyethyl, 3-acetyloxypropyl or propionyloxymethyl, even more preferably an acetyloxymethyl, 2-acetyloxyethyl or 3-acetyloxypropyl group, and particularly preferably an acetyloxymethyl group.

The "lower alkoxycarbonyl group" in the definition of Substituent group α, the lower alkoxycarbonyl portion of the "lower alkoxycarbonylalkyl group" in the definition of $R^4$, and the lower alkoxycarbonyl portion of the "lower alkoxycarbonyl lower alkoxyalkyl group" in the definition of $R^a$ and $R^b$ mean a group in which the aforementioned "lower alkoxy group" is bonded to a carbonyl group, and preferably it is a $C_2$-$C_5$ alkoxycarbonyl group such as methoxycarbonyl, ethoxycarbonyl, propoxycarbonyl, butoxycarbonyl, s-butoxycarbonyl, tert-butoxycarbonyl or isobutoxycarbonyl.

The "lower alkoxycarbonylalkyl group" in the definition of $R^4$ means a group in which the aforementioned "lower alkyl group" is substituted with the aforementioned "lower alkoxycarbonyl group", preferably it is a $C_3$-$C_9$ alkoxycarbonylalkyl group, more preferably a $C_3$-$C_7$ alkoxycarbonylalkyl group such as methoxycarbonylmethyl, 2-methoxycarbonylethyl, 3-methoxycarbonylpropyl, ethoxylcarbonylmethyl, 2-ethoxycarbonylethyl, 3-ethoxycarbonylpropyl, propoxycarbonylmethyl, 2-propoxycarbonylethyl or 3-propoxycarbonylpropyl, still more preferably a $C_1$-$C_4$ alkyl group substituted with ethoxycarbonyl, and particularly preferably ethoxycarbonylmethyl, 2-ethoxycarbonylethyl or 3-ethoxycarbonylpropyl.

The "hydroxy lower alkoxy group" in the definitions of $R^a$, $R^b$ and Substituent group α means a group in which the aforementioned "lower alkoxy group" is substituted with a hydroxyl group, examples of which include hydroxymethoxy, 2-hydroxyethoxy, 2,3-dihydroxypropoxy, 3-hydroxypropoxy, 3,4-dihydroxybutoxy and 4-hydroxybutoxy, preferably it is hydroxymethoxy, 2-hydroxyethoxy, 3-hydroxypropoxy or 4-hydroxybutoxy, and more preferably 2-hydroxyethoxy or 3-hydroxypropoxy.

The "hydroxy lower alkoxyalkyl group" in the definitions of $R^a$, $R^b$ and Substituent group α means a group in which the aforementioned "lower alkoxyalkyl group" is substituted with a hydroxyl group, preferably it is a $C_3$-$C_9$ hydroxyalkoxyalkyl group, more preferably a $C_3$-$C_7$ hydroxyalkoxyalkyl group such as hydroxymethoxymethyl, 2-(hydroxymethoxy)ethyl, 3-(hydroxymethoxy)propyl, 2-hydroxyethoxymethyl, 2-(2-hydroxyethoxy)ethyl, 3-(2-hydroxyethoxy)propyl, 3-hydroxypropoxymethyl, 2-(3-hydroxypropoxy)ethyl or 3-(3-hydroxypropoxy)propyl, still more preferably a $C_1$-$C_4$ alkyl group substituted with 2-hydroxyethoxy, particularly preferably 2-hydroxyethoxymethyl, 2-(2-hydroxyethoxy)ethyl or 3-(2-hydroxyethoxy)propyl, and most preferably 2-(2-hydroxyethoxy)ethyl.

The "lower alkoxy lower alkoxyalkyl group" in the definitions of $R^a$ and $R^b$ means a group in which the aforementioned "lower alkoxyalkyl group" is substituted with a lower alkoxy group, preferably it is a $C_1$-$C_4$ alkoxy $C_3$-$C_9$ alkoxyalkyl group, more preferably a $C_1$-$C_2$ alkoxy $C_3$-$C_4$ alkoxyalkyl group, particularly preferably 2-methoxyethoxymethyl or 2-(2-methoxyethoxy)ethyl, and most preferably 2-(2-methoxyethoxy)ethyl.

The "cyano lower alkyl group" in the definitions of $R^a$ and $R^b$ means a group in which the aforementioned "lower alkyl group" is substituted with a cyano group, examples of which include cyanomethyl, 2-cyanoethyl, 3-cyanopropyl and 4-cyanobutyl, and preferably it is 2-cyanoethyl or 3-cyanopropyl.

The "cyano lower alkoxyalkyl group" in the definitions of $R^a$ and $R^b$ means a group in which the aforementioned "lower alkoxyalkyl group" is substituted with a cyano group, preferably it is a cyano $C_3$-$C_9$ alkoxyalkyl group, more preferably a cyano $C_3$-$C_4$ alkoxyalkyl group, particularly preferably 2-cyanoethoxymethyl or 2-(2-cyanoethoxy)ethyl, and most preferably 2-(2-cyanoethoxy)ethyl.

The "carboxy lower alkyl group" in the definitions of $R^a$, $R^b$ and Substituent group α means a group in which the aforementioned "lower alkyl group" is substituted with a carboxy group, examples of which include carboxymethyl, 2-carboxyethyl, 3-carboxypropyl and 4-carboxybutyl, and preferably it is 2-carboxyethyl or 3-carboxypropyl.

The "carboxy lower alkoxyalkyl group" in the definitions of $R^a$, $R^b$ and Substituent group α means a group in which the aforementioned "lower alkoxyalkyl group" is substituted with a carboxy group, preferably it is a carboxy $C_3$-$C_9$ alkoxyalkyl group, more preferably a carboxy $C_3$-$C_4$ alkoxyalkyl group, particularly preferably 2-carboxyethoxymethyl or 2-(2-carboxyethoxy)ethyl, and most preferably 2-(2-carboxyethoxy)ethyl.

The "lower alkoxycarbonyl lower alkoxyalkyl group" in the definitions of $R^a$ and $R^b$ means a group in which the aforementioned "lower alkoxyalkyl group" is substituted with a lower alkoxycarbonyl group, preferably it is a methoxycarbonyl $C_3$-$C_9$ alkoxyalkyl group, more preferably a methoxycarbonyl $C_3$-$C_4$ alkoxyalkyl group, particularly preferably 2-methoxycarbonylethoxymethyl or 2-(2-methoxycarbonylethoxy)ethyl, and most preferably 2-(2-methoxycarbonylethoxy)ethyl.

The "carbamoyl lower alkyl group" in the definitions of $R^a$ and $R^b$ means a group in which the aforementioned "lower alkyl group" is substituted with a carbamoyl group, examples of which include carbamoylmethyl, 2-carbamoylethyl, 3-carbamoylpropyl and 4-carbamoylbutyl, and preferably it is 2-carbamoylethyl or 3-carbamoylpropyl.

The "carbamoyl lower alkoxyalkyl group" in the definitions of $R^a$ and $R^b$ means a group in which the aforementioned "lower alkoxyalkyl group" is substituted with a carbamoyl group, preferably it is a carbamoyl $C_3$-$C_9$ alkoxyalkyl group, more preferably a carbamoyl $C_3$-$C_4$ alkoxyalkyl group, particularly preferably 2-carbamoylethoxymethyl or 2-(2-carbamoylethoxy)ethyl, and most preferably 2-(2-carbamoylethoxy)ethyl.

The "lower aliphatic acylamino group" in the definition of Substituent group α and the lower aliphatic acylamino portion of the "lower aliphatic acylamino lower alkyl group" and "lower aliphatic acylamino lower alkoxyalkyl group" in the definitions of $R^a$ and $R^b$ mean an amino group substituted with the aforementioned "lower aliphatic acyl group", examples of which include formylamino, acetylamino, propionylamino, butyrylamino, isobutyrylamino, pentanoylamino, pivaloylamino, valerylamino and isovalerylamino, preferably it is formylamino, acetylamino or propionylamino, and particularly preferably acetylamino.

The "lower aliphatic-acylamino lower alkyl group" in the definitions of $R^a$ and $R^b$ means a group in which the aforementioned "lower alkyl group" is substituted with the aforementioned "lower aliphatic acylamino group", particularly preferably it is a $C_1$-$C_4$ alkyl group substituted with acetylamino, and most preferably 2-acetylaminoethyl, 3-acetylaminopropyl or 4-acetylaminobutyl.

The "lower aliphatic acylamino lower alkoxyalkyl group" in the definitions of $R^a$ and $R^b$ means a group in which the aforementioned "lower alkoxyalkyl group" is substituted with a lower aliphatic acylamino group, preferably it is an acetylamino $C_3$-$C_9$ alkoxyalkyl group, more preferably an acetylamino $C_3$-$C_4$ alkoxyalkyl group, particularly preferably 2-acetylaminoethoxymethyl or 2-(2-acetylaminoethoxy)ethyl, and most preferably 2-(2-acetylaminoethoxy)ethyl.

The "lower alkylsulfonylamino lower alkyl group" in the definitions of $R^a$ and $R^b$ is preferably a $C_1$-$C_2$ alkyl-$SO_2NH$—$C_1$-$C_4$ alkyl group, more preferably a $C_1$-$C_4$ alkyl group substituted with methylsulfonylamino, and most preferably 2-methylsulfonylaminoethyl, 3-methylsulfonylaminopropyl or 4-methylsulfonylaminobutyl.

The "lower alkylsulfonylamino lower alkoxyalkyl group" in the definitions of $R^a$ and $R^b$ is preferably a $C_1$-$C_2$ alkyl-$SO_2NH$—$C_3$-$C_9$ alkoxyalkyl group, more preferably a methylsulfonylamino-$C_3$-$C_4$ alkoxyalkyl group, particularly preferably 2-methylsulfonylaminoethoxymethyl or 2-(2-methylsulfonylaminoethoxy)ethyl, and most preferably 2-(2-methylsulfonylaminoethoxy)ethyl.

The "(N-hydroxy-N-methylcarbamoyl) lower alkyl group" in the definitions of $R^a$, $R^b$ and Substituent group α is preferably a $C_1$-$C_4$ alkyl group substituted with N-hydroxy-N-methylcarbamoyl, and most preferably 2-(N-hydroxy-N-methylcarbamoyl)ethyl, 3-(N-hydroxy-N-methylcarbamoyl)propyl or 4-(N-hydroxy-N-methylcarbamoyl)butyl.

The "(N-hydroxy-N-methylcarbamoyl) lower alkoxyalkyl group" in the definitions of $R^a$ and $R^b$ is preferably a $C_3$-$C_9$ alkoxyalkyl group substituted with N-hydroxy-N-methylcarbamoyl, more preferably a $C_3$-$C_4$ alkoxyalkyl group substituted with N-hydroxy-N-methylcarbamoyl, particularly preferably 2-(N-hydroxy-N-methylcarbamoyl)ethoxymethyl or 2-[2-(N-hydroxy-N-methylcarbamoyl)ethoxy]ethyl, and most preferably 2-[2-(N-hydroxy-N-methylcarbamoyl)ethoxy]ethyl.

The "(N-lower alkoxy-N-methylcarbamoyl) lower alkyl group" in the definitions of $R^a$, $R^b$ and Substituent group α is preferably an N-($C_1$-$C_2$ alkoxy)-N-methylcarbamoyl-$C_1$-$C_4$ alkyl group, more preferably a $C_1$-$C_4$ alkyl group substituted with N-methoxy-N-methylcarbamoyl, and most preferably 2-(N-methoxy-N-methylcarbamoyl)ethyl, 3-(N-methoxy-N-methylcarbamoyl)propyl or 4-(N-methoxy-N-methylcarbamoyl)butyl.

The "(N-lower alkoxy-N-methylcarbamoyl) lower alkoxyalkyl group" in the definitions of $R^a$ and $R^b$ is preferably an N-($C_1$-$C_2$ alkoxy)-N-methylcarbamoyl $C_3$-$C_9$ alkoxyalkyl group, more preferably a $C_3$-$C_4$ alkoxyalkyl group substituted with N-methoxy-N-methylcarbamoyl, particularly preferably 2-(N-methoxy-N-methylcarbamoyl)ethoxymethyl or 2-[2-(N-methoxy-N-methylcarbamoyl)ethoxy]ethyl, and most preferably 2-[2-(N-methoxy-N-methylcarbamoyl)ethoxy]ethyl.

The "nitrogen-containing heterocyclic group" and the nitrogen-containing heterocyclic group of the "nitrogen-containing heterocyclic group substituted with 1 to 3 groups selected from Substituent group α", which are formed by $R^a$ and $R^b$, together with the nitrogen atom to which they are attached, is a 4- to 7-membered heterocyclic group containing at least one nitrogen atom and optionally containing an oxygen atom or sulfur atom, preferably a 4- to 6-membered heterocyclic group containing at least one nitrogen atom and optionally containing an oxygen atom or sulfur atom, more preferably azetidino, pyrrolidino, imidazolidino, 1-pyrazolidinyl, piperidino, 4-oxopiperidino, piperazino, 3-oxopiperazino, morpholino or thiomorpholino, particularly preferably azetidino, pyrrolidino, piperidino, 4-oxopiperidino, piperazino, 3-oxopiperazino, morpholino or thiomorpholino, and most preferably pyrrolidino, piperidino or piperazino.

In the case of $R^a$ and $R^b$, together with the nitrogen atom to which they are attached, forming a "nitrogen-containing heterocyclic group substituted with 1 to 3 groups selected from Substituent group α", said group is preferably a nitrogen-containing heterocyclic group substituted with one group selected from Substituent group α, more preferably a nitrogen-containing heterocyclic group substituted with a hydroxy lower alkyl group, hydroxy lower alkoxy group, hydroxy lower alkoxy lower alkyl group, lower aliphatic acyl group, hydroxyl lower aliphatic acylamino group, hydroxyl group or carbamoyl group, and most preferably pyrrolidino, piperidino or piperazino substituted with a hydroxy lower alkyl group, hydroxy lower alkoxy group, hydroxy lower alkoxy lower alkyl group, lower aliphatic acyl group, hydroxy lower aliphatic acylamino group or hydroxyl group.

The "$C_1$-$C_4$ alkylene group" in the definitions of B and E is, for example, methylene, methylmethylene, ethylene, propylene, trimethylene, tetramethylene, 1-methyltrimethylene, 2-methyltrimethylene or 3-methyltrimethylene, and preferably $C_1$-$C_3$ alkylene. B is particularly preferably methylene. E is particularly preferably ethylene or trimethylene, and most preferably ethylene.

The "$C_2$-$C_4$ alkenylene group" in the definitions of B and E is, for example, ethenylene, 2-propenylene, 1-methyl-2-propenylene, 2-methyl-2-propenylene, 2-ethyl-2-propenylene or 2-butenylene, preferably ethenylene, 2-propenylene or 3-butenylene, and more preferably ethenylene or 2-propenylene.

The "halogen atom" in the definition of Substituent group α is a fluorine atom, chlorine atom, bromine atom or iodine atom, and preferably a fluorine atom or a chlorine atom.

The "hydroxy lower aliphatic acylamino group" in the definition of Substituent group α means a group in which the aforementioned "lower aliphatic acylamino group" is substituted with a hydroxyl group, examples of which include hydroxyacetylamino, 3-hydroxypropionylamino, 4-hydroxybutyrylamino and 3-hydroxyisobutyrylamino, preferably it is hydroxyacetylamino or 3-hydroxypropionylamino, and particularly preferably a hydroxyacetylamino group.

The "pharmacologically acceptable salt thereof" represents a salt of compound (I) of the present invention since said compound (I) of the present invention can be converted to a salt by reacting with an acid in the case of a compound having a basic functional group such as an amino group, or by reacting with base in the case of a compound having an acidic functional group such as a carboxyl group.

Examples of salts based on basic functional groups include inorganic acid salts such as hydrohalides, e.g. hydrochloride, hydrobromide or hydroiodide, nitrates, perchlorates, sulfates or phosphates; organic acid salts such as lower alkane sulfonates, e.g. methanesulfonate, trifluoromethanesulfonate or ethanesulfonate, aryl sulfonates, e.g. benzene sulfonate or p-toluene sulfonate, or carboxylic acid salts, e.g. acetates, malates, fumarates, succinates, citrates, ascorbates, tartrates, oxalates or maleates; and, amino acid salts such as glycine salts, lysine salts, arginine salts, ornithine salts, glutamates or aspartates.

Examples of salts based on acidic functional groups include metal salts such as alkali metal salts, e.g. sodium salts, potassium salts or lithium salts, alkaline earth metal salts, e.g. calcium salts or magnesium salts, aluminium salts, or iron salts; ammonium salts; organic amine salts such as t-octylamine salts, dibenzylamine salts, morpholine salts, glucosamine salts, phenylglycine alkyl ester salts, ethylene diamine salts, N-methylglucamine salts, guanidine salts, diethylamine salts, triethylamine salts, dicyclohexylamine salts, N,N'-dibenzyl ethylene diamine salts, chloroprocaine salts, procaine salts, diethanolamine salts, N-benzyl phenethylamine salts, piperazine salts, tetramethyl ammonium salts or tris(hydroxymethyl)aminomethane salts; and, amino acid salts such as glycine salts, lysine salts, arginine salts, ornithine salts, glutamates or aspartates.

A compound having the general formula (I) of the present invention, or a pharmacologically acceptable salt thereof, may absorb moisture, retain adhered moisture or form a hydrate as a result of being exposed to the atmosphere or recrystallizing, and such hydrates are also included in the present invention.

A compound having the general formula (I) of the present invention may have optical isomers based on an asymmetric center in the molecule thereof. In a compound of the present invention, all of these isomers and mixtures thereof are represented with a single formula, namely the general formula (I). Thus, the present invention includes all of these isomers and mixtures of these isomers at arbitrary ratios.

Specific examples of compounds having the general formula (I) of the present invention include those compounds described in the following Compound List 1 and Compound List 2.

In the following lists of compounds, "Ac" represents acetyl, "Me" methyl, "Et" ethyl, "Pr" propyl, "iPr" isopropyl, "Bu" butyl, "iBu" isobutyl, "Pn" pentyl, "iPn" isopentyl, "tBu" tert-butyl, "cPr" cyclopropyl, "cBu" cyclobutyl, "cPn" cyclopentyl, "cHx" cyclohexyl, "Mor" morpholino, "Pip" piperidino (for example, "4-($H_2$NCO)-Pip" represents 4-aminocarbonylpiperazino), "Pipr" piperazino, "Aze" azetidino, and "Pyrr" pyrrolidino.

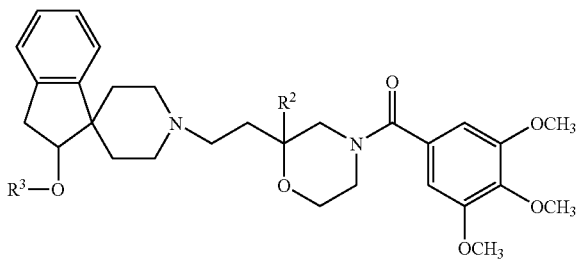

(I-1)

[Compound List 1]

| Compound No. | $R^2$ | $R^3$ |
|---|---|---|
| 1-1 | 3,4-diF—Ph | Me—CO—O—$CH_2$—CO |
| 1-2 | 3,4-diF—Ph | Me—CO |
| 1-3 | 3,4-diF—Ph | Et—CO |
| 1-4 | 3,4-diF—Ph | Pr—CO |
| 1-5 | 3,4-diF—Ph | iPr—CO |
| 1-6 | 3,4-diF—Ph | Bu—CO |
| 1-7 | 3,4-diF—Ph | iBu—CO |
| 1-8 | 3,4-diF—Ph | Pn—CO |
| 1-9 | 3,4-diF—Ph | iPn—CO |
| 1-10 | 3,4-diF—Ph | tBu—$CH_2$—CO |
| 1-11 | 3,4-diF—Ph | cPr—CO |
| 1-12 | 3,4-diF—Ph | cBu—CO |
| 1-13 | 3,4-diF—Ph | cPn—CO |
| 1-14 | 3,4-diF—Ph | cHx—CO |
| 1-15 | 3,4-diF—Ph | MeO—$CH_2$—CO |
| 1-16 | 3,4-diF—Ph | Mor—$CH_2$—CO |
| 1-17 | 3,4-diF—Ph | Mor—$(CH_2)_2$—CO |
| 1-18 | 3,4-diF—Ph | Mor—$(CH_2)_3$—CO |
| 1-19 | 3,4-diF—Ph | Pip—$CH_2$—CO |
| 1-20 | 3,4-diF—Ph | Pip—$(CH_2)_2$—CO |
| 1-21 | 3,4-diF—Ph | Pip—$(CH_2)_3$—CO |
| 1-22 | 3,4-diF—Ph | Pipr—$CH_2$—CO |
| 1-23 | 3,4-diF—Ph | Pipr—$(CH_2)_2$—CO |
| 1-24 | 3,4-diF—Ph | Pipr—$(CH_2)_3$—CO |
| 1-25 | 3,4-diF—Ph | EtO—CO |
| 1-26 | 3,4-diF—Ph | MeO—$(CH_2)_2$—O—CO |
| 1-27 | 3,4-diF—Ph | F—$(CH_2)_2$—O—CO |
| 1-28 | 3,4-diF—Ph | Propargyl—O—CO |
| 1-29 | 3,4-diF—Ph | EtO—CO—$CH_2$—NH—CO |
| 1-30 | 3,4-diF—Ph | EtO—CO—$(CH_2)_2$—NH—CO |
| 1-31 | 3,4-diF—Ph | Eto—CO—$(CH_2)_3$—NH—CO |

-continued

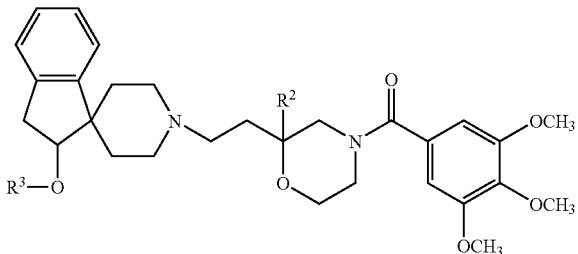

(I-1)

[Compound List 1]

| Compound No. | R² | R³ |
|---|---|---|
| 1-32 | 3,4-diF—Ph | Et—NH—CO |
| 1-33 | 3,4-diF—Ph | HO—(CH₂)₂—N(Me)—CH₂—CO |
| 1-34 | 3,4-diF—Ph | EtO—(CH₂)₂—NH—CH₂—CO |
| 1-35 | 3,4-diF—Ph | Me—NH—CH₂—CO |
| 1-36 | 3,4-diF—Ph | Et—NH—CH₂—CO |
| 1-37 | 3,4-diF—Ph | Pr—NH—CH₂—CO |
| 1-38 | 3,4-diF—Ph | iPr—NH—CH₂—CO |
| 1-39 | 3,4-diF—Ph | (Me)₂N—CH₂—CO |
| 1-40 | 3,4-diF—Ph | (Et)₂N—CH₂—CO |
| 1-41 | 3,4-diF—Ph | (Pr)₂N—CH₂—CO |
| 1-42 | 3,4-diF—Ph | (iPr)₂N—CH₂—CO |
| 1-43 | 3,4-diF—Ph | (MeO—CH₂)₂N—CH₂—CO |
| 1-44 | 3,4-diF—Ph | (MeO—CH₂—CH₂)2N—CH₂—CO |
| 1-45 | 3,4-diF—Ph | Aze—CH₂—CO |
| 1-46 | 3,4-diF—Ph | Pyrr—CH₂—CO |
| 1-47 | 3,4-diF—Ph | Pip—CH₂—CO |
| 1-48 | 3,4-diF—Ph | 4-(H₂NCO)—Pip—CH₂—CO |
| 1-49 | 3,4-diF—Ph | 4-(HO—CH₂)—Pip—CH₂—CO |
| 1-50 | 3,4-diF—Ph | 4-(HO—CH₂—CH₂)—Pip—CH₂—CO |
| 1-51 | 3,4-diF—Ph | HO—CO—CH₂ |
| 1-52 | 3,4-diF—Ph | MeO—CO—CH₂ |
| 1-53 | 3,4-diF—Ph | EtO—CO—CH₂ |
| 1-54 | 3,4-diF—Ph | H₂N—CO—CH₂ |
| 1-55 | 3,4-diF—Ph | (Me)₂N—CO—CH₂ |
| 1-56 | 3,4-diF—Ph | (Et)₂N—CO—CH₂ |
| 1-57 | 3,4-diF—Ph | (HO—CH₂—CH₂)₂N—CO—CH₂ |
| 1-58 | 3,4-diF—Ph | HO—CH₂—CH₂—NH—CO—CH₂ |
| 1-59 | 3,4-diF—Ph | HO—CH₂—CH₂—N(Me)—CO—CH₂ |
| 1-60 | 3,4-diF—Ph | Mor—CO—CH₂ |
| 1-61 | 3,4-diF—Ph | Pip—CO—CH₂ |
| 1-62 | 3,4-diF—Ph | Pipr—CO—CH₂ |
| 1-63 | 3,4-diF—Ph | HO—(CH₂)₂ |
| 1-64 | 3,4-diF—Ph | H₂N—(CH₂)₂ |
| 1-65 | 3,4-diF—Ph | (Me)₂N—(CH₂)₂ |
| 1-66 | 3,4-diF—Ph | (Et)₂N—(CH₂)₂ |
| 1-67 | 3,4-diF—Ph | (HO—CH₂—CH₂)₂N—(CH₂)₂ |
| 1-68 | 3,4-diF—Ph | HO—CH₂—CH₂—NH—(CH₂)₂ |
| 1-69 | 3,4-diF—Ph | HO—CH₂—CH₂—N(Me)—(CH₂)₂ |
| 1-70 | 3,4-diF—Ph | Mor—(CH₂)₂ |
| 1-71 | 3,4-diF—Ph | Pip—(CH₂)₂ |
| 1-72 | 3,4-diF—Ph | Pipr—(CH₂)₂ |
| 1-73 | 3,4-diF—Ph | H₂N—CO—NH—CO |
| 1-74 | 3,4-diF—Ph | (Me)₂N—CO—NH—CO |
| 1-75 | 3,4-diF—Ph | (Et)₂N—CO—NH—CO |
| 1-76 | 3,4-diF—Ph | (HO—CH₂—CH₂)₂N—CO—NH—CO |
| 1-77 | 3,4-diF—Ph | HO—CH₂—CH₂—NH—CO—NH—CO |
| 1-78 | 3,4-diF—Ph | HO—CH₂—CH₂—N(Me)—CO—NH—CO |
| 1-79 | 3,4-diF—Ph | Mor—CO—NH—CO |
| 1-80 | 3,4-diF—Ph | Pip—CO—NH—CO |
| 1-81 | 3,4-diF—Ph | Pipr—CO—NH—CO |
| 1-82 | 3,4-diF—Ph | H₂N—SO₂—NH—CO |
| 1-83 | 3,4-diF—Ph | (Me)₂N—SO₂—NH—CO |
| 1-84 | 3,4-diF—Ph | (Et)₂N—SO₂—NH—CO |
| 1-85 | 3,4-diF—Ph | (HO—CH₂—CH₂)₂N—SO₂—NH—CO |
| 1-86 | 3,4-diF—Ph | HO—CH₂—CH₂—NH—SO₂—NH—CO |
| 1-87 | 3,4-diF—Ph | HO—CH₂—CH₂—N(Me)—SO₂—NH—CO |
| 1-88 | 3,4-diF—Ph | Mor—SO₂—NH—CO |
| 1-89 | 3,4-diF—Ph | Pip—SO₂—NH—CO |
| 1-90 | 3,4-diF—Ph | Pipr—SO₂—NH—CO |
| 1-91 | 3,4-diF—Ph | Mor—CH₂—CO—NH—CO |

-continued

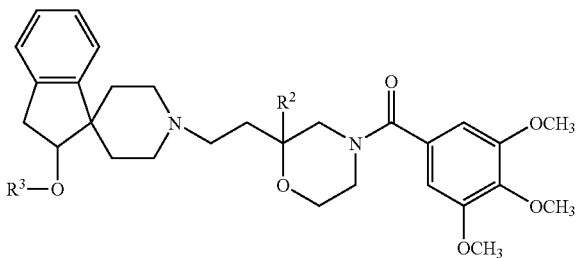

(I-1)

[Compound List 1]

| Compound No. | R² | R³ |
|---|---|---|
| 1-92 | 3,4-diF—Ph | Pip—CH₂—CO—NH—CO |
| 1-93 | 3,4-diF—Ph | Pipr—CH₂—CO—NH—CO |
| 1-94 | 3,4-diF—Ph | H₂N—CO |
| 1-95 | 3,4-diF—Ph | MeO—(CH₂)₂—O—CH₂ |
| 1-96 | 3,4-diF—Ph | MeO—CH₂ |
| 1-97 | 3,4-diCl—Ph | Me—CO—O—CH₂—CO |
| 1-98 | 3,4-diCl—Ph | Me—CO |
| 1-99 | 3,4-diCl—Ph | Et—CO |
| 1-100 | 3,4-diCl—Ph | Pr—CO |
| 1-101 | 3,4-diCl—Ph | iPr—CO |
| 1-102 | 3,4-diCl—Ph | Bu—CO |
| 1-103 | 3,4-diCl—Ph | iBu—CO |
| 1-104 | 3,4-diCl—Ph | Pn—CO |
| 1-105 | 3,4-diCl—Ph | iPn—CO |
| 1-106 | 3,4-diCl—Ph | tBu—CH₂—CO |
| 1-107 | 3,4-diCl—Ph | cPr—CO |
| 1-108 | 3,4-diCl—Ph | cBu—CO |
| 1-109 | 3,4-diCl—Ph | cPn—CO |
| 1-110 | 3,4-diCl—Ph | cHx—CO |
| 1-111 | 3,4-diCl—Ph | MeO—CH₂—CO |
| 1-112 | 3,4-diCl—Ph | Mor—CH₂—CO |
| 1-113 | 3,4-diCl—Ph | Mor—(CH₂)₂—CO |
| 1-114 | 3,4-diCl—Ph | Mor—(CH₂)₃—CO |
| 1-115 | 3,4-diCl—Ph | Pip—CH₂—CO |
| 1-116 | 3,4-diCl—Ph | Pip—(CH₂)₂—CO |
| 1-117 | 3,4-diCl—Ph | Pip—(CH₂)₃—CO |
| 1-118 | 3,4-diCl—Ph | Pipr—CH₂—CO |
| 1-119 | 3,4-diCl—Ph | Pipr—(CH₂)₂—CO |
| 1-120 | 3,4-diCl—Ph | Pipr—(CH₂)₃—CO |
| 1-121 | 3,4-diCl—Ph | EtO—CO |
| 1-122 | 3,4-diCl—Ph | MeO—(CH₂)₂—O—CO |
| 1-123 | 3,4-diCl—Ph | F—(CH₂)₂—O—CO |
| 1-124 | 3,4-diCl—Ph | Propargyl—O—CO |
| 1-125 | 3,4-diCl—Ph | EtO—CO—CH₂—NH—CO |
| 1-126 | 3,4-diCl—Ph | EtO—CO—(CH₂)₂—NH—CO |
| 1-127 | 3,4-diCl—Ph | EtO—CO—(CH₂)₃—NH—CO |
| 1-128 | 3,4-diCl—Ph | Et—NH—CO |
| 1-129 | 3,4-diCl—Ph | HO—(CH₂)₂—N(Me)—CH₂—CO |
| 1-130 | 3,4-diCl—Ph | EtO—(CH₂)₂—NH—CH₂—CO |
| 1-131 | 3,4-diCl—Ph | Me—NH—CH₂—CO |
| 1-132 | 3,4-diCl—Ph | Et—NH—CH₂—CO |
| 1-133 | 3,4-diCl—Ph | Pr—NH—CH₂—CO |
| 1-134 | 3,4-diCl—Ph | iPr—NH—CH₂—CO |
| 1-135 | 3,4-diCl—Ph | (Me)₂N—CH₂—CO |
| 1-136 | 3,4-diCl—Ph | (Et)₂N—CH₂—CO |
| 1-137 | 3,4-diCl—Ph | (Pr)₂N—CH₂—CO |
| 1-138 | 3,4-diCl—Ph | (iPr)₂N—CH₂—CO |
| 1-139 | 3,4-diCl—Ph | (MeO—CH₂)₂N—CH₂—CO |
| 1-140 | 3,4-diCl—Ph | (MeO—CH₂—CH₂)₂N—CH₂—CO |
| 1-141 | 3,4-diCl—Ph | Aze—CH₂—CO |
| 1-142 | 3,4-diCl—Ph | Pyrr—CH₂—CO |
| 1-143 | 3,4-diCl—Ph | Pip—CH₂—CO |
| 1-144 | 3,4-diCl—Ph | 4-(H₂NCO)—Pip—CH₂—CO |
| 1-145 | 3,4-diCl—Ph | 4-(HO—CH₂)—Pip—CH₂—CO |
| 1-146 | 3,4-diCl—Ph | 4-(HO—CH₂—CH₂)—Pip—CH₂—CO |
| 1-147 | 3,4-diCl—Ph | HO—CO—CH₂ |
| 1-148 | 3,4-diCl—Ph | MeO—CO—CH₂ |
| 1-149 | 3,4-diCl—Ph | EtO—CO—CH₂ |
| 1-150 | 3,4-diCl—Ph | H₂N—CO—CH₂ |
| 1-151 | 3,4-diCl—Ph | (Me)₂N—CO—CH₂ |

-continued

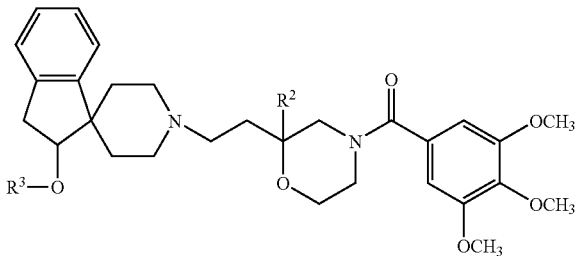

(I-1)

[Compound List 1]

| Compound No. | $R^2$ | $R^3$ |
|---|---|---|
| 1-152 | 3,4-diCl—Ph | (Et)$_2$N—CO—CH$_2$ |
| 1-153 | 3,4-diCl—Ph | (HO—CH$_2$—CH$_2$)$_2$N—CO—CH$_2$ |
| 1-154 | 3,4-diCl—Ph | HO—CH$_2$—CH$_2$—NH—CO—CH$_2$ |
| 1-155 | 3,4-diCl—Ph | HO—CH$_2$—CH$_2$—N(Me)—CO—CH$_2$ |
| 1-156 | 3,4-diCl—Ph | Mor—CO—CH$_2$ |
| 1-157 | 3,4-diCl—Ph | Pip—CO—CH$_2$ |
| 1-158 | 3,4-diCl—Ph | Pipr—CO—CH$_2$ |
| 1-159 | 3,4-diCl—Ph | HO—(CH$_2$)$_2$ |
| 1-160 | 3,4-diCl—Ph | H$_2$N—(CH$_2$)$_2$ |
| 1-161 | 3,4-diCl—Ph | (Me)$_2$N—(CH$_2$)$_2$ |
| 1-162 | 3,4-diCl—Ph | (Et)$_2$N—(CH$_2$)$_2$ |
| 1-163 | 3,4-diCl—Ph | (HO—CH$_2$—CH$_2$)$_2$N—(CH$_2$)$_2$ |
| 1-164 | 3,4-diCl—Ph | HO—CH$_2$—CH$_2$—NH—(CH$_2$)$_2$ |
| 1-165 | 3,4-diCl—Ph | HO—CH$_2$—CH$_2$—N(Me)—(CH$_2$)$_2$ |
| 1-166 | 3,4-diCl—Ph | Mor—(CH$_2$)$_2$ |
| 1-167 | 3,4-diCl—Ph | Pip—(CH$_2$)$_2$ |
| 1-168 | 3,4-diCl—Ph | Pipr—(CH$_2$)$_2$ |
| 1-169 | 3,4-diCl—Ph | H$_2$N—CO—NH—CO |
| 1-170 | 3,4-diCl—Ph | (Me)$_2$N—CO—NH—CO |
| 1-171 | 3,4-diCl—Ph | (Et)$_2$N—CO—NH—CO |
| 1-172 | 3,4-diCl—Ph | (HO—CH$_2$—CH$_2$)$_2$N—CO—NH—CO |
| 1-173 | 3,4-diCl—Ph | HO—CH$_2$—CH$_2$—NH—CO—NH—CO |
| 1-174 | 3,4-diCl—Ph | HO—CH$_2$—CH$_2$—N(Me)—CO—NH—CO |
| 1-175 | 3,4-diCl—Ph | Mor—CO—NH—CO |
| 1-176 | 3,4-diCl—Ph | Pip—CO—NH—CO |
| 1-177 | 3,4-diCl—Ph | Pipr—CO—NH—CO |
| 1-178 | 3,4-diCl—Ph | H$_2$N—SO$_2$—NH—CO |
| 1-179 | 3,4-diCl—Ph | (Me)$_2$N—SO$_2$—NH—CO |
| 1-180 | 3,4-diCl—Ph | (Et)$_2$N—SO$_2$—NH—CO |
| 1-181 | 3,4-diCl—Ph | (HO—CH$_2$—CH$_2$)$_2$N—SO$_2$—NH—CO |
| 1-182 | 3,4-diCl—Ph | HO—CH$_2$—CH$_2$—NH—SO$_2$—NH—CO |
| 1-183 | 3,4-diCl—Ph | HO—CH$_2$—CH$_2$—N(Me)—SO$_2$—NH—CO |
| 1-184 | 3,4-diCl—Ph | Mor—SO$_2$—NH—CO |
| 1-185 | 3,4-diCl—Ph | Pip—SO$_2$—NH—CO |
| 1-186 | 3,4-diCl—Ph | Pipr—SO$_2$—NH—CO |
| 1-187 | 3,4-diCl—Ph | Mor—CH$_2$—CO—NH—CO |
| 1-188 | 3,4-diCl—Ph | Pip—CH$_2$—CO—NH—CO |
| 1-189 | 3,4-diCl—Ph | Pipr—CH$_2$—CO—NH—CO |
| 1-190 | 3,4-diCl—Ph | H$_2$N—CO |
| 1-191 | 3,4-diCl—Ph | MeO—(CH$_2$)$_2$—O—CH$_2$ |
| 1-192 | 3,4-diCl—Ph | MeO—CH$_2$ |
| 1-193 | 3,4-diF—Ph | MeO—NH—CO—CH$_2$ |
| 1-194 | 3,4-diF—Ph | EtO—NH—CO—CH$_2$ |
| 1-195 | 3,4-diF—Ph | PrO—NH—CO—CH$_2$ |
| 1-196 | 3,4-diF—Ph | BuO—NH—CO—CH$_2$ |
| 1-197 | 3,4-diF—Ph | PnO—NH—CO—CH$_2$ |
| 1-198 | 3,4-diF—Ph | HxO—NH—CO—CH$_2$ |
| 1-199 | 3,4-diF—Ph | HO—(CH$_2$)$_3$—NH—CO—CH$_2$ |
| 1-200 | 3,4-diF—Ph | HO—(CH$_2$)$_4$—NH—CO—CH$_2$ |
| 1-201 | 3,4-diF—Ph | HO—(CH$_2$)$_5$—NH—CO—CH$_2$ |
| 1-202 | 3,4-diF—Ph | HO—(CH$_2$)$_2$—O—(CH$_2$)$_2$—NH—CO—CH$_2$ |
| 1-203 | 3,4-diF—Ph | Me—CH(OH)—(CH$_2$)$_3$—NH—CO—CH$_2$ |
| 1-204 | 3,4-diF—Ph | HO—(CH$_2$)$_6$—NH—CO—CH$_2$ |
| 1-205 | 3,4-diF—Ph | HO—C(Me)(Me)—(CH$_2$)$_3$—NH—CO—CH$_2$ |
| 1-206 | 3,4-diF—Ph | HO—(CH$_2$)$_3$—N(Me)—CO—CH$_2$ |
| 1-207 | 3,4-diF—Ph | HO—(CH$_2$)$_4$—N(Me)—CO—CH$_2$ |
| 1-208 | 3,4-diF—Ph | HO—(CH$_2$)$_5$—N(Me)—CO—CH$_2$ |
| 1-209 | 3,4-diF—Ph | Me—CH(OH)—(CH$_2$)$_3$—N(Me)—CO—CH$_2$ |
| 1-210 | 3,4-diF—Ph | HO—(CH$_2$)$_6$—N(Me)—CO—CH$_2$ |
| 1-211 | 3,4-diF—Ph | HO—(CH$_2$)$_2$—O—(CH$_2$)$_2$—N(Me)—CO—CH$_2$ |

-continued

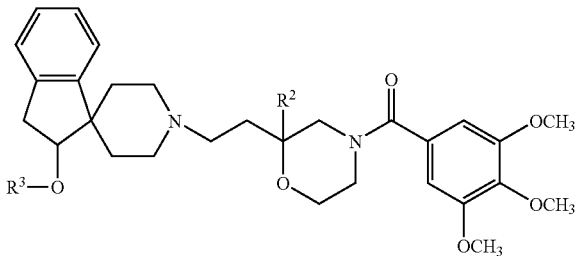

(I-1)

[Compound List 1]

| Compound No. | R² | R³ |
|---|---|---|
| 1-212 | 3,4-diF—Ph | HO—C(Me)(Me)—(CH₂)₃—N(Me)—CO—CH₂ |
| 1-213 | 3,4-diF—Ph | HO—(CH₂)₂—N(Et)—CO—CH₂ |
| 1-214 | 3,4-diF—Ph | HO—(CH₂)₃—N(Et)—CO—CH₂ |
| 1-215 | 3,4-diF—Ph | HO—(CH₂)₄—N(Et)—CO—CH₂ |
| 1-216 | 3,4-diF—Ph | HO—(CH₂)₅—N(Et)—CO—CH₂ |
| 1-217 | 3,4-diF—Ph | HO—(CH₂)₆—N(Et)—CO—CH₂ |
| 1-218 | 3,4-diF—Ph | HO—(CH₂)₂—O—(CH₂)₂—N(Et)—CO—CH₂ |
| 1-219 | 3,4-diF—Ph | HO—C(Me)(Me)—(CH₂)₃—N(Et)—CO—CH₂ |
| 1-220 | 3,4-diF—Ph | HO—(CH₂)₂—N(Pr)—CO—CH₂ |
| 1-221 | 3,4-diF—Ph | HO—(CH₂)₃—N(Pr)—CO—CH₂ |
| 1-222 | 3,4-diF—Ph | HO—(CH₂)₄—N(Pr)—CO—CH₂ |
| 1-223 | 3,4-diF—Ph | HO—(CH₂)₅—N(Pr)—CO—CH₂ |
| 1-224 | 3,4-diF—Ph | HO—(CH₂)₆—N(Pr)—CO—CH₂ |
| 1-225 | 3,4-diF—Ph | HO—(CH₂)₂—O—(CH₂)₂—N(Pr)—CO—CH₂ |
| 1-226 | 3,4-diF—Ph | HO—C(Me)(Me)—(CH₂)₃—N(Pr)—CO—CH₂ |
| 1-227 | 3,4-diF—Ph | HO—(CH₂)₂—N(Bu)—CO—CH₂ |
| 1-228 | 3,4-diF—Ph | HO—(CH₂)₃—N(Bu)—CO—CH₂ |
| 1-229 | 3,4-diF—Ph | HO—(CH₂)₄—N(Bu)—CO—CH₂ |
| 1-230 | 3,4-diF—Ph | HO—(CH₂)₅—N(Bu)—CO—CH₂ |
| 1-231 | 3,4-diF—Ph | HO—(CH₂)₆—N(Bu)—CO—CH₂ |
| 1-232 | 3,4-diF—Ph | HO—(CH₂)₂—O—(CH₂)₂—N(Bu)—CO—CH₂ |
| 1-233 | 3,4-diF—Ph | HO—C(Me)(Me)—(CH₂)₃—N(Bu)—CO—CH₂ |
| 1-234 | 3,4-diF—Ph | HO—(CH₂)₂—N(cPr)—CO—CH₂ |
| 1-235 | 3,4-diF—Ph | HO—(CH₂)₃—N(cPr)—CO—CH₂ |
| 1-236 | 3,4-diF—Ph | HO—(CH₂)₄—N(cPr)—CO—CH₂ |
| 1-237 | 3,4-diF—Ph | HO—(CH₂)₅—N(cPr)—CO—CH₂ |
| 1-238 | 3,4-diF—Ph | HO—(CH₂)₆—N(cPr)—CO—CH₂ |
| 1-239 | 3,4-diF—Ph | HO—(CH₂)₂—O—(CH₂)₂—N(cPr)—CO—CH₂ |
| 1-240 | 3,4-diF—Ph | HO—(CH₂)₂—N(HO)—CO—CH₂ |
| 1-241 | 3,4-diF—Ph | HO—(CH₂)₃—N(HO)—CO—CH₂ |
| 1-242 | 3,4-diF—Ph | HO—(CH₂)₄—N(HO)—CO—CH₂ |
| 1-243 | 3,4-diF—Ph | HO—(CH₂)₅—N(HO)—CO—CH₂ |
| 1-244 | 3,4-diF—Ph | HO—(CH₂)₆—N(HO)—CO—CH₂ |
| 1-245 | 3,4-diF—Ph | HO—C(Me)(Me)—(CH₂)₂—N(HO)—CO—CH₂ |
| 1-246 | 3,4-diF—Ph | HO—C(Me)(Me)—(CH₂)₃—N(HO)—CO—CH₂ |
| 1-247 | 3,4-diF—Ph | HO—(CH₂)₂—N(MeO)—CO—CH₂ |
| 1-248 | 3,4-diF—Ph | HO—(CH₂)₃—N(MeO)—CO—CH₂ |
| 1-249 | 3,4-diF—Ph | HO—(CH₂)₄—N(MeO)—CO—CH₂ |
| 1-250 | 3,4-diF—Ph | HO—(CH₂)₅—N(MeO)—CO—CH₂ |
| 1-251 | 3,4-diF—Ph | HO—(CH₂)₆—N(MeO)—CO—CH₂ |
| 1-252 | 3,4-diF—Ph | HO—C(Me)(Me)—(CH₂)₂—N(MeO)—CO—CH₂ |
| 1-253 | 3,4-diF—Ph | HO—C(Me)(Me)—(CH₂)₃—N(MeO)—CO—CH₂ |
| 1-254 | 3,4-diF—Ph | MeO—(CH₂)₂—N(Me)—CO—CH₂ |
| 1-255 | 3,4-diF—Ph | MeO—(CH₂)₃—N(Me)—CO—CH₂ |
| 1-256 | 3,4-diF—Ph | MeO—(CH₂)₄—N(Me)—CO—CH₂ |
| 1-257 | 3,4-diF—Ph | MeO—(CH₂)₅—N(Me)—CO—CH₂ |
| 1-258 | 3,4-diF—Ph | MeO—(CH₂)₆—N(Me)—CO—CH₂ |
| 1-259 | 3,4-diF—Ph | MeO—(CH₂)₂—O—(CH₂)₂—N(Me)—CO—CH₂ |
| 1-260 | 3,4-diF—Ph | MeO—C(Me)(Me)—(CH₂)₃—N(Me)—CO—CH₂ |
| 1-261 | 3,4-diF—Ph | NC—CH₂—NH—CO—CH₂ |
| 1-262 | 3,4-diF—Ph | NC—(CH₂)₂—NH—CO—CH₂ |
| 1-263 | 3,4-diF—Ph | NC—(CH₂)₃—NH—CO—CH₂ |
| 1-264 | 3,4-diF—Ph | NC—(CH₂)₄—NH—CO—CH₂ |
| 1-265 | 3,4-diF—Ph | NC—(CH₂)₅—NH—CO—CH₂ |
| 1-266 | 3,4-diF—Ph | NC—(CH₂)₆—NH—CO—CH₂ |
| 1-267 | 3,4-diF—Ph | NC—(CH₂)₂—O—(CH₂)₂—NH—CO—CH₂ |
| 1-268 | 3,4-diF—Ph | NC—CH₂—N(Me)—CO—CH₂ |
| 1-269 | 3,4-diF—Ph | NC—(CH₂)₂—N(Me)—CO—CH₂ |
| 1-270 | 3,4-diF—Ph | NC—(CH₂)₃—N(Me)—CO—CH₂ |
| 1-271 | 3,4-diF—Ph | NC—(CH₂)₄—N(Me)—CO—CH₂ |

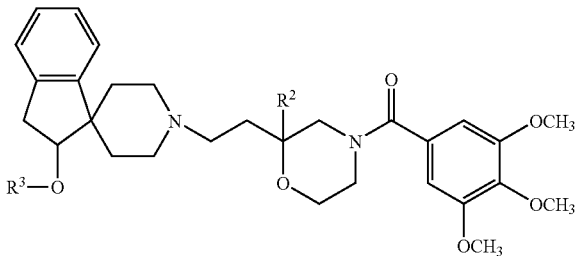

(I-1)

[Compound List 1]

| Compound No. | R² | R³ |
|---|---|---|
| 1-272 | 3,4-diF—Ph | NC—(CH₂)₅—N(Me)—CO—CH₂ |
| 1-273 | 3,4-diF—Ph | NC—(CH₂)₆—N(Me)—CO—CH₂ |
| 1-274 | 3,4-diF—Ph | NC—(CH₂)₂—O—(CH₂)₂—N(Me)—CO—CH₂ |
| 1-275 | 3,4-diF—Ph | HO—CO—CH₂—NH—CO—CH₂ |
| 1-276 | 3,4-diF—Ph | HO—CO—(CH₂)₂—NH—CO—CH₂ |
| 1-277 | 3,4-diF—Ph | HO—CO—(CH₂)₃—NH—CO—CH₂ |
| 1-278 | 3,4-diF—Ph | HO—CO—(CH₂)₄—MH—CO—CH₂ |
| 1-279 | 3,4-diF—Ph | HO—CO—(CH₂)₅—NH—CO—CH₂ |
| 1-280 | 3,4-diF—Ph | HO—CO—(CH₂)₆—NH—CO—CH₂ |
| 1-281 | 3,4-diF—Ph | HO—CO—(CH₂)₂—O—(CH₂)₂—NH—CO—CH₂ |
| 1-282 | 3,4-diF—Ph | HO—CO—CH₂—N(Me)—CO—CH₂ |
| 1-283 | 3,4-diF—Ph | HO—CO—(CH₂)₂—N(Me)—CO—CH₂ |
| 1-284 | 3,4-diF—Ph | HO—CO—(CH₂)₃—N(Me)—CO—CH₂ |
| 1-285 | 3,4-diF—Ph | HO—CO—(CH₂)₄—N(Me)—CO—CH₂ |
| 1-286 | 3,4-diF—Ph | HO—CO—(CH₂)₅—N(Me)—CO—CH₂ |
| 1-287 | 3,4-diF—Ph | HO—CO—(CH₂)₆—N(Me)—CO—CH₂ |
| 1-288 | 3,4-diF—Ph | HO—CO—(CH₂)₂—O—(CH₂)₂—N(Me)—CO—CH₂ |
| 1-289 | 3,4-diF—Ph | MeO—CO—CH₂—NH—CO—CH₂ |
| 1-290 | 3,4-diF—Ph | MeO—CO—(CH₂)₂—NH—CO—CH₂ |
| 1-291 | 3,4-diF—Ph | MeO—CO—(CH₂)₃—NH—CO—CH₂ |
| 1-292 | 3,4-diF—Ph | MeO—CO—(CH₂)₄—NH—CO—CH₂ |
| 1-293 | 3,4-diF—Ph | MeO—CO—(CH₂)₅—NH—CO—CH₂ |
| 1-294 | 3,4-diF—Ph | MeO—CO—(CH₂)₆—NH—CO—CH₂ |
| 1-295 | 3,4-diF—Ph | MeO—CO—(CH₂)₂—O—(CH₂)₂—NH—CO—CH₂ |
| 1-296 | 3,4-diF—Ph | MeO—CO—CH₂—N(Me)—CO—CH₂ |
| 1-297 | 3,4-diF—Ph | MeO—CO—(CH₂)₂—N(Me)—CO—CH₂ |
| 1-298 | 3,4-diF—Ph | MeO—CO—(CH₂)₃—N(Me)—CO—CH₂ |
| 1-299 | 3,4-diF—Ph | MeO—CO—(CH₂)₄—N(Me)—CO—CH₂ |
| 1-300 | 3,4-diF—Ph | MeO—CO—(CH₂)₅—N(Me)—CO—CH₂ |
| 1-301 | 3,4-diF—Ph | MeO—CO—(CH₂)₆—N(Me)—CO—CH₂ |
| 1-302 | 3,4-diF—Ph | MeO—CO—(CH₂)₂—O—(CH₂)₂—N(Me)—CO—CH₂ |
| 1-303 | 3,4-diF—Ph | H₂N—CO—CH₂—NH—CO—CH₂ |
| 1-304 | 3,4-diF—Ph | H₂N—CO—(CH₂)₂—N2H—CO—CH₂ |
| 1-305 | 3,4-diF—Ph | H₂N—CO—(CH₂)₃—NH—CO—CH₂ |
| 1-306 | 3,4-diF—Ph | H₂N—CO—(CH₂)₄—NH—CO—CH₂ |
| 1-307 | 3,4-diF—Ph | H₂N—CO—(CH₂)₅—MH—CO—CH₂ |
| 1-308 | 3,4-diF—Ph | H₂N—CO—(CH₂)₆—NH—CO—CH₂ |
| 1-309 | 3,4-diF—Ph | H₂N—CO—(CH₂)₂—O—(CH₂)₂—NH—CO—CH₂ |
| 1-310 | 3,4-diF—Ph | H₂N—CO—CH₂—N(Me)—CO—CH₂ |
| 1-311 | 3,4-diF—Ph | H₂N—CO—(CH₂)₂—N(Me)—CO—CH₂ |
| 1-312 | 3,4-diF—Ph | H₂N—CO—(CH₂)₃—N(Me)—CO—CH₂ |
| 1-313 | 3,4-diF—Ph | H₂N—CO—(CH₂)₄—N(Me)—CO—CH₂ |
| 1-314 | 3,4-diF—Ph | H₂N—CO—(CH₂)₅—N(Me)—CO—CH₂ |
| 1-315 | 3,4-diF—Ph | H₂N—CO—(CH₂)₆—N(Me)—CO—CH₂ |
| 1-316 | 3,4-diF—Ph | H₂N—CO—(CH₂)₂—O—(CH₂)₂—N(Me)—CO—CH₂ |
| 1-317 | 3,4-diF—Ph | HO—N(Me)—CO—CH₂—N(Me)—CO—CH₂ |
| 1-318 | 3,4-diF—Ph | HO—N(Me)—CO—(CH₂)₂—N(Me)—CO—CH₂ |
| 1-319 | 3,4-diF—Ph | HO—N(Me)—CO—(CH₂)₃—N(Me)—CO—CH₂ |
| 1-320 | 3,4-diF—Ph | HO—N(Me)—CO—(CH₂)₄—N(Me)—CO—CH₂ |
| 1-321 | 3,4-diF—Ph | HO—N(Me)—CO—(CH₂)₅—N(Me)—CO—CH₂ |
| 1-322 | 3,4-diF—Ph | HO—N(Me)—CO—(CH₂)₆—N(Me)—CO—CH₂ |
| 1-323 | 3,4-diF—Ph | HO—N(Me)—CO—(CH₂)₂—O—(CH₂)₂—N(Me)—CO—CH₂ |
| 1-324 | 3,4-diF—Ph | MeO—N(Me)—CO—CH₂—N(Me)—CO—CH₂ |
| 1-325 | 3,4-diF—Ph | MeO—N(Me)—CO—(CH₂)₂—N(Me)—CO—CH₂ |
| 1-326 | 3,4-diF—Ph | MeO—N(Me)—CO—(CH₂)₃—N(Me)—CO—CH₂ |
| 1-327 | 3,4-diF—Ph | MeO—N(Me)—CO—(CH₂)₄—N(Me)—CO—CH₂ |
| 1-328 | 3,4-diF—Ph | MeO—N(Me)—CO—(CH₂)₅—N(Me)—CO—CH₂ |
| 1-329 | 3,4-diF—Ph | MeO—N(Me)—CO—(CH₂)₆—N(Me)—CO—CH₂ |
| 1-330 | 3,4-diF—Ph | MeO—N(Me)—CO—(CH₂)₂—O—(CH₂)₂—N(Me)—CO—CH₂ |
| 1-331 | 3,4-diF—Ph | Ac—CH₂—N(Me)—CO—CH₂ |

-continued

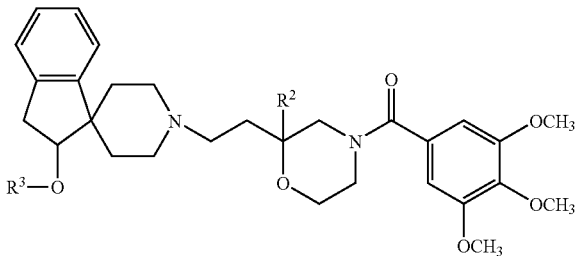

(I-1)

[Compound List 1]

| Compound No. | R² | R³ |
|---|---|---|
| 1-332 | 3,4-diF—Ph | Ac—(CH₂)₂—N(Me)—CO—CH₂ |
| 1-333 | 3,4-diF—Ph | Ac—(CH₂)₃—N(Me)—CO—CH₂ |
| 1-334 | 3,4-diF—Ph | Ac—(CH₂)₄—N(Me)—CO—CH₂ |
| 1-335 | 3,4-diF—Ph | Ac—(CH₂)₅—N(Me)—CO—CH₂ |
| 1-336 | 3,4-diF—Ph | Ac—(CH₂)₆—N(Me)—CO—CH₂ |
| 1-337 | 3,4-diF—Ph | Ac—(CH₂)₂—O—(CH₂)₂—N(Me)—CO—CH₂ |
| 1-338 | 3,4-diF—Ph | HO—(CH₂)₂—O—N(Me)—CO—CH₂ |
| 1-339 | 3,4-diF—Ph | HO—(CH₂)₃—O—N(Me)—CO—CH₂ |
| 1-340 | 3,4-diF—Ph | HO—(CH₂)₄—O—N(Me)—CO—CH₂ |
| 1-341 | 3,4-diF—Ph | HO—(CH₂)₅—O—N(Me)—CO—CH₂ |
| 1-342 | 3,4-diF—Ph | HO—(CH₂)₆—O—N(Me)—CO—CH₂ |
| 1-343 | 3,4-diF—Ph | HO—(CH₂)₂—O—(CH₂)₂—O—N(Me)—CO—CH₂ |
| 1-344 | 3,4-diF—Ph | (Me)₂N—(CH₂)₂—N(Me)—CO—CH₂ |
| 1-345 | 3,4-diF—Ph | (Me)₂N—(CH₂)₃—N(Me)—CO—CH₂ |
| 1-346 | 3,4-diF—Ph | (Me)₂N—(CH₂)₄—N(Me)—CO—CH₂ |
| 1-347 | 3,4-diF—Ph | (Me)₂N—(CH₂)₅—N(Me)—CO—CH₂ |
| 1-348 | 3,4-diF—Ph | (Me)₂N—(CH₂)₆—N(Me)—CO—CH₂ |
| 1-349 | 3,4-diF—Ph | (Me)₂N—(CH₂)₂—O—(CH₂)₂—N(Me)—CO—CH₂ |
| 1-350 | 3,4-diF—Ph | AcNH—(CH₂)₂—N(Me)—CO—CH₂ |
| 1-351 | 3,4-diF—Ph | AcNH—(CH₂)₃—N(Me)—CO—CH₂ |
| 1-352 | 3,4-diF—Ph | AcNH—(CH₂)₄—N(Me)—CO—CH₂ |
| 1-353 | 3,4-diF—Ph | AcNH—(CH₂)₅—N(Me)—CO—CH₂ |
| 1-354 | 3,4-diF—Ph | AcNH—(CH₂)₆—N(Me)—CO—CH₂ |
| 1-355 | 3,4-diF—Ph | AcNH—(CH₂)₂—O—(CH₂)₂—N(Me)—CO—CH₂ |
| 1-356 | 3,4-diF—Ph | Me—SO₂NH—(CH₂)₂—N(Me)—CO—CH₂ |
| 1-357 | 3,4-diF—Ph | Me—SO₂NH—(CH₂)₃—N(Me)—CO—CH₂ |
| 1-358 | 3,4-diF—Ph | Me—SO₂NH—(CH₂)₄—N(Me)—CO—CH₂ |
| 1-359 | 3,4-diF—Ph | Me—SO₂NH—(CH₂)₅—N(Me)—CO—CH₂ |
| 1-360 | 3,4-diF—Ph | Me—SO₂NH—(CH₂)₆—N(Me)—CO—CH₂ |
| 1-361 | 3,4-diF—Ph | Me—SO₂NH—(CH₂)₂—O—(CH₂)₂—N(Me)—CO—CH₂ |
| 1-362 | 3,4-diF—Ph | 2-(HO—(CH₂)₂)—Pyrr—CO—CH₂ |
| 1-363 | 3,4-diF—Ph | 2-(HO—(CH₂)₃)—Pyrr—CO—CH₂ |
| 1-364 | 3,4-diF—Ph | 2-(HO—(CH₂)₄)—Pyrr—CO—CH₂ |
| 1-365 | 3,4-diF—Ph | 2-(HO—CO—CH₂)—Pyrr—CO—CH₂ |
| 1-366 | 3,4-diF—Ph | 2-(HO—CO—(CH₂)₂)—Pyrr—CO—CH₂ |
| 1-367 | 3,4-diF—Ph | 2-(HO—CO—(CH₂)₃)—Pyrr—CO—CH₂ |
| 1-368 | 3,4-diF—Ph | 4-Oxo—Pip—CO—CH₂ |
| 1-369 | 3,4-diF—Ph | 4-HO—Pip—CO—CH₂ |
| 1-370 | 3,4-diF—Ph | 4-(HO—CH₂)—Pip—CO—CH₂ |
| 1-371 | 3,4-diF—Ph | 4-(HO—(CH₂)₂)—Pip—CO—CH₂ |
| 1-372 | 3,4-diF—Ph | 4-(HO—(CH₂)₃)—Pip—CO—CH₂ |
| 1-373 | 3,4-diF—Ph | 4-(HO—(CH₂)₄)—Pip—CO—CH₂ |
| 1-374 | 3,4-diF—Ph | 4-(HO—CH₂—O)—Pip—CO—CH₂ |
| 1-375 | 3,4-diF—Ph | 4-(HO—(CH₂)₂—O)—Pip—CO—CH₂ |
| 1-376 | 3,4-diF—Ph | 4-(HO—(CH₂)₃—O)—Pip—CO—CH₂ |
| 1-377 | 3,4-diF—Ph | 4-H₂N—Pip—CO—CH₂ |
| 1-378 | 3,4-diF—Ph | 4-(AcNH)—Pip—CO—CH₂ |
| 1-379 | 3,4-diF—Ph | 4-(HO—CH₂—CONH)—Pip—CO—CH₂ |
| 1-380 | 3,4-diF—Ph | 4-(HO—(CH₂)₂—O—CH₂)—Pip—CO—CH₂ |
| 1-381 | 3,4-diF—Ph | 4-(HO—CO)—Pip—CO—CH₂ |
| 1-382 | 3,4-diF—Ph | 4-(HO—CO—CH₂)—Pip—CO—CH₂ |
| 1-383 | 3,4-diF—Ph | 4-(HO—CO—(CH₂)₂)—Pip—CO—CH₂ |
| 1-384 | 3,4-diF—Ph | 4-(HO—CO—(CH₂)₃)—Pip—CO—CH₂ |
| 1-385 | 3,4-diF—Ph | 4-(HO—CO—(CH₂)₄)—Pip—CO—CH₂ |
| 1-386 | 3,4-diF—Ph | 4-(H₂N—CO)—Pip—CO—CH₂ |
| 1-387 | 3,4-diF—Ph | 4-(H₂N—CO—CH₂)—Pip—CO—CH₂ |
| 1-388 | 3,4-diF—Ph | 4-(H₂N—CO—(CH₂)₂)—Pip—CO—CH₂ |
| 1-389 | 3,4-diF—Ph | 4-(H₂N—CO—(CH₂)₃)—Pip—CO—CH₂ |
| 1-390 | 3,4-diF—Ph | 4-(H₂N—CO—(CH₂)₄)—Pip—CO—CH₂ |
| 1-391 | 3,4-diF—Ph | 4-(HO—N(Me)—CO)—Pip—CO—CH₂ |

-continued

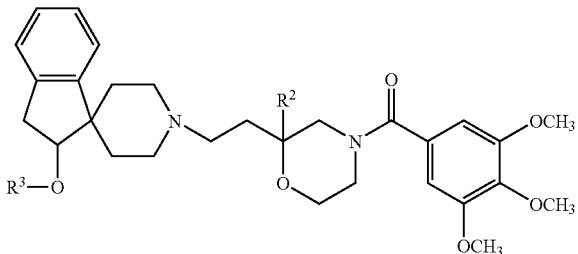

(I-1)

[Compound List 1]

| Compound No. | R² | R³ |
|---|---|---|
| 1-392 | 3,4-diF—Ph | 4-(HO—N(Me)—CO—CH₂)—Pip—CO—CH₂ |
| 1-393 | 3,4-diF—Ph | 4-(HO—N(Me)—CO—(CH₂)₂)—Pip—CO—CH₂ |
| 1-394 | 3,4-diF—Ph | 4-(HO—N(Me)—CO—(CH₂)₃)—Pip—CO—CH₂ |
| 1-395 | 3,4-diF—Ph | 4-(HO—N(Me)—CO—(CH₂)₄)—Pip—CO—CH₂ |
| 1-396 | 3,4-diF—Ph | 4-(MeO—N(Me)—CO)—Pip—CO—CH₂ |
| 1-397 | 3,4-diF—Ph | 4-(MeO—N(Me)—CO—CH₂)—Pip—CO—CH₂ |
| 1-398 | 3,4-diF—Ph | 4-(MeO—N(Me)—CO—(CH₂)₂)—Pip—CO—CH₂ |
| 1-399 | 3,4-diF—Ph | 4-(MeO—N(Me)—CO—(CH₂)₃)—Pip—CO—CH₂ |
| 1-400 | 3,4-diF—Ph | 4-(MeO—N(Me)—CO—(CH₂)₄)—Pip—CO—CH₂ |
| 1-401 | 3,4-diF—Ph | 3-Oxo—Pipr—CO—CH₂ |
| 1-402 | 3,4-diF—Ph | 4-Ac—Pipr—CO—CH₂ |
| 1-403 | 3,4-diF—Ph | 4-(HO—(CH₂)₂)—Pipr—CO—CH₂ |
| 1-404 | 3,4-diCl—Ph | MeO—NH—CO—CH₂ |
| 1-405 | 3,4-diCl—Ph | EtO—NH—CO—CH₂ |
| 1-406 | 3,4-diCl—Ph | PrO—NH—CO—CH₂ |
| 1-407 | 3,4-diCl—Ph | BuO—NH—CO—CH₂ |
| 1-408 | 3,4-diCl—Ph | PnO—NH—CO—CH₂ |
| 1-409 | 3,4-diCl—Ph | HxO—NH—CO—CH₂ |
| 1-410 | 3,4-diCl—Ph | HO—(CH₂)₃—NH—CO—CH₂ |
| 1-411 | 3,4-diCl—Ph | HO—(CH₂)₄—NH—CO—CH₂ |
| 1-412 | 3,4-diCl—Ph | HO—(CH₂)₅—NH—CO—CH₂ |
| 1-413 | 3,4-diCl—Ph | HO—(CH₂)₂—O—(CH₂)₂—NH—CO—CH₂ |
| 1-414 | 3,4-diCl—Ph | Me—CH(OH)—(CH₂)₃—NH—CO—CH₂ |
| 1-415 | 3,4-diCl—Ph | HO—(CH₂)₆—NH—CO—CH₂ |
| 1-416 | 3,4-diCl—Ph | HO—C(Me)(Me)—(CH₂)₃—NH—CO—CH₂ |
| 1-417 | 3,4-diCl—Ph | HO—(CH₂)₃—N(Me)—CO—CH₂ |
| 1-418 | 3,4-diCl—Ph | HO—(CH₂)₄—N(Me)—CO—CH₂ |
| 1-419 | 3,4-diCl—Ph | HO—(CH₂)₅—N(Me)—CO—CH₂ |
| 1-420 | 3,4-diCl—Ph | Me—CH(OH)—(CH₂)₃—N(Me)—CO—CH₂ |
| 1-421 | 3,4-diCl—Ph | HO—(CH₂)₆—N(Me)—CO—CH₂ |
| 1-422 | 3,4-diCl—Ph | HO—(CH₂)₂—O—(CH₂)₂—N(Me)—CO—CH₂ |
| 1-423 | 3,4-diCl—Ph | HO—C(Me)(Me)—(CH₂)₃—N(Me)—CO—CH₂ |
| 1-424 | 3,4-diCl—Ph | HO—(CH₂)₂—N(Et)—CO—CH₂ |
| 1-425 | 3,4-diCl—Ph | HO—(CH₂)₃—N(Et)—CO—CH₂ |
| 1-426 | 3,4-diCl—Ph | HO—(CH₂)₄—N(Et)—CO—CH₂ |
| 1-427 | 3,4-diCl—Ph | HO—(CH₂)₅—N(Et)—CO—CH₂ |
| 1-428 | 3,4-diCl—Ph | HO—(CH₂)₆—N(Et)—CO—CH₂ |
| 1-429 | 3,4-diCl—Ph | HO—(CH₂)₂—O—(CH₂)₂—N(Et)—CO—CH₂ |
| 1-430 | 3,4-diCl—Ph | HO—C(Me)(Me)—(CH₂)₃—N(Et)—CO—CH₂ |
| 1-431 | 3,4-diCl—Ph | HO—(CH₂)₂—N(Pr)—CO—CH₂ |
| 1-432 | 3,4-diCl—Ph | HO—(CH₂)₃—N(Pr)—CO—CH₂ |
| 1-433 | 3,4-diCl—Ph | HO—(CH₂)₄—N(Pr)—CO—CH₂ |
| 1-434 | 3,4-diCl—Ph | HO—(CH₂)₅—N(Pr)—CO—CH₂ |
| 1-435 | 3,4-diCl—Ph | HO—(CH₂)₆—N(Pr)—CO—CH₂ |
| 1-436 | 3,4-diCl—Ph | HO—(CH₂)₂—O—(CH₂)₂—N(Pr)—CO—CH₂ |
| 1-437 | 3,4-diCl—Ph | HO—C(Me)(Me)—(CH₂)₃—N(Pr)—CO—CH₂ |
| 1-438 | 3,4-diCl—Ph | HO—(CH₂)₂—N(Bu)—CO—CH₂ |
| 1-439 | 3,4-diCl—Ph | HO—(CH₂)₃—N(Bu)—CO—CH₂ |
| 1-440 | 3,4-diCl—Ph | HO—(CH₂)₄—N(Bu)—CO—CH₂ |
| 1-441 | 3,4-diCl—Ph | HO—(CH₂)₅—N(Bu)—CO—CH₂ |
| 1-442 | 3,4-diCl—Ph | HO—(CH₂)₆—N(Bu)—CO—CH₂ |
| 1-443 | 3,4-diCl—Ph | HO—(CH₂)₂—O—(CH₂)₂—N(Bu)—CO—CH₂ |
| 1-444 | 3,4-diCl—Ph | HO—C(Me)(Me)—(CH₂)₃—N(Bu)—CO—CH₂ |
| 1-445 | 3,4-diCl—Ph | HO—(CH₂)₂—N(cPr)—CO—CH₂ |
| 1-446 | 3,4-diCl—Ph | HO—(CH₂)₃—N(cPr)—CO—CH₂ |
| 1-447 | 3,4-diCl—Ph | HO—(CH₂)₄—N(cPr)—CO—CH₂ |
| 1-448 | 3,4-diCl—Ph | HO—(CH₂)₅—N(cPr)—CO—CH₂ |
| 1-449 | 3,4-diCl—Ph | HO—(CH₂)₆—N(cPr)—CO—CH₂ |
| 1-450 | 3,4-diCl—Ph | HO—(CH₂)₂—O—(CH₂)₂—N(cPr)—CO—CH₂ |
| 1-451 | 3,4-diCl—Ph | HO—(CH₂)₂—N(HO)—CO—CH₂ |

(I-1)

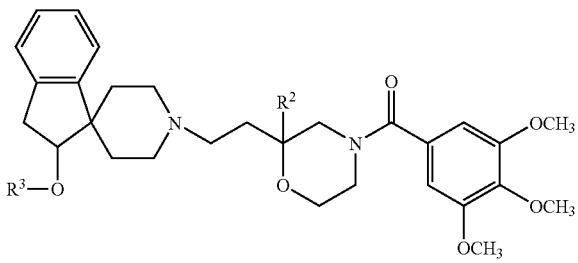

[Compound List 1]

| Compound No. | R² | R³ |
|---|---|---|
| 1-452 | 3,4-diCl—Ph | HO—(CH₂)₃—N(HO)—CO—CH₂ |
| 1-453 | 3,4-diCl—Ph | HO—(CH₂)₄—N(HO)—CO—CH₂ |
| 1-454 | 3,4-diCl—Ph | HO—(CH₂)₅—N(HO)—CO—CH₂ |
| 1-455 | 3,4-diCl—Ph | HO—(CH₂)₆—N(HO)—CO—CH₂ |
| 1-456 | 3,4-diCl—Ph | HO—C(Me)(Me)—(CH₂)₂—N(HO)—CO—CH₂ |
| 1-457 | 3,4-diCl—Ph | HO—C(Me)(Me)—(CH₂)₃—N(HO)—CO—CH₂ |
| 1-458 | 3,4-diCl—Ph | HO—(CH₂)₂—N(MeO)—CO—CH₂ |
| 1-459 | 3,4-diCl—Ph | HO—(CH₂)₃—N(MeO)—CO—CH₂ |
| 1-460 | 3,4-diCl—Ph | HO—(CH₂)₄—N(MeO)—CO—CH₂ |
| 1-461 | 3,4-diCl—Ph | HO—(CH₂)₅—N(MeO)—CO—CH₂ |
| 1-462 | 3,4-diCl—Ph | HO—(CH₂)₆—N(MeO)—CO—CH₂ |
| 1-463 | 3,4-diCl—Ph | HO—C(Me)(Me)—(CH₂)₂—N(MeO)—CO—CH₂ |
| 1-464 | 3,4-diCl—Ph | HO—C(Me)(Me)—(CH₂)₃—N(MeO)—CO—CH₂ |
| 1-465 | 3,4-diCl—Ph | MeO—(CH₂)₂—N(Me)—CO—CH₂ |
| 1-466 | 3,4-diCl—Ph | MeO—(CH₂)₃—N(Me)—CO—CH₂ |
| 1-467 | 3,4-diCl—Ph | MeO—(CH₂)₄—N(Me)—CO—CH₂ |
| 1-468 | 3,4-diCl—Ph | MeO—(CH₂)₅—N(Me)—CO—CH₂ |
| 1-469 | 3,4-diCl—Ph | MeO—(CH₂)₆—N(Me)—CO—CH₂ |
| 1-470 | 3,4-diCl—Ph | MeO—(CH₂)₂—O—(CH₂)₂—N(Me)—CO—CH₂ |
| 1-471 | 3,4-diCl—Ph | MeO—C(Me)(Me)—(CH₂)₃—N(Me)—CO—CH₂ |
| 1-472 | 3,4-diCl—Ph | NC—CH₂—NH—CO—CH₂ |
| 1-473 | 3,4-diCl—Ph | NC—(CH₂)₂—NH—CO—CH₂ |
| 1-474 | 3,4-diCl—Ph | NC—(CH₂)₃—NH—CO—CH₂ |
| 1-475 | 3,4-diCl—Ph | NC—(CH₂)₄—NH—CO—CH₂ |
| 1-476 | 3,4-diCl—Ph | NC—(CH₂)₅—NH—CO—CH₂ |
| 1-477 | 3,4-diCl—Ph | NC—(CH₂)₆—NH—CO—CH₂ |
| 1-478 | 3,4-diCl—Ph | NC—(CH₂)₂—O—(CH₂)₂—NH—CO—CH₂ |
| 1-479 | 3,4-diCl—Ph | NC—CH₂—N(Me)—CO—CH₂ |
| 1-480 | 3,4-diCl—Ph | NC—(CH₂)₂—N(Me)—CO—CH₂ |
| 1-481 | 3,4-diCl—Ph | NC—(CH₂)₃—N(Me)—CO—CH₂ |
| 1-482 | 3,4-diCl—Ph | NC—(CH₂)₄—N(Me)—CO—CH₂ |
| 1-483 | 3,4-diCl—Ph | NC—(CH₂)₅—N(Me)—CO—CH₂ |
| 1-484 | 3,4-diCl—Ph | NC—(CH₂)₆—N(Me)—CO—CH₂ |
| 1-485 | 3,4-diCl—Ph | NC—(CH₂)₂—O—(CH₂)₂—N(Me)—CO—CH₂ |
| 1-486 | 3,4-diCl—Ph | HO—CO—CH₂—NH—CO—CH₂ |
| 1-487 | 3,4-diCl—Ph | HO—CO—(CH₂)₂—NH—CO—CH₂ |
| 1-488 | 3,4-diCl—Ph | HO—CO—(CH₂)₃—NH—CO—CH₂ |
| 1-489 | 3,4-diCl—Ph | HO—CO—(CH₂)₄—NH—CO—CH₂ |
| 1-490 | 3,4-diCl—Ph | HO—CO—(CH₂)₅—NH—CO—CH₂ |
| 1-491 | 3,4-diCl—Ph | HO—CO—(CH₂)₆—NH—CO—CH₂ |
| 1-492 | 3,4-diCl—Ph | HO—CO—(CH₂)₂—O—(CH₂)₂—NH—CO—CH₂ |
| 1-493 | 3,4-diCl—Ph | HO—CO—CH₂—N(Me)—CO—CH₂ |
| 1-494 | 3,4-diCl—Ph | HO—CO—(CH₂)₂—N(Me)—CO—CH₂ |
| 1-495 | 3,4-diCl—Ph | HO—CO—(CH₂)₃—N(Me)—CO—CH₂ |
| 1-496 | 3,4-diCl—Ph | HO—CO—(CH₂)₄—N(Me)—CO—CH₂ |
| 1-497 | 3,4-diCl—Ph | HO—CO—(CH₂)₅—N(Me)—CO—CH₂ |
| 1-498 | 3,4-diCl—Ph | HO—CO—(CH₂)₆—N(Me)—CO—CH₂ |
| 1-499 | 3,4-diCl—Ph | HO—CO—(CH₂)₂—O—(CH₂)₂—N(Me)—CO—CH₂ |
| 1-500 | 3,4-diCl—Ph | MeO—CO—CH₂—NH—CO—CH₂ |
| 1-501 | 3,4-diCl—Ph | MeO—CO—(CH₂)₂—NH—CO—CH₂ |
| 1-502 | 3,4-diCl—Ph | MeO—CO—(CH₂)₃—NH—CO—CH₂ |
| 1-503 | 3,4-diCl—Ph | MeO—CO—(CH₂)₄—NH—CO—CH₂ |
| 1-504 | 3,4-diCl—Ph | MeO—CO—(CH₂)₅—NH—CO—CH₂ |
| 1-505 | 3,4-diCl—Ph | MeO—CO—(CH₂)₆—NH—CO—CH₂ |
| 1-506 | 3,4-diCl—Ph | MeO—CO—(CH₂)₂—O—(CH₂)₂—NH—CO—CH₂ |
| 1-507 | 3,4-diCl—Ph | MeO—CO—CH₂—N(Me)—CO—CH₂ |
| 1-508 | 3,4-diCl—Ph | MeO—CO—(CH₂)₂—N(Me)—CO—CH₂ |
| 1-509 | 3,4-diCl—Ph | MeO—CO—(CH₂)₃—N(Me)—CO—CH₂ |
| 1-510 | 3,4-diCl—Ph | MeO—CO—(CH₂)₄—N(Me)—CO—CH₂ |
| 1-511 | 3,4-diCl—Ph | MeO—CO—(CH₂)₅—N(Me)—CO—CH₂ |

-continued

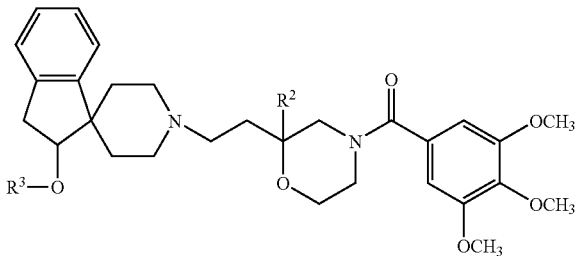

(I-1)

[Compound List 1]

| Compound No. | R² | R³ |
|---|---|---|
| 1-512 | 3,4-diCl—Ph | MeO—CO—(CH₂)₆—N(Me)—CO—CH₂ |
| 1-513 | 3,4-diCl—Ph | MeO—CO—(CH₂)₂—O—(CH₂)₂—N(Me)—CO—CH₂ |
| 1-514 | 3,4-diCl—Ph | H₂N—CO—CH₂—NH—CO—CH₂ |
| 1-515 | 3,4-diCl—Ph | H₂N—CO—(CH₂)₂—NH—CO—CH₂ |
| 1-516 | 3,4-diCl—Ph | H₂N—CO—(CH₂)₃—NH—CO—CH₂ |
| 1-517 | 3,4-diCl—Ph | H₂N—CO—(CH₂)₄—NH—CO—CH₂ |
| 1-518 | 3,4-diCl—Ph | H₂N—CO—(CH₂)₅—NH—CO—CH₂ |
| 1-519 | 3,4-diCl—Ph | H₂N—CO—(CH₂)₆—NH—CO—CH₂ |
| 1-520 | 3,4-diCl—Ph | H₂N—CO—(CH₂)₂—O—(CH₂)₂—NH—CO—CH₂ |
| 1-521 | 3,4-diCl—Ph | H₂N—CO—CH₂—N(Me)—CO—CH₂ |
| 1-522 | 3,4-diCl—Ph | H₂N—CO—(CH₂)₂—N(Me)—CO—CH₂ |
| 1-523 | 3,4-diCl—Ph | H₂N—CO—(CH₂)₃—N(Me)—CO—CH₂ |
| 1-524 | 3,4-diCl—Ph | H₂N—CO—(CH₂)₄—N(Me)—CO—CH₂ |
| 1-525 | 3,4-diCl—Ph | H₂N—CO—(CH₂)₅—N(Me)—CO—CH₂ |
| 1-526 | 3,4-diCl—Ph | H₂N—CO—(CH₂)₆—N(Me)—CO—CH₂ |
| 1-527 | 3,4-diCl—Ph | H₂N—CO—(CH₂)₂—O—(CH₂)₂—N(Me)—CO—CH₂ |
| 1-528 | 3,4-diCl—Ph | HO—N(Me)—CO—CH₂—N(Me)—CO—CH₂ |
| 1-529 | 3,4-diCl—Ph | HO—N(Me)—CO—(CH₂)₂—N(Me)—CO—CH₂ |
| 1-530 | 3,4-diCl—Ph | HO—N(Me)—CO—(CH₂)₃—N(Me)—CO—CH₂ |
| 1-531 | 3,4-diCl—Ph | HO—N(Me)—CO—(CH₂)₄—N(Me)—CO—CH₂ |
| 1-532 | 3,4-diCl—Ph | HO—N(Me)—CO—(CH₂)₅—N(Me)—CO—CH₂ |
| 1-533 | 3,4-diCl—Ph | HO—N(Me)—CO—(CH₂)₆—N(Me)—CO—CH₂ |
| 1-534 | 3,4-diCl—Ph | HO—N(Me)—CO—(CH₂)₂—O—(CH₂)₂—N(Me)—CO—CH₂ |
| 1-535 | 3,4-diCl—Ph | MeO—N(Me)—CO—CH₂—N(Me)—CO—CH₂ |
| 1-536 | 3,4-diCl—Ph | MeO—N(Me)—CO—(CH₂)₂—N(Me)—CO—CH₂ |
| 1-537 | 3,4-diCl—Ph | MeO—N(Me)—CO—(CH₂)₃—N(Me)—CO—CH₂ |
| 1-538 | 3,4-diCl—Ph | MeO—N(Me)—CO—(CH₂)₄—N(Me)—CO—CH₂ |
| 1-539 | 3,4-diCl—Ph | MeO—N(Me)—CO—(CH₂)₅—N(Me)—CO—CH₂ |
| 1-540 | 3,4-diCl—Ph | MeO—N(Me)—CO—(CH₂)₆—N(Me)—CO—CH₂ |
| 1-541 | 3,4-diCl—Ph | MeO—N(Me)—CO—(CH₂)₂—O—(CH₂)₂—N(Me)—CO—CH₂ |
| 1-542 | 3,4-diCl—Ph | Ac—CH₂—N(Me)—CO—CH₂ |
| 1-543 | 3,4-diCl—Ph | Ac—(CH₂)₂—N(Me)—CO—CH₂ |
| 1-544 | 3,4-diCl—Ph | Ac—(CH₂)₃—N(Me)—CO—CH₂ |
| 1-545 | 3,4-diCl—Ph | Ac—(CH₂)₄—N(Me)—CO—CH₂ |
| 1-546 | 3,4-diCl—Ph | Ac—(CH₂)₅—N(Me)—CO—CH₂ |
| 1-547 | 3,4-diCl—Ph | Ac—(CH₂)₆—N(Me)—CO—CH₂ |
| 1-548 | 3,4-diCl—Ph | Ac—(CH₂)₂—O—(CH₂)₂—N(Me)—CO—CH₂ |
| 1-549 | 3,4-diCl—Ph | HO—(CH₂)₂—O—N(Me)—CO—CH₂ |
| 1-550 | 3,4-diCl—Ph | HO—(CH₂)₃—O—N(Me)—CO—CH₂ |
| 1-551 | 3,4-diCl—Ph | HO—(CH₂)₄—O—N(Me)—CO—CH₂ |
| 1-552 | 3,4-diCl—Ph | HO—(CH₂)₅—O—N(Me)—CO—CH₂ |
| 1-553 | 3,4-diCl—Ph | HO—(CH₂)₆—O—N(Me)—CO—CH₂ |
| 1-554 | 3,4-diCl—Ph | HO—(CH₂)₂—O—(CH₂)₂—O—N(Me)—CO—CH₂ |
| 1-555 | 3,4-diCl—Ph | (Me)₂N—(CH₂)₂—N(Me)—CO—CH₂ |
| 1-556 | 3,4-diCl—Ph | (Me)₂N—(CH₂)₃—N(Me)—CO—CH₂ |
| 1-557 | 3,4-diCl—Ph | (Me)₂N—(CH₂)₄—N(Me)—CO—CH₂ |
| 1-558 | 3,4-diCl—Ph | (Me)₂N—(CH₂)₅—N(Me)—CO—CH₂ |
| 1-559 | 3,4-diCl—Ph | (Me)₂N—(CH₂)₆—N(Me)—CO—CH₂ |
| 1-560 | 3,4-diCl—Ph | (Me)₂N—(CH₂)₂—O—(CH₂)₂—N(Me)—CO—CH₂ |
| 1-561 | 3,4-diCl—Ph | AcNH—(CH₂)₂—N(Me)—CO—CH₂ |
| 1-562 | 3,4-diCl—Ph | AcNH—(CH₂)₃—N(Me)—CO—CH₂ |
| 1-563 | 3,4-diCl—Ph | AcNH—(CH₂)₄—N(Me)—CO—CH₂ |
| 1-564 | 3,4-diCl—Ph | AcNH—(CH₂)₅—N(Me)—CO—CH₂ |
| 1-565 | 3,4-diCl—Ph | AcNH—(CH₂)₆—N(Me)—CO—CH₂ |
| 1-566 | 3,4-diCl—Ph | AcNH—(CH₂)₂—O—(CH₂)₂—N(Me)—CO—CH₂ |
| 1-567 | 3,4-diCl—Ph | Me—SO₂NH—(CH₂)₂—N(Me)—CO—CH₂ |
| 1-568 | 3,4-diCl—Ph | Me—SO₂NH—(CH₂)₃—N(Me)—CO—CH₂ |
| 1-569 | 3,4-diCl—Ph | Me—SO₂NH—(CH₂)₄—N(Me)—CO—CH₂ |
| 1-570 | 3,4-diCl—Ph | Me—SO₂NH—(CH₂)₅—N(Me)—CO—CH₂ |
| 1-571 | 3,4-diCl—Ph | Me—SO₂NH—(CH₂)₆—N(Me)—CO—CH₂ |

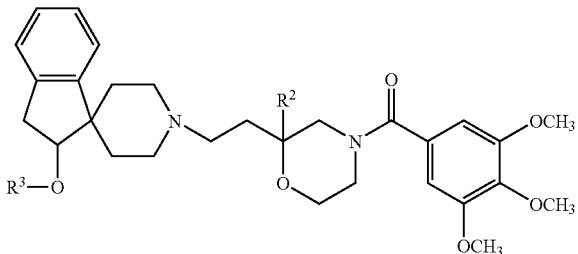

(I-1)

[Compound List 1]

| Compound No. | R² | R³ |
|---|---|---|
| 1-572 | 3,4-diCl—Ph | Me—SO₂NH—(CH₂)₂—O—(CH₂)₂—N(Me)—CO—CH₂ |
| 1-573 | 3,4-diCl—Ph | 2-(HO—(CH₂)₂)—Pyrr—CO—CH₂ |
| 1-574 | 3,4-diCl—Ph | 2-(HO—(CH₂)₃)—Pyrr—CO—CH₂ |
| 1-575 | 3,4-diCl—Ph | 2-(HO—(CH₂)₄)—Pyrr—CO—CH₂ |
| 1-576 | 3,4-diCl—Ph | 2-(HO—CO—CH₂)—Pyrr—CO—CH₂ |
| 1-577 | 3,4-diCl—Ph | 2-(HO—CO—(CH₂)₂)—Pyrr—CO—CH₂ |
| 1-578 | 3,4-diCl—Ph | 2-(HO—CO—(CH₂)₃)—Pyrr—CO—CH₂ |
| 1-579 | 3,4-diCl—Ph | 4-Oxo—Pip—CO—CH₂ |
| 1-580 | 3,4-diCl—Ph | 4-HO—Pip—CO—CH₂ |
| 1-581 | 3,4-diCl—Ph | 4-(HO—CH₂)—Pip—CO—CH₂ |
| 1-582 | 3,4-diCl—Ph | 4-(HO—(CH₂)₂)—Pip—CO—CH₂ |
| 1-583 | 3,4-diCl—Ph | 4-(HO—(CH₂)₃)—Pip—CO—CH₂ |
| 1-584 | 3,4-diCl—Ph | 4-(HO—(CH₂)₄)—Pip—CO—CH₂ |
| 1-585 | 3,4-diCl—Ph | 4-(HO—CH₂—O)—Pip—CO—CH₂ |
| 1-586 | 3,4-diCl—Ph | 4-(HO—(CH₂)₂—O)—Pip—CO—CH₂ |
| 1-587 | 3,4-diCl—Ph | 4-(HO—(CH₂)₃—O)—Pip—CO—CH₂ |
| 1-588 | 3,4-diCl—Ph | 4-H₂N—Pip—CO—CH₂ |
| 1-589 | 3,4-diCl—Ph | 4-(AcNH)—Pip—CO—CH₂ |
| 1-590 | 3,4-diCl—Ph | 4-(HO—CH₂—CONH)—Pip—CO—CH₂ |
| 1-591 | 3,4-diCl—Ph | 4-(HO—(CH₂)₂—O—CH₂)—Pip—CO—CH₂ |
| 1-592 | 3,4-diCl—Ph | 4-(HO—CO)—Pip—CO—CH₂ |
| 1-593 | 3,4-diCl—Ph | 4-(HO—CO—CH₂)—Pip—CO—CH₂ |
| 1-594 | 3,4-diCl—Ph | 4-(HO—CO—(CH₂)₂)—Pip—CO—CH₂ |
| 1-595 | 3,4-diCl—Ph | 4-(HO—CO—(CH₂)₃)—Pip—CO—CH₂ |
| 1-596 | 3,4-diCl—Ph | 4-(HO—CO—(CH₂)₄)—Pip—CO—CH₂ |
| 1-597 | 3,4-diCl—Ph | 4-(H₂N—CO)—Pip—CO—CH₂ |
| 1-598 | 3,4-diCl—Ph | 4-(H₂N—CO—CH₂)—Pip—CO—CH₂ |
| 1-599 | 3,4-diCl—Ph | 4-(H₂N—CO—(CH₂)₂)—Pip—CO—CH₂ |
| 1-600 | 3,4-diCl—Ph | 4-(H₂N—CO—(CH₂)₃)—Pip—CO—CH₂ |
| 1-601 | 3,4-diCl—Ph | 4-(H₂N—CO—(CH₂)₄)—Pip—CO—CH₂ |
| 1-602 | 3,4-diCl—Ph | 4-(HO—N(Me)—CO)—Pip—CO—CH₂ |
| 1-603 | 3,4-diCl—Ph | 4-(HO—N(Me)—CO—CH₂)—Pip—CO—CH₂ |
| 1-604 | 3,4-diCl—Ph | 4-(HO—N(Me)—CO—(CH₂)₂)—Pip—CO—CH₂ |
| 1-605 | 3,4-diCl—Ph | 4-(HO—N(Me)—CO—(CH₂)₃)—Pip—CO—CH₂ |
| 1-606 | 3,4-diCl—Ph | 4-(HO—N(Me)—CO—(CH₂)₄)—Pip—CO—CH₂ |
| 1-607 | 3,4-diCl—Ph | 4-(MeO—N(Me)—CO)—Pip—CO—CH₂ |
| 1-608 | 3,4-diCl—Ph | 4-(MeO—N(Me)—CO—CH₂)—Pip—CO—CH₂ |
| 1-609 | 3,4-diCl—Ph | 4-(MeO—N(Me)—CO—(CH₂)₂)—Pip—CO—CH₂ |
| 1-610 | 3,4-diCl—Ph | 4-(MeO—N(Me)—CO—(CH₂)₃)—Pip—CO—CH₂ |
| 1-611 | 3,4-diCl—Ph | 4-(MeO—N(Me)—CO—(CH₂)₄)—Pip—CO—CH₂ |
| 1-612 | 3,4-diCl—Ph | 3-Oxo—Pipr—CO—CH₂ |
| 1-613 | 3,4-diCl—Ph | 4-Ac—Pipr—CO—CH₂ |
| 1-614 | 3,4-diCl—Ph | 4-(HO—(CH₂)₂)—Pipr—CO—CH₂ |
| 1-615 | 3,4-diF—Ph | 3-CHO—(CH₂)₂)—Pyrr—CO—CH₂ |
| 1-616 | 3,4-diF—Ph | 3-(HO—(CH₂)₃)—Pyrr—CO—CH₂ |
| 1-617 | 3,4-diF—Ph | 3-(HO—(CH₂)₄)—Pyrr—CO—CH₂ |
| 1-618 | 3,4-diF—Ph | 3-(HO—CO—CH₂)—Pyrr—CO—CH₂ |
| 1-619 | 3,4-diF—Ph | 3-(HO—CO—(CH₂)₂)—Pyrr—CO—CH₂ |
| 1-620 | 3,4-diF—Ph | 3-(HO—CO—(CH₂)₃)—Pyrr—CO—CH₂ |
| 1-621 | 3,4-diF—Ph | 3-(HO—CH₂)—Pip—CO—CH₂ |
| 1-622 | 3,4-diF—Ph | 3-(HO—(CH₂)₂)—Pip—CO—CH₂ |
| 1-623 | 3,4-diF—Ph | 3-(HO—(CH₂)₃)—Pip—CO—CH₂ |
| 1-624 | 3,4-diF—Ph | 3-(HO—(CH₂)₄)—Pip—CO—CH₂ |
| 1-625 | 3,4-diF—Ph | 3-(HO—CH₂—O)—Pip—CO—CH₂ |
| 1-626 | 3,4-diF—Ph | 3-(HO—(CH₂)₂—O)—Pip—CO—CH₂ |
| 1-627 | 3,4-diF—Ph | 3-(HO—(CH₂)₃—O)—Pip—CO—CH₂ |
| 1-628 | 3,4-diF—Ph | 3-(HO—CH₂—CONH)—Pip—CO—CH₂ |
| 1-629 | 3,4-diF—Ph | 3-(HO—(CH₂)₂—O—CH₂)—Pip—CO—CH₂ |
| 1-630 | 3,4-diF—Ph | 3-(HO—N(Me)—CO)—Pip—CO—CH₂ |
| 1-631 | 3,4-diF—Ph | 3-(HO—N(Me)—CO—CH₂)—Pip—CO—CH₂ |

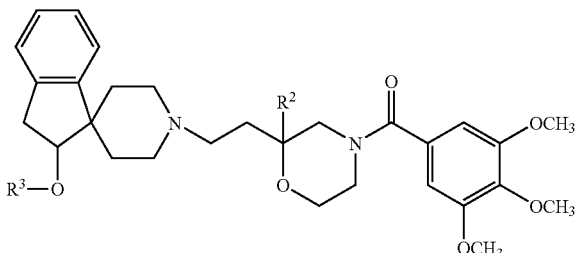

[Compound List 1]

| Compound No. | R² | R³ |
|---|---|---|
| 1-632 | 3,4-diF—Ph | 3-(HO—N(Me)—CO—(CH₂)₂)—Pip—CO—CH₂ |
| 1-633 | 3,4-diF—Ph | 3-(HO—N(Me)—CO—(CH₂)₃)—Pip—CO—CH₂ |
| 1-634 | 3,4-diF—Ph | 3-(HO—N(Me)—CO—(CH₂)₄)—Pip—CO—CH₂ |
| 1-635 | 3,4-diF—Ph | 3-(MeO—N(Me)—CO)—Pip—CO—CH₂ |
| 1-636 | 3,4-diF—Ph | 3-(MeO—N(Me)—CO—CH₂)—Pip—CO—CH₂ |
| 1-637 | 3,4-diF—Ph | 3-(MeO—N(Me)—CO—(CH₂)₂)—Pip—CO—CH₂ |
| 1-638 | 3,4-diF—Ph | 3-(MeO—N(Me)—CO—(CH₂)₃)—Pip—CO—CH₂ |
| 1-639 | 3,4-diF—Ph | 3-(MeO—N(Me)—CO—(CH₂)₄)—Pip—CO—CH₂ |
| 1-640 | 3,4-diF—Ph | 3-(HO—(CH₂)₂)—Pipr—CO—CH₂ |
| 1-641 | 3,4-diCl—Ph | 3-(HO—(CH₂)₂)—Pyrr—CO—CH₂ |
| 1-642 | 3,4-diCl—Ph | 3-(HO—(CH₂)₃)—Pyrr—CO—CH₂ |
| 1-643 | 3,4-diCl—Ph | 3-(HO—(CH₂)₄)—Pyrr—CO—CH₂ |
| 1-644 | 3,4-diCl—Ph | 3-(HO—CO—CH₂)—Pyrr—CO—CH₂ |
| 1-645 | 3,4-diCl—Ph | 3-(HO—CO—(CH₂)₂)—Pyrr—CO—CH₂ |
| 1-646 | 3,4-diCl—Ph | 3-(HO—CO—(CH₂)₃)—Pyrr—CO—CH₂ |
| 1-647 | 3,4-diCl—Ph | 3-(HO—CH₂)—Pip—CO—CH₂ |
| 1-648 | 3,4-diCl—Ph | 3-(HO—(CH₂)₂)—Pip—CO—CH₂ |
| 1-649 | 3,4-diCl—Ph | 3-(HO—(CH₂)₃)—Pip—CO—CH₂ |
| 1-650 | 3,4-diCl—Ph | 3-(HO—(CH₂)₄)—Pip—CO—CH₂ |
| 1-651 | 3,4-diCl—Ph | 3-(HO—CH₂—O)—Pip—CO—CH₂ |
| 1-652 | 3,4-diCl—Ph | 3-(HO—(CH₂)₂—O)—Pip—CO—CH₂ |
| 1-653 | 3,4-diCl—Ph | 3-(HO—(CH₂)₃—O)—Pip—CO—CH₂ |
| 1-654 | 3,4-diCl—Ph | 3-(HO—CH₂—CONH)—Pip—CO—CH₂ |
| 1-655 | 3,4-diCl—Ph | 3-(HO—(CH₂)₂—O—CH₂)—Pip—CO—CH₂ |
| 1-656 | 3,4-diCl—Ph | 3-(HO—N(Me)—CO)—Pip—CO—CH₂ |
| 1-657 | 3,4-diCl—Ph | 3-(HO—N(Me)—CO—CH₂)—Pip—CO—CH₂ |
| 1-658 | 3,4-diCl—Ph | 3-(HO—N(Me)—CO—(CH₂)₂)—Pip—CO—CH₂ |
| 1-659 | 3,4-diCl—Ph | 3-(HO—N(Me)—CO—(CH₂)₃)—Pip—CO—CH₂ |
| 1-660 | 3,4-diCl—Ph | 3-(HO—N(Me)—CO—(CH₂)₄)—Pip—CO—CH₂ |
| 1-661 | 3,4-diCl—Ph | 3-(MeO—N(Me)—CO)—Pip—CO—CH₂ |
| 1-662 | 3,4-diCl—Ph | 3-(MeO—N(Me)—CO—CH₂)—Pip—CO—CH₂ |
| 1-663 | 3,4-diCl—Ph | 3-(MeO—N(Me)—CO—(CH₂)₂)—Pip—CO—CH₂ |
| 1-664 | 3,4-diCl—Ph | 3-(MeO—N(Me)—CO—(CH₂)₃)—Pip—CO—CH₂ |
| 1-665 | 3,4-diCl—Ph | 3-(MeO—N(Me)—CO—(CH₂)₄)—Pip—CO—CH₂ |
| 1-666 | 3,4-diCl—Ph | 3-(HO—(CH₂)₂)—Pipr—CO—CH₂ |

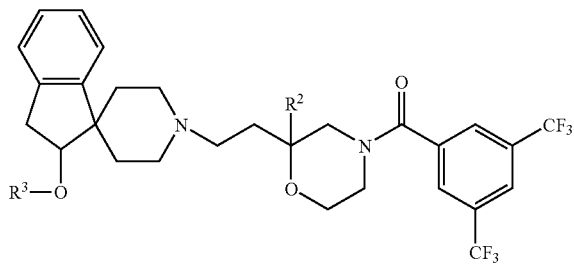

[Compound List 2]

| Compound No. | R² | R³ |
|---|---|---|
| 2-1 | 3,4-diF—Ph | Me—CO—O—CH₂—CO |
| 2-2 | 3,4-diF—Ph | Me—CO |

-continued

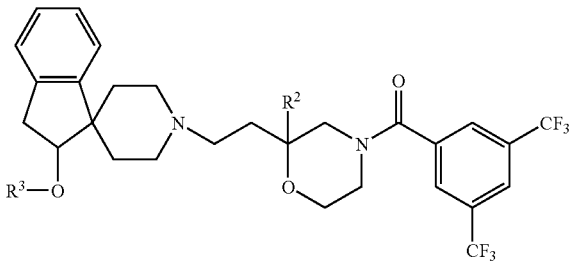

(I-2)

[Compound List 2]

| Compound No. | R² | R³ |
|---|---|---|
| 2-3 | 3,4-diF—Ph | Et—CO |
| 2-4 | 3,4-diF—Ph | Pr—CO |
| 2-5 | 3,4-diF—Ph | iPr—CO |
| 2-6 | 3,4-diF—Ph | Bu—CO |
| 2-7 | 3,4-diF—Ph | iBu—CO |
| 2-8 | 3,4-diF—Ph | Pn—CO |
| 2-9 | 3,4-diF—Ph | iPn—CO |
| 2-10 | 3,4-diF—Ph | tBu—CH₂—CO |
| 2-11 | 3,4-diF—Ph | cPr—CO |
| 2-12 | 3,4-diF—Ph | cBu—CO |
| 2-13 | 3,4-diF—Ph | cPn—CO |
| 2-14 | 3,4-diF—Ph | cHx—CO |
| 2-15 | 3,4-diF—Ph | MeO—CH₂—CO |
| 2-16 | 3,4-diF—Ph | Mor—CH₂—CO |
| 2-17 | 3,4-diF—Ph | Mor—(CH₂)₂—CO |
| 2-18 | 3,4-diF—Ph | Mor—(CH₂)₃—CO |
| 2-19 | 3,4-diF—Ph | Pip—CH₂—CO |
| 2-20 | 3,4-diF—Ph | Pip—(CH₂)₂—CO |
| 2-21 | 3,4-diF—Ph | Pip—(CH₂)₃—CO |
| 2-22 | 3,4-diF—Ph | Pipr—CH₂—CO |
| 2-23 | 3,4-diF—Ph | Pipr—(CH₂)₂—CO |
| 2-24 | 3,4-diF—Ph | Pipr—(CH₂)₃—CO |
| 2-25 | 3,4-diF—Ph | EtO—CO |
| 2-26 | 3,4-diF—Ph | MeO—(CH₂)₂—O—CO |
| 2-27 | 3,4-diF—Ph | F—(CH₂)₂—O—CO |
| 2-28 | 3,4-diF—Ph | Propargyl—O—CO |
| 2-29 | 3,4-diF—Ph | EtO—CO—CH₂—NH—CO |
| 2-30 | 3,4-diF—Ph | EtO—CO—(CH₂)₂—NH—CO |
| 2-31 | 3,4-diF—Ph | Eto—CO—(CH₂)₃—NH—CO |
| 2-32 | 3,4-diF—Ph | Et—NH—CO |
| 2-33 | 3,4-diF—Ph | HO—(CH₂)₂—N(Me)—CH₂—CO |
| 2-34 | 3,4-diF—Ph | EtO—(CH₂)₂—NH—CH₂—CO |
| 2-35 | 3,4-diF—Ph | Me—NH—CH₂—CO |
| 2-36 | 3,4-diF—Ph | Et—NH—CH₂—CO |
| 2-37 | 3,4-diF—Ph | Pr—NH—CH₂—CO |
| 2-38 | 3,4-diF—Ph | iPr—NH—CH₂—CO |
| 2-39 | 3,4-diF—Ph | (Me)₂N—CH₂—CO |
| 2-40 | 3,4-diF—Ph | (Et)₂N—CH₂—CO |
| 2-41 | 3,4-diF—Ph | (Pr)₂N—CH₂—CO |
| 2-42 | 3,4-diF—Ph | (iPr)₂N—CH₂—CO |
| 2-43 | 3,4-diF—Ph | (MeO—CH₂)₂N—CH₂—CO |
| 2-44 | 3,4-diF—Ph | (MeO—CH₂—CH₂)₂N—CH₂—CO |
| 2-45 | 3,4-diF—Ph | Aze—CH₂—CO |
| 2-46 | 3,4-diF—Ph | Pyrr—CH₂—CO |
| 2-47 | 3,4-diF—Ph | Pip—CH₂—CO |
| 2-48 | 3,4-diF—Ph | 4-(H₂NCO)—Pip—CH₂—CO |
| 2-49 | 3,4-diF—Ph | 4-(HO—CH₂)—Pip—CH₂—CO |
| 2-50 | 3,4-diF—Ph | 4-(HO—CH₂—CH₂)—Pip—CH₂—CO |
| 2-51 | 3,4-diF—Ph | HO—CO—CH₂ |
| 2-52 | 3,4-diF—Ph | MeO—CO—CH₂ |
| 2-53 | 3,4-diF—Ph | EtO—CO—CH₂ |
| 2-54 | 3,4-diF—Ph | H₂N—CO—CH₂ |
| 2-55 | 3,4-diF—Ph | (Me)₂N—CO—CH₂ |
| 2-56 | 3,4-diF—Ph | (Et)₂N—CO—CH₂ |
| 2-57 | 3,4-diF—Ph | (HO—CH₂—CH₂)₂N—CO—CH₂ |
| 2-58 | 3,4-diF—Ph | HO—CH₂—CH₂—NH—CO—CH₂ |
| 2-59 | 3,4-diF—Ph | HO—CH₂—CH₂—N(Me)—CO—CH₂ |
| 2-60 | 3,4-diF—Ph | Mor—CO—CH₂ |
| 2-61 | 3,4-diF—Ph | Pip—CO—CH₂ |
| 2-62 | 3,4-diF—Ph | Pipr—CO—CH₂ |

-continued

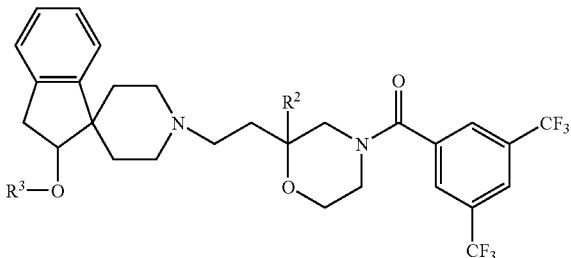

(I-2)

[Compound List 2]

| Compound No. | R² | R³ |
|---|---|---|
| 2-63 | 3,4-diF—Ph | HO—(CH₂)₂ |
| 2-64 | 3,4-diF—Ph | H₂N—(CH₂)₂ |
| 2-65 | 3,4-diF—Ph | (Me)₂N—(CH₂)₂ |
| 2-66 | 3,4-diF—Ph | (Et)₂N—(CH₂)₂ |
| 2-67 | 3,4-diF—Ph | (HO—CH₂—CH₂)₂N—(CH₂)₂ |
| 2-68 | 3,4-diF—Ph | HO—CH₂—CH₂—NH—(CH₂)₂ |
| 2-69 | 3,4-diF—Ph | HO—CH₂—CH₂—N(Me)—(CH₂)₂ |
| 2-70 | 3,4-diF—Ph | Mor—(CH₂)₂ |
| 2-71 | 3,4-diF—Ph | Pip—(CH₂)₂ |
| 2-72 | 3,4-diF—Ph | Pipr—(CH₂)₂ |
| 2-73 | 3,4-diF—Ph | H₂N—CO—NH—CO |
| 2-74 | 3,4-diF—Ph | (Me)₂N—CO—NH—CO |
| 2-75 | 3,4-diF—Ph | (Et)₂N—CO—NH—CO |
| 2-76 | 3,4-diF—Ph | (HO—CH₂—CH₂)₂N—CO—NH—CO |
| 2-77 | 3,4-diF—Ph | HO—CH₂—CH₂—NH—CO—NH—CO |
| 2-78 | 3,4-diF—Ph | HO—CH₂—CH₂—N(Me)—CO—NH—CO |
| 2-79 | 3,4-diF—Ph | Mor—CO—NH—CO |
| 2-80 | 3,4-diF—Ph | Pip—CO—NH—CO |
| 2-81 | 3,4-diF—Ph | Pipr—CO—NH—CO |
| 2-82 | 3,4-diF—Ph | H₂N—SO₂—NH—CO |
| 2-83 | 3,4-diF—Ph | (Me)₂N—SO₂—NH—CO |
| 2-84 | 3,4-diF—Ph | (Et)₂N—SO₂—NH—CO |
| 2-85 | 3,4-diF—Ph | (HO—CH₂—CH₂)₂N—SO₂—NH—CO |
| 2-86 | 3,4-diF—Ph | HO—CH₂—CH₂—NH—SO₂—NH—CO |
| 2-87 | 3,4-diF—Ph | HO—CH₂—CH₂—N(Me)—SO₂—NH—CO |
| 2-88 | 3,4-diF—Ph | Mor—SO₂—NH—CO |
| 2-89 | 3,4-diF—Ph | Pip—SO₂—NH—CO |
| 2-90 | 3,4-diF—Ph | Pipr—SO₂—NH—CO |
| 2-91 | 3,4-diF—Ph | Mor—CH₂—CO—NH—CO |
| 2-92 | 3,4-diF—Ph | Pip—CH₂—CO—NH—CO |
| 2-93 | 3,4-diF—Ph | Pipr—CH₂—CO—NH—CO |
| 2-94 | 3,4-diF—Ph | H₂N—CO |
| 2-95 | 3,4-diF—Ph | MeO—(CH₂)₂—O—CH₂ |
| 2-96 | 3,4-diF—Ph | MeO—CH₂ |
| 2-97 | 3,4-diCl—Ph | Me—CO—O—CH₂—CO |
| 2-98 | 3,4-diCl—Ph | Me—CO |
| 2-99 | 3,4-diCl—Ph | Et—CO |
| 2-100 | 3,4-diCl—Ph | Pr—CO |
| 2-101 | 3,4-diCl—Ph | iPr—CO |
| 2-102 | 3,4-diCl—Ph | Bu—CO |
| 2-103 | 3,4-diCl—Ph | iBu—CO |
| 2-104 | 3,4-diCl—Ph | Pn—CO |
| 2-105 | 3,4-diCl—Ph | iPn—CO |
| 2-106 | 3,4-diCl—Ph | tBu—CH₂—CO |
| 2-107 | 3,4-diCl—Ph | cPr—CO |
| 2-108 | 3,4-diCl—Ph | cBu—CO |
| 2-109 | 3,4-diCl—Ph | cPn—CO |
| 2-110 | 3,4-diCl—Ph | cHx—CO |
| 2-111 | 3,4-diCl—Ph | MeO—CH₂—CO |
| 2-112 | 3,4-diCl—Ph | Mor—CH₂—CO |
| 2-113 | 3,4-diCl—Ph | Mor—(CH₂)₂—CO |
| 2-114 | 3,4-diCl—Ph | Mor—(CH₂)₃—CO |
| 2-115 | 3,4-diCl—Ph | Pip—CH₂—CO |
| 2-116 | 3,4-diCl—Ph | Pip—(CH₂)₂—CO |
| 2-117 | 3,4-diCl—Ph | Pip—(CH₂)₃—CO |
| 2-118 | 3,4-diCl—Ph | Pipr—CH₂—CO |
| 2-119 | 3,4-diCl—Ph | Pipr—(CH₂)₂—CO |
| 2-120 | 3,4-diCl—Ph | Pipr—(CH₂)₃—CO |
| 2-121 | 3,4-diCl—Ph | EtO—CO |
| 2-122 | 3,4-diCl—Ph | MeO—(CH₂)₂—O—CO |

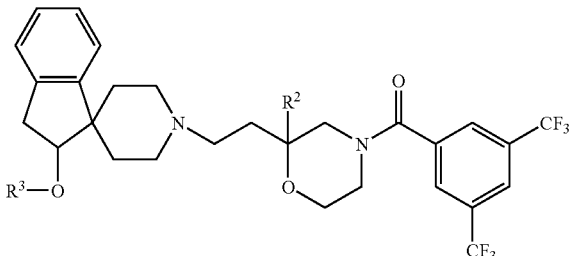
(I-2)

[Compound List 2]

| Compound No. | R² | R³ |
|---|---|---|
| 2-123 | 3,4-diCl—Ph | F—(CH₂)₂—O—CO |
| 2-124 | 3,4-diCl—Ph | Propargyl—O—CO |
| 2-125 | 3,4-diCl—Ph | EtO—CO—CH₂—NH—CO |
| 2-126 | 3,4-diCl—Ph | EtO—CO—(CH₂)₂—NH—CO |
| 2-127 | 3,4-diCl—Ph | EtO—CO—(CH₂)₃—NH—CO |
| 2-128 | 3,4-diCl—Ph | Et—NH—CO |
| 2-129 | 3,4-diCl—Ph | HO—(CH₂)₂—N(Me)—CH₂—CO |
| 2-130 | 3,4-diCl—Ph | EtO—(CH₂)₂—NH—CH₂—CO |
| 2-131 | 3,4-diCl—Ph | Me—NH—CH₂—CO |
| 2-132 | 3,4-diCl—Ph | Et—NH—CH₂—CO |
| 2-133 | 3,4-diCl—Ph | Pr—NH—CH₂—CO |
| 2-134 | 3,4-diCl—Ph | iPr—NH—CH₂—CO |
| 2-135 | 3,4-diCl—Ph | (Me)₂N—CH₂—CO |
| 2-136 | 3,4-diCl—Ph | (Et)₂N—CH₂—CO |
| 2-137 | 3,4-diCl—Ph | (Pr)₂N—CH₂—CO |
| 2-138 | 3,4-diCl—Ph | (iPr)₂N—CH₂—CO |
| 2-139 | 3,4-diCl—Ph | (MeO—CH₂)₂N—CH₂—CO |
| 2-140 | 3,4-diCl—Ph | (MeO—CH₂—CH₂)₂N—CH₂—CO |
| 2-141 | 3,4-diCl—Ph | Aze—CH₂—CO |
| 2-142 | 3,4-diCl—Ph | Pyrr—CH₂—CO |
| 2-143 | 3,4-diCl—Ph | Pip—CH₂—CO |
| 2-144 | 3,4-diCl—Ph | 4-(H₂NCO)—Pip—CH₂—CO |
| 2-145 | 3,4-diCl—Ph | 4-(HO—CH₂)—Pip—CH₂—CO |
| 2-146 | 3,4-diCl—Ph | 4-(HO—CH₂—CH₂)—Pip—CH₂—CO |
| 2-147 | 3,4-diCl—Ph | HO—CO—CH₂ |
| 2-148 | 3,4-diCl—Ph | MeO—CO—CH₂ |
| 2-149 | 3,4-diCl—Ph | EtO—CO—CH₂ |
| 2-150 | 3,4-diCl—Ph | H₂N—CO—CH₂ |
| 2-151 | 3,4-diCl—Ph | (Me)₂N—CO—CH₂ |
| 2-152 | 3,4-diCl—Ph | (Et)₂N—CO—CH₂ |
| 2-153 | 3,4-diCl—Ph | (HO—CH₂—CH₂)₂N—CO—CH₂ |
| 2-154 | 3,4-diCl—Ph | HO—CH₂—CH₂—NH—CO—CH₂ |
| 2-155 | 3,4-diCl—Ph | HO—CH₂—CH₂—N(Me)—CO—CH₂ |
| 2-156 | 3,4-diCl—Ph | Mor—CO—CH₂ |
| 2-157 | 3,4-diCl—Ph | Pip—CO—CH₂ |
| 2-158 | 3,4-diCl—Ph | Pipr—CO—CH₂ |
| 2-159 | 3,4-diCl—Ph | HO—(CH₂)₂ |
| 2-160 | 3,4-diCl—Ph | H₂N—(CH₂)₂ |
| 2-161 | 3,4-diCl—Ph | (Me)₂N—(CH₂)₂ |
| 2-162 | 3,4-diCl—Ph | (Et)₂N—(CH₂)₂ |
| 2-163 | 3,4-diCl—Ph | (HO—CH₂—CH₂)₂N—(CH₂)₂ |
| 2-164 | 3,4-diCl—Ph | HO—CH₂—CH₂—NH—(CH₂)₂ |
| 2-165 | 3,4-diCl—Ph | HO—CH₂—CH₂—N(Me)—(CH₂)₂ |
| 2-166 | 3,4-diCl—Ph | Mor—(CH₂)₂ |
| 2-167 | 3,4-diCl—Ph | Pip—(CH₂)₂ |
| 2-168 | 3,4-diCl—Ph | Pipr—(CH₂)₂ |
| 2-169 | 3,4-diCl—Ph | H₂N—CO—NH—CO |
| 2-170 | 3,4-diCl—Ph | (Me)₂N—CO—NH—CO |
| 2-171 | 3,4-diCl—Ph | (Et)₂N—CO—NH—CO |
| 2-172 | 3,4-diCl—Ph | (HO—CH₂—CH₂)₂N—CO—NH—CO |
| 2-173 | 3,4-diCl—Ph | HO—CH₂—CH₂—NH—CO—NH—CO |
| 2-174 | 3,4-diCl—Ph | HO—CH₂—CH₂—N(Me)—CO—NH—CO |
| 2-175 | 3,4-diCl—Ph | Mor—CO—NH—CO |
| 2-176 | 3,4-diCl—Ph | Pip—CO—NH—CO |
| 2-177 | 3,4-diCl—Ph | Pipr—CO—NH—CO |
| 2-178 | 3,4-diCl—Ph | H₂N—SO₂—NH—CO |
| 2-179 | 3,4-diCl—Ph | (Me)₂N—SO₂—NH—CO |
| 2-180 | 3,4-diCl—Ph | (Et)₂N—SO₂—NH—CO |
| 2-181 | 3,4-diCl—Ph | (HO—CH₂—CH₂)₂N—SO₂—NH—CO |
| 2-182 | 3,4-diCl—Ph | HO—CH₂—CH₂—NH—SO₂—NH—CO |

-continued

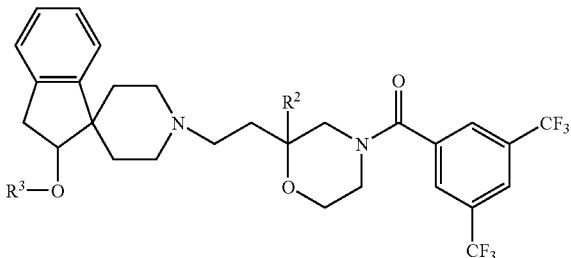

(I-2)

[Compound List 2]

| Compound No. | R² | R³ |
|---|---|---|
| 2-183 | 3,4-diCl—Ph | HO—CH₂—CH₂—N(Me)—SO₂—NH—CO |
| 2-184 | 3,4-diCl—Ph | Mor—SO₂—NH—CO |
| 2-185 | 3,4-diCl—Ph | Pip—SO₂—NH—CO |
| 2-186 | 3,4-diCl—Ph | Pipr—SO₂—NH—CO |
| 2-187 | 3,4-diCl—Ph | Mor—CH₂—CO—NH—CO |
| 2-188 | 3,4-diCl—Ph | Pip—CH₂—CO—NH—CO |
| 2-189 | 3,4-diCl—Ph | Pipr—CH₂—CO—NH—CO |
| 2-190 | 3,4-diCl—Ph | H₂N—CO |
| 2-191 | 3,4-diCl—Ph | MeO—(CH₂)₂—O—CH₂ |
| 2-192 | 3,4-diCl—Ph | MeO—CH₂ |
| 2-193 | 3,4-diF—Ph | MeO—NH—CO—CH₂ |
| 2-194 | 3,4-diF—Ph | EtO—NH—CO—CH₂ |
| 2-195 | 3,4-diF—Ph | PrO—NH—CO—CH₂ |
| 2-196 | 3,4-diF—Ph | BuO—NH—CO—CH₂ |
| 2-197 | 3,4-diF—Ph | PnO—NH—CO—CH₂ |
| 2-198 | 3,4-diF—Ph | HxO—NH—CO—CH₂ |
| 2-199 | 3,4-diF—Ph | HO—(CH₂)₃—NH—CO—CH₂ |
| 2-200 | 3,4-diF—Ph | HO—(CH₂)₄—NH—CO—CH₂ |
| 2-201 | 3,4-diF—Ph | HO—(CH₂)₅—NH—CO—CH₂ |
| 2-202 | 3,4-diF—Ph | HO—(CH₂)₂—O—(CH₂)₂—NH—CO—CH₂ |
| 2-203 | 3,4-diF—Ph | Me—CH(OH)—(CH₂)₃—NH—CO—CH₂ |
| 2-204 | 3,4-diF—Ph | HO—(CH₂)₆—NH—CO—CH₂ |
| 2-205 | 3,4-diF—Ph | HO—C(Me)(Me)—(CH₂)₃—NH—CO—CH₂ |
| 2-206 | 3,4-diF—Ph | HO—(CH₂)₃—N(Me)—CO—CH₂ |
| 2-207 | 3,4-diF—Ph | HO—(CH₂)₄—N(Me)—CO—CH₂ |
| 2-208 | 3,4-diF—Ph | HO—(CH₂)₅—N(Me)—CO—CH₂ |
| 2-209 | 3,4-diF—Ph | Me—CH(OH)—(CH₂)₃—N(Me)—CO—CH₂ |
| 2-210 | 3,4-diF—Ph | HO—(CH₂)₆—N(Me)—CO—CH₂ |
| 2-211 | 3,4-diF—Ph | HO—(CH₂)₂—O—(CH₂)₂—N(Me)—CO—CH₂ |
| 2-212 | 3,4-diF—Ph | HO—C(Me)(Me)—(CH₂)₃—N(Me)—CO—CH₂ |
| 2-213 | 3,4-diF—Ph | HO—(CH₂)₂—N(Et)—CO—CH₂ |
| 2-214 | 3,4-diF—Ph | HO—(CH₂)₃—N(Et)—CO—CH₂ |
| 2-215 | 3,4-diF—Ph | HO—(CH₂)₄—N(Et)—CO—CH₂ |
| 2-216 | 3,4-diF—Ph | HO—(CH₂)₅—N(Et)—CO—CH₂ |
| 2-217 | 3,4-diF—Ph | HO—(CH₂)₆—N(Et)—CO—CH₂ |
| 2-218 | 3,4-diF—Ph | HO—(CH₂)₂—O—(CH₂)₂—N(Et)—CO—CH₂ |
| 2-219 | 3,4-diF—Ph | HO—C(Me)(Me)—(CH₂)₃—N(Et)—CO—CH₂ |
| 2-220 | 3,4-diF—Ph | HO—(CH₂)₂—N(Pr)—CO—CH₂ |
| 2-221 | 3,4-diF—Ph | HO—(CH₂)₃—N(Pr)—CO—CH₂ |
| 2-222 | 3,4-diF—Ph | HO—(CH₂)₄—N(Pr)—CO—CH₂ |
| 2-223 | 3,4-diF—Ph | HO—(CH₂)₅—N(Pr)—CO—CH₂ |
| 2-224 | 3,4-diF—Ph | HO—(CH₂)₆—N(Pr)—CO—CH₂ |
| 2-225 | 3,4-diF—Ph | HO—(CH₂)₂—O—(CH₂)₂—N(Pr)—CO—CH₂ |
| 2-226 | 3,4-diF—Ph | HO—C(Me)(Me)—(CH₂)₃—N(Pr)—CO—CH₂ |
| 2-227 | 3,4-diF—Ph | HO—(CH₂)₂—N(Bu)—CO—CH₂ |
| 2-228 | 3,4-diF—Ph | HO—(CH₂)₃—N(Bu)—CO—CH₂ |
| 2-229 | 3,4-diF—Ph | HO—(CH₂)₄—N(Bu)—CO—CH₂ |
| 2-230 | 3,4-diF—Ph | HO—(CH₂)₅—N(Bu)—CO—CH₂ |
| 2-231 | 3,4-diF—Ph | HO—(CH₂)₆—N(Bu)—CO—CH₂ |
| 2-232 | 3,4-diF—Ph | HO—(CH₂)₂—O—(CH₂)₂—N(Bu)—CO—CH₂ |
| 2-233 | 3,4-diF—Ph | HO—C(Me)(Me)—(CH₂)₃—N(Bu)—CO—CH₂ |
| 2-234 | 3,4-diF—Ph | HO—(CH₂)₂—N(cPr)—CO—CH₂ |
| 2-235 | 3,4-diF—Ph | HO—(CH₂)₃—N(cPr)—CO—CH₂ |
| 2-236 | 3,4-diF—Ph | HO—(CH₂)₄—N(cPr)—CO—CH₂ |
| 2-237 | 3,4-diF—Ph | HO—(CH₂)₅—N(cPr)—CO—CH₂ |
| 2-238 | 3,4-diF—Ph | HO—(CH₂)₆—N(cPr)—CO—CH₂ |
| 2-239 | 3,4-diF—Ph | HO—(CH₂)₂—O—(CH₂)₂—N(cPr)—CO—CH₂ |
| 2-240 | 3,4-diF—Ph | HO—(CH₂)₂—N(HO)—CO—CH₂ |
| 2-241 | 3,4-diF—Ph | HO—(CH₂)₃—N(HO)—CO—CH₂ |
| 2-242 | 3,4-diF—Ph | HO—(CH₂)₄—N(HO)—CO—CH₂ |

-continued

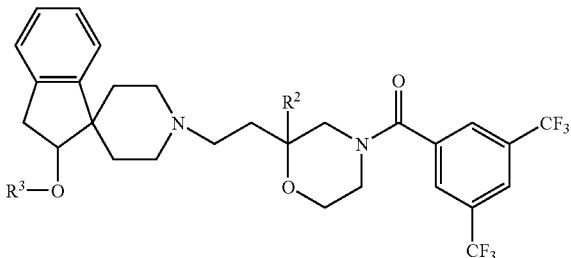

(I-2)

[Compound List 2]

| Compound No. | R² | R³ |
|---|---|---|
| 2-243 | 3,4-diF—Ph | HO—(CH₂)₅—N(HO)—CO—CH₂ |
| 2-244 | 3,4-diF—Ph | HO—(CH₂)₆—N(HO)—CO—CH₂ |
| 2-245 | 3,4-diF—Ph | HO—C(Me)(Me)—(CH₂)₂—N(HO)—CO—CH₂ |
| 2-246 | 3,4-diF—Ph | HO—C(Me)(Me)—(CH₂)₃—N(HO)—CO—CH₂ |
| 2-247 | 3,4-diF—Ph | HO—(CH₂)₂—N(MeO)—CO—CH₂ |
| 2-248 | 3,4-diF—Ph | HO—(CH₂)₃—N(MeO)—CO—CH₂ |
| 2-249 | 3,4-diF—Ph | HO—(CH₂)₄—N(MeO)—CO—CH₂ |
| 2-250 | 3,4-diF—Ph | HO—(CH₂)₅—N(MeO)—CO—CH₂ |
| 2-251 | 3,4-diF—Ph | HO—(CH₂)₆—N(MeO)—CO—CH₂ |
| 2-252 | 3,4-diF—Ph | HO—C(Me)(Me)—(CH₂)₂—N(MeO)—CO—CH₂ |
| 2-253 | 3,4-diF—Ph | HO—C(Me)(Me)—(CH₂)₃—N(MeO)—CO—CH₂ |
| 2-254 | 3,4-diF—Ph | MeO—(CH₂)₂—N(Me)—CO—CH₂ |
| 2-255 | 3,4-diF—Ph | MeO—(CH₂)₃—N(Me)—CO—CH₂ |
| 2-256 | 3,4-diF—Ph | MeO—(CH₂)₄—N(Me)—CO—CH₂ |
| 2-257 | 3,4-diF—Ph | MeO—(CH₂)₅—N(Me)—CO—CH₂ |
| 2-258 | 3,4-diF—Ph | MeO—(CH₂)₆—N(Me)—CO—CH₂ |
| 2-259 | 3,4-diF—Ph | MeO—(CH₂)₂—O—(CH₂)₂—N(Me)—CO—CH₂ |
| 2-260 | 3,4-diF—Ph | MeO—C(Me)(Me)—(CH₂)₃—N(Me)—CO—CH₂ |
| 2-261 | 3,4-diF—Ph | NC—CH₂—NH—CO—CH₂ |
| 2-262 | 3,4-diF—Ph | NC—(CH₂)₂—NH—CO—CH₂ |
| 2-263 | 3,4-diF—Ph | NC—(CH₂)₃—NH—CO—CH₂ |
| 2-264 | 3,4-diF—Ph | NC—(CH₂)₄—NH—CO—CH₂ |
| 2-265 | 3,4-diF—Ph | NC—(CH₂)₅—NH—CO—CH₂ |
| 2-266 | 3,4-diF—Ph | NC—(CH₂)₆—NH—CO—CH₂ |
| 2-267 | 3,4-diF—Ph | NC—(CH₂)₂—O—(CH₂)₂—NH—CO—CH₂ |
| 2-268 | 3,4-diF—Ph | NC—CH₂—N(Me)—CO—CH₂ |
| 2-269 | 3,4-diF—Ph | NC—(CH₂)₂—N(Me)—CO—CH₂ |
| 2-270 | 3,4-diF—Ph | NC—(CH₂)₃—N(Me)—CO—CH₂ |
| 2-271 | 3,4-diF—Ph | NC—(CH₂)₄—N(Me)—CO—CH₂ |
| 2-272 | 3,4-diF—Ph | NC—(CH₂)₅—N(Me)—CO—CH₂ |
| 2-273 | 3,4-diF—Ph | NC—(CH₂)₆—N(Me)—CO—CH₂ |
| 2-274 | 3,4-diF—Ph | NC—(CH₂)₂—O—(CH₂)₂—N(Me)—CO—CH₂ |
| 2-275 | 3,4-diF—Ph | HO—CO—CH₂—NH—CO—CH₂ |
| 2-276 | 3,4-diF—Ph | HO—CO—(CH₂)₂—NH—CO—CH₂ |
| 2-277 | 3,4-diF—Ph | HO—CO—(CH₂)₃—NH—CO—CH₂ |
| 2-278 | 3,4-diF—Ph | HO—CO—(CH₂)₄—MH—CO—CH₂ |
| 2-279 | 3,4-diF—Ph | HO—CO—(CH₂)₅—NH—CO—CH₂ |
| 2-280 | 3,4-diF—Ph | HO—CO—(CH₂)₆—NH—CO—CH₂ |
| 2-281 | 3,4-diF—Ph | HO—CO—(CH₂)₂—O—(CH₂)₂—NH—CO—CH₂ |
| 2-282 | 3,4-diF—Ph | HO—CO—CH₂—N(Me)—CO—CH₂ |
| 2-283 | 3,4-diF—Ph | HO—CO—(CH₂)₂—N(Me)—CO—CH₂ |
| 2-284 | 3,4-diF—Ph | HO—CO—(CH₂)₃—N(Me)—CO—CH₂ |
| 2-285 | 3,4-diF—Ph | HO—CO—(CH₂)₄—N(Me)—CO—CH₂ |
| 2-286 | 3,4-diF—Ph | HO—CO—(CH₂)₅—N(Me)—CO—CH₂ |
| 2-287 | 3,4-diF—Ph | HO—CO—(CH₂)₆—N(Me)—CO—CH₂ |
| 2-288 | 3,4-diF—Ph | HO—CO—(CH₂)₂—O—(CH₂)₂—N(Me)—CO—CH₂ |
| 2-289 | 3,4-diF—Ph | MeO—CO—CH₂—NH—CO—CH₂ |
| 2-290 | 3,4-diF—Ph | MeO—CO—(CH₂)₂—NH—CO—CH₂ |
| 2-291 | 3,4-diF—Ph | MeO—CO—(CH₂)₃—NH—CO—CH₂ |
| 2-292 | 3,4-diF—Ph | MeO—CO—(CH₂)₄—NH—CO—CH₂ |
| 2-293 | 3,4-diF—Ph | MeO—CO—(CH₂)₅—NH—CO—CH₂ |
| 2-294 | 3,4-diF—Ph | MeO—CO—(CH₂)₆—NH—CO—CH₂ |
| 2-295 | 3,4-diF—Ph | MeO—CO—(CH₂)₂—O—(CH₂)₂—NH—CO—CH₂ |
| 2-296 | 3,4-diF—Ph | MeO—CO—CH₂—N(Me)—CO—CH₂ |
| 2-297 | 3,4-diF—Ph | MeO—CO—(CH₂)₂—N(Me)—CO—CH₂ |
| 2-298 | 3,4-diF—Ph | MeO—CO—(CH₂)₃—N(Me)—CO—CH₂ |
| 2-299 | 3,4-diF—Ph | MeO—CO—(CH₂)₄—N(Me)—CO—CH₂ |
| 2-300 | 3,4-diF—Ph | MeO—CO—(CH₂)₅—N(Me)—CO—CH₂ |
| 2-301 | 3,4-diF—Ph | MeO—CO—(CH₂)₆—N(Me)—CO—CH₂ |
| 2-302 | 3,4-diF—Ph | MeO—CO—(CH₂)₂—O—(CH₂)₂—N(Me)—CO—CH₂ |

-continued

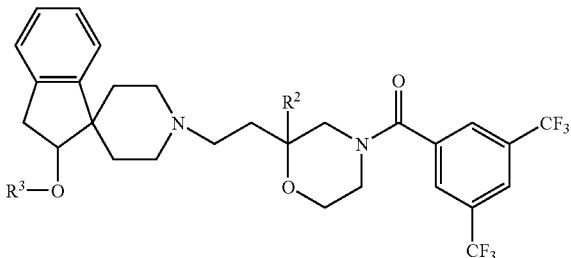

(I-2)

[Compound List 2]

| Compound No. | R² | R³ |
|---|---|---|
| 2-303 | 3,4-diF—Ph | H₂N—CO—CH₂—NH—CO—CH₂ |
| 2-304 | 3,4-diF—Ph | H₂N—CO—(CH₂)₂—NH—CO—CH₂ |
| 2-305 | 3,4-diF—Ph | H₂N—CO—(CH₂)₃—NH—CO—CH₂ |
| 2-306 | 3,4-diF—Ph | H₂N—CO—(CH₂)₄—NH—CO—CH₂ |
| 2-307 | 3,4-diF—Ph | H₂N—CO—(CH₂)₅—NH—CO—CH₂ |
| 2-308 | 3,4-diF—Ph | H₂N—CO—(CH₂)₆—NH—CO—CH₂ |
| 2-309 | 3,4-diF—Ph | H₂N—CO—(CH₂)₂—O—(CH₂)₂—NH—CO—CH₂ |
| 2-310 | 3,4-diF—Ph | H₂N—CO—CH₂—N(Me)—CO—CH₂ |
| 2-311 | 3,4-diF—Ph | H₂N—CO—(CH₂)₂—N(Me)—CO—CH₂ |
| 2-312 | 3,4-diF—Ph | H₂N—CO—(CH₂)₃—N(Me)—CO—CH₂ |
| 2-313 | 3,4-diF—Ph | H₂N—CO—(CH₂)₄—N(Me)—CO—CH₂ |
| 2-314 | 3,4-diF—Ph | H₂N—CO—(CH₂)₅—N(Me)—CO—CH₂ |
| 2-315 | 3,4-diF—Ph | H₂N—CO—(CH₂)₆—N(Me)—CO—CH₂ |
| 2-316 | 3,4-diF—Ph | H₂N—CO—(CH₂)₂—O—(CH₂)₂—N(Me)—CO—CH₂ |
| 2-317 | 3,4-diF—Ph | HO—N(Me)—CO—CH₂—N(Me)—CO—CH₂ |
| 2-318 | 3,4-diF—Ph | HO—N(Me)—CO—(CH₂)₂—N(Me)—CO—CH₂ |
| 2-319 | 3,4-diF—Ph | HO—N(Me)—CO—(CH₂)₃—N(Me)—CO—CH₂ |
| 2-320 | 3,4-diF—Ph | HO—N(Me)—CO—(CH₂)₄—N(Me)—CO—CH₂ |
| 2-321 | 3,4-diF—Ph | HO—N(Me)—CO—(CH₂)₅—N(Me)—CO—CH₂ |
| 2-322 | 3,4-diF—Ph | HO—N(Me)—CO—(CH₂)₆—N(Me)—CO—CH₂ |
| 2-323 | 3,4-diF—Ph | HO—N(Me)—CO—(CH₂)₂—O—(CH₂)₂—N(Me)—CO—CH₂ |
| 2-324 | 3,4-diF—Ph | MeO—N(Me)—CO—CH₂—N(Me)—CO—CH₂ |
| 2-325 | 3,4-diF—Ph | MeO—N(Me)—CO—(CH₂)₂—N(Me)—CO—CH₂ |
| 2-326 | 3,4-diF—Ph | MeO—N(Me)—CO—(CH₂)₃—N(Me)—CO—CH₂ |
| 2-327 | 3,4-diF—Ph | MeO—N(Me)—CO—(CH₂)₄—N(Me)—CO—CH₂ |
| 2-328 | 3,4-diF—Ph | MeO—N(Me)—CO—(CH₂)₅—N(Me)—CO—CH₂ |
| 2-329 | 3,4-diF—Ph | MeO—N(Me)—CO—(CH₂)₆—N(Me)—CO—CH₂ |
| 2-330 | 3,4-diF—Ph | MeO—N(Me)—CO—(CH₂)₂—O—(CH₂)₂—N(Me)—CO—CH₂ |
| 2-331 | 3,4-diF—Ph | Ac—CH₂—N(Me)—CO—CH₂ |
| 2-332 | 3,4-diF—Ph | Ac—(CH₂)₂—N(Me)—CO—CH₂ |
| 2-333 | 3,4-diF—Ph | Ac—(CH₂)₃—N(Me)—CO—CH₂ |
| 2-334 | 3,4-diF—Ph | Ac—(CH₂)₄—N(Me)—CO—CH₂ |
| 2-335 | 3,4-diF—Ph | Ac—(CH₂)₅—N(Me)—CO—CH₂ |
| 2-336 | 3,4-diF—Ph | Ac—(CH₂)₆—N(Me)—CO—CH₂ |
| 2-337 | 3,4-diF—Ph | Ac—(CH₂)₂—O—(CH₂)₂—N(Me)—CO—CH₂ |
| 2-338 | 3,4-diF—Ph | HO—(CH₂)₂—O—N(Me)—CO—CH₂ |
| 2-339 | 3,4-diF—Ph | HO—(CH₂)₃—O—N(Me)—CO—CH₂ |
| 2-340 | 3,4-diF—Ph | HO—(CH₂)₄—O—N(Me)—CO—CH₂ |
| 2-341 | 3,4-diF—Ph | HO—(CH₂)₅—O—N(Me)—CO—CH₂ |
| 2-342 | 3,4-diF—Ph | HO—(CH₂)₆—O—N(Me)—CO—CH₂ |
| 2-343 | 3,4-diF—Ph | HO—(CH₂)₂—O—(CH₂)₂—O—N(Me)—CO—CH₂ |
| 2-344 | 3,4-diF—Ph | (Me)₂N—(CH₂)₂—N(Me)—CO—CH₂ |
| 2-345 | 3,4-diF—Ph | (Me)₂N—(CH₂)₃—N(Me)—CO—CH₂ |
| 2-346 | 3,4-diF—Ph | (Me)₂N—(CH₂)₄—N(Me)—CO—CH₂ |
| 2-347 | 3,4-diF—Ph | (Me)₂N—(CH₂)₅—N(Me)—CO—CH₂ |
| 2-348 | 3,4-diF—Ph | (Me)₂N—(CH₂)₆—N(Me)—CO—CH₂ |
| 2-349 | 3,4-diF—Ph | (Me)₂N—(CH₂)₂—O—(CH₂)₂—N(Me)—CO—CH₂ |
| 2-350 | 3,4-diF—Ph | AcNH—(CH₂)₂—N(Me)—CO—CH₂ |
| 2-351 | 3,4-diF—Ph | AcNH—(CH₂)₃—N(Me)—CO—CH₂ |
| 2-352 | 3,4-diF—Ph | AcNH—(CH₂)₄—N(Me)—CO—CH₂ |
| 2-353 | 3,4-diF—Ph | AcNH—(CH₂)₅—N(Me)—CO—CH₂ |
| 2-354 | 3,4-diF—Ph | AcNH—(CH₂)₆—N(Me)—CO—CH₂ |
| 2-355 | 3,4-diF—Ph | AcNH—(CH₂)₂—O—(CH₂)₂—N(Me)—CO—CH₂ |
| 2-356 | 3,4-diF—Ph | Me—SO₂NH—(CH₂)₂—N(Me)—CO—CH₂ |
| 2-357 | 3,4-diF—Ph | Me—SO₂NH—(CH₂)₃—N(Me)—CO—CH₂ |
| 2-358 | 3,4-diF—Ph | Me—SO₂NH—(CH₂)₄—N(Me)—CO—CH₂ |
| 2-359 | 3,4-diF—Ph | Me—SO₂NH—(CH₂)₅—N(Me)—CO—CH₂ |
| 2-360 | 3,4-diF—Ph | Me—SO₂NH—(CH₂)₆—N(Me)—CO—CH₂ |
| 2-361 | 3,4-diF—Ph | Me—SO₂NH—(CH₂)₂—O—(CH₂)₂—N(Me)—CO—CH₂ |
| 2-362 | 3,4-diF—Ph | 2-(HO—(CH₂)₂)—Pyrr—CO—CH₂ |

-continued

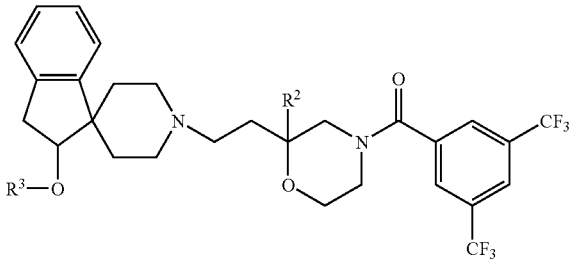

(I-2)

[Compound List 2]

| Compound No. | $R^2$ | $R^3$ |
|---|---|---|
| 2-363 | 3,4-diF—Ph | 2-(HO—(CH$_2$)$_3$)—Pyrr—CO—CH$_2$ |
| 2-364 | 3,4-diF—Ph | 2-(HO—(CH$_2$)$_4$)—Pyrr—CO—CH$_2$ |
| 2-365 | 3,4-diF—Ph | 2-(HO—CO—CH$_2$)—Pyrr—CO—CH$_2$ |
| 2-366 | 3,4-diF—Ph | 2-(HO—CO—(CH$_2$)$_2$)—Pyrr—CO—CH$_2$ |
| 2-367 | 3,4-diF—Ph | 2-(HO—CO—(CH$_2$)$_3$)—Pyrr—CO—CH$_2$ |
| 2-368 | 3,4-diF—Ph | 4-Oxo—Pip—CO—CH$_2$ |
| 2-369 | 3,4-diF—Ph | 4-HO—Pip—CO—CH$_2$ |
| 2-370 | 3,4-diF—Ph | 4-(HO—CH$_2$)—Pip—CO—CH$_2$ |
| 2-371 | 3,4-diF—Ph | 4-(HO—(CH$_2$)$_2$)—Pip—CO—CH$_2$ |
| 2-372 | 3,4-diF—Ph | 4-(HO—(CH$_2$)$_3$)—Pip—CO—CH$_2$ |
| 2-373 | 3,4-diF—Ph | 4-(HO—(CH$_2$)$_4$)—Pip—CO—CH$_2$ |
| 2-374 | 3,4-diF—Ph | 4-(HO—CH$_2$—O)—Pip—CO—CH$_2$ |
| 2-375 | 3,4-diF—Ph | 4-(HO—(CH$_2$)$_2$—O)—Pip—CO—CH$_2$ |
| 2-376 | 3,4-diF—Ph | 4-(HO—(CH$_2$)$_3$—O)—Pip—CO—CH$_2$ |
| 2-377 | 3,4-diF—Ph | 4-H$_2$N—Pip—CO—CH$_2$ |
| 2-378 | 3,4-diF—Ph | 4-(AcNH)—Pip—CO—CH$_2$ |
| 2-379 | 3,4-diF—Ph | 4-(HO—CH$_2$—CONH)—Pip—CO—CH$_2$ |
| 2-380 | 3,4-diF—Ph | 4-(HO—(CH$_2$)$_2$—O—CH$_2$)—Pip—CO—CH$_2$ |
| 2-381 | 3,4-diF—Ph | 4-(HO—CO)—Pip—CO—CH$_2$ |
| 2-382 | 3,4-diF—Ph | 4-(HO—CO—CH$_2$)—Pip—CO—CH$_2$ |
| 2-383 | 3,4-diF—Ph | 4-(HO—CO—(CH$_2$)$_2$)—Pip—CO—CH$_2$ |
| 2-384 | 3,4-diF—Ph | 4-(HO—CO—(CH$_2$)$_3$)—Pip—CO—CH$_2$ |
| 2-385 | 3,4-diF—Ph | 4-(HO—CO—(CH$_2$)$_4$)—Pip—CO—CH$_2$ |
| 2-386 | 3,4-diF—Ph | 4-(H$_2$N—CO)—Pip—CO—CH$_2$ |
| 2-387 | 3,4-diF—Ph | 4-(H$_2$N—CO—CH$_2$)—Pip—CO—CH$_2$ |
| 2-388 | 3,4-diF—Ph | 4-(H$_2$N—CO—(CH$_2$)$_2$)—Pip—CO—CH$_2$ |
| 2-389 | 3,4-diF—Ph | 4-(H$_2$N—CO—(CH$_2$)$_3$)—Pip—CO—CH$_2$ |
| 2-390 | 3,4-diF—Ph | 4-(H$_2$N—CO—(CH$_2$)$_4$)—Pip—CO—CH$_2$ |
| 2-391 | 3,4-diF—Ph | 4-(HO—N(Me)—CO)—Pip—CO—CH$_2$ |
| 2-392 | 3,4-diF—Ph | 4-(HO—N(Me)—CO—CH$_2$)—Pip—CO—CH$_2$ |
| 2-393 | 3,4-diF—Ph | 4-(HO—N(Me)—CO—(CH$_2$)$_2$)—Pip—CO—CH$_2$ |
| 2-394 | 3,4-diF—Ph | 4-(HO—N(Me)—CO—(CH$_2$)$_3$)—Pip—CO—CH$_2$ |
| 2-395 | 3,4-diF—Ph | 4-(HO—N(Me)—CO—(CH$_2$)$_4$)—Pip—CO—CH$_2$ |
| 2-396 | 3,4-diF—Ph | 4-(MeO—N(Me)—CO)—Pip—CO—CH$_2$ |
| 2-397 | 3,4-diF—Ph | 4-(MeO—N(Me)—CO—CH$_2$)—Pip—CO—CH$_2$ |
| 2-398 | 3,4-diF—Ph | 4-(MeO—N(Me)—CO—(CH$_2$)$_2$)—Pip—CO—CH$_2$ |
| 2-399 | 3,4-diF—Ph | 4-(MeO—N(Me)—CO—(CH$_2$)$_3$)—Pip—CO—CH$_2$ |
| 2-400 | 3,4-diF—Ph | 4-(MeO—N(Me)—CO—(CH$_2$)$_4$)—Pip—CO—CH$_2$ |
| 2-401 | 3,4-diF—Ph | 3-Oxo—Pipr—CO—CH$_2$ |
| 2-402 | 3,4-diF—Ph | 4-Ac—Pipr—CO—CH$_2$ |
| 2-403 | 3,4-diF—Ph | 4-(HO—(CH$_2$)$_2$)—Pipr—CO—CH$_2$ |
| 2-404 | 3,4-diCl—Ph | MeO—NH—CO—CH$_2$ |
| 2-405 | 3,4-diCl—Ph | EtO—NH—CO—CH$_2$ |
| 2-406 | 3,4-diCl—Ph | PrO—NH—CO—CH$_2$ |
| 2-407 | 3,4-diCl—Ph | BuO—NH—CO—CH$_2$ |
| 2-408 | 3,4-diCl—Ph | PnO—NH—CO—CH$_2$ |
| 2-409 | 3,4-diCl—Ph | HxO—NH—CO—CH$_2$ |
| 2-410 | 3,4-diCl—Ph | HO—(CH$_2$)$_3$—NH—CO—CH$_2$ |
| 2-411 | 3,4-diCl—Ph | HO—(CH$_2$)$_4$—NH—CO—CH$_2$ |
| 2-412 | 3,4-diCl—Ph | HO—(CH$_2$)$_5$—NH—CO—CH$_2$ |
| 2-413 | 3,4-diCl—Ph | HO—(CH$_2$)$_2$—O—(CH$_2$)$_2$—NH—CO—CH$_2$ |
| 2-414 | 3,4-diCl—Ph | Me—CH(OH)—(CH$_2$)$_3$—NH—CO—CH$_2$ |
| 2-415 | 3,4-diCl—Ph | HO—(CH$_2$)$_6$—NH—CO—CH$_2$ |
| 2-416 | 3,4-diCl—Ph | HO—C(Me)(Me)—(CH$_2$)$_3$—NH—CO—CH$_2$ |
| 2-417 | 3,4-diCl—Ph | HO—(CH$_2$)$_3$—N(Me)—CO—CH$_2$ |
| 2-418 | 3,4-diCl—Ph | HO—(CH$_2$)$_4$—N(Me)—CO—CH$_2$ |
| 2-419 | 3,4-diCl—Ph | HO—(CH$_2$)$_5$—N(Me)—CO—CH$_2$ |
| 2-420 | 3,4-diCl—Ph | Me—CH(OH)—(CH$_2$)$_3$—N(Me)—CO—CH$_2$ |
| 2-421 | 3,4-diCl—Ph | HO—(CH$_2$)$_6$—N(Me)—CO—CH$_2$ |
| 2-422 | 3,4-diCl—Ph | HO—(CH$_2$)$_2$—O—(CH$_2$)$_2$—N(Me)—CO—CH$_2$ |

-continued

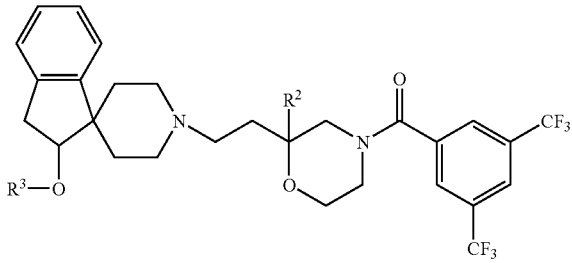

(I-2)

[Compound List 2]

| Compound No. | R² | R³ |
|---|---|---|
| 2-423 | 3,4-diCl—Ph | HO—C(Me)(Me)—(CH₂)₃—N(Me)—CO—CH₂ |
| 2-424 | 3,4-diCl—Ph | HO—(CH₂)₂—N(Et)—CO—CH₂ |
| 2-425 | 3,4-diCl—Ph | HO—(CH₂)₃—N(Et)—CO—CH₂ |
| 2-426 | 3,4-diCl—Ph | HO—(CH₂)₄—N(Et)—CO—CH₂ |
| 2-427 | 3,4-diCl—Ph | HO—(CH₂)₅—N(Et)—CO—CH₂ |
| 2-428 | 3,4-diCl—Ph | HO—(CH₂)₆—N(Et)—CO—CH₂ |
| 2-429 | 3,4-diCl—Ph | HO—(CH₂)₂—O—(CH₂)₂—N(Et)—CO—CH₂ |
| 2-430 | 3,4-diCl—Ph | HO—C(Me)(Me)—(CH₂)₃—N(Et)—CO—CH₂ |
| 2-431 | 3,4-diCl—Ph | HO—(CH₂)₂—N(Pr)—CO—CH₂ |
| 2-432 | 3,4-diCl—Ph | HO—(CH₂)₃—N(Pr)—CO—CH₂ |
| 2-433 | 3,4-diCl—Ph | HO—(CH₂)₄—N(Pr)—CO—CH₂ |
| 2-434 | 3,4-diCl—Ph | HO—(CH₂)₅—N(Pr)—CO—CH₂ |
| 2-435 | 3,4-diCl—Ph | HO—(CH₂)₆—N(Pr)—CO—CH₂ |
| 2-436 | 3,4-diCl—Ph | HO—(CH₂)₂—O—(CH₂)₂—N(Pr)—CO—CH₂ |
| 2-437 | 3,4-diCl—Ph | HO—C(Me)(Me)—(CH₂)₃—N(Pr)—CO—CH₂ |
| 2-438 | 3,4-diCl—Ph | HO—(CH₂)₂—N(Bu)—CO—CH₂ |
| 2-439 | 3,4-diCl—Ph | HO—(CH₂)₃—N(Bu)—CO—CH₂ |
| 2-440 | 3,4-diCl—Ph | HO—(CH₂)₄—N(Bu)—CO—CH₂ |
| 2-441 | 3,4-diCl—Ph | HO—(CH₂)₅—N(Bu)—CO—CH₂ |
| 2-442 | 3,4-diCl—Ph | HO—(CH₂)₆—N(Bu)—CO—CH₂ |
| 2-443 | 3,4-diCl—Ph | HO—(CH₂)₂—O—(CH₂)₂—N(Bu)—CO—CH₂ |
| 2-444 | 3,4-diCl—Ph | HO—C(Me)(Me)—(CH₂)₃—N(Bu)—CO—CH₂ |
| 2-445 | 3,4-diCl—Ph | HO—(CH₂)₂—N(cPr)—CO—CH₂ |
| 2-446 | 3,4-diCl—Ph | HO—(CH₂)₃—N(cPr)—CO—CH₂ |
| 2-447 | 3,4-diCl—Ph | HO—(CH₂)₄—N(cPr)—CO—CH₂ |
| 2-448 | 3,4-diCl—Ph | HO—(CH₂)₅—N(cPr)—CO—CH₂ |
| 2-449 | 3,4-diCl—Ph | HO—(CH₂)₆—N(cPr)—CO—CH₂ |
| 2-450 | 3,4-diCl—Ph | HO—(CH₂)₂—O—(CH₂)₂—N(cPr)—CO—CH₂ |
| 2-451 | 3,4-diCl—Ph | HO—(CH₂)₂—N(HO)—CO—CH₂ |
| 2-452 | 3,4-diCl—Ph | HO—(CH₂)₃—N(HO)—CO—CH₂ |
| 2-453 | 3,4-diCl—Ph | HO—(CH₂)₄—N(HO)—CO—CH₂ |
| 2-454 | 3,4-diCl—Ph | HO—(CH₂)₅—N(HO)—CO—CH₂ |
| 2-455 | 3,4-diCl—Ph | HO—(CH₂)₆—N(HO)—CO—CH₂ |
| 2-456 | 3,4-diCl—Ph | HO—C(Me)(Me)—(CH₂)₂—N(HO)—CO—CH₂ |
| 2-457 | 3,4-diCl—Ph | HO—C(Me)(Me)—(CH₂)₃—N(HO)—CO—CH₂ |
| 2-458 | 3,4-diCl—Ph | HO—(CH₂)₂—N(MeO)—CO—CH₂ |
| 2-459 | 3,4-diCl—Ph | HO—(CH₂)₃—N(MeO)—CO—CH₂ |
| 2-460 | 3,4-diCl—Ph | HO—(CH₂)₄—N(MeO)—CO—CH₂ |
| 2-461 | 3,4-diCl—Ph | HO—(CH₂)₅—N(MeO)—CO—CH₂ |
| 2-462 | 3,4-diCl—Ph | HO—(CH₂)₆—N(MeO)—CO—CH₂ |
| 2-463 | 3,4-diCl—Ph | HO—C(Me)(Me)—(CH₂)₂—N(MeO)—CO—CH₂ |
| 2-464 | 3,4-diCl—Ph | HO—C(Me)(Me)—(CH₂)₃—N(MeO)—CO—CH₂ |
| 2-465 | 3,4-diCl—Ph | MeO—(CH₂)₂—N(Me)—CO—CH₂ |
| 2-466 | 3,4-diCl—Ph | MeO—(CH₂)₃—N(Me)—CO—CH₂ |
| 2-467 | 3,4-diCl—Ph | MeO—(CH₂)₄—N(Me)—CO—CH₂ |
| 2-468 | 3,4-diCl—Ph | MeO—(CH₂)₅—N(Me)—CO—CH₂ |
| 2-469 | 3,4-diCl—Ph | MeO—(CH₂)₆—N(Me)—CO—CH₂ |
| 2-470 | 3,4-diCl—Ph | MeO—(CH₂)₂—O—(CH₂)₂—N(Me)—CO—CH₂ |
| 2-471 | 3,4-diCl—Ph | MeO—C(Me)(Me)—(CH₂)₃—N(Me)—CO—CH₂ |
| 2-472 | 3,4-diCl—Ph | NC—CH₂—NH—CO—CH₂ |
| 2-473 | 3,4-diCl—Ph | NC—(CH₂)₂—NH—CO—CH₂ |
| 2-474 | 3,4-diCl—Ph | NC—(CH₂)₃—NH—CO—CH₂ |
| 2-475 | 3,4-diCl—Ph | NC—(CH₂)₄—NH—CO—CH₂ |
| 2-476 | 3,4-diCl—Ph | NC—(CH₂)₅—NH—CO—CH₂ |
| 2-477 | 3,4-diCl—Ph | NC—(CH₂)₆—NH—CO—CH₂ |
| 2-478 | 3,4-diCl—Ph | NC—(CH₂)₂—O—(CH₂)₂—NH—CO—CH₂ |
| 2-479 | 3,4-diCl—Ph | NC—CH₂—N(Me)—CO—CH₂ |
| 2-480 | 3,4-diCl—Ph | NC—(CH₂)₂—N(Me)—CO—CH₂ |
| 2-481 | 3,4-diCl—Ph | NC—(CH₂)₃—N(Me)—CO—CH₂ |
| 2-482 | 3,4-diCl—Ph | NC—(CH₂)₄—N(Me)—CO—CH₂ |

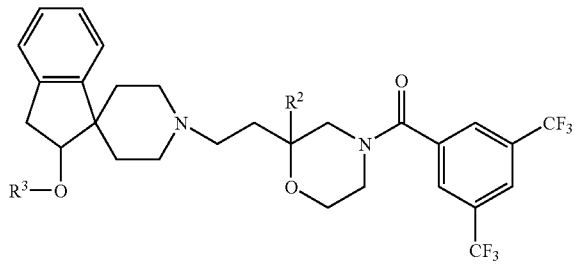

(I-2)

[Compound List 2]

| Compound No. | R² | R³ |
|---|---|---|
| 2-483 | 3,4-diCl—Ph | NC—(CH₂)₅—N(Me)—CO—CH₂ |
| 2-484 | 3,4-diCl—Ph | NC—(CH₂)₆—N(Me)—CO—CH₂ |
| 2-485 | 3,4-diCl—Ph | NC—(CH₂)₂—O—(CH₂)₂—N(Me)—CO—CH₂ |
| 2-486 | 3,4-diCl—Ph | HO—CO—CH₂—NH—CO—CH₂ |
| 2-487 | 3,4-diCl—Ph | HO—CO—(CH₂)₂—NH—CO—CH₂ |
| 2-488 | 3,4-diCl—Ph | HO—CO—(CH₂)₃—NH—CO—CH₂ |
| 2-489 | 3,4-diCl—Ph | HO—CO—(CH₂)₄—NH—CO—CH₂ |
| 2-490 | 3,4-diCl—Ph | HO—CO—(CH₂)₅—NH—CO—CH₂ |
| 2-491 | 3,4-diCl—Ph | HO—CO—(CH₂)₆—NH—CO—CH₂ |
| 2-492 | 3,4-diCl—Ph | HO—CO—(CH₂)₂—O—(CH₂)₂—NH—CO—CH₂ |
| 2-493 | 3,4-diCl—Ph | HO—CO—CH₂—N(Me)—CO—CH₂ |
| 2-494 | 3,4-diCl—Ph | HO—CO—(CH₂)₂—N(Me)—CO—CH₂ |
| 2-495 | 3,4-diCl—Ph | HO—CO—(CH₂)₃—N(Me)—CO—CH₂ |
| 2-496 | 3,4-diCl—Ph | HO—CO—(CH₂)₄—N(Me)—CO—CH₂ |
| 2-497 | 3,4-diCl—Ph | HO—CO—(CH₂)₅—N(Me)—CO—CH₂ |
| 2-498 | 3,4-diCl—Ph | HO—CO—(CH₂)₆—N(Me)—CO—CH₂ |
| 2-499 | 3,4-diCl—Ph | HO—CO—(CH₂)₂—O—(CH₂)₂—N(Me)—CO—CH₂ |
| 2-500 | 3,4-diCl—Ph | MeO—CO—CH₂—NH—CO—CH₂ |
| 2-501 | 3,4-diCl—Ph | MeO—CO—(CH₂)₂—NH—CO—CH₂ |
| 2-502 | 3,4-diCl—Ph | MeO—CO—(CH₂)₃—NH—CO—CH₂ |
| 2-503 | 3,4-diCl—Ph | MeO—CO—(CH₂)₄—NH—CO—CH₂ |
| 2-504 | 3,4-diCl—Ph | MeO—CO—(CH₂)₅—NH—CO—CH₂ |
| 2-505 | 3,4-diCl—Ph | MeO—CO—(CH₂)₆—NH—CO—CH₂ |
| 2-506 | 3,4-diCl—Ph | MeO—CO—(CH₂)₂—O—(CH₂)₂—NH—CO—CH₂ |
| 2-507 | 3,4-diCl—Ph | MeO—CO—CH₂—N(Me)—CO—CH₂ |
| 2-508 | 3,4-diCl—Ph | MeO—CO—(CH₂)₂—N(Me)—CO—CH₂ |
| 2-509 | 3,4-diCl—Ph | MeO—CO—(CH₂)₃—N(Me)—CO—CH₂ |
| 2-510 | 3,4-diCl—Ph | MeO—CO—(CH₂)₄—N(Me)—CO—CH₂ |
| 2-511 | 3,4-diCl—Ph | MeO—CO—(CH₂)₅—N(Me)—CO—CH₂ |
| 2-512 | 3,4-diCl—Ph | MeO—CO—(CH₂)₆—N(Me)—CO—CH₂ |
| 2-513 | 3,4-diCl—Ph | MeO—CO—(CH₂)₂—O—(CH₂)₂—N(Me)—CO—CH₂ |
| 2-514 | 3,4-diCl—Ph | H₂N—CO—CH₂—NH—CO—CH₂ |
| 2-515 | 3,4-diCl—Ph | H₂N—CO—(CH₂)₂—NH—CO—CH₂ |
| 2-516 | 3,4-diCl—Ph | H₂N—CO—(CH₂)₃—NH—CO—CH₂ |
| 2-517 | 3,4-diCl—Ph | H₂N—CO—(CH₂)₄—NH—CO—CH₂ |
| 2-518 | 3,4-diCl—Ph | H₂N—CO—(CH₂)₅—NH—CO—CH₂ |
| 2-519 | 3,4-diCl—Ph | H₂N—CO—(CH₂)₆—NH—CO—CH₂ |
| 2-520 | 3,4-diCl—Ph | H₂N—CO—(CH₂)₂—O—(CH₂)₂—NH—CO—CH₂ |
| 2-521 | 3,4-diCl—Ph | H₂N—CO—CH₂—N(Me)—CO—CH₂ |
| 2-522 | 3,4-diCl—Ph | H₂N—CO—(CH₂)₂—N(Me)—CO—CH₂ |
| 2-523 | 3,4-diCl—Ph | H₂N—CO—(CH₂)₃—N(Me)—CO—CH₂ |
| 2-524 | 3,4-diCl—Ph | H₂N—CO—(CH₂)₄—N(Me)—CO—CH₂ |
| 2-525 | 3,4-diCl—Ph | H₂N—CO—(CH₂)₅—N(Me)—CO—CH₂ |
| 2-526 | 3,4-diCl—Ph | H₂N—CO—(CH₂)₆—N(Me)—CO—CH₂ |
| 2-527 | 3,4-diCl—Ph | H₂N—CO—(CH₂)₂—O—(CH₂)₂—N(Me)—CO—CH₂ |
| 2-528 | 3,4-diCl—Ph | HO—N(Me)—CO—CH₂—N(Me)—CO—CH₂ |
| 2-529 | 3,4-diCl—Ph | HO—N(Me)—CO—(CH₂)₂—N(Me)—CO—CH₂ |
| 2-530 | 3,4-diCl—Ph | HO—N(Me)—CO—(CH₂)₃—N(Me)—CO—CH₂ |
| 2-531 | 3,4-diCl—Ph | HO—N(Me)—CO—(CH₂)₄—N(Me)—CO—CH₂ |
| 2-532 | 3,4-diCl—Ph | HO—N(Me)—CO—(CH₂)₅—N(Me)—CO—CH₂ |
| 2-533 | 3,4-diCl—Ph | HO—N(Me)—CO—(CH₂)₆—N(Me)—CO—CH₂ |
| 2-534 | 3,4-diCl—Ph | HO—N(Me)—CO—(CH₂)₂—O—(CH₂)₂—N(Me)—CO—CH₂ |
| 2-535 | 3,4-diCl—Ph | MeO—N(Me)—CO—CH₂—N(Me)—CO—CH₂ |
| 2-536 | 3,4-diCl—Ph | MeO—N(Me)—CO—(CH₂)₂—N(Me)—CO—CH₂ |
| 2-537 | 3,4-diCl—Ph | MeO—N(Me)—CO—(CH₂)₃—N(Me)—CO—CH₂ |
| 2-538 | 3,4-diCl—Ph | MeO—N(Me)—CO—(CH₂)₄—N(Me)—CO—CH₂ |
| 2-539 | 3,4-diCl—Ph | MeO—N(Me)—CO—(CH₂)₅—N(Me)—CO—CH₂ |
| 2-540 | 3,4-diCl—Ph | MeO—N(Me)—CO—(CH₂)₆—N(Me)—CO—CH₂ |
| 2-541 | 3,4-diCl—Ph | MeO—N(Me)—CO—(CH₂)₂—O—(CH₂)₂—N(Me)—CO—CH₂ |
| 2-542 | 3,4-diCl—Ph | Ac—CH₂—N(Me)—CO—CH₂ |

-continued

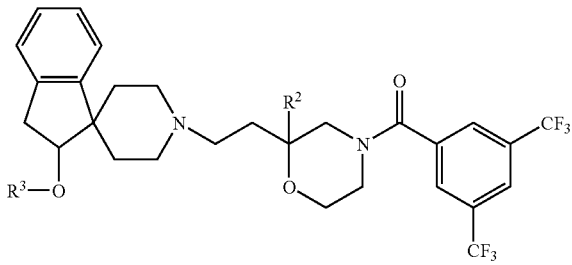
(I-2)

[Compound List 2]

| Compound No. | R² | R³ |
|---|---|---|
| 2-543 | 3,4-diCl—Ph | Ac—(CH₂)₂—N(Me)—CO—CH₂ |
| 2-544 | 3,4-diCl—Ph | Ac—(CH₂)₃—N(Me)—CO—CH₂ |
| 2-545 | 3,4-diCl—Ph | Ac—(CH₂)₄—N(Me)—CO—CH₂ |
| 2-546 | 3,4-diCl—Ph | Ac—(CH₂)₅—N(Me)—CO—CH₂ |
| 2-547 | 3,4-diCl—Ph | Ac—(CH₂)₆—N(Me)—CO—CH₂ |
| 2-548 | 3,4-diCl—Ph | Ac—(CH₂)₂—O—(CH₂)₂—N(Me)—CO—CH₂ |
| 2-549 | 3,4-diCl—Ph | HO—(CH₂)₂—O—N(Me)—CO—CH₂ |
| 2-550 | 3,4-diCl—Ph | HO—(CH₂)₃—O—N(Me)—CO—CH₂ |
| 2-551 | 3,4-diCl—Ph | HO—(CH₂)₄—O—N(Me)—CO—CH₂ |
| 2-552 | 3,4-diCl—Ph | HO—(CH₂)₅—O—N(Me)—CO—CH₂ |
| 2-553 | 3,4-diCl—Ph | HO—(CH₂)₆—O—N(Me)—CO—CH₂ |
| 2-554 | 3,4-diCl—Ph | HO—(CH₂)₂—O—(CH₂)₂—O—N(Me)—CO—CH₂ |
| 2-555 | 3,4-diCl—Ph | (Me)₂N—(CH₂)₂—N(Me)—CO—CH₂ |
| 2-556 | 3,4-diCl—Ph | (Me)₂N—(CH₂)₃—N(Me)—CO—CH₂ |
| 2-557 | 3,4-diCl—Ph | (Me)₂N—(CH₂)₄—N(Me)—CO—CH₂ |
| 2-558 | 3,4-diCl—Ph | (Me)₂N—(CH₂)₅—N(Me)—CO—CH₂ |
| 2-559 | 3,4-diCl—Ph | (Me)₂N—(CH₂)₆—N(Me)—CO—CH₂ |
| 2-560 | 3,4-diCl—Ph | (Me)₂N—(CH₂)₂—O—(CH₂)₂—N(Me)—CO—CH₂ |
| 2-561 | 3,4-diCl—Ph | AcNH—(CH₂)₂—N(Me)—CO—CH₂ |
| 2-562 | 3,4-diCl—Ph | AcNH—(CH₂)₃—N(Me)—CO—CH₂ |
| 2-563 | 3,4-diCl—Ph | AcNH—(CH₂)₄—N(Me)—CO—CH₂ |
| 2-564 | 3,4-diCl—Ph | AcNH—(CH₂)₅—N(Me)—CO—CH₂ |
| 2-565 | 3,4-diCl—Ph | AcNH—(CH₂)₆—N(Me)—CO—CH₂ |
| 2-566 | 3,4-diCl—Ph | AcNH—(CH₂)₂—O—(CH₂)₂—N(Me)—CO—CH₂ |
| 2-567 | 3,4-diCl—Ph | Me—SO₂NH—(CH₂)₂—N(Me)—CO—CH₂ |
| 2-568 | 3,4-diCl—Ph | Me—SO₂NH—(CH₂)₃—N(Me)—CO—CH₂ |
| 2-569 | 3,4-diCl—Ph | Me—SO₂NH—(CH₂)₄—N(Me)—CO—CH₂ |
| 2-570 | 3,4-diCl—Ph | Me—SO₂NH—(CH₂)₅—N(Me)—CO—CH₂ |
| 2-571 | 3,4-diCl—Ph | Me—SO₂NH—(CH₂)₆—N(Me)—CO—CH₂ |
| 2-572 | 3,4-diCl—Ph | Me—SO₂NH—(CH₂)₂—O—(CH₂)₂—N(Me)—CO—CH₂ |
| 2-573 | 3,4-diCl—Ph | 2-(HO—(CH₂)₂)—Pyrr—CO—CH₂ |
| 2-574 | 3,4-diCl—Ph | 2-(HO—(CH₂)₃)—Pyrr—CO—CH₂ |
| 2-575 | 3,4-diCl—Ph | 2-(HO—(CH₂)₄)—Pyrr—CO—CH₂ |
| 2-576 | 3,4-diCl—Ph | 2-(HO—CO—CH₂)—Pyrr—CO—CH₂ |
| 2-577 | 3,4-diCl—Ph | 2-(HO—CO—(CH₂)₂)—Pyrr—CO—CH₂ |
| 2-578 | 3,4-diCl—Ph | 2-(HO—CO—(CH₂)₃)—Pyrr—CO—CH₂ |
| 2-579 | 3,4-diCl—Ph | 4-Oxo—Pip—CO—CH₂ |
| 2-580 | 3,4-diCl—Ph | 4-HO—Pip—CO—CH₂ |
| 2-581 | 3,4-diCl—Ph | 4-(HO—CH₂)—Pip—CO—CH₂ |
| 2-582 | 3,4-diCl—Ph | 4-(HO—(CH₂)₂)—Pip—CO—CH₂ |
| 2-583 | 3,4-diCl—Ph | 4-(HO—(CH₂)₃)—Pip—CO—CH₂ |
| 2-584 | 3,4-diCl—Ph | 4-(HO—(CH₂)₄)—Pip—CO—CH₂ |
| 2-585 | 3,4-diCl—Ph | 4-(HO—CH₂—O)—Pip—CO—CH₂ |
| 2-586 | 3,4-diCl—Ph | 4-(HO—(CH₂)₂—O)—Pip—CO—CH₂ |
| 2-587 | 3,4-diCl—Ph | 4-(HO—(CH₂)₃—O)—Pip—CO—CH₂ |
| 2-588 | 3,4-diCl—Ph | 4-H₂N—Pip—CO—CH₂ |
| 2-589 | 3,4-diCl—Ph | 4-(AcNH)—Pip—CO—CH₂ |
| 2-590 | 3,4-diCl—Ph | 4-(HO—CH₂—CONH)—Pip—CO—CH₂ |
| 2-591 | 3,4-diCl—Ph | 4-(HO—(CH₂)₂—O—CH₂)—Pip—CO—CH₂ |
| 2-592 | 3,4-diCl—Ph | 4-(HO—CO)—Pip—CO—CH₂ |
| 2-593 | 3,4-diCl—Ph | 4-(HO—CO—CH₂)—Pip—CO—CH₂ |
| 2-594 | 3,4-diCl—Ph | 4-(HO—CO—(CH₂)₂)—Pip—CO—CH₂ |
| 2-595 | 3,4-diCl—Ph | 4-(HO—CO—(CH₂)₃)—Pip—CO—CH₂ |
| 2-596 | 3,4-diCl—Ph | 4-(HO—CO—(CH₂)₄)—Pip—CO—CH₂ |
| 2-597 | 3,4-diCl—Ph | 4-(H₂N—CO)—Pip—CO—CH₂ |
| 2-598 | 3,4-diCl—Ph | 4-(H₂N—CO—CH₂)—Pip—CO—CH₂ |
| 2-599 | 3,4-diCl—Ph | 4-(H₂N—CO—(CH₂)₂)—Pip—CO—CH₂ |
| 2-600 | 3,4-diCl—Ph | 4-(H₂N—CO—(CH₂)₃)—Pip—CO—CH₂ |
| 2-601 | 3,4-diCl—Ph | 4-(H₂N—CO—(CH₂)₄)—Pip—CO—CH₂ |
| 2-602 | 3,4-diCl—Ph | 4-(HO—N(Me)—CO)—Pip—CO—CH₂ |

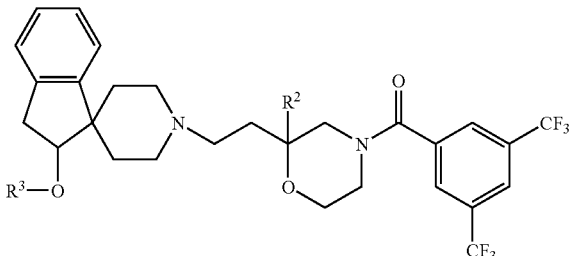

(I-2)

[Compound List 2]

| Compound No. | R² | R³ |
|---|---|---|
| 2-603 | 3,4-diCl—Ph | 4-(HO—N(Me)—CO—CH₂)—Pip—CO—CH₂ |
| 2-604 | 3,4-diCl—Ph | 4-(HO—N(Me)—CO—(CH₂)₂)—Pip—CO—CH₂ |
| 2-605 | 3,4-diCl—Ph | 4-(HO—N(Me)—CO—(CH₂)₃)—Pip—CO—CH₂ |
| 2-606 | 3,4-diCl—Ph | 4-(HO—N(Me)—CO—(CH₂)₄)—Pip—CO—CH₂ |
| 2-607 | 3,4-diCl—Ph | 4-(MeO—N(Me)—CO)—Pip—CO—CH₂ |
| 2-608 | 3,4-diCl—Ph | 4-(MeO—N(Me)—CO—CH₂)—Pip—CO—CH₂ |
| 2-609 | 3,4-diCl—Ph | 4-(MeO—N(Me)—CO—(CH₂)₂)—Pip—CO—CH₂ |
| 2-610 | 3,4-diCl—Ph | 4-(MeO—N(Me)—CO—(CH₂)₃)—Pip—CO—CH₂ |
| 2-611 | 3,4-diCl—Ph | 4-(MeO—N(Me)—CO—(CH₂)₄)—Pip—CO—CH₂ |
| 2-612 | 3,4-diCl—Ph | 3-Oxo—Pipr—CO—CH₂ |
| 2-613 | 3,4-diCl—Ph | 4-Ac—Pipr—CO—CH₂ |
| 2-614 | 3,4-diCl—Ph | 4-(HO—(CH₂)₂)—Pipr—CO—CH₂ |
| 2-615 | 3,4-diF—Ph | 3-CHO—(CH₂)₂)—Pyrr—CO—CH₂ |
| 2-616 | 3,4-diF—Ph | 3-(HO—(CH₂)₃)—Pyrr—CO—CH₂ |
| 2-617 | 3,4-diF—Ph | 3-(HO—(CH₂)₄)—Pyrr—CO—CH₂ |
| 2-618 | 3,4-diF—Ph | 3-(HO—CO—CH₂)—Pyrr—CO—CH₂ |
| 2-619 | 3,4-diF—Ph | 3-(HO—CO—(CH₂)₂)—Pyrr—CO—CH₂ |
| 2-620 | 3,4-diF—Ph | 3-(HO—CO—(CH₂)₃)—Pyrr—CO—CH₂ |
| 2-621 | 3,4-diF—Ph | 3-(HO—CH₂)—Pip—CO—CH₂ |
| 2-622 | 3,4-diF—Ph | 3-(HO—(CH₂)₂)—Pip—CO—CH₂ |
| 2-623 | 3,4-diF—Ph | 3-(HO—(CH₂)₃)—Pip—CO—CH₂ |
| 2-624 | 3,4-diF—Ph | 3-(HO—(CH₂)₄)—Pip—CO—CH₂ |
| 2-625 | 3,4-diF—Ph | 3-(HO—CH₂—O)—Pip—CO—CH₂ |
| 2-626 | 3,4-diF—Ph | 3-(HO—(CH₂)₂—O)—Pip—CO—CH₂ |
| 2-627 | 3,4-diF—Ph | 3-(HO—(CH₂)₃—O)—Pip—CO—CH₂ |
| 2-628 | 3,4-diF—Ph | 3-(HO—CH₂—CONH)—Pip—CO—CH₂ |
| 2-629 | 3,4-diF—Ph | 3-(HO—(CH₂)₂—O—CH₂)—Pip—CO—CH₂ |
| 2-630 | 3,4-diF—Ph | 3-(HO—N(Me)—CO)—Pip—CO—CH₂ |
| 2-631 | 3,4-diF—Ph | 3-(HO—N(Me)—CO—CH₂)—Pip—CO—CH₂ |
| 2-632 | 3,4-diF—Ph | 3-(HO—N(Me)—CO—(CH₂)₂)—Pip—CO—CH₂ |
| 2-633 | 3,4-diF—Ph | 3-(HO—N(Me)—CO—(CH₂)₃)—Pip—CO—CH₂ |
| 2-634 | 3,4-diF—Ph | 3-(HO—N(Me)—CO—(CH₂)₄)—Pip—CO—CH₂ |
| 2-635 | 3,4-diF—Ph | 3-(MeO—N(Me)—CO)—Pip—CO—CH₂ |
| 2-636 | 3,4-diF—Ph | 3-(MeO—N(Me)—CO—CH₂)—Pip—CO—CH₂ |
| 2-637 | 3,4-diF—Ph | 3-(MeO—N(Me)—CO—(CH₂)₂)—Pip—CO—CH₂ |
| 2-638 | 3,4-diF—Ph | 3-(MeO—N(Me)—CO—(CH₂)₃)—Pip—CO—CH₂ |
| 2-639 | 3,4-diF—Ph | 3-(MeO—N(Me)—CO—(CH₂)₄)—Pip—CO—CH₂ |
| 2-640 | 3,4-diF—Ph | 3-(HO—(CH₂)₂)—Pipr—CO—CH₂ |
| 2-641 | 3,4-diCl—Ph | 3-(HO—(CH₂)₂)—Pyrr—CO—CH₂ |
| 2-642 | 3,4-diCl—Ph | 3-(HO—(CH₂)₃)—Pyrr—CO—CH₂ |
| 2-643 | 3,4-diCl—Ph | 3-(HO—(CH₂)₄)—Pyrr—CO—CH₂ |
| 2-644 | 3,4-diCl—Ph | 3-(HO—CO—CH₂)—Pyrr—CO—CH₂ |
| 2-645 | 3,4-diCl—Ph | 3-(HO—CO—(CH₂)₂)—Pyrr—CO—CH₂ |
| 2-646 | 3,4-diCl—Ph | 3-(HO—CO—(CH₂)₃)—Pyrr—CO—CH₂ |
| 2-647 | 3,4-diCl—Ph | 3-(HO—CH₂)—Pip—CO—CH₂ |
| 2-648 | 3,4-diCl—Ph | 3-(HO—(CH₂)₂)—Pip—CO—CH₂ |
| 2-649 | 3,4-diCl—Ph | 3-(HO—(CH₂)₃)—Pip—CO—CH₂ |
| 2-650 | 3,4-diCl—Ph | 3-(HO—(CH₂)₄)—Pip—CO—CH₂ |
| 2-651 | 3,4-diCl—Ph | 3-(HO—CH₂—O)—Pip—CO—CH₂ |
| 2-652 | 3,4-diCl—Ph | 3-(HO—(CH₂)₂—O)—Pip—CO—CH₂ |
| 2-653 | 3,4-diCl—Ph | 3-(HO—(CH₂)₃—O)—Pip—CO—CH₂ |
| 2-654 | 3,4-diCl—Ph | 3-(HO—CH₂—CONH)—Pip—CO—CH₂ |
| 2-655 | 3,4-diCl—Ph | 3-(HO—(CH₂)₂—O—CH₂)—Pip—CO—CH₂ |
| 2-656 | 3,4-diCl—Ph | 3-(HO—N(Me)—do)—Pip—CO—CH₂ |
| 2-657 | 3,4-diCl—Ph | 3-(HO—N(Me)—CO—CH₂)—Pip—CO—CH₂ |
| 2-658 | 3,4-diCl—Ph | 3-(HO—N(Me)—CO—(CH₂)₂)—Pip—CO—CH₂ |
| 2-659 | 3,4-diCl—Ph | 3-(HO—N(Me)—CO—(CH₂)₃)—Pip—CO—CH₂ |
| 2-660 | 3,4-diCl—Ph | 3-(HO—N(Me)—CO—(CH₂)₄)—Pip—CO—CH₂ |
| 2-661 | 3,4-diCl—Ph | 3-(MeO—N(Me)—CO)—Pip—CO—CH₂ |
| 2-662 | 3,4-diCl—Ph | 3-(MeO—N(Me)—CO—CH₂)—Pip—CO—CH₂ |

-continued

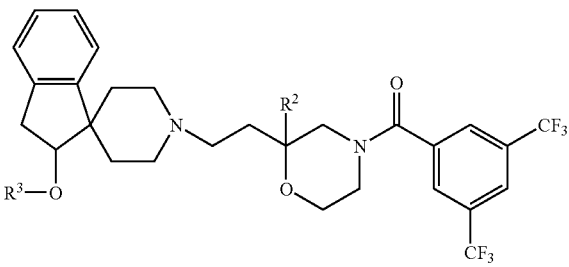

(I-2)

[Compound List 2]

| Compound No. | R² | R³ |
|---|---|---|
| 2-663 | 3,4-diCl—Ph | 3-(MeO—N(Me)—CO—(CH₂)₂)—Pip—CO—CH₂ |
| 2-664 | 3,4-diCl—Ph | 3-(MeO—N(Me)—CO—(CH₂)₃)—Pip—CO—CH₂ |
| 2-665 | 3,4-diCl—Ph | 3-(MeO—N(Me)—CO—(CH₂)₄)—Pip—CO—CH₂ |
| 2-666 | 3,4-diCl—Ph | 3-(HO—(CH₂)₂)—Pipr—CO—CH₂ |

MODE FOR CARRYING OUT THE INVENTION

A Compound (I) of the present invention can be produced according to the methods described below.

Among the Compounds (I), a compound wherein $R^3$ is —CO—$R^4$ can be produced according to the following Method A.

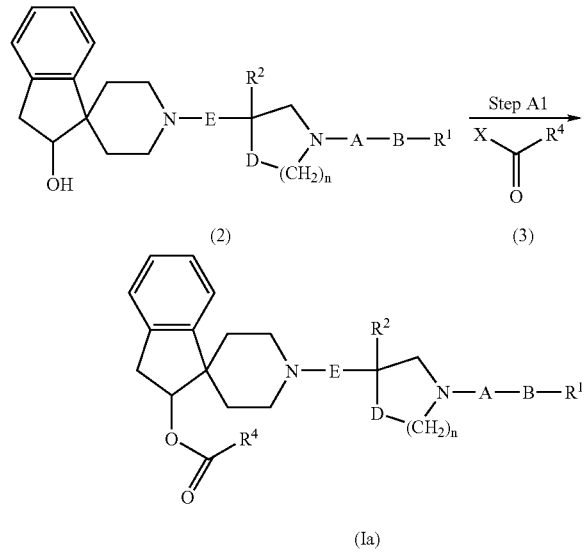

<Method A>

In the above formulae, A, B, D, E, $R^1$, $R^2$, $R^4$ and n are the same as previously defined, and X represents a hydroxyl group or a leaving group.

There are no particular limitations on the "leaving group" in the definition of X provided that it is a leaving group that is used in the field of organic synthesis chemistry, and is preferably a halogen atom such as a chlorine atom, bromine atom or iodine atom; a lower alkane sulfonyl group such as methane sulfonyl or ethane sulfonyl; a halogeno lower alkane sulfonyl group such as trifluoromethane sulfonyl or pentafluoroethane sulfonyl; or an aryl sulfonyl group such as benzene sulfonyl, p-toluene sulfonyl or p-nitrobenzene sulfonyl, more preferably a halogen atom, and particularly preferably a chlorine atom or a bromine atom.

(Step A1)

Step A1 is a step wherein a compound having the general formula (Ia) is produced by condensing Compound (2) and Compound (3) in an inert solvent in the presence or absence of a condensing agent and in the presence or absence of a base.

There is no particular limitation on the inert solvent to be used provided that it is inert in the present reaction, examples of which include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorbne or cyclohexanone; nitriles such as acetonitrile or isobutyl nitrile; amides such as formamide, N,N-dimethylformamide, N,N-dimethylacetamide or hexamethylphosphoric triamide; sulfoxides such as dimethyl sulfoxide; and sulfones such as sulfolan, preferably halogenated hydrocarbons, and most preferably methylene chloride.

Examples of "condensing agents" to be used include:

(1) combinations of phosphoric acid esters such as diethyl phosphoryl cyanide or diphenyl phosphoryl azide and the bases indicated below;

(2) carbodiimides such as 1,3-dicyclohexylcarbodiimide, 1,3-diisopropylcarbodiimide or 1-ethyl-3-(3-dimethylaminopropyl)carbodiimide; combinations of the aforementioned carbodiimides and the bases indicated below; or combinations of the aforementioned carbodiimides and N-hydroxy compounds such as N-hydroxysuccinimide, 1-hydroxybenzotriazole or N-hydroxy-5-norbornene-2,3-dicarboxyimide;

(3) combinations of disulfides such as 2,2'-dipyridyl disulfide or 2,2'-dibenzothiazolyl disulfide and phosphines such as triphenyl phosphine or tributyl phosphine;

(4) carbonates such as N,N'-disuccinimidyl carbonate, di-2-pyridyl carbonate or S,S'-bis(1-phenyl-1H-tetrazol-5-yl) dithiocarbonate;
(5) phosphinic acid chlorides such as N,N'-bis(2-oxo-3-oxazolidinyl)-phosphinic chloride;
(6) oxalates such as N,N'-disuccinimidyl oxalate, N,N'-diphthalimido oxalate, N,N'-bis(5-norbornene-2,3-dicarboxyimidyl)oxalate, 1,1'-bis(benzotriazolyl)oxalate, 1,1'-bis(6-chlorobenzotriazolyl)oxalate or 1,1'-bis(6-trifluoromethylbenzotriazolyl)oxalate;
(7) combinations of the aforementioned phosphines and an azodicarboxylic acid ester or azodicarboxyamide such as diethyl diazocarboxylate or 1,1'-(azodicarbonyl)dipiperidine; or, a combination of the aforementioned phosphines and the bases indicated below;
(8) N-lower alkyl-5-arylisoxazolium-3-sulfonates such as N-ethyl-5-phenylisoxazolium-3'-sulfonate;
(9) diheteroaryl diselenides such as di-2-pyridyl selenide;
(10) aryl sulfonyl triazolides such as p-nitrobenzene sulfonyl triazolide;
(11) 2-halo-1-lower alkyl pyridinium halides such as 2-chloro-1-methyl pyridinium iodide;
(12) imidazoles such as 1,1'-oxalyl diimidazole or N,N'-carbonyl diimidazole;
(13) 3-lower alkyl-2-halogen-benzothiazolium fluoroborates such as 3-ethyl-2-chloro-benzothiazolium fluoroborate;
(14) 3-lower alkyl-benzothiazole-2-selones such as 3-methyl-benzothiazole-2-selone;
(15) phosphates such as phenyldichlorophosphate or polyphosphate esters;
(16) halogenosulfonyl isocyanates such as chlorosulfonyl isocyanate;
(17) halogenosilanes such as trimethylsilyl chloride or triethylsilyl chloride;
(18) combinations of lower alkane sulfonyl halides such as methane sulfonyl chloride and the bases indicated below; and,
(19) N,N,N',N'-tetra lower alkyl halogeno formamidium chlorides such as N,N,N',N'-tetramethylchloroformamidium chloride, and (5) described above is preferred.

There are no particular limitations on the base provided that it is a base that is used in ordinary alkylation reactions, examples of which include alkali metal carbonates such as lithium carbonate, sodium carbonate or potassium carbonate; alkaline metal bicarbonates such as lithium hydrogencarbonate, sodium hydrogencarbonate or potassium hydrogencarbonate; alkaline metal hydrides such as lithium hydride, sodium hydride or potassium hydride; alkaline metal hydroxides such as lithium hydroxide, sodium hydroxide or potassium hydroxide; alkaline metal alkoxides such as lithium methoxide, sodium methoxide, sodium ethoxide or potassium t-butoxide; and, organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]-7-undecene (DBU), preferably organic amines, and most preferably triethylamine.

While the reaction temperature varies depending on the types of starting materials, condensing agent, base, solvent and so forth, it is normally from –20° C. to 200° C. (preferably from 0° C. to 120° C.).

While the reaction time varies depending on the starting materials, condensing agent, base, solvent, reaction temperature and so forth, it is normally from 5 minutes to 48 hours (preferably from 15 minutes to 24 hours).

Furthermore, in the case of using Compound (3) in which X is a hydroxyl group, the reaction is preferably carried out in the presence of a condensing agent. In addition, in the present step, an acid anhydride (such as a compound having the general formula: $R^4$—CO—O—CO—$R^4$ or an acid anhydride of Compound (3) and an organic acid such as acetic acid) can also be used instead of Compound (3).

Following completion of the reaction, the desired compound is collected from the reaction mixture in accordance with ordinary methods. For example, after suitably neutralizing the reaction mixture or removing insoluble matter by filtration in cases where insoluble matter is present, an immiscible organic solvent such as water or ethyl acetate is added, and after washing with water and so forth, the organic layer containing the desired compound is separated, and after drying with anhydrous magnesium sulfate or anhydrous sodium sulfate, the desired compound is obtained by distilling off the solvent. The resulting desired compound is purified in accordance with ordinary methods if necessary. For example, methods such as recrystallization, reprecipitation or methods used to separate and purify ordinary organic compounds can be suitably combined to separate and purify by eluting with a suitable eluent, examples of which include adsorption column chromatography using a carrier such as silica gel, alumina or magnesium-silica gel-based Florisil; methods using a synthetic adsorbent such as partition column chromatography using a carrier such as Sephadex LH-20 (Pharmacia), Amberlite XAD-11 (Rohm & Haas) or Diaion HP-20 (Mitsubishi Chemical); and methods using ion exchange chromatography or forward/reverse-phase column chromatography using silica gel or alkylated silica gel (and preferably high-performance liquid chromatography).

Among the Compounds (I), a compound in which $R^3$ is —CO—O—$R^4$ can be produced according to the following Method B.

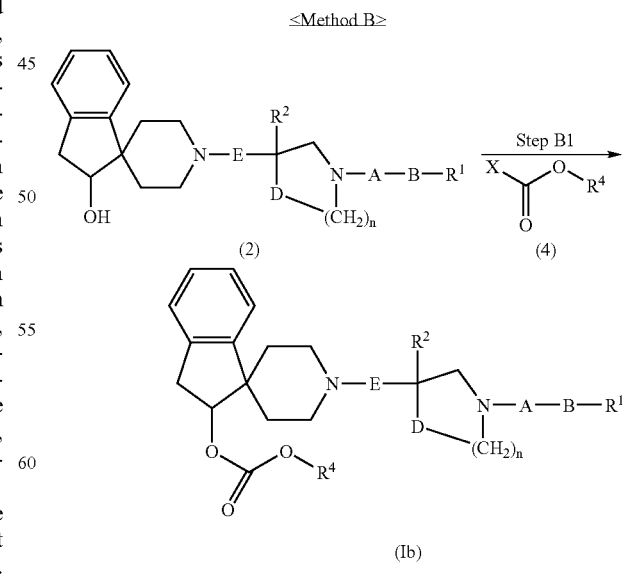

In the above formulae, A, B, D, E, $R^1$, $R^2$, $R^4$, X and n are the same as previously defined.

(Step B1)

Step B1 is a step wherein a compound having the general formula (Ib) is produced by condensing Compound (2) and Compound (4) in an inert solvent in the presence or absence of a condensing agent and in the presence of a base.

In the present step, the same inert solvent, condensing agent and base described in "Step A1" can be used. (However, the base used in the present step is most preferably diisopropylethylamine.)

While the reaction temperature varies depending on the types of starting materials, condensing agent, base, solvent and so forth, it is normally from −20° C. to 200° C. (preferably from 0° C. to 120° C.).

While the reaction time varies depending on the starting materials, condensing agent, base, solvent, reaction temperature and so forth, it is normally from 5 minutes to 48 hours (and preferably from 15 minutes to 24 hours).

Following to the completion of the reaction, the desired compound can be purified by the same methods as those described in "Step A1" if necessary.

Among the Compounds (I), a compound in which $R^3$ is —CO—NH—$R^4$ or —CO—NH$_2$ in Compound (I) can be produced according to the following Method C.

While the reaction time varies depending on the starting materials, base, solvent, reaction temperature and so forth, it is normally from 5 minutes to 48 hours (and preferably from 15 minutes to 24 hours).

In the present step, a compound in which $R^3$ is —CO—NH$_2$ can be produced if isocyanic acid is used instead of Compound (5).

Following completion of the reaction, the desired compound can be purified by the same methods as those described in "Step A1" as necessary.

Among the Compounds (I), a compound in which $R^3$ is —CO—CH$^2$—N($R^a$)$R^b$ can be produced according to the following Method D.

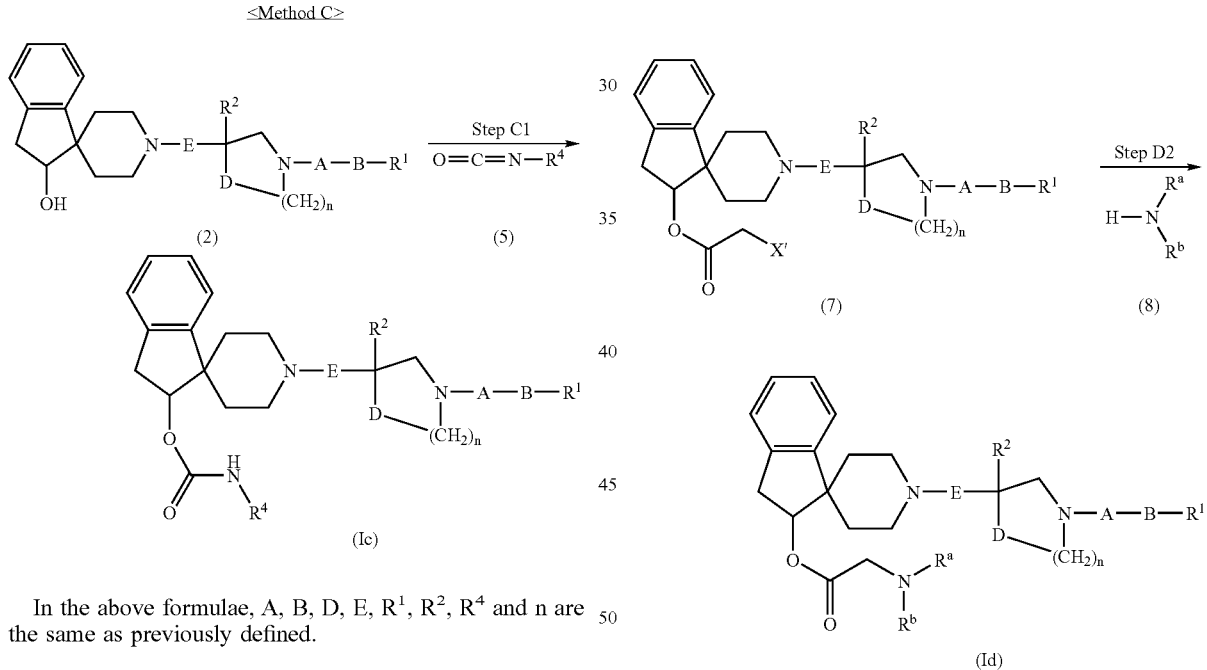

In the above formulae, A, B, D, E, $R^1$, $R^2$, $R^4$ and n are the same as previously defined.

(Step C1)

Step C1 is a step wherein a compound having the general formula (Ic) is produced by reacting Compound (2) and Compound (5) in an inert solvent in the presence or absence of a base.

In the present step, the same inert solvents and bases described in "Step A1" can be used. (However, in the present step, preferably an aromatic hydrocarbon, halogenated hydrocarbon or nitrile (more preferably an aromatic hydrocarbon) is used as solvent, and preferably an organic amine (more preferably diisopropylethylamine) is used as a base).

While the reaction temperature varies depending on the types of starting materials, base, solvent and so forth, it is normally from −20° C. to 200° C. (preferably from 0° C. to 120° C.)

In the above formulae, A, B, D, E, $R^1$, $R^2$, $R^a$, $R^b$, X and n are the same as previously defined, and X' represents a leaving group.

The same groups as the leaving groups in the definition of X can be used for the "leaving group" in the definition of X', and is preferably a halogen atom, particularly preferably a chlorine atom or a bromine atom, and most preferably a bromine atom.

(Step D1)

Step D1 is a step wherein Compound (7) is produced by reacting Compound (2) and Compound (6) in an inert solvent in the presence of a base.

In the present step, the same inert solvents and bases described in "Step A1" can be used. (However, the base used in the present step is most preferably diisopropylethylamine).

While the reaction temperature varies depending on the types of starting materials, base, solvent and so forth, it is normally from −20° C. to 200° C. (and preferably from 0 to 120° C.).

While the reaction time varies depending on the starting materials, base, solvent, reaction temperature and so forth, it is normally from 5 minutes to 48 hours (and preferably from 15 minutes to 24 hours).

Following completion of the reaction, the desired compound can be purified by the same methods as those described in "Step A1" if necessary.

(Step D2)

Step D2 is a step wherein a compound having the general formula (Id) is produced by reacting Compound (7) and Compound (8) in an inert solvent in the presence or absence of a base.

In the present step, the same inert solvents and bases described in "Step A1" can be used. (However, in the present step, preferably a nitrile (and particularly preferably acetonitrile) is used as the solvent.) While the reaction temperature varies depending on the types of starting materials, base, solvent and so forth, it is normally from −20° C. to 200° C. (and preferably from 0 to 120° C.).

While the reaction time varies depending on the starting materials, base, solvent, reaction temperature and so forth, it is normally from 5 minutes to 48 hours (and preferably from 15 minutes to 24 hours).

Following completion of the reaction, the desired compound can be purified by the same methods as those described in "Step A1" if necessary.

Among the Compounds (I), compound in which $R^3$ is $-(CH^2)_m-CO-R^5$ can be produced according to the following Method E.

<Method E>

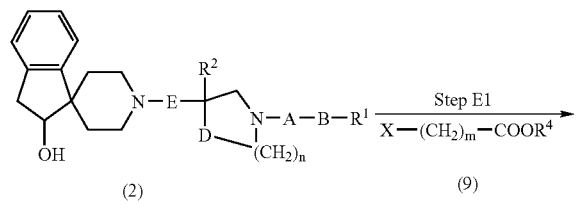

(2)

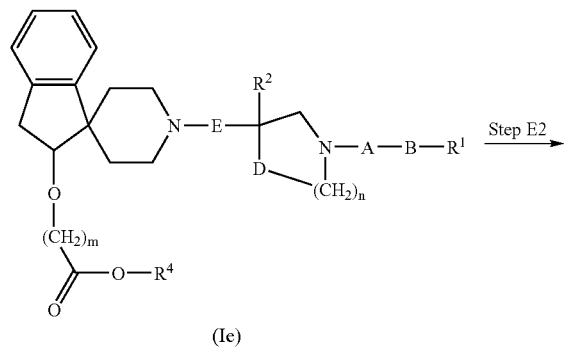

(Ie)

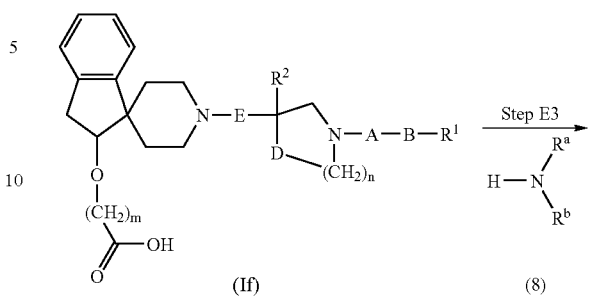

(If)            (8)

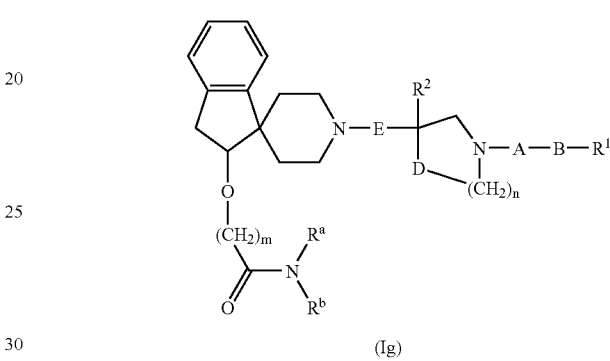

(Ig)

In the above formulae, A, B, D, E, $R^1$, $R^2$, $R^4$, $R^a$, $R^b$, X, m and n are the same as previously defined.

(Step E1)

Step E1 is a step wherein a compound having the general formula (Ie) is produced by reacting Compound (2) and Compound (9) in an inert solvent in the presence of a base.

There is no particular limitation on the inert solvent to be used provided that it is inert in the present reaction, examples of which include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitriles such as acetonitrile or isobutyl nitrile; amides such as formamide, N,N-dimethylformamide, N,N-dimethylacetamide or hexamethylphosphoric triamide; sulfoxides such as dimethyl sulfoxide; and sulfones such as sulfolan; or mixed solvents thereof, preferably aliphatic hydrocarbons, aromatic hydrocarbons, ethers or mixed solvents thereof, and more preferably aromatic hydrocarbons, ethers or mixed solvents thereof.

There is no particular limitation on the base provided that it is a base that is used in ordinary alkylation reactions, examples of which include alkali metal carbonates such as lithium carbonate, sodium carbonate or potassium carbonate; alkali metal bicarbonates such as lithium hydrogencarbonate, sodium hydrogencarbonate or potassium hydrogencarbonate; alkali metal hydrides such as lithium hydride, sodium hydride or potassium hydride; alkaline metal hydroxides such as lithium hydroxide, sodium hydroxide or potassium hydroxide; alkali metal alkoxides such as lithium methoxide, sodium methoxide, sodium ethoxide or potassium t-butoxide; organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]-7-undecene (DBU); and, amides such as potassium bis(trimethylsilyl)amide, preferably amides, and most preferably potassium bis(trimethylsilyl)amide.

While the reaction temperature varies depending on the types of starting materials, base, solvent and so forth, it is normally from −20° C. to 200° C. (preferably from 0° C. to 120° C.).

While the reaction time varies depending on the starting materials, base, solvent, reaction temperature and so forth, it is normally from 5 minutes to 48 hours (and preferably from 15 minutes to 24 hours).

Following completion of the reaction, the desired compound can be purified by the same methods as those described in "Step A1" if necessary.

(Step E2)

Step E2 is a step wherein a compound having the general formula (If) is produced by hydrolyzing a compound having the general formula (Ie) in an inert solvent in the presence of an acid or a base.

There is no particular limitation on the inert solvent to be used provided that it is inert in the present reaction, examples of which include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitriles such as acetonitrile or isobutyl nitrile; amides such as formamide, N,N-dimethylformamide, N,N-dimethylacetamide or hexamethylphosphoric triamide; sulfoxides such as dimethyl sulfoxide; or sulfones such as sulfolan; alcohols such as methanol, ethanol, propanol, 2-propanol, butanol, ethylene glycol or diethylene glycol; water; and, mixed solvents of water and the aforementioned organic solvents, preferably halogenated hydrocarbons, and most preferably methylene chloride.

Examples of acids to be used include inorganic acids such as hydrochloric acid, sulfuric acid, phosphoric acid or hydrobromic acid; sulfonic acids such as methanesulfonic acid or ethanesulfonic acid; and carboxylic acids such as acetic acid, propionic acid or trifluoroacetic acid, preferably it is hydrochloric acid, sulfuric acid or trifluoroacetic acid, and particularly preferably trifluoroacetic acid.

Examples of bases to be used include alkali metal hydroxides such as sodium hydroxide, potassium hydroxide, barium hydroxide or lithium hydroxide, and it is preferably sodium hydroxide or potassium hydroxide.

While the reaction temperature varies depending on the types of starting material, acid, base, solvent and so forth, it is normally from −20° C. to 200° C. (and preferably from 0° C. to 120° C.)

While the reaction time varies depending on the starting material, acid, base, solvent, reaction temperature and so forth, it is normally from 5 minutes to 48 hours (and preferably from 15 minutes to 24 hours).

Following completion of the reaction, the desired compound can be purified by the same methods as those described in "Step A1" if necessary.

(Step E3)

Step E3 is a step wherein a compound having the general formula (Ig) is produced by reacting a compound having the general formula (If) with Compound (8) in an inert solvent, in the presence or absence of a condensing agent, and in the presence or absence of a base.

There is no particular limitation on the inert solvent to be used provided that it is inert in the present reaction, examples of which include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitriles such as acetonitrile or isobutyl nitrile; amides such as formamide, N,N-dimethylformamide, N,N-dimethylacetamide or hexamethylphosphoric triamide; sulfoxides such as dimethyl sulfoxide; sulfones such as sulfolan; and mixed solvents thereof, preferably halogenated hydrocarbons, amides or mixed solvents thereof, and it is most preferably methylene chloride, N,N-dimethylformamide or mixed solvents thereof.

In the present step, the same condensing agents and bases as those described in "Step A1" can be used.

While the reaction temperature varies depending on the types of starting materials, condensing agent, base, solvent and so forth, it is normally from −20° C. to 200° C. (preferably from 0° C. to 120° C.).

While the reaction time varies depending on the starting materials, condensing agent, base, solvent, reaction temperature and so forth, it is normally from 5 minutes to 48 hours (preferably from 15 minutes to 24 hours).

Following completion of the reaction, the desired compound can be purified by the same methods as those described in "Step A1" if necessary.

Furthermore, the present step can also be carried out by, for example, reacting Compound (If) with a halogenating agent (such as thionyl chloride or oxalyl chloride) in the aforementioned solvents, and then reacting the resulting reactive derivative (acyl halide derivative) and Compound (8) in the aforementioned solvents.

Among the Compounds (I), a compound in which $R^3$ is $-(CH_2)_m-R^5$ and in which m is from 2 to 6 can be produced according to the following Method F.

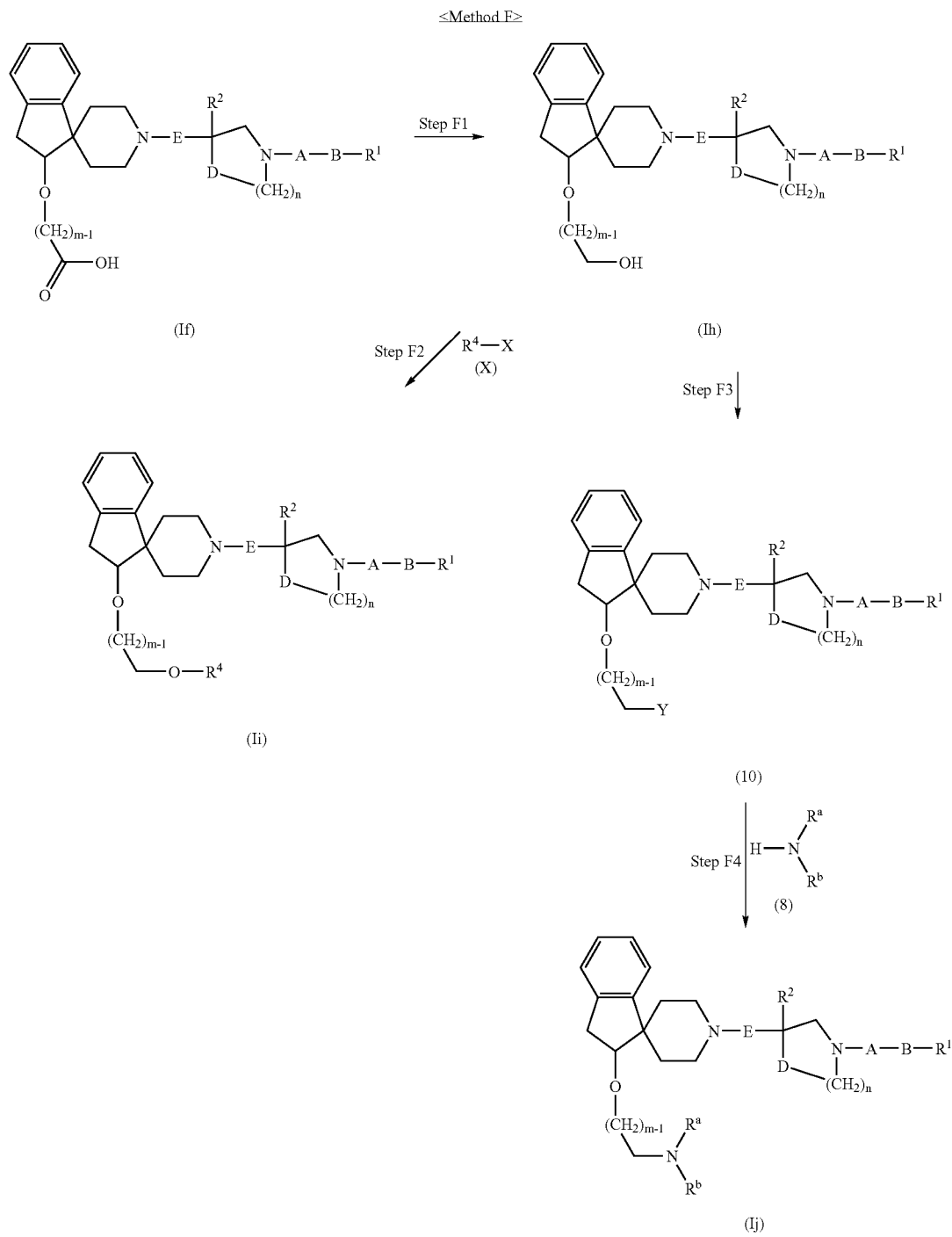

In the above formulae, A, B, D, E, $R^1$, $R^2$, $R^4$, $R^a$, $R^b$, X, m and n are the same as previously defined (however, m is an integer of 2 to 6 in the aforementioned reaction scheme), and Y represents a leaving group.

There is no particular limitation on the "leaving group" in the definition of Y provided that it is a leaving group that is used in the field of organic synthesis chemistry, and is preferably a halogen atom such as a chlorine atom, bromine atom or iodine atom; a lower alkane sulfonyloxy group such as methane sulfonyloxy or ethane sulfonyloxy; a halogeno lower alkane sulfonyloxy group such as trifluoromethane sulfonyloxy or pentafluoroethane sulfonyloxy; or an aryl sulfonyloxy group such as benzene sulfonyloxy, p-toluene sulfonyloxy or p-nitrobenzene sulfonyloxy, more preferably a halogen atom, lower alkane sulfonyloxy group or halogeno lower alkane sulfonyloxy group, even more preferably a chlorine atom, bromine atom, methane sulfonyloxy or trifluoromethane sulfonyloxy, and particularly preferably methane sulfonyloxy.

(Step F1)

Step F1 is a step wherein a compound having the general formula (Ih) is produced by reducing a compound having the general formula (If) in an inert solvent with using a reducing agent.

There is no particular limitation on the inert solvent to be used provided that it is inert in the present reaction, examples of which include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitriles such as acetonitrile or isobutyl nitrile; amides such as formamide, N,N-dimethylformamide, N,N-dimethylacetamide or hexamethylphosphoric triamide; sulfoxides such as dimethyl sulfoxide; and sulfones such as sulfolan, preferably aromatic hydrocarbons or ethers, still more preferably ethers, and particularly preferably diethyl ether or tetrahydrofuran.

Examples of reducing agents to be used include borane, diborane, borane-dimethyl sulfide complex and borane-tetrahydrofuran complex; alkali metal borohydrides such as sodium cyanoborohydride, sodium borohydride, zinc borohydride or lithium borohydride; and, aluminium hydride compounds such as lithium aluminium hydride or tri-tert-butyl aluminium hydride; preferably borane, borane-dimethyl sulfide complex or borane-tetrahydrofuran complex, and particularly preferably borane-tetrahydrofuran complex.

While the reaction temperature varies depending on the types of starting material, reducing agent, solvent and so forth, it is normally from −20° C. to 200° C. (preferably from 0° C. to 120° C.).

While the reaction time varies depending on the starting material, reducing agent, solvent, reaction temperature and so forth, it is normally from 5 minutes to 48 hours (and preferably from 15 minutes to 24 hours).

Following completion of the reaction, the desired compound can be purified by the same methods as those described in "Step A1" if necessary.

(Step F2)

Step F2 is a step wherein a compound having the general formula (Ii) is produced by reacting a compound having the general formula (Ih) with Compound (X) in an inert solvent, in the presence or absence of a condensing agent, and in the presence or absence of a base, and is carried out in the same manner as the aforementioned "Step A1".

Following completion of the reaction, the desired compound can be purified by the same methods as those described in "Step A1" if necessary.

(Step F3)

Step F3 is a step wherein Compound (10) is produced by reacting a compound having the general formula (Ih) with a halogenating agent (such as thionyl chloride or oxalyl chloride) or a sulfonylating agent (such as methane sulfonyl chloride, trifluoromethane sulfonyl chloride, benzene sulfonyl chloride or p-toluene sulfonyl chloride) in an inert solvent in the presence or absence of a base.

In the present step, the same inert solvent and base as those described in "Step A1" can be used.

While the reaction temperature varies depending on the types of the starting material, halogenating agent or sulfonylating agent, base, solvent and so forth, it is normally from −20° C. to 200° C. (and preferably from 0° C. to 120° C.).

While the reaction time varies depending on the starting material, halogenating agent or sulfonylating agent, base, solvent, reaction temperature and so forth, it is normally from 5 minutes to 48 hours (and preferably from 15 minutes to 24 hours).

Following completion of the reaction, the desired compound can be purified by the same methods as those described in "Step A1" as necessary.

(Step F4)

Step F4 is a step wherein a compound having the general formula (Ij) is produced by reacting Compound (10) with Compound (8) in an inert solvent in the presence of a base, and is carried out in the same manner as the aforementioned "Step D2". (However, in the present step, preferably an amide (particularly preferably N,N-dimethylacetamide) is used as the solvent, and preferably an alkali metal bicarbonate (particularly preferably sodium hydrogencarbonate) is used as the base.)

Following completion of the reaction, the desired compound can be purified by the same methods as those described in "Step A1" as necessary.

Among the Compounds (I), a compound in which $R^3$ is —CO—NH—CO—N($R^a$)$R^b$ can be produced according to the following Method G.

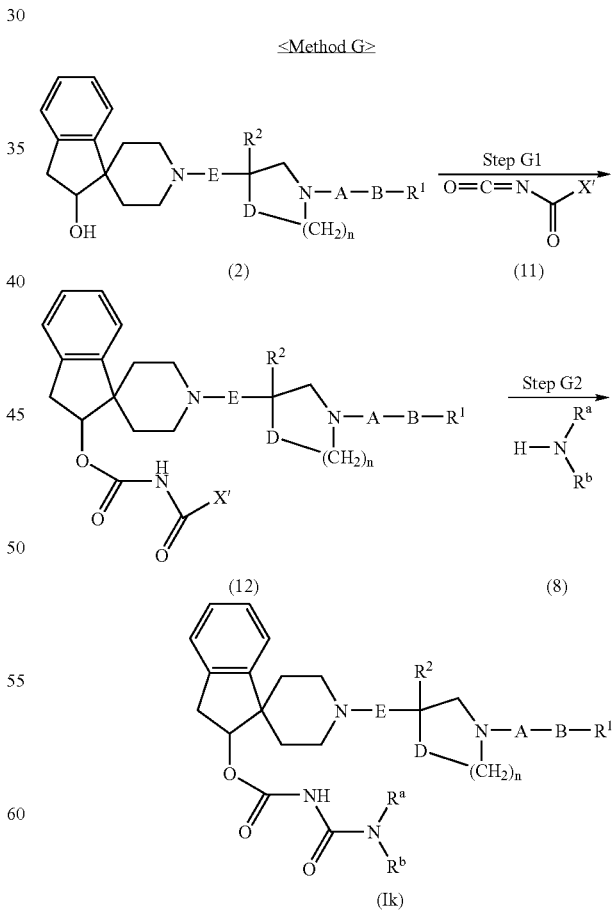

In the above formula, A, B, D, E, $R^1$, $R^2$, $R^a$, $R^b$, X' and n are the same as previously defined.

(Step G1)

Step G1 is a step wherein Compound (12) is produced by reacting Compound (2) with Compound (11) in an inert solvent in the presence or absence of a base, and is carried out in the same manner as the aforementioned "Step C1". (However, in the present step, preferably a halogenated hydrocarbon (particularly preferably methylene chloride) is used as the solvent.)

Following completion of the reaction, the desired compound can be purified by the same methods as those described in "Step A1" if necessary.

(Step G2)

Step G2 is a step wherein a compound having the general formula (Ik) is produced by reacting Compound (12) with Compound (8) in an inert solvent in the presence of a base, and is carried out in the same manner as the aforementioned "Step D2". (However, in the present step, preferably a halogenated hydrocarbon (particularly preferably methylene chloride) is used as the solvent.)

Following completion of the reaction, the desired compound can be purified by the same methods as those described in "Step A1" if necessary.

Among the Compounds (I), a compound in which $R^3$ is —CO—NH—SO$^2$—N(R$^a$)R$^b$ can be produced according to the following Method H.

(Step H2)

Step H2 is a step wherein a compound having the general formula (Im) is produced by reacting Compound (14) with Compound (8) in an inert solvent in the presence or absence of a base, and is carried out in the same manner as the aforementioned "Step D2". (However, in the present step, preferably a halogenated hydrocarbon (particularly preferably methylene chloride) is used as the solvent.)

Following completion of the reaction, the desired compound can be purified by the same methods as those described in "Step A1" if necessary.

Among the Compounds (I), a compound in which $R^3$ is —CO—NH—CO—(CH$^2$)$_m$—N(R$^a$)R$^b$ can be produced according to the following Method I.

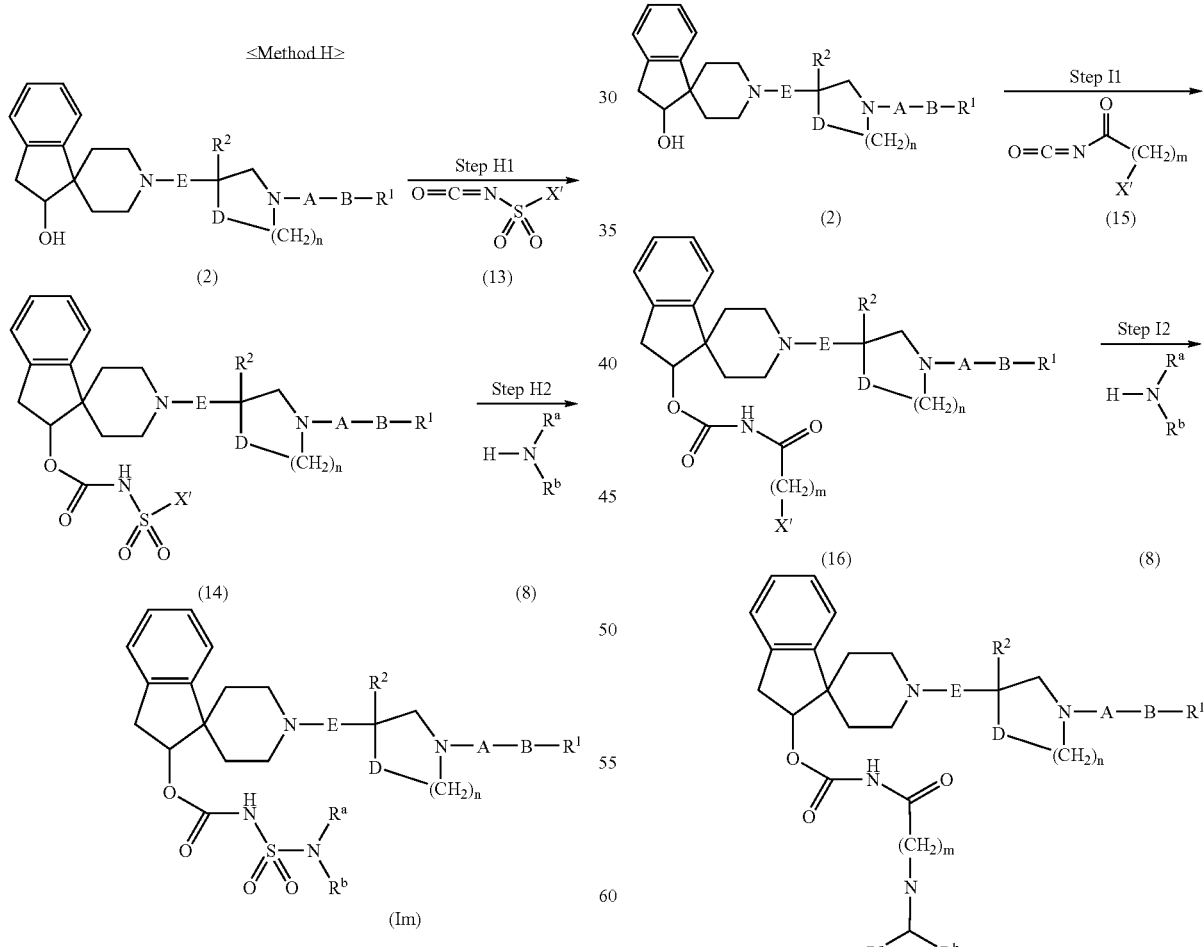

In the above formula, A, B, D, E, R$^1$, R$^2$, R$^a$, R$^b$, X' and n are the same as previously defined.

(Step H1)

Step H1 is a step wherein Compound (14) is produced by reacting Compound (2) with Compound (13) in an inert solvent In the above formula, A, B, D, E, R$^1$, R$^2$, R$^a$, R$^b$, X', m and n are the same as previously defined.

(Step I1)

Step I1 is a step wherein Compound (16) is produced by reacting Compound (2) with Compound (15) in an inert solvent in the presence or absence of a base, and is carried out in the same manner as the aforementioned "Step C1". (However, in the present step, preferably a halogenated hydrocarbon (particularly preferably methylene chloride) is used as the solvent.)

Following completion of the reaction, the desired compound can be purified by the same methods as those described in "Step A1" if necessary.

(Step I2)

Step I2 is a step wherein a compound having the general formula (In) is produced by reacting Compound (16) with Compound (8) in an inert solvent in the presence or absence of a base, and is carried out in the same manner as the aforementioned "Step D2". (However, in the present step, preferably a halogenated hydrocarbon (particularly preferably methylene chloride) is used as the solvent.)

Following completion of the reaction, the desired compound can be purified by the same methods as those described in Step A1 if necessary.

Among the Compounds (I), a compound in which $R^3$ is $-(CH_2)_m-R^5$ and in which m is from 1 to 6 can be produced according to the following Method J.

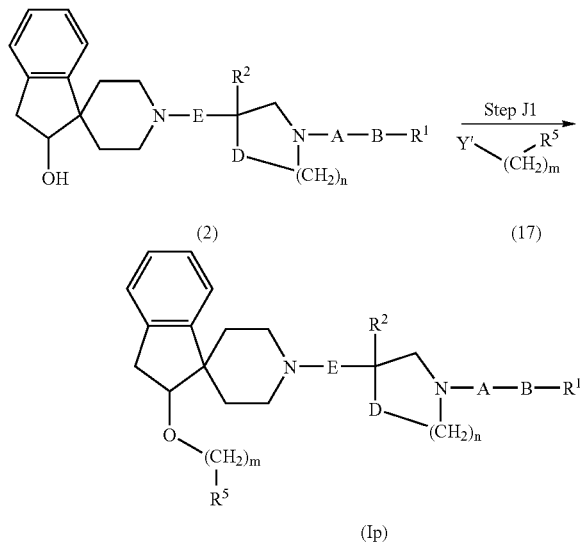

In the above formula, A, B, D, E, $R^1$, $R^2$, $R^5$, m and n are the same as previously defined, and Y' represents a leaving group.

The same groups as those described in the definition of Y can be used for the leaving group in the definition of Y', and is preferably a halogen atom, more preferably a chlorine atom or a bromine atom, and particularly preferably a chlorine atom.

(Step J1)

Step J1 is a step wherein a compound having the general formula (Ip) is produced by reacting Compound (2) with Compound (17) in an inert solvent, in the presence or absence of a condensing agent, and in the presence or absence of a base, and is carried out in the same manner as the aforementioned "Step E1".

Following completion of the reaction, the desired compound can be purified by the same methods as those described in Step A1 if necessary.

Each starting material in the aforementioned Methods A to J is a known compound or can be easily produced from a known compound in accordance with known methods in the field of organic chemistry.

For example, Compound (2) can be produced according to the method disclosed in columns 11 to 13 of U.S. Pat. No. 6,511,975. In addition, compounds having a leaving group such as Compounds (3), (4), (9) and (10) can easily be produced by, for example, halogenating and sulfonylating the corresponding carboxylic acid compound or alcohol compound in accordance with the method described in the aforementioned Step F3. Moreover, Compounds (4), (5) and (9) can easily be produced by reacting $R^4-X$ (wherein, $R^4$ and X are the same as previously defined) with a suitable compound in accordance with the method described in the aforementioned Step A1 or Step D2.

Since a compound having the general formula (I) and a pharmacologically acceptable salt thereof of the present invention have antagonistic activity on neurokinin receptors ($NK_1$, $NK_2$ and $NK_3$ receptors), they can be used as a pharmaceutical. Such a pharmaceutical can be administered for $NK_1$, $NK_2$ and/or $NK_3$ receptor-mediated diseases, and examples of such diseases include central nervous system diseases including anxiety, depression, mental illness and schizophrenia; neurodegenerative diseases including AIDS-associated dementia, Alzheimer-type senile dementia, Alzheimer's disease, Down's syndrome, demyelinating disease, amyotrophic lateral sclerosis, neuropathy, peripheral neuropathy and neuralgia; respiratory diseases including chronic obstructive lung disease, bronchitis, pneumonia, bronchial constriction, asthma and cough; inflammatory diseases including inflammatory bowel disease (IBD), psoriasis, fibrositis, osteoarthritis, degenerative arthritis and rheumatoid arthritis; eczema; allergic diseases including rhinitis; hypersensitivity diseases including diseases of hypersensitivity to vine plants; ophthalmological diseases including conjunctivitis, vernal conjunctivitis, vernal catarrh, destruction of the blood-aqueous humor barrier accompanying various inflammatory eye diseases, increased intraocular pressure and miosis; skin diseases including contact dermatitis, atopic dermatitis, urticaria and other eczema-like dermatitis; addictions including alcoholism; stress-induced somatic diseases; sympathetic reflex dystrophy including shoulder-hand syndrome; dysthymia; diseases related to undesirable immune reactions including transplant rejections and immunoenhancement or immunosuppression including systemic lupus erythematosus; digestive organ diseases including diseases caused by abnormalities in nerves regulating internal organs, colitis, ulcerative colitis, irritable bowel syndrome and Crohn's disease; emesis including that induced by X-ray irradiation and chemotherapeutic agents, poisons, toxins, pregnancy, vestibular disorders, post-operative illnesses, gastrointestinal obstruction, gastrointestinal dysmotility, visceralgia, migraine headache, increased intracranial pressure, decreased intracranial pressure or adverse side effects accompanying administration of various pharmaceuticals; urinary bladder function diseases including cystitis and urinary incontinence; eosinophilia caused by collagen diseases, scleroderma or Fasciola hepatica infection; diseases caused by circulation abnormalities due to vascular dilation or constriction including angina pectoris, migraine headache and Raynaud's disease; pain associated with reception of pain penetration including migraine headache, headache and toothache; and, sleep apnea syndrome. The aforementioned pharmaceuticals can be used as a prophylactic or therapeutic for respiratory diseases such as asthma, bronchitis and chronic obstructive lung disease; allergic diseases such as rhinitis; and/or urinary incontinence in particular.

Examples of the administration form of a compound having the general formula (I) of the present invention, or pharmacologically acceptable salt thereof, include oral administration by tablets, capsules, granules, powders or syrups, and parenteral administration by injection or suppositories. Moreover, a compound having the general formula (I) or a pharmacologically acceptable salt thereof of the present invention can also be administered by pulmonary administration in the form of a powder, solution or suspension. Preparations for these administrations are produced by known methods using additives such as excipients, lubricants, binders, disintegrants, stabilizers, corrigents, diluents and so forth.

Examples of excipients include organic excipients such as sugar derivatives, e.g. lactose, sucrose, glucose, mannitol or sorbitol, starch derivatives, e.g. corn starch, potato starch, α-starch, dextrin or carboxymethyl starch, cellulose derivatives, e.g. crystalline cellulose, low substituted hydroxypropyl cellulose, hydroxypropyl methyl cellulose, carboxymethyl cellulose, calcium carboxymethyl cellulose or internally crosslinked sodium carboxymethyl cellulose, and gum Arabic, dextran or pullulan; and, inorganic excipients such as silicate derivatives, e.g. light anhydrous silicic acid, synthetic aluminium silicate or magnesium aluminium metasilicate, phosphates, e.g. calcium phosphate, carbonates, e.g. calcium carbonate, or sulfates, e.g. calcium sulfate.

Examples of lubricants include stearic acid and metal stearates such as calcium stearate or magnesium stearate; talc; colloidal silica; waxes such as bee gum or spermaceti; boric acid; adipic acid; sulfates such as sodium sulfate; glycol; fumaric acid; sodium benzoate; DL-leucine; sodium fatty acid salts; lauryl sulfates such as sodium lauryl sulfate or magnesium lauryl sulfate; silicic acids such as silicic anhydride or silicate hydrate; and, starch derivatives.

Examples of binders include polyvinylpyrrolidone, Macrogol and compounds similar to the aforementioned excipients.

Examples of disintegrants agents include compounds similar to the aforementioned excipients, and chemically crosslinked starches and celluloses such as cross sodium carmellose, sodium carboxymethyl starch or crosslinked polyvinylpyrrolidone.

Examples of stabilizers include paraoxybenzoate esters such as methyl paraben or propyl paraben; alcohols such as chlorobutanol, benzyl alcohol or phenyl ethyl alcohol; benzalkonium chloride; phenols such as phenol or cresol; thimerosal; dehydroacetic acid; and, sorbic acid.

Examples of corrigents include ordinarily used sweeteners, sour flavourings and fragrances.

In the case of producing a solution or suspension for pulmonary administration of a compound having the general formula (I) or pharmacologically acceptable salt thereof of the present invention, for example, said solution or suspension can be produced by dissolving or suspending crystals of the present invention in water or in a mixture of water and an auxiliary solvent (e.g., ethanol, propylene glycol or polyethylene glycol). Such a solution or suspension may also contain an antiseptic (e.g., benzalkonium chloride), solubilizing agent (e.g., a polysorbate such as Tween 80 or Span 80 or surface activator such as benzalkonium chloride), buffer, isotonic agent (e.g., sodium chloride), absorption promoter and/or thickener. In addition, the suspension may additionally contain a suspending agent (such as microcrystalline cellulose or sodium carboxymethyl cellulose).

A composition for pulmonary administration produced in the manner described above is administered directly into the nasal cavity or oral cavity by a typical means in the field of inhalants (using, for example, a dropper, pipette, cannula or atomizer). In the case of using an atomizer, crystals of the present invention can be atomized as an aerosol in the form of a pressurized pack together with a suitable nebula (for example, a chlorofluorocarbon such as dichlorofluoromethane, trichlorofluoromethane or dichlorotetrafluoroethane, or a gas such as carbon dioxide), or they can be administered using a nebulizer.

While the amount of a compound having the general formula (I) or pharmacologically acceptable salt thereof of the present invention used varies depending on the symptoms, age, administration method and so forth, it is desired to administer in an amount of 0.1 mg as a lower limit (preferably 1 mg and more preferably 5 mg) and 1000 mg as an upper limit (preferably 100 mg and more preferably 50 mg) per day to an adult human either in a single dose or by dividing into multiple doses according to the symptoms in the case of oral administration, for example. In the case of intravenous administration, it is desired to administer in an amount of 0.01 mg as a lower limit (preferably 0.1 mg) and 100 mg as an upper limit (preferably 10 mg) per day to an adult human in a single dose or by dividing into multiple doses according to the symptoms.

In addition, while the amount of a compound having the general formula (I) or pharmacologically acceptable salt used varies depending on the symptoms, age, gender and so forth, it is desired to administer in an amount of 0.01 µg/kg as a lower limit (preferably 0.05 µg/kg) and 1000 µg/kg as an upper limit (preferably 100 µg/kg and more preferably 20 µg/kg) per day to an adult human in a single dose or by dividing into multiple doses according to the symptoms, in the case of pulmonary administration.

BEST MODE FOR CARRYING OUT THE INVENTION

Although the following provides a more detailed explanation of the present invention through its examples, reference examples, preparation examples and test examples, the present invention is not limited thereto.

EXAMPLE

Example 1

1-(2-{(2R)-2-(3,4-Dichlorophenyl)-4-[3,5-bis(trifluoromethyl)benzoyl]morpholin-2-yl}ethyl)spiro{(2S)-2-[(acetoxy)acetoxy]}indane-1,4'-piperidine hydrochloride (Exemplary compound No. 2-97 hydrochloride)

0.07 mL of acetoxyacetyl chloride was added to a solution of 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 320 mg (1.07 mmol, 3.3 mmol/g) of PS-diisopropylethylamine in toluene (3.0 mL). After the mixture was stirred at room temperature for 20 hours, the resin was removed by filtration. After the residue obtained by evaporating the solvent under reduced pressure was purified by silica gel chromatography (eluting solvent: methylene chloride/methanol=10/1), it was dissolved in ethanol (5.0 mL) and 4N hydrochloric acid-dioxane solution (0.5 mL) was added thereto. The solvent was distilled off again under reduced pressure, followed by azeotropy with diethyl ether twice. The thus obtained residue was recrystalized from hexane to obtain 171 mg (yield: 95%) of the title compound as a white crystal.

¹H-NMR spectrum (400 MHz, DMSO-d₆) δ ppm: 8.45-8.01 (3H, m), 7.85-7.12 (7H, m), 5.43 (1H, bs), 4.56 (2H, bs), 4.21-1.62 (24H, m).

IR spectrum ν max cm⁻¹ (KBr): 2961, 1748, 1646, 1474, 1439, 1376, 1282, 1186, 1137, 905, 681.

Mass spectrum (FAB) m/z: 801 ((M+H)⁺, free form)

Elementary analysis (for $C_{38}H_{37}Cl_3F_6N_2O_6$) Calculated (%): C, 54.46; H, 4.45; N, 3.34; F, 13.60; Cl, 12.69. Found (%): C, 52.13; H, 4.54; N, 3.43; F, 12.23; Cl, 11.83.

Optical rotation: $[\alpha]_D^{20}$=+39.5 (c=1.00, methanol)

Example 2

1-(2-{(2R)-2-(3,4-Dichlorophenyl)-4-[3,5-bis(trifluoromethyl)benzoyl]morpholin-2-yl}ethyl)spiro{(2S)-2-[(3,3-dimethylbutanoyl)oxy]}indane-1,4'-piperidine hydrochloride (Exemplary compound No. 2-106 hydrochloride)

The reaction was carried out in similar procedure to Example 1 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 3,3-dimethylbutanoic chloride to obtain 143 mg (yield: 80%) of the title compound as a white crystal.

IR spectrum ν max cm⁻¹ (KBr): 2960, 2658, 2553, 1725, 1647, 1475, 1439, 1375, 1281, 1240, 1186, 1139, 905, 757, 681.

Mass spectrum (FAB) m/z: 799 ((M+H)⁺, free form)

Example 3

1-(2-{(2R)-2-(3,4-Dichlorophenyl)-4-[3,5-bis(trifluoromethyl)benzoyl]morpholin-2-yl}ethyl)spiro{(2S)-2-[(cyclohexylcarbonyl)oxy]}indane-1,4'-piperidine hydrochloride (Exemplary compound No. 2-110 hydrochloride)

The reaction was carried out in similar procedure to Example 1 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and cyclohexanecarboxylic chloride to obtain 185 mg (yield: 99%) of the title compound as a white crystal.

IR spectrum ν max cm⁻¹ (KBr): 2933, 2857, 2657, 2477, 1726, 1647, 1473, 1452, 1440, 1376, 1281, 1246, 1185, 1170, 1138, 1029, 905, 757, 681.

Mass spectrum (FAB) m/z: 811 ((M+H)⁺, free form)

Example 4

1-(2-{(2R)-2-(3,4-Dichlorophenyl)-4-[3,5-bis(trifluoromethyl)benzoyl]morpholin-2-yl}ethyl)spiro{(2S)-2-[(methoxyacetyl)oxy]}indane-1,4'-piperidine hydrochloride (Exemplary compound No. 2-111 hydrochloride)

The reaction was carried out in similar procedure to Example 1 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and methoxyacetyl chloride to obtain 98.0 mg (yield: 57%) of the title compound as a white crystal.

IR spectrum ν max cm⁻¹ (KBr): 2930, 2655, 2508, 1749, 1645, 1473, 1457, 1439, 1376, 1363, 1282, 1186, 1136, 1028, 905, 758, 681.

Mass spectrum (FAB) m/z: 773 ((M+H)⁺, free form)

Example 5

1-(2-{(2R)-2-(3,4-Dichlorophenyl)-4-[3,5-bis(trifluoromethyl)benzoyl]morpholin-2-yl}ethyl)spiro{(2S)-2-[(cyclopropylcarbonyl)oxy]}indane-1,4'-piperidine hydrochloride (Exemplary compound No. 2-107 hydrochloride)

The reaction was carried out in similar procedure to Example 1 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and cyclopropanecarboxylic chloride to obtain 72.0 mg (yield: 42%) of the title compound as a white crystal.

IR spectrum ν max cm⁻¹ (KBr): 2926, 2482, 2406, 1724, 1646, 1473, 1439, 1392, 1376, 1281, 1172, 1139, 1071, 1029, 905, 758, 681.

Mass spectrum (FAB) m/z: 801 ((M+H)⁺, free form)

Example 6

1-(2-{(2R)-2-(3,4-Dichlorophenyl)-4-[3,5-bis(trifluoromethyl)benzoyl]morpholin-2-yl}ethyl)spiro((2S)-2-{[(morpholin-1-yl)acetyl]oxy})indane-1,4'-piperidine dihydrochloride (Exemplary compound No. 2-112 dihydrochloride)

435 mg (1.71 mmol) of N,N-bis(2-oxo-3-oxazolidinyl)phosphinic chloride and 7 mg (0.057 mmol) of 4-(dimethylamino)pyridine were added to a solution of 400 mg (0.57 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine, 248 mg (1.71 mmol) of 2-morpholine acetic acid and 0.48 mL (3.42 mmol) of triethylamine in 12 mL of methylene chloride under ice-cooling with stirring and the mixture was stirred at room temperature for 1 hour. The reaction mixture was washed with water and a saturated NaCl solution and dried over anhydrous magnesium sulfate. The residue obtained by evaporating the solvent under reduced pressure was purified by silica gel chromatography (eluting solvent: methylene chloride/methanol=50/1-100/3) to obtain 337 mg (yield: 71%) of the free form of the title compound.

5 mL of ethanol was added to 336 mg (0.405 mmol) of the free form of title compound thus obtained to dissolve it and 0.51 mL of 4N hydrochloric acid-dioxane solution was added thereto. After the reaction mixture was stirred under ice-cooling for 10 minutes, the solvent was distilled off under reduced pressure, followed by azeotropy with diethyl ether. Ether was added to the thus obtained residue to collect it by filtration to obtain 341 mg (yield: 93%) of the title compound as a white solid.

¹H-NMR spectrum (400 MHz, CD₃OD) δ ppm: 8.20-7.92 (3H, m), 7.87-7.20 (7H, m), 5.70-5.40 (1H, m), 4.55-1.80 (30H, m).

IR spectrum ν max cm⁻¹ (KBr): 3422, 2928, 2873, 2646, 2551, 2424, 1750, 1695, 1645, 1473, 1457, 1440, 1376, 1281, 1240, 1224, 1206, 1186, 1138, 1109, 1098, 1073, 1049, 1027, 905, 757, 681.

Mass spectrum (FAB) m/z: 828 ((M+H)⁺, free form)

Elementary analysis (for $C_{40}H_{41}Cl_2F_6N_3O_5$ 2HCl) Calculated (%): C, 53.29; H, 4.81; N, 4.66; F, 12.64; Cl, 15.73. Found (%): C, 51.97; H, 5.05; N, 4.60; F, 11.48; Cl, 15.39.

Optical rotation: $[\alpha]_D^{20}$=+44.2 (c=1.00, methanol)

Example 7

1-{2-[(2R)-2-(3,4-Dichlorophenyl)-4-(3,4,5-trimethoxybenzoyl)morpholin-2-yl]ethyl}spiro((2S)-2-{[(morpholin-1-yl)acetyl]oxy})indane-1,4'-piperidine dihydrochloride (Exemplary compound No. 1-112 dihydrochloride)

The reaction was carried out in similar procedure to Example 6 using 350 mg (0.534 mmol) of 1-{2-[(2R)-2-(3,4-dichlorophenyl)-4-(3,4,5-trimethoxybenzoyl)morpholin-2-yl]ethyl}spiro[(2S)-2-hydroxy]indane-1,4'-piperidine, 232 mg (1.60 mmol) of 2-morpholine acetic acid, 0.45 mL (3.20 mmol) of triethylamine, 408 mg (1.60 mmol) of N,N-bis(2-oxo-3-oxazolidinyl)-phosphinic chloride and 7 mg (0.057 mmol) of 4-(dimethylamino)pyridine to obtain 404 mg (yield: 83%) of the title compound as a white solid.

$^1$H-NMR spectrum (400 MHz, CD$_3$OD) δ ppm: 7.87-7.20 (7H, m), 6.70-6.60 (2H, m), 5.70-5.38 (1H, m), 4.50-1.80 (30H, m)

IR spectrum ν max cm$^{-1}$ (KBr): 3426, 2936, 2872, 2644, 2537, 2423, 1750, 1634, 1583, 1505, 1462, 1427, 1415, 1380, 1330, 1269, 1228, 1207, 1125, 1075, 1026, 1004, 927, 901, 871, 831, 762, 723, 678.

Mass spectrum (FAB) m/z: 782 ((M+H)$^+$, free form)

Elementary analysis (for C$_{41}$H$_{49}$Cl$_2$N$_3$O$_8$ 2HCl 1.5H$_2$O) Calculated (%): C, 55.79; H, 6.17; N, 4.76; Cl, 16.07. Found (%): C, 55.87; H, 6.07; N, 4.69; Cl, 16.37.

Optical rotation: [α]$_D^{20}$=+39.5 (c=1.00, methanol)

Example 8

1-(2-{(2R)-2-(3,4-Dichlorophenyl)-4-[3,5-bis(trifluoromethyl)benzoyl]morpholin-2-yl}ethyl)spiro((2S)-2-{[(4-morpholin-4-yl)butanoyl]oxy})indane-1,4'-piperidine dihydrochloride (Exemplary compound No. 2-114 dihydrochloride)

The reaction was carried out in similar procedure to Example 6 using 212 mg (0.302 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine, 262 mg (1.51 mmol) of 4-morpholine butyric acid, 0.42 mL (3.02 mmol) of triethylamine, 384 mg (1.51 mmol) of N,N-bis(2-oxo-3-oxazolidinyl)-phosphinic chloride and 4 mg (0.03 mmol) of 4-(dimethylamino)pyridine to obtain 182 mg (yield: 67%) of the title compound as a white solid.

IR spectrum ν max cm$^{-1}$ (KBr): 3436, 2927, 2874, 2653, 2558, 2461, 1733, 1644, 1472, 1457, 1440, 1376, 1282, 1243, 1183, 1138, 1108, 1096, 1028, 981, 928, 905, 759, 681.

Mass spectrum (FAB) m/z: 856 ((M+H)$^+$, free form)

Example 9

1-(2-{(2R)-2-(3,4-Dichlorophenyl)-4-[3,5-bis(trifluoromethyl)benzoyl]morpholin-2-yl}ethyl)spiro((2S)-2-{[(3-morpholin-4-yl)propanoyl]oxy})indane-1,4'-piperidine dihydrochloride (Exemplary compound No. 2-113 dihydrochloride)

The reaction was carried out in similar procedure to Example 6 using 218 mg (0.311 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine, 247 mg (1.55 mmol) of 3-morpholinepropionic acid, 0.43 mL (3.10 mmol) of triethylamine, 395 mg (1.55 mmol) of N,N-bis(2-oxo-3-oxazolidinyl)-phosphinic chloride and 5 mg (0.03 mmol) of 4-(dimethylamino)pyridine to obtain 158 mg (yield: 63%) of the title compound as a white solid.

IR spectrum ν max cm$^{-1}$ (KBr): 3438, 2928, 2873, 2653, 2560, 2458, 1737, 1644, 1473, 1458, 1440, 1376, 1319, 1282, 1185, 1137, 1110, 1095, 1047, 1028, 987, 905, 759, 707, 681.

Mass spectrum (FAB) m/z: 842 ((M+H)$^+$, free form)

Example 10

1-(2-{(2R)-2-(3,4-Dichlorophenyl)-4-[3,5-bis(trifluoromethyl)benzoyl]morpholin-2-yl}ethyl)spiro((2S)-2-{[(2-methoxy)ethoxycarbonyl]oxy})indane-1,4'-piperidine hydrochloride (Exemplary compound No. 2-122 hydrochloride)

The reaction was carried out in similar procedure to Example 1 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 2-methoxyethyl chloroformate to obtain 172 mg (yield: 96%) of the title compound as a white crystal.

IR spectrum ν max cm$^{-1}$ (KBr): 2928, 2481, 2393, 1746, 1646, 1473, 1440, 1363, 1282, 1266, 1186, 1137, 1027, 905, 681.

Mass spectrum (FAB) m/z: 803 ((M+H)$^+$, free form)

Example 11

1-(2-{(2R)-2-(3,4-Dichlorophenyl)-4-[3,5-bis(trifluoromethyl)benzoyl]morpholin-2-yl}ethyl)spiro{(2S)-2-[(ethoxycarbonyl)oxy]}indane-1,4'-piperidine hydrochloride (Exemplary compound No. 2-121 hydrochloride)

The reaction was carried out in similar procedure to Example 1 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and ethyl chloroformate to obtain 165 mg (yield: 93%) of the title compound as a white crystal.

IR spectrum ν max cm$^{-1}$ (KBr): 2927, 2481, 2404, 1743, 1647, 1473, 1439, 1375, 1281, 1266, 1186, 1139, 905, 681.

Mass spectrum (FAB) m/z: 773 ((M+H)$^+$, free form)

Example 12

1-(2-{(2R)-2-(3,4-Dichlorophenyl)-4-[3,5-bis(trifluoromethyl)benzoyl]morpholin-2-yl}ethyl)spiro((2S)-2-{[(2-fluoro)ethoxycarbonyl]oxy})indane-1,4'-piperidine hydrochloride (Exemplary compound No. 2-123 hydrochloride)

The reaction was carried out in similar procedure to Example 1 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and ethyl chloroformate to obtain 50.0 mg (yield: 28%) of the title compound as a white crystal.

IR spectrum ν max cm$^{-1}$ (KBr): 2960, 2481, 2400, 1748, 1646, 1473, 1440, 1377, 1282, 1267, 1186, 1138, 905, 873, 681.

Mass spectrum (FAB) m/z: 791 ((M+H)$^+$, free form)

Example 13

1-(2-{(2R)-2-(3,4-Dichlorophenyl)-4-[3,5-bis(trifluoromethyl)benzoyl]morpholin-2-yl}ethyl)spiro((2S)-2-{[(2-propargyl)oxycarbonyl]oxy})indane-1,4'-piperidine hydrochloride (Exemplary compound No. 2-124 hydrochloride)

The reaction was carried out in similar procedure to Example 1 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and propargyl chloroformate to obtain 170 mg (yield: 97%) of the title compound as a white crystal.

IR spectrum ν max cm$^{-1}$ (KBr): 2925, 2484, 2410, 1750, 1645, 1473, 1439, 1377, 1281, 1264, 1186, 1139, 905, 681.

Mass spectrum (FAB) m/z: 783 ((M+H)$^+$, free form)

Example 14

1-(2-{(2R)-2-(3,4-Dichlorophenyl)-4-[3,5-bis(trifluoromethyl)benzoyl]morpholin-2-yl}ethyl)spiro[(2S)-2-({[2-(ethoxycarbonyl)ethyl]carbamoyl}oxy)]indane-1,4'-piperidine hydrochloride (Exemplary compound No. 2-126 hydrochloride)

0.08 mL of ethoxycarbonylethyl isocyanate was added to a solution of 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxyoxy]indane-1,4'-piperidine and 320 mg (1.07 mmol, 3.3 mmol/g) of PS-diisopropylethylamine in toluene (3.0 mL). After the mixture was stirred at 80° C. for 20 hours, the resin was removed by filtration. After the residue obtained by evaporating the solvent under reduced pressure was purified by silica gel chromatography (eluting solvent: methylene chloride/methanol=10/1), it was dissolved in ethanol (5.0 mL) and 4N hydrochloric acid-dioxane solution (0.5 mL) was added thereto. The solvent was distilled off again under reduced pressure, followed by azeotropy with diethyl ether twice. The thus obtained residue was recrystallized from hexane to obtain 45.0 mg (yield: 24%) of the title compound as a white crystal.

$^1$H-NMR spectrum (400 MHz, DMSO-d$_6$) δ ppm: 8.31-7.98 (3H, m), 7.88-7.08 (7H, m), 5.24 (1H, bs), 4.18-1.57 (31H, m).

IR spectrum ν max cm$^{-1}$ (KBr): 2958, 2657, 2564, 1723, 1644, 1525, 1376, 1282, 1186, 1139, 758, 681.

Mass spectrum (FAB) m/z: 844 ((M+H)$^+$, free form)

Elementary analysis (for C$_{40}$H$_{42}$Cl$_3$F$_6$N$_3$O$_6$) Calculated (%): C, 54.52; H, 4.80; N, 4.77; F, 12.94; Cl, 12.07. Found (%): C, 51.32; H, 4.77; N, 5.35; F, 10.92; Cl, 12.04.

Optical rotation: [α]$_D^{20}$=+42.1 (c=1.00, methanol)

Example 15

1-(2-{(2R)-2-(3,4-Dichlorophenyl)-4-[3,5-bis(trifluoromethyl)benzoyl]morpholin-2-yl}ethyl)spiro[(2S)-2-({[3-(ethoxycarbonyl)propyl]carbamoyl}oxy)]indane-1,4'-piperidine hydrochloride (Exemplary compound No. 2-127 hydrochloride)

The reaction was carried out in similar procedure to Example 14 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and ethoxycarbonylpropyl isocyanate to obtain 38.0 mg (yield: 20%) of the title compound as a white crystal.

IR spectrum ν max cm$^{-1}$ (KBr): 2953, 2655, 2560, 1720, 1644, 1527, 1440, 1376, 1282, 1185, 1139, 1029, 758, 681.

Mass spectrum (FAB) m/z: 858 ((M+H)$^+$, free form)

Example 16

1-(2-{(2R)-2-(3,4-Dichlorophenyl)-4-[3,5-bis(trifluoromethyl)benzoyl]morpholin-2-yl}ethyl)spiro[(2S)-2-(2-(ethylcarbamoyloxy)]indane-1,4'-piperidine hydrochloride (Exemplary compound No. 2-128 hydrochloride)

The reaction was carried out in similar procedure to Example 14 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and ethyl isocyanate to obtain 68.0 mg (yield: 39%) of the title compound as a white crystal.

IR spectrum ν max cm$^{-1}$ (KBr): 2971, 2495, 2417, 1714, 1645, 1518, 1473, 1440, 1376, 1281, 1186, 1139, 1029, 905, 681.

Mass spectrum (FAB) m/z: 772 ((M+H)$^+$, free form)

Example 17

1-(2-{(2R)-2-(3,4-Dichlorophenyl)-4-[3,5-bis(trifluoromethyl)benzoyl]morpholin-2-yl}ethyl)spiro[(2S)-2-(ethoxycarbonylmethylcarbamoyloxy)]indane-1,4'-piperidine hydrochloride (Exemplary compound No. 2-125 hydrochloride)

The reaction was carried out in similar procedure to Example 14 using 150 mg (0.214 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and ethoxycarbonylmethyl isocyanate to obtain 53.0 mg (yield: 29%) of the title compound as a white crystal.

IR spectrum ν max cm$^{-1}$ (KBr): 2961, 2657, 2562, 1722, 1645, 1521, 1474, 1440, 1376, 1282, 1186, 1139, 905, 758, 681.

Mass spectrum (FAB) m/z: 830 ((M+H)$^+$, free form)

Example 18

1-(2-{(2R)-2-(3,4-Dichlorophenyl)-4-[3,5-bis(trifluoromethyl)benzoyl]morpholin-2-yl}ethyl)spiro[(2S)-2-({[N-(hydroxyethyl)-N-methylamino]acetyl}oxy)]indane-1,4'-piperidine dihydrochloride (Exemplary compound No. 2-129 dihydrochloride)

Example 18a 1-(2-{(2R)-2-(3,4-Dichlorophenyl)-4-[3,5-bis(trifluoromethyl)benzoyl]morpholin-2-yl}ethyl)spiro[(2S)-2-(bromoacetyl)oxy]indane-1,4'-piperidine Bromoacetyl bromide was added dropwise to a solution of 10.0 g (14.3 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 2.78 mL of triethylamine in 200 mL of methylene chloride under ice-cooling with stirring and the mixture was stirred as such for 35 minutes. The reaction solution was washed with a saturated aqueous ammonium chloride solution and dried over anhydrous magnesium sulfate. The residue obtained by evaporating the solvent under reduced pressure was purified by silica gel chromatography (eluting solvent: methylene chloride/methanol=25/1-20/1) to obtain 11.48 g (yield: 98%) of the title compound as a white solid.

$^1$H-NMR spectrum (400 MHz, CDCl$_3$) δ ppm: 8.20-7.10 (10H, m), 5.80-5.30 (1H, m), 4.65-1.40 (22H, m).

IR spectrum ν max cm$^{-1}$ (KBr): 2974, 1741, 1645, 1473, 1458, 1437, 1375, 1280, 1185, 1163, 1139, 1109, 1047, 1029, 992, 927, 905, 849, 758, 722, 705, 681.

Mass spectrum (FAB) m/z: 821 ((M+H)$^+$)

Example 18b 1-(2-{(2R)-2-(3,4-Dichlorophenyl)-4-[3,5-bis(trifluoromethyl)benzoyl]morpholin-2-yl}ethyl)spiro[(2S)-2-({[N-(2-hydroxyethyl)-N-methylamino]acetyl}oxy)]indane-1,4'-piperidine dihydrochloride 60 μL (0.75 mmol) of N-methylethanolamine was added to a solution of 200 mg (0.243 mmol) of 1-(2-{(2R)-2-(3,4-dichlorophenyl)-4-[3,5-bis(trifluoromethyl)benzoyl]morpholin-2-yl}ethyl)spiro[(2S)-2-(bromoacetyl)oxy]indane-1,4'-piperidine, obtained in Example 18a, in acetonitrile and the mixture was stirred at 50° C. for 5 hours. Methylene chloride was added to the reaction solution and the organic layer was washed with a saturated NaCl solution and dried over anhydrous magnesium sulfate. The residue obtained by evaporating the solvent under reduced pressure was purified by silica gel chromatography (eluting solvent: methylene chloride/2-propanol=10/1-5/1) and dissolved in 5.0 mL of methanol and 1.0 mL of 4N hydrochloric acid-dioxane solution was added thereto. The solvent was distilled off again under reduced pressure, followed by azeotropy twice with diethyl ether. Ether was added to the thus obtained residue to collect it by filtration to obtain 39 mg (yield: 18%) of the title compound as a white solid.

$^1$H-NMR spectrum (400 MHz, CD$_3$OD) δ ppm: 8.20-7.91 (3H, m), 7.86-7.08 (7H, m), 5.72-5.32 (1H, m), 4.55-1.65 (29H, m).

IR spectrum ν max cm$^{-1}$ (KBr): 3344, 2926, 1645, 1474, 1458, 1439, 1376, 1281, 1186, 1165, 1139, 1109, 1047, 1029, 988, 972, 927, 905, 849, 830, 758, 722, 707, 681, 623.

Mass spectrum (FAB) m/z: 816 ((M+H)$^+$, free form)

Elementary analysis (for C$_{39}$H$_{41}$Cl$_2$F$_6$N$_3$O$_5$ 2HCl) Calculated: C, 52.66; H, 4.87; N, 4.72. Found: C, 52.72; H, 4.59; N, 3.73.

Optical rotation: [α]$_D^{20}$=+36.3 (c=1.00, methanol)

Example 19

1-(2-{(2R)-2-(3,4-Dichlorophenyl)-4-[3,5-bis(trifluoromethyl)benzoyl]morpholin-2-yl}ethyl)spiro[(2S)-2-({[4-(aminocarbonyl)piperidin-1-yl]acetyl}oxy)]indane-1,4'-piperidine dihydrochloride (Exemplary compound No. 2-144 dihydrochloride)

The reaction was carried out in similar procedure to Example 18b using 200 mg (0.243 mmol) of 1-(2-{(2R)-2-(3,4-dichlorophenyl)-4-[3,5-bis(trifluoromethyl)benzoyl]morpholin-2-yl}ethyl)spiro[(2S)-2-(bromoacetyl)oxy]indane-1,4'-piperidine, obtained in Example 18a, and 86 mg (0.75 mmol) of isonipecotamide to obtain 43 mg (yield: 19%) of the title compound as a white solid.

$^1$H-NMR spectrum (400 MHz, CD$_3$OD) δ ppm: 8.20-7.90 (3H, m), 7.86-7.11 (7H, m), 5.73-5.33 (1H, m), 4.55-1.70 (30H, m).

IR spectrum νmax cm$^{-1}$ (KBr): 3384, 3180, 2929, 2651, 2553, 1750, 1646, 1472, 1456, 1438, 1402, 1376, 1282, 1241, 1186, 1140, 1109, 1098, 1028, 952, 905, 757, 723, 707, 682, 637, 622, 543.

Mass spectrum (FAB) m/z: 869 ((M+H)$^+$, free form)

Elementary analysis (for C$_{42}$H$_{46}$Cl$_2$F$_6$N$_4$O$_5$ 2HCl 5H$_2$O) Calculated (%): C, 48.85; H, 5.47; N, 5.43. Found (%): C, 48.61; H, 5.23; N, 5.27.

Optical rotation: [α]$_D^{20}$=+49.9 (c=0.80, methanol)

Example 20

1-(2-{(2R)-2-(3,4-Dichlorophenyl)-4-[3,5-bis(trifluoromethyl)benzoyl]morpholin-2-yl}ethyl)spiro((2S)-2-{[(pyrrolidin-1-yl)acetyl]oxy})indane-1,4'-piperidine dihydrochloride (Exemplary compound No. 2-142 dihydrochloride)

The reaction was carried out in similar procedure to Example 18b using 200 mg (0.243 mmol) of 1-(2-{(2R)-2-(3,4-dichlorophenyl)-4-[3,5-bis(trifluoromethyl)benzoyl]morpholin-2-yl}ethyl)spiro[(2S)-2-(bromoacetyl)oxy]indane-1,4'-piperidine, obtained in Example 18a, and 52 mg (0.73 mmol) of pyrrolidine to obtain 91 mg (yield: 45%) of the title compound as a white solid.

IR spectrum ν max cm$^{-1}$ (KBr): 2955, 2927, 2647, 2555, 2468, 1751, 1645, 1472, 1457, 1438, 1376, 1282, 1237, 1186, 1138, 1109, 1029, 986, 905, 849, 757, 722, 707, 681.

Mass spectrum (FAB) m/z: 812 ((M+H)$^+$, free form)

Example 21

1-(2-{(2R)-2-(3,4-Dichlorophenyl)-4-[3,5-bis(trifluoromethyl)benzoyl]morpholin-2-yl}ethyl)spiro((2S)-2-{[(azetidin-1-yl)acetyl]oxy})indane-1,4'-piperidine dihydrochloride (Exemplary compound No. 2-141 dihydrochloride)

The reaction was carried out in similar procedure to Example 18b using 200 mg (0.243 mmol) of 1-(2-{(2R)-2-(3,4-dichlorophenyl)-4-[3,5-bis(trifluoromethyl)benzoyl]morpholin-2-yl}ethyl)spiro[(2S)-2-(bromoacetyl)oxy]indane-1,4'-piperidine, obtained in Example 18a, and 52 mg (0.75 mmol) of azetidine to obtain 37 mg (yield: 17%) of the title compound as a white solid.

IR spectrum ν max cm$^{-1}$ (KBr): 3402, 2930, 2658, 2574, 2414, 1752, 1645, 1560, 1473, 1438, 1376, 1281, 1238, 1186, 1139, 1109, 1098, 1078, 1029, 985, 949, 905, 758, 722, 707, 681.

Mass spectrum (FAB) m/z: 798 ((M+H)$^+$, free form)

Example 22

1-(2-{(2R)-2-(3,4-Dichlorophenyl)-4-[3,5-bis(trifluoromethyl)benzoyl]morpholin-2-yl}ethyl)spiro[(2S)-2-({[4-(hydroxymethyl)piperidin-1-yl]acetyl}oxy)]indane-1,4'-piperidine dihydrochloride (Exemplary compound No. 2-145 dihydrochloride)

The reaction was carried out in similar procedure to Example 18b using 200 mg (0.243 mmol) of 1-(2-{(2R)-2-(3,4-dichlorophenyl)-4-[3,5-bis(trifluoromethyl)benzoyl]morpholin-2-yl}ethyl)spiro[(2S)-2-(bromoacetyl)oxy]indane-1,4'-piperidine, obtained in Example 18a, and 96 mg (0.75 mmol) of 4-(hydroxymethyl)piperidine to obtain 58 mg (yield: 26%) of the title compound as a white solid.

IR spectrum ν max cm⁻¹ (KBr): 3374, 2927, 2876, 2650, 2552, 1751, 1645, 1473, 1457, 1439, 1405, 1376, 1330, 1281, 1241, 1186, 1164, 1138, 1109, 1075, 1040, 1028, 1001, 985, 949, 905, 757, 722, 707, 681.

Mass spectrum (FAB) m/z: 856 ((M+H)⁺, free form)

Example 23

1-(2-{(2R)-2-(3,4-Dichlorophenyl)-4-[3,5-bis(trifluoromethyl)benzoyl]morpholin-2-yl}ethyl)spiro[(2S)-2-({[N-(2-ethoxyethyl)-N-methylamino]acetyl}oxy)]indane-1,4'-piperidine dihydrochloride (Exemplary compound No. 2-130 dihydrochloride)

The reaction was carried out in similar procedure to Example 18b using 200 mg (0.243 mmol) of 1-(2-{(2R)-2-(3,4-dichlorophenyl)-4-[3,5-bis(trifluoromethyl)benzoyl]morpholin-2-yl}ethyl)spiro[(2S)-2-(bromoacetyl)oxy]indane-1,4'-piperidine, obtained in Example 18a, and 105 μL (0.75 mmol) of 2-ethoxyethylamine to obtain 68 mg (yield: 31%) of the title compound as a white solid.

IR spectrum ν max cm⁻¹ (KBr): 3372, 3068, 2928, 2653, 2552, 1751, 1645, 1473, 1457, 1439, 1406, 1376, 1280, 1241, 1186, 1138, 1109, 1076, 1028, 987, 905, 758, 681.

Mass spectrum (FAB) m/z: 830 ((M+H)⁺, free form)

Example 24

1-(2-{(2R)-2-(3,4-Dichlorophenyl)-4-[3,5-bis(trifluoromethyl)benzoyl]morpholin-2-yl}ethyl)spiro[(2S)-2-({[4-(2-hydroxyethyl)piperidin-1-yl]acetyl}oxy)]indane-1,4'-piperidine dihydrochloride (Exemplary compound No. 2-146 dihydrochloride)

The reaction was carried out in similar procedure to Example 18b using 200 mg (0.243 mmol) of 1-(2-{(2R)-2-(3,4-dichlorophenyl)-4-[3,5-bis(trifluoromethyl)benzoyl]morpholin-2-yl}ethyl)spiro[(2S)-2-(bromoacetyl)oxy]indane-1,4'-piperidine, obtained in Example 18a, and 92 mg (0.75 mmol) of 4-piperidine ethanol to obtain 48 mg (yield: 21%) of the title compound as a white solid.

IR spectrum ν max cm⁻¹ (KBr): 3372, 3068, 2928, 2653, 2552, 1751, 1645, 1473, 1457, 1439, 1406, 1376, 1280, 1241, 1186, 1138, 1109, 1076, 1028, 987, 905, 758, 681.

Mass spectrum (FAB) m/z: 870 ((M+H)⁺, free form)

Example 25

1-(2-{(2R)-2-(3,4-Dichlorophenyl)-4-[3,5-bis(trifluoromethyl)benzoyl]morpholin-2-yl}ethyl)spiro((2S)-2-{[(isopropylamino)acetyl]oxy})indane-1,4'-piperidine dihydrochloride (Exemplary compound No. 2-134 dihydrochloride)

The reaction was carried out in similar procedure to Example 18b using 200 mg (0.243 mmol) of 1-(2-{(2R)-2-(3,4-dichlorophenyl)-4-[3,5-bis(trifluoromethyl)benzoyl]morpholin-2-yl}ethyl)spiro[(2S)-2-(bromoacetyl)oxy]indane-1,4'-piperidine, obtained in Example 18a, and 64 μL (0.75 mmol) of 2-propylamine to obtain 50 mg (yield: 24%) of the title compound as a white solid.

IR spectrum ν max cm⁻¹ (KBr): 3400, 2931, 2664, 2569, 2423, 1752, 1645, 1473, 1458, 1439, 1376, 1320, 1281, 1240, 1207, 1186, 1139, 1109, 1098, 1075, 1129, 905, 707, 681.

Mass spectrum (FAB) m/z: 800 ((M+H)⁺, free form)

Example 26

1-(2-{(2R)-2-(3,4-Dichlorophenyl)-4-[3,5-bis(trifluoromethyl)benzoyl]morpholin-2-yl}ethyl)spiro[(2S)-2-({[bis(2-methoxyethyl)amino]acetyl}oxy)]indane-1,4'-piperidine dihydrochloride (Exemplary compound No. 2-140 dihydrochloride)

The reaction was carried out in similar procedure to Example 18b using 200 mg (0.243 mmol) of 1-(2-{(2R)-2-(3,4-dichlorophenyl)-4-[3,5-bis(trifluoromethyl)benzoyl]morpholin-2-yl}ethyl)spiro[(2S)-2-(bromoacetyl)oxy]indane-1,4'-piperidine, obtained in Example 18a, and 97 μL (0.75 mmol) of bis(2-methoxyethyl)amine to obtain 74 mg (yield: 32%) of the title compound as a white solid.

IR spectrum ν max cm⁻¹ (KBr): 3407, 2931, 2652, 2527, 2424, 1751, 1645, 1473, 1458, 1440, 1376, 1282, 1240, 1223, 1187, 1164, 1137, 1028, 989, 905, 757, 707, 681.

Mass spectrum (FAB) m/z: 874 ((M+H)⁺, free form)

Example 27

1-(2-{(2R)-2-(3,4-Dichlorophenyl)-4-[3,5-bis(trifluoromethyl)benzoyl]morpholin-2-yl}ethyl)spiro{(2S)-2-[(carboxymethyl)oxy]}indane-1,4'-piperidine sodium salt (Exemplary compound No. 2-147 sodium salt)

Example 27a 1-(2-{(2R)-2-(3,4-Dichlorophenyl)-4-[3,5-bis(trifluoromethyl)benzoyl]morpholin-2-yl}ethyl)spiro[(2S)-2-(t-butoxycarbonylmethoxy)]indane-1,4'-piperidine 5 g (7.13 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine was dissolved in 6 mL of tetrahydrofuran and 21 mL (10.5 mmol) of potassium bis(trimethylsilyl)amide (0.5 mol/L toluene solution) was added dropwise thereto under ice-cooling over 10 minutes. After the mixture was stirred under ice-cooling for 10 minutes, 1.58 mL (10.7 mmol) of t-butyl bromoacetate was added thereto. After the mixture was stirred under ice-cooling for 10 minutes, the temperature of the mixture was returned to room temperature and the mixture was stirred for 1 hour. Water was added and the mixture was quenched and extracted with ethyl acetate. The organic layer was washed successively with water and a saturated NaCl solution and dried over anhydrous sodium sulfate. The solvent was distilled off under reduced pressure and the residue was purified by silica gel chromatography (eluting solvent: ethyl acetate/n-hexane=4/1) to obtain 3.45 g (yield: 59%) of the title compound.

¹H-NMR spectrum (500 MHz, CD₃OD) δ ppm: 8.34-7.98 (3H, m), 7.78-7.03 (7H, m), 4.52-4.33 (1H, m), 4.15-1.65 (22H, m), 1.39 (9H, s).

IR spectrum ν max cm⁻¹ (KBr): 2926, 1749, 1646, 1473, 1375, 1280, 1137.

Mass spectrum (FAB) m/z: 815 ((M+H)⁺, free form)

Example 27b 1-(2-{(2R)-2-(3,4-Dichlorophenyl)-4-[3,5-bis(trifluoromethyl)benzoyl]morpholin-2-yl}ethyl)spiro{(2S)-2-[(carboxymethyl)oxy]}indane-1,4'-piperidine 7.5 g (9.19 mmol) of 1-(2-{(2R)-2-(3,4-dichlorophenyl)-4-[3,5-bis(trifluoromethyl)benzoyl]morpholin-2-yl}ethyl)spiro[(2S)-2-(t-butoxycarbonylmethoxy)]indane-1,4'-piperidine, obtained in Example 27a, was dissolved in 75 mL of methylene chloride and 75 mL of a 90% aqueous trifluoroacetic acid solution was added dropwise thereto over 5 minutes. After the mixture was stirred at room temperature for 2 hours, the solvent was distilled off under reduced pressure. The thus obtained residue was dissolved in ethyl acetate, washed successively with water and a saturated NaCl solution and dried over anhydrous sodium sulfate. The solvent was distilled off under reduced pressure to obtain 6.5 g (yield: 96%) of the title compound.

$^1$H-NMR spectrum (500 MHz, CD$_3$OD) δ ppm: 8.20-7.90 (3H, m), 7.86-7.10 (7H, m), 4.55-1.55 (23H, m).

IR spectrum ν max cm$^{-1}$ (KBr): 2930, 1726, 1645, 1474, 1376, 1281, 1138.

Mass spectrum (FAB) m/z: 759 ((M+H)$^+$, free form)

Example 27c 1-(2-{(2R)-2-(3,4-Dichlorophenyl)-4-[3,5-bis(trifluoromethyl)benzoyl]morpholin-2-yl}ethyl)spiro{(2S)-2-[(carboxymethyl)oxy]}indane-1,4'-piperidine sodium salt 300 mg (0.39 mmol) of 1-(2-{(2R)-2-(3,4-dichlorophenyl)-4-[3,5-bis(trifluoromethyl)benzoyl]morpholin-2-yl}ethyl)spiro{(2S)-2-[(carboxymethyl)oxy]}indane-1,4'-piperidine, obtained in Example 27b, was dissolved in 15 mL of 1N aqueous sodium hydroxide solution and the mixture was extracted twice with ethyl acetate, washed with a saturated NaCl solution and dried over anhydrous sodium sulfate. The solvent was distilled off under reduced pressure and the thus obtained residue was recrystallized from n-hexane to obtain 135 mg (yield: 44%) of the title compound as a white crystal.

$^1$H-NMR spectrum (500 MHz, CD$_3$OD) δ ppm: 8.34-7.98 (3H, m), 7.79-7.01 (7H, m), 4.59-4.42 (1H, m), 4.21-4.05 (2H, m), 3.96-2.83 (10H, m), 2.70-1.60 (10H, m).

IR spectrum ν max cm$^{-1}$ (KBr): 2922, 1645, 1615, 1280, 1138.

Mass spectrum (FAB) m/z: 759 ((M+H)$^+$, free form)

Elementary analysis (for C$_{36}$H$_{33}$Cl$_2$F$_6$N$_2$NaO$_5$ 4H$_2$O) Calculated (%): C, 50.65; H, 4.84; Cl, 8.31; F, 13.35; N, 3.28; Na, 2.69. Found (%): C, 50.59; H, 4.32; Cl, 7.94; F, 13.07; N, 3.36; Na, 3.63.

Optical rotation: [α]$_D^{20}$=+43.4 (c=0.50, methanol)

Example 28

1-(2-{(2R)-2-(3,4-Dichlorophenyl)-4-[3,5-bis(trifluoromethyl)benzoyl]morpholin-2-yl}ethyl)spiro{(2S)-2-[2-(morpholin-4-yl)-2-oxoethoxy]}indane-1,4'-piperidine hydrochloride (Exemplary compound No. 2-156 hydrochloride)

300 mg (0.39 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, obtained in Example 27b, was dissolved in 5 mL of methylene chloride and 57 μL (0.79 mmol) of thionyl chloride was added thereto. One drop of dimethylformamide was added to the mixture, followed by stirring at room temperature for 2 hours. The solvent was distilled off under reduced pressure, 5 mL of methylene chloride was added to the obtained residue and 103 μL (1.18 mmol) of morpholine was added thereto under ice-cooling. After the mixture was stirred at room temperature for 2 hours, it was washed successively with water and a saturated NaCl solution and dried over anhydrous sodium sulfate. The solvent was distilled off under reduced pressure and the thus obtained residue was purified by thin layer chromatography (eluting solvent: methylene chloride/methanol=9/1) to obtain 105 mg (yield: 32%) of 1-(2-{(2R)-2-(3,4-dichlorophenyl)-4-[3,5-bis(trifluoromethyl)benzoyl]morpholin-2-yl}ethyl)spiro{(2S)-2-[2-(morpholin-4-yl)-2-oxoethoxy]}indane-1,4'-piperidine.

The thus obtained 1-(2-{(2R)-2-(3,4-dichlorophenyl)-4-[3,5-bis(trifluoromethyl)benzoyl]morpholin-2-yl}ethyl)spiro{(2S)-2-[2-(morpholin-4-yl)-2-oxoethoxy]}indane-1,4'-piperidine was dissolved in 4 mL of ethanol and 0.5 mL of 4N hydrochloric acid-dioxane was added thereto. The solvent was distilled off under reduced pressure, followed by azeotropy twice with diethyl ether. The thus obtained residue was recrystallized from hexane to obtain 70 mg (yield: 64%) of the title compound as a white crystal.

$^1$H-NMR spectrum (500 MHz, CD$_3$OD) δ ppm: 8.35-8.00 (3H, m), 7.85-7.08 (7H, m), 4.37-1.58 (31H, m).

IR spectrum ν max cm$^{-1}$ (KBr): 2923, 1650, 1437, 1375, 1280, 1138.

Mass spectrum (FAB) m/z: 828 ((M+H)$^+$, free form)

Elementary analysis (for C$_{40}$H$_{42}$Cl$_3$F$_6$N$_3$O$_4$ 3H$_2$O) Calculated (%): C, 52.27; H, 5.26; Cl, 11.57; F, 12.40; N, 4.57. Found (%): C, 52.56; H, 5.05; Cl, 12.14; F, 12.67; N, 4.70.

Optical rotation: [α]$_D^{20}$=+52.2 (c=0.50, methanol)

Example 29

1-(2-{(2R)-2-(3,4-Dichlorophenyl)-4-[3,5-bis(trifluoromethyl)benzoyl]morpholin-2-yl}ethyl)spiro[(2S)-2-(2-amino-2-oxoethoxy)]indane-1,4'-piperidine hydrochloride (Exemplary compound No. 2-150 hydrochloride)

The reaction was carried out in similar procedure to Example 28 using 300 mg (0.39 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine and 2.5 mL of ammonia water to obtain 162 mg (yield: 52%) of the title compound as a white crystal.

$^1$H-NMR spectrum (500 MHz, CD$_3$OD) δ ppm: 8.32-7.98 (3H, m), 7.87-6.88 (7H, m), 4.30-1.53 (23H, m).

IR spectrum ν max cm$^{-1}$ (KBr): 2928, 1645, 1438, 1376, 1280, 1137.

Mass spectrum (FAB) m/z: 758 ((M+H)$^+$, free form)

Elementary analysis (for C$_{36}$H$_{36}$Cl$_3$F$_6$N$_3$O$_4$ 4H$_2$O) Calculated (%): C, 49.87; H, 5.11; Cl, 12.27; F, 13.15; N, 4.85. Found (%): C, 49.84; H, 4.81; Cl, 14.91; F, 13.70; N, 4.83.

Optical rotation: [α]$_D^{20}$=+55.5 (c=0.50, methanol)

Example 30

1-(2-{(2R)-2-(3,4-Dichlorophenyl)-4-[3,5-bis(trifluoromethyl)benzoyl]morpholin-2-yl}ethyl)spiro{(2S)-2-[2-(N,N-dimethyamino)-2-oxoethoxy]}indane-1,4'-piperidine hydrochloride (Exemplary compound No. 2-151 hydrochloride)

The reaction was carried out in similar procedure to Example 28 using 300 mg (0.39 mmol) of 1-(2-{(2R)-2-(3,4-dichlorophenyl)-4-[3,5-bis(trifluoromethyl)benzoyl]morpholin-2-yl}ethyl)spiro{[(2S)-2-carboxymethoxy]}indane-1,4'-piperidine and 2.5 mL of an aqueous dimethylamine solution to obtain 166 mg (yield: 51%) of the title compound as a white crystal.

$^1$H-NMR spectrum (500 MHz, CD$_3$OD) δ ppm: 8.34-8.30 (3H, m), 7.85-7.05 (7H, m), 4.31-1.58 (29H, m).

IR spectrum ν max cm$^{-1}$ (KBr): 2929, 1650, 1439, 1376, 1280, 1137.

Mass spectrum (FAB) m/z: 786 ((M+H)$^+$, free form)

Elementary analysis (for C$_{38}$H$_{40}$Cl$_3$F$_6$N$_3$O$_4$ 2H$_2$O) Calculated (%): C, 53.13; H, 5.16; Cl, 12.38; F, 13.27; N, 4.89. Found (%): C, 53.37; H, 5.75; Cl, 13.39; F, 12.96; N, 4.60.

Optical rotation: $[α]_D^{20}$=+49.1 (c=0.50, methanol)

Example 31

1-(2-{(2R)-2-(3,4-Dichlorophenyl)-4-[3,5-bis(trifluoromethyl)benzoyl]morpholin-2-yl}ethyl)spiro((2S)-2-{2-[bis(2-hydroxyethyl)amino]-2-oxoethoxy})indane-1,4'-piperidine dihydrochloride (Exemplary compound No. 2-153 dihydrochloride)

The reaction was carried out in similar procedure to Example 28 using 300 mg (0.39 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine and 113 μL (1.18 mmol) of diethanolamine to obtain 87 mg (yield: 25%) of the title compound as a white crystal.

$^1$H-NMR spectrum (500 MHz, CD$_3$OD) δ ppm: 8.33-8.01 (3H, m), 7.85-7.06 (7H, m), 4.41-1.58 (31H, m).

IR spectrum ν max cm$^{-1}$ (KBr): 2683, 1753, 1645, 1439, 1376, 1281, 1136.

Mass spectrum (FAB) m/z: 846 ((M+H)$^+$, free form)

Elementary analysis (for C$_{40}$H$_{45}$Cl$_4$F$_6$N$_3$O$_6$ 4H$_2$O) Calculated (%): C, 48.45; H, 5.39; Cl, 14.30; F, 11.49; N, 4.24. Found (%): C, 48.51; H, 4.99; Cl, 15.23; F, 11.77; N, 4.28.

Optical rotation: $[α]_D^{20}$=+45.8 (c=0.50, methanol)

Example 32

1-(2-{(2R)-2-(3,4-Dichlorophenyl)-4-[3,5-bis(trifluoromethyl)benzoyl]morpholin-2-yl}ethyl)spiro((2S)-2-{[N-(2-hydroxyethyl)-N-methylamino]-2-oxoethoxy})indane-1,4'-piperidine hydrochloride (Exemplary compound No. 2-155 hydrochloride)

The reaction was carried out in similar procedure to Example 28 using 300 mg (0.39 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine and 95 μL (1.18 mmol) of 2-(methylamino)ethanol to obtain 162 mg (yield: 48%) of the title compound as a white crystal.

$^1$H-NMR spectrum (500 MHz, CD$_3$OD) δ ppm: 8.31-7.99 (3H, m), 7.88-7.06 (7H, m), 4.40-1.55 (30H, m).

IR spectrum ν max cm$^{-1}$ (KBr): 2928, 1753, 1647, 1473, 1438, 1376, 1280, 1137.

Mass spectrum (FAB) m/z: 816 ((M+H)$^+$, free form)

Elementary analysis (for C$_{39}$H$_{41}$Cl$_2$F$_6$N$_3$O$_5$ 4/3HCl 3H$_2$O) Calculated (%): C, 50.95; H, 5.30; Cl, 12.85; F, 12.40; N, 4.57. Found (%): C, 50.63; H, 5.13; Cl, 13.77; F, 13.05; N, 4.49.

Optical rotation: $[α]_D^{20}$=+50.3 (c=0.33, methanol)

Example 33

1-(2-{(2R)-2-(3,4-Dichlorophenyl)-4-[3,5-bis(trifluoromethyl)benzoyl]morpholin-2-yl}ethyl)spiro((2S)-2-{2-[N-(2-hydroxyethyl)amino]-2-oxoethoxy})indane-1,4'-piperidine hydrochloride (Exemplary compound No. 2-154 hydrochloride)

The reaction was carried out in similar procedure to Example 28 using 300 mg (0.39 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine and 71 μL (1.18 mmol) of ethanolamine to obtain 142 mg (yield: 43%) of the title compound as a white crystal.

$^1$H-NMR spectrum (500 MHz, CD$_3$OD) δ ppm: 8.33-7.98 (3H, m), 7.86-7.08 (7H, m), 4.32-1.53 (27H, m).

IR spectrum ν max cm$^{-1}$ (KBr): 2928, 1647, 1439, 1376, 1280, 1137.

Mass spectrum (FAB) m/z: 802((M+H)$^+$, free form)

Elementary analysis (for C$_{38}$H$_{40}$Cl$_3$F$_6$N$_3$O$_5$ 3H$_2$O) Calculated (%): C, 51.10; H, 5.19; Cl, 11.91; F, 12.76; N, 4.70. Found (%): C, 51.00; H, 4.95; Cl, 12.76; F, 13.00; N, 4.72.

Optical rotation: $[α]_D^{20}$=+58.4 (c=0.50, methanol)

Example 34

1-(2-{(2R)-2-(3,4-Dichlorophenyl)-4-[3,5-bis(trifluoromethyl)benzoyl]morpholin-2-yl}ethyl)spiro{(2S)-2-[2-(piperidin-1-yl)-2-oxoethoxy]}indane-1,4'-piperidine hydrochloride (Exemplary compound No. 2-157 hydrochloride)

The reaction was carried out in similar procedure to Example 28 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 119 μL (1.18 mmol) of piperidine to obtain 168 mg (yield: 50%) of the title compound as a white crystal.

IR spectrum ν max cm$^{-1}$ (KBr): 3358, 2931, 1720, 1645, 1476, 1376, 1280, 1139.

Mass spectrum (FAB) m/z: 831 ((M+H)$^+$, free form)

Example 35

1-(2-{(2R)-2-(3,4-Dichlorophenyl)-4-[3,5-bis(trifluoromethyl)benzoyl]morpholin-2-yl}ethyl)spiro[(2S)-2-(2-hydroxyethoxy)]indane-1,4'-piperidine hydrochloride (Exemplary compound No. 2-159 hydrochloride)

Example 35

1-(2-{(2R)-2-(3,4-Dichlorophenyl)-4-[3,5-bis(trifluoromethyl)benzoyl]morpholin-2-yl}ethyl)spiro[(2S)-2-(2-hydroxyethoxy)]indane-1,4'-piperidine 3 g (3.95 mmol) of 1-(2-{(2R)-2-(3,4-dichlorophenyl)-4-[3,5-bis(trifluoromethyl)benzoyl]morpholin-2-yl}ethyl)

spiro[(2S)-2-carboxymethoxy]indane-1,4'-piperidine, obtained in Example 27b, was dissolved in 30 mL of tetrahydrofuran and 5.9 mL (5.9 mmol) of borane-tetrahydrofuran complex (1 mol/L tetrahydrofuran solution) was added dropwise thereto under ice-cooling over 10 minutes. After the mixture was stirred under ice-cooling for 30 minutes, the temperature of the mixture was returned to room temperature, followed by stirring for 1 hour. Water was added thereto and the mixture was quenched and extracted with ethyl acetate. The extract was washed successively with water and a saturated NaCl solution and dried over anhydrous sodium sulfate. The solvent was distilled off under reduced pressure, and the thus obtained residue was purified by silica gel chromatography (eluting solvent: ethyl acetate/methanol=100/2) to obtain 2.1 g (yield: 71%) of the title compound.

$^1$H-NMR spectrum (500 MHz, CD$_3$OD) δ ppm: 8.20-7.90 (3H, m), 7.82-7.06 (7H, m), 4.40-1.42 (25H, m).

IR spectrum ν max cm$^{-1}$ (KBr): 2924, 1645, 1473, 1375, 1281, 1139.

Mass spectrum (FAB) m/z: 7745 ((M+H)$^+$, free form)

Example 35b 1-(2-{(2R)-2-(3,4-Dichlorophenyl)-4-[3,5-bis(trifluoromethyl)benzoyl]morpholin-2-yl}ethyl)spiro[(2S)-2-(2-hydroxyethoxy)]indane-1,4'-piperidine hydrochloride 300 mg (0.4 mmol) of 1-(2-{(2R)-2-(3,4-dichlorophenyl)-4-[3,5-bis(trifluoromethyl)benzoyl]morpholin-2-yl}ethyl)spiro[(2S)-2-(2-hydroxyethoxy)]indane-1,4'-piperidine, obtained in Example 35a, was dissolved in 6 mL of ethanol and 0.5 mL of 4N hydrochloric acid-dioxane was added thereto. The solvent was distilled off under reduced pressure, followed by azeotropy twice with diethyl ether. The thus obtained residue was recrystallized from hexane to obtain 215 mg (yield: 68%) of the title compound as a white crystal.

$^1$H-NMR spectrum (500 MHz, CD3OD) δ ppm: 8.31-8.00 (3H, m), 7.85-7.05 (7H, m), 4.20-1.50 (25H, m).

IR spectrum ν max cm$^{-1}$ (KBr): 2928, 1645, 1438, 1376, 1280, 1137.

Mass spectrum (FAB) m/z: 745 ((M+H)$^+$, free form)

Elementary analysis (for C$_{36}$H$_{37}$Cl$_3$F$_6$N$_2$O$_4$ 2H$_2$O) Calculated (%): C, 52.92; H, 4.93; Cl, 13.02; F, 13.95; N, 3.43. Found (%): C, 52.61; H, 4.70; Cl, 12.68; F, 14.22; N, 3.48.

Optical rotation: $[\alpha]_D^{20}$=+43.3 (c=0.50, methanol)

Example 36

1-(2-{(2R)-2-(3,4-Dichlorophenyl)-4-[3,5-bis(trifluoromethyl)benzoyl]morpholin-2-yl}ethyl)spiro{(2S)-2-[2-(morpholin-4-yl)ethoxy]}indane-1,4'-piperidine dihydrochloride (Exemplary compound No. 2-166 dihydrochloride)

200 mg (0.27 mmol) of 1-(2-{(2R)-2-(3,4-dichlorophenyl)-4-[3,5-bis(trifluoromethyl)benzoyl]morpholin-2-yl}ethyl)spiro[(2S)-2-(2-hydroxyethoxy)]indane-1,4'-piperidine, obtained in Example 35b, was dissolved in 4 mL of methylene chloride and 56 μL (0.4 mmol) of triethylamine was added thereto, and 27 μL (0.35 mmol) of methanesulfonyl chloride was added to the mixture under ice-cooling, followed by stirring at room temperature for 30 minutes. Water was added to the reaction mixture and the methylene chloride layer was washed with water and a saturated NaCl solution and dried over anhydrous sodium sulfate. The solvent was distilled off under reduced pressure and the thus obtained residue was dissolved in 6 mL of dimethylacetamide. 34 mg (0.35 mmol) of sodium hydrogencarbonate, 66 mg (0.35 mmol) of potassium iodide and 35 μL (0.35 mmol) of morpholine were added to the solution, and the mixture was stirred at 80° C. for 8 hours. The temperature of the reaction mixture was returned to room temperature, and the mixture was poured into water, followed by twice extraction with ethyl acetate. The ethyl acetate layer was combined, washed successively with water and a saturated NaCl solution and dried over anhydrous sodium sulfate. The solvent was distilled off under reduced pressure and the obtained residue was purified by thin layer chromatography (eluting solvent: methylene chloride/methanol=9/1) to obtain 125 mg (yield: 57%) of 1-(2-{(2R)-2-(3,4-dichlorophenyl)-4-[3,5-bis(trifluoromethyl)benzoyl]morpholin-2-yl}ethyl)spiro{(2S)-2-[2-[(morpholin-4-yl)ethoxy]]}indane-1,4'-piperidine.

125 mg (0.15 mmol) of the obtained 1-(2-{(2R)-2-(3,4-dichlorophenyl)-4-[3,5-bis(trifluoromethyl)benzoyl]morpholin-2-yl}ethyl)spiro{(2S)-2-[2-(morpholin-4-yl)ethoxy]}indane-1,4'-piperidine was dissolved in 3 mL of ethanol and 0.5 mL of 4N hydrochloric acid-dioxane was added thereto. The solvent was distilled off under reduced pressure, followed by azeotropy twice with diethyl ether. The thus obtained residue was recrystallized from hexane to obtain 97 mg (yield: 74%) of the title compound as a white crystal.

$^1$H-NMR spectrum (500 MHz, CD$_3$OD) δ ppm: 8.35-8.01 (3H, m), 7.88-7.08 (7H, m), 4.29-1.60 (33H, m).

IR spectrum ν max cm$^{-1}$ (KBr): 2927, 2571, 1644, 1439, 1376, 1281, 1136.

Mass spectrum (FAB) m/z: 814 ((M+H)$^+$, free form)

Elementary analysis (for C$_{40}$H$_{45}$Cl$_4$F$_6$N$_3$O$_4$ 4H$_2$O) Calculated (%): C, 50.06; H, 5.57; Cl, 14.78; F, 11.88; N, 4.38. Found (%): C, 48.62; H, 5.03; Cl, 15.27; F, 11.61; N, 3.48.

Optical rotation: $[\alpha]_D^{20}$=+48.7 (c=0.50, methanol)

Example 37

1-(2-{(2R)-2-(3,4-Dichlorophenyl)-4-[3,5-bis(trifluoromethyl)benzoyl]morpholin-2-yl}ethyl)spiro{(2S)-2-[2-(piperidin-1-yl)ethoxy]}indane-1,4'-piperidine dihydrochloride (Exemplary compound No. 2-167 dihydrochloride)

The reaction was carried out in similar procedure to Example 36 using 200 mg (0.27 mmol) of 1-(2-{(2R)-2-(3,4-dichlorophenyl)-4-[3,5-bis(trifluoromethyl)benzoyl]morpholin-2-yl}ethyl)spiro[(2S)-2-(2-hydroxyethoxy)]indane-1,4'-piperidine and 40 μL (0.4 mmol) of piperidine to obtain 32 mg (yield: 14%) of the title compound as a white crystal.

$^1$H-NMR spectrum (500 MHz, CD$_3$OD) δ ppm: 8.31-8.00 (3H, m), 7.88-7.07 (7H, m), 4.31-1.51 (35H, m).

IR spectrum ν max cm$^{-1}$ (KBr): 2943, 2650, 1644, 1439, 1376, 1281, 1137.

Mass spectrum (FAB) m/z: 812 ((M+H)$^+$, free form)

Elementary analysis (for C$_{41}$H$_{47}$Cl$_4$F$_6$N$_3$O$_3$ 8H$_2$O) Calculated (%): C, 47.82; H, 6.17; Cl, 13.77; F, 11.07; N, 4.08. Found (%): C, 48.29; H, 5.26; Cl, 15.53; F, 11.03; N, 4.27.

Optical rotation: $[\alpha]_D^{20}$=+44.0 (c=0.50, methanol)

Example 38

1-(2-{(2R)-2-(3,4-Dichlorophenyl)-4-[3,5-bis(trifluoromethyl)benzoyl]morpholin-2-yl}ethyl)spiro{(2S)-2-[2-(N,N-dimethylamino)ethoxy]}indane-1,4'-piperidine dihydrochloride (Exemplary compound No. 2-161 dihydrochloride)

The reaction was carried out in similar procedure to Example 36 using 200 mg (0.27 mmol) of 1-(2-{(2R)-2-(3,4-dichlorophenyl)-4-[3,5-bis(trifluoromethyl)benzoyl]morpholin-2-yl}ethyl)spiro[(2S)-2-(2-hydroxyethoxy)]indane-1,4'-piperidine and 33 mg (0.4 mmol) of dimethylamine hydrochloride to obtain 54 mg (yield: 25%) of the title compound as a white crystal.

$^1$H-NMR spectrum (500 MHz, CD$_3$OD) δ ppm: 8.31-8.00 (3H, m), 7.87-7.08 (7H, m), 4.35-1.53 (31H, m).

IR spectrum ν max cm$^{-1}$ (KBr): 2927, 2654, 1644, 1474, 1376, 1281, 1137.

Mass spectrum (FAB) m/z: 772 ((M+H)$^+$, free form)

Elementary analysis (for C$_{38}$H$_{43}$Cl$_4$F$_6$N$_3$O$_3$ 3H$_2$O) Calculated (%): C, 50.73; H, 5.49; Cl, 15.76; F, 12.67; N, 4.67. Found (%): C, 47.55; H, 5.23; Cl, 16.68; F, 12.43; N, 4.48.

Optical rotation: $[α]_D^{20}$=+50.5 (c=0.50, methanol)

Example 39

1-(2-{(2R)-2-(3,4-Dichlorophenyl)-4-[3,5-bis(trifluoromethyl)benzoyl]morpholin-2-yl}ethyl)spiro((2S)-2-{2-[N-(2-hydroxyethyl)-N-methylamino]ethoxy})indane-1,4'-piperidine dihydrochloride (Exemplary compound No. 2-165 dihydrochloride)

The reaction was carried out in similar procedure to Example 36 using 200 mg (0.27 mmol) of 1-(2-{(2R)-2-(3,4-dichlorophenyl)-4-[3,5-bis(trifluoromethyl)benzoyl]morpholin-2-yl}ethyl)spiro[(2S)-2-(2-hydroxyethoxy)]indane-1,4'-piperidine and 32 μL (0.4 mmol) of 2-(methylamino)ethanol to obtain 158 mg (yield: 70%) of the title compound as a white crystal.

$^1$H-NMR spectrum (500 MHz, CD$_3$OD) δ ppm: 8.30-8.01 (3H, m), 7.87-7.08 (7H, m), 4.28-1.54 (32H, m).

IR spectrum ν max cm$^{-1}$ (KBr): 2928, 2654, 1644, 1473, 1376, 1281, 1138.

Mass spectrum (FAB) m/z: 802 ((M+H)$^+$, free form)

Elementary analysis (for C$_{39}$H$_{45}$Cl$_4$F$_6$N$_3$O$_4$ 3H$_2$O) Calculated (%): C, 50.39; H, 5.53; Cl, 15.25; F, 12.26; N, 4.52. Found (%): C, 50.00; H, 5.50; Cl, 15.22; F, 11.16; N, 4.30.

Optical rotation: $[α]_D^{20}$=+52.3 (c=0.50, methanol)

Example 40

1-(2-{(2R)-2-(3,4-Dichlorophenyl)-4-[3,5-bis(trifluoromethyl)benzoyl]morpholin-2-yl}ethyl)spiro((2S)-2-{2-[N-(2-hydroxyethyl)amino]ethoxy})indane-1,4'-piperidine dihydrochloride (Exemplary compound No. 2-164 dihydrochloride)

The reaction was carried out in similar procedure to Example 36 using 200 mg (0.27 mmol) of 1-(2-{(2R)-2-(3,4-dichlorophenyl)-4-[3,5-bis(trifluoromethyl)benzoyl]morpholin-2-yl}ethyl)spiro[(2S)-2-(2-hydroxyethoxy)]indane-1,4'-piperidine and 24 μL (0.4 mmol) of ethanolamine to obtain 96 mg (yield: 43%) of the title compound as a white crystal.

$^1$H-NMR spectrum (500 MHz, CD$_3$OD) δ ppm: 8.30-8.02 (3H, m) 7.87-7.06 (7H, m), 4.28-1.50 (29H, m).

IR spectrum ν max cm$^{-1}$ (KBr): 2930, 2681, 1644, 1439, 1376, 1280, 1138.

Mass spectrum (FAB) m/z: 788 ((M+H)$^+$, free form)

Elementary analysis (for C$_{38}$H$_{43}$Cl$_4$F$_6$N$_3$O$_4$ 4H$_2$O) Calculated (%): C, 48.89; H, 5.51; Cl, 15.19; F, 12.21; N, 4.50. Found (%): C, 48.75; H, 4.79; Cl, 15.85; F, 12.20; N, 4.57.

Optical rotation: $[α]_D^{20}$=+52.5 (c=0.50, methanol)

Example 41

1-(2-{(2R)-2-(3,4-Dichlorophenyl)-4-[3,5-bis(trifluoromethyl)benzoyl]morpholin-2-yl}ethyl)spiro((2S)-2-{2-[bis(2-hydroxyethyl)amino]ethoxy})indane-1,4'-piperidine dihydrochloride (Exemplary compound No. 2-163 dihydrochloride)

The reaction was carried out in similar procedure to Example 36 using 200 mg (0.27 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 33 μL (0.35 mmol) of diethanolamine to obtain 90 mg (yield: 39%) of the title compound as a white crystal.

IR spectrum ν max cm$^{-1}$ (KBr): 3358, 2931, 1720, 1645, 1476, 1376, 1280, 1139.

Mass spectrum (FAB) m/z: 832 ((M+H)$^+$, free form)

Example 42

1-(2-{(2R)-2-(3,4-Dichlorophenyl)-4-[3,5-bis(trifluoromethyl)benzoyl]morpholin-2-yl}ethyl)spiro((2S)-2-{[({[bis(2-hydroxyethyl)amino]carbonyl}amino)carbonyl]oxy})indane-1,4'-piperidine hydrochloride (Exemplary compound No. 2-172 hydrochloride)

300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine was dissolved in 5 mL of methylene chloride and 55 μL (0.64 mmol) of N-(chlorocarbonyl)isocyanate was added thereto under ice-cooling. After the mixture was stirred under ice-cooling for 30 minutes, 61 μL (0.64 mmol) of diethanolamine was added thereto and the mixture was stirred under ice-cooling for 30 minutes. After the temperature of the mixture was returned to room temperature and the mixture was stirred for 1 hour, it was washed successively with 1N aqueous hydrochloric acid, water and a saturated NaCl solution and dried over anhydrous sodium sulfate. The solvent was distilled off under reduced pressure and the thus obtained residue was purified by thin layer chromatography (eluting solvent: methylene chloride/methanol=9/1) to obtain 223 mg (yield: 60%) of 1-(2-{(2R)-2-(3,4-dichlorophenyl)-4-[3,5-bis(trifluoromethyl)benzoyl]morpholin-2-yl}ethyl)spiro{(2S)-2-{[({[bis(2-hydroxyethyl)amino]carbonyl}amino)carbonyl]oxy}indane-1,4'-piperidine.

223 mg (0.25 mmol) of the obtained 1-(2-{(2R)-2-(3,4-dichlorophenyl)-4-[3,5-bis(trifluoromethyl)benzoyl]morpholin-2-yl}ethyl)spiro[(2S)-2-{[({[bis(2-hydroxyethyl)amino]carbonyl}amino)carbonyl]oxy}indane-1,4'-piperidine was dissolved in 4 mL of ethanol and 0.5 mL of 4N hydrochloric acid-dioxane was added thereto. The solvent was distilled off under reduced pressure, followed by azeotropy twice with diethyl ether. The thus obtained residue was recrystallized from hexane to obtain 179 mg (yield: 77%) of the title compound as a white crystal.

$^1$H-NMR spectrum (500 MHz, CD$_3$OD) δ ppm: 8.33-7.99 (3H, m), 7.85-7.06 (7H, m), 5.34-5.20 (1H, m), 4.15-1.65 (29H, m).

IR spectrum ν max cm$^{-1}$ (KBr): 3394, 2931, 1764, 1646, 1474, 1376, 1281, 1138.
Mass spectrum (FAB) m/z: 875 ((M+H)$^+$, free form)
Elementary analysis (for C$_{40}$H$_{43}$Cl$_3$F$_6$N$_4$O$_7$ 4H$_2$O) Calculated (%): C, 48.81; H, 5.22; Cl, 10.81; F, 11.58; N, 5.69. Found (%): C, 49.02; H, 4.92; Cl, 11.62; F, 11.50; N, 5.86.
Optical rotation: [α]$_D^{20}$=+54.3 (c=0.50, methanol)

Example 43

1-(2-{(2R)-2-(3,4-Dichlorophenyl)-4-[3,5-bis(trifluoromethyl)benzoyl]morpholin-2-yl}ethyl)spiro{(2S)-2-[({[(morpholin-4-yl)carbonyl]amino}carbonyl)oxy]}indane-1,4'-piperidine hydrochloride (Exemplary compound No. 2-175 hydrochloride)

The reaction was carried out in similar procedure to Example 42 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 56 μL (0.64 mmol) of morpholine to obtain 240 mg (yield: 63%) of the title compound as a white crystal.
IR spectrum ν max cm$^{-1}$ (KBr): 3358, 2931, 1720, 1645, 1476, 1376, 1280, 1139.
Mass spectrum (FAB) m/z: 857 ((M+H)$^+$, free form)

Example 44

1-(2-{(2R)-2-(3,4-Dichlorophenyl)-4-[3,5-bis(trifluoromethyl)benzoyl]morpholin-2-yl}ethyl)spiro{(2S)-2-[({[(piperidin-1-yl)carbonyl]amino}carbonyl)oxy]]indane-1,4'-piperidine hydrochloride (Exemplary compound No. 2-176 hydrochloride)

The reaction was carried out in similar procedure to Example 42 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 64 μL (0.64 mmol) of piperidine to obtain 143 mg (yield: 38%) of the title compound as a white crystal.
IR spectrum ν max cm$^{-1}$ (KBr): 3358, 2931, 1720, 1645, 1476, 1376, 1280, 1139.
Mass spectrum (FAB) m/z: 855 ((M+H)$^+$, free form)

Example 45

1-(2-{(2R)-2-(3,4-Dichlorophenyl)-4-[3,5-bis(trifluoromethyl)benzoyl]morpholin-2-yl}ethyl)spiro((2S)-2-{[({[N-(2-hydroxyethyl)-N-methylamino]carbonyl}amino)carbonyl]oxy})indane-1,4'-piperidine hydrochloride (Exemplary compound No. 2-174 hydrochloride)

The reaction was carried out in similar procedure to Example 42 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 52 μL (0.64 mmol) of 2-(methylamino)ethanol to obtain 181 mg (yield: 48%) of the title compound as a white crystal.
$^1$H-NMR spectrum (500 MHz, CD$_3$OD) δ ppm: 8.34-7.98 (3H, m), 7.84-7.10 (7H, m), 5.34-5.20 (1H, m), 4.17-1.64 (28H, m).
IR spectrum ν max cm$^{-1}$ (KBr): 3272, 2930, 1765, 1646, 1475, 1376, 1280, 1138.

Mass spectrum (FAB) m/z: 845 ((M+H)$^+$, free form)
Elementary analysis (for C$_{39}$H$_{41}$Cl$_3$F$_6$N$_4$O$_6$ 3H$_2$O) Calculated (%): C, 50.04; H, 5.06; Cl, 11.36; F, 12.18; N, 5.06. Found (%): C, 50.69; H, 4.82; Cl, 11.00; F, 11.66; N, 6.20.
Optical rotation: [α]$_D^{20}$=+55.8 (c=0.50, methanol)

Example 46

1-(2-{(2R)-2-(3,4-Dichlorophenyl)-4-[3,5-bis(trifluoromethyl)benzoyl]morpholin-2-yl}ethyl)spiro((2S)-2-{[({[N-(2-hydroxyethyl)amino]carbonyl}amino)carbonyl]oxy})indane-1,4'-piperidine hydrochloride (Exemplary compound No. 2-173 hydrochloride)

The reaction was carried out in similar procedure to Example 42 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 39 μL (0.64 mmol) of ethanolamine to obtain 192 mg (yield: 52%) of the title compound as a white crystal.
$^1$H-NMR spectrum (500 MHz, CD$_3$OD) δ ppm: 8.31-7.98 (3H, m), 7.90-7.10 (7H, m), 5.24-5.11 (1H, m), 4.15-1.65 (25H, m).
IR spectrum ν max cm$^{-1}$ (KBr): 3358, 2931, 1720, 1645, 1476, 1376, 1280, 1139.
Mass spectrum (FAB) m/z: 831 ((M+H)$^+$, free form)
Elementary analysis (for C$_{38}$H$_{39}$Cl$_3$F$_6$N$_4$O$_6$ 2H$_2$O) Calculated (%): C, 50.48; H, 4.79; Cl, 11.76; F, 12.61; N, 6.20. Found (%): C, 50.69; H, 4.82; Cl, 11.93; F, 12.09; N, 6.20.
Optical rotation: [α]$_D^{20}$=+69.3 (c=0.50, methanol)

Example 47

1-(2-{(2R)-2-(3,4-Dichlorophenyl)-4-[3,5-bis(trifluoromethyl)benzoyl]morpholin-2-yl}ethyl)spiro{(2S)-2-[({[(morpholin-4-yl)sulfonyl]amino}carbonyl)oxy]}indane-1,4'-piperidine hydrochloride (Exemplary compound No. 2-184 hydrochloride)

300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine was dissolved in 5 mL of methylene chloride and 63 μL (0.64 mmol) of sulfonylisocyanate chloride was added thereto under ice-cooling. After the mixture was stirred under ice-cooling for 30 minutes, 56 μL (0.64 mmol) of morpholine was added thereto and the mixture was stirred under ice-cooling for 30 minutes. After the temperature of the mixture was returned to room temperature and the mixture was stirred for 1 hour, the mixture was washed successively with 1N hydrochloric acid solution, water and a saturated NaCl solution and dried over anhydrous sodium sulfate. The solvent was distilled off under reduced pressure and the thus obtained residue was recrystallized from methanol-water to obtain 215 mg (yield: 56%) of 1-(2-{(2R)-2-(3,4-dichlorophenyl)-4-[3,5-bis(trifluoromethyl)benzoyl]morpholin-2-yl}ethyl)spiro[(2S)-2-({[(morpholin-4-yl-sulfonyl)amino]carbonyl}oxy)]indane-1,4'-piperidine.

215 mg (0.24 mmol) of the obtained 1-(2-{(2R)-2-(3,4-dichlorophenyl)-4-[3,5-bis(trifluoromethyl)benzoyl]morpholin-2-yl}ethyl)spiro[(2S)-2-({[(morpholin-4-yl-sulfonyl)amino]carbonyl}oxy)]indane-1,4'-piperidine was dissolved in 4 mL of ethanol and 0.5 mL of 4N hydrochloric acid-dioxane was added thereto. The solvent was distilled off under reduced pressure, followed by azeotropy twice with diethyl ether. The thus obtained residue was recrystallized from hexane to obtain 181 mg (yield: 81%) of the title compound as a white crystal.

$^1$H-NMR spectrum (500 MHz, CD$_3$OD) δ ppm: 8.31-7.99 (3H, m), 7.87-7.10 (7H, m), 5.35-5.25 (1H, m), 4.21-1.68 (28H, m).

IR spectrum ν max cm$^{-1}$ (KBr): 2926, 1741, 1645, 1455, 1375, 1281, 1162.

Mass spectrum (FAB) m/z: 893 ((M+H)$^+$, free form)

Elementary analysis (for C$_{39}$H$_{41}$Cl$_3$F$_6$N$_4$O$_7$S 2H$_2$O) Calculated (%): C, 48.48; H, 4.69; Cl, 11.01; F, 11.80, N, 5.80; S, 3.32. Found (%): C, 48.11; H, 4.66; Cl, 11.25; F, 11.83, N, 5.87; S, 3.38.

Optical rotation: [α]$_D^{20}$=+61.7 (c=0.50, DMSO)

Example 48

1-(2-{(2R)-2-(3,4-Dichlorophenyl)-4-[3,5-bis(trifluoromethyl)benzoyl]morpholin-2-yl}ethyl)spiro[(2S)-2-({[(aminosulfonyl)amino]carbonyl}oxy)]indane-1,4'-piperidine hydrochloride (Exemplary compound No. 2-178 hydrochloride)

The reaction was carried out in similar procedure to Example 47 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 2.5 mL of ammonia water to obtain 70 mg (yield: 12%) of the title compound as a white crystal.

$^1$H-NMR spectrum (500 MHz, CD$_3$OD) δ ppm: 8.35-7.97 (3H, m), 7.81-7.08 (7H, m), 5.48-5.19 (1H, m), 4.01-1.70 (20H, m).

IR spectrum ν max cm$^{-1}$ (KBr): 2927, 1644, 1439, 1376, 1280, 1139.

Mass spectrum (FAB) m/z: 823 ((M+H)$^+$, free form)

Elementary analysis (for C$_{35}$H$_{34}$Cl$_2$F$_6$N$_4$O$_6$S 1/3HCl 2H$_2$O) Calculated (%): C, 48.22; H, 4.43; Cl, 9.49; F, 13.07; N, 6.43; S, 3.68. Found (%): C, 48.21; H, 4.29; Cl, 10.09; F, 13.39; N, 6.34; S, 3.58.

Optical rotation: [α]$_D^{20}$=+55.0 (c=0.50, DMSO)

Example 49

1-(2-{(2R)-2-(3,4-Dichlorophenyl)-4-[3,5-bis(trifluoromethyl)benzoyl]morpholin-2-yl}ethyl)spiro[(2S)-2-({[(N,N-dimethylaminosulfonyl)amino]carbonyl}oxy)]indane-1,4'-piperidine hydrochloride (Exemplary compound No. 2-179 hydrochloride)

The reaction was carried out in similar procedure to Example 47 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 2.5 mL of an aqueous dimethylamine solution to obtain 90 mg (yield: 25%) of the title compound as a white crystal.

$^1$H-NMR spectrum (500 MHz, CD$_3$OD) δ ppm: 8.36-7.98 (3H, m), 7.82-7.10 (7H, m), 5.35-5.29 (1H, m), 3.99-1.65 (26H, m).

IR spectrum ν max cm$^{-1}$ (KBr): 2954, 1643, 1473, 1375, 1281, 1138.

Mass spectrum (FAB) m/z: 851 ((M+H)$^+$, free form)

Elementary analysis (for C$_{37}$H$_{38}$Cl$_2$F$_6$N$_4$O$_6$S 1/4HCl H$_2$O) Calculated (%): C, 50.57; H, 4.62; Cl, 9.08; F, 12.97; N, 6.38; S, 3.65. Found (%): C, 50.45; H, 4.43; Cl, 9.12; F, 13.31; N, 6.24; S, 3.71.

Optical rotation: [α]$_D^{20}$=+57.8 (c=0.50, DMSO)

Example 50

1-(2-{(2R)-2-(3,4-Dichlorophenyl)-4-[3,5-bis(trifluoromethyl)benzoyl]morpholin-2-yl}ethyl)spiro([2S)-2-({[({N-(2-hydroxyethyl)-N-methylamino]sulfonyl}amino)carbonyl]oxy})indane-1,4'-piperidine (Exemplary compound No. 2-183)

The reaction was carried out in similar procedure to Example 47 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 52 μL (0.64 mmol) of 2-(methylamino)ethanol to obtain 30 mg (yield: 8%) of the title compound as a white crystal.

$^1$H-NMR spectrum (500 MHz, CD$_3$OD) δ ppm: 8.35-7.98 (3H, m), 7.84-7.06 (7H, m), 5.38-5.23 (1H, m), 3.98-1.70 (27H, m).

IR spectrum ν max cm$^{-1}$ (KBr): 2928, 1642, 1473, 1376, 1281, 1139.

Mass spectrum (FAB) m/z: 881 ((M+H)$^+$, free form)

Elementary analysis (for C$_{38}$H$_{40}$Cl$_2$F$_6$N$_4$O$_7$S 3H$_2$O) Calculated (%): C, 48.78; H, 4.95; Cl, 7.58; F, 12.18; N, 5.99; S, 3.43. Found (%): C, 48.52; H, 4.40; Cl, 7.81; F, 11.81; N, 6.22; S, 3.21.

Optical rotation: [α]$_D^{20}$=+39.7 (c=0.50, DMSO)

Example 51

1-(2-{(2R)-2-(3,4-Dichlorophenyl)-4-[3,5-bis(trifluoromethyl)benzoyl]morpholin-2-yl}ethyl)spiro((2S)-2-{[({N-(2-hydroxyethyl)amino]sulfonyl}amino)carbonyl]oxy})indane-1,4'-piperidine (Exemplary compound No. 2-182)

The reaction was carried out in similar procedure to Example 47 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 39 μL (0.64 mmol) of ethanolamine to obtain 67 mg (yield: 17%) of the title compound as a white crystal.

$^1$H-NMR spectrum (500 MHz, CD$_3$OD) δ ppm: 8.31-7.97 (3H, m), 7.78-7.03 (7H, m), 5.37-5.20 (1H, m), 3.98-1.68 (24H, m).

IR spectrum ν max cm$^{-1}$ (KBr): 2927, 1642, 1475, 1376, 1281, 1138.

Mass spectrum (FAB) m/z: 867 ((M+H)$^+$, free form)

Elementary analysis (for C$_{37}$H$_{38}$Cl$_2$F$_6$N$_4$O$_7$S 2H$_2$O) Calculated (%): C, 49.18; H, 4.68; Cl, 7.85; F, 12.61; N, 6.20; S, 3.55. Found (%): C, 49.10; H, 4.45; Cl, 8.53; F, 12.67; N, 6.23; S, 3.29.

Optical rotation: [α]$_D^{20}$=+47.6 (c=0.50, DMSO)

Example 52

1-(2-{(2R)-2-(3,4-Dichlorophenyl)-4-[3,5-bis(trifluoromethyl)benzoyl]morpholin-2-yl}ethyl)spiro((2S)-2-{[({bis(2-hydroxyethyl)amino]sulfonyl}amino)carbonyl]oxy})indane-1,4'-piperidine hydrochloride (Exemplary compound No. 2-181 hydrochloride)

The reaction was carried out in similar procedure to Example 47 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 61 µL (0.64 mmol) of diethanolamine to obtain 60 mg (yield: 16%) of the title compound as a white crystal.

IR spectrum ν max cm$^{-1}$ (KBr): 3406, 2930, 1733, 1643, 1473, 1376, 1281, 1139.

Mass spectrum (FAB) m/z: 911 ((M+H)$^+$, free form)

Example 53

1-(2-{(2R)-2-(3,4-Dichlorophenyl)-4-[3,5-bis(trifluoromethyl)benzoyl]morpholin-2-yl}ethyl)spiro{(2S)-2-[({[(morpholin-4-yl)acetyl]amino}carbonyl)oxy]}indane-1,4'-piperidine hydrochloride (Exemplary compound No. 2-187 hydrochloride)

300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine was dissolved in 5 mL of methylene chloride and 55 µL (0.64 mmol) of N-(chloroacetyl)isocyanate was added thereto under ice-cooling. After the mixture was stirred under ice-cooling for 30 minutes, 56 µL (0.64 mmol) of morpholine was added thereto, followed by stirring under ice-cooling for 30 minutes. After the temperature of the mixture was returned to room temperature and the mixture was stirred for 1 hour, it was washed successively with 1N hydrochloric acid solution, water and a saturated NaCl solution and dried over anhydrous sodium sulfate. The solvent was distilled off under reduced pressure and the thus obtained residue was purified by thin layer chromatography (eluting solvent: methylene chloride/methanol=9/1) to obtain 248 mg (yield: 67%) of 1-(2-{(2R)-2-(3,4-dichlorophenyl)-4-[3,5-bis(trifluoromethyl)benzoyl]morpholin-2-yl}ethyl)spiro{(2S)-2-[({[(morpholin-4-yl)acetyl]amino}carbonyl)oxy]}indane-1,4'-piperidine.

248 mg (0.29 mmol) of the obtained 1-(2-{(2R)-2-(3,4-dichlorophenyl)-4-[3,5-bis(trifluoromethyl)benzoyl]morpholin-2-yl}ethyl)spiro{(2S)-2-[({[(morpholin-4-yl)acetyl]amino}carbonyl)oxy]}indane-1,4'-piperidine was dissolved in 4 mL of ethanol and 0.5 mL of 4N hydrochloric acid-dioxane was added thereto. The solvent was distilled off under reduced pressure, followed by azeotropy twice with diethyl ether. The thus obtained residue was recrystallized from hexane to obtain 224 mg (yield: 84%) of the title compound as a white crystal.

$^1$H-NMR spectrum (500 MHz, CD$_3$OD) δ ppm: 8.34-7.79 (3H, m), 7.86-7.11 (7H, m), 5.35-5.27 (1H, m), 4.55-1.66 (30H, m).

IR spectrum ν max cm$^{-1}$ (KBr): 2932, 1785, 1719, 1644, 1475, 1376, 1281, 1137.

Mass spectrum (FAB) m/z: 871 ((M+H)$^+$, free form)

Elementary analysis (for C$_{41}$H$_{44}$Cl$_4$F$_6$N$_4$O$_6$ 3H$_2$O) Calculated (%): C, 49.31; H, 5.05; Cl, 14.20; F, 11.41; N, 5.61. Found (%): C, 49.21; H, 4.91; Cl, 14.76; F, 11.62; N, 5.64. Optical rotation: [α]$_D^{20}$=+59.4 (c=0.50, methanol)

Example 54

1-(2-{(2R)-2-(3,4-Dichlorophenyl)-4-[3,5-bis(trifluoromethyl)benzoyl]morpholin-2-yl}ethyl)spiro{(2S)-2-[(aminocarbonyl)oxy]}indane-1,4'-piperidine hydrochloride (Exemplary compound No. 2-190 hydrochloride)

The reaction was carried out in similar procedure to Example 53 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 1 mL of ammonia water to obtain 134 mg (yield: 40%) of the title compound as a white crystal.

IR spectrum ν max cm$^{-1}$ (KBr): 2928, 1726, 1645, 1438, 1376, 1281, 1138.

Mass spectrum (FAB) m/z: 744 ((M+H)$^+$, free form)

Example 55

1-(2-{(2R)-2-(3,4-Dichlorophenyl)-4-[3,5-bis(trifluoromethyl)benzoyl]morpholin-2-yl}ethyl)spiro{(2S)-2-[({[(piperidin-1-yl)acetyl]amino}carbonyl)oxy]}indane-1,4'-piperidine hydrochloride (Exemplary compound No. 2-188 hydrochloride)

The reaction was carried out in similar procedure to Example 53 using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 64 µL (0.64 mmol) of piperidine to obtain 217 mg (yield: 56%) of the title compound as a white crystal.

IR spectrum ν max cm$^{-1}$ (KBr): 3358, 2931, 1720, 1645, 1476, 1376, 1280, 1139.

Mass spectrum (FAB) m/z: 869 ((M+H)$^+$, free form)

Example 56

1-(2-{(2R)-2-(3,4-Dichlorophenyl)-4-[3,5-bis(trifluoromethyl)benzoyl]morpholin-2-yl}ethyl)spiro{(2S)-2-[(2-methoxyethoxy)methoxy]}indane-1,4'-piperidine (Exemplary compound No. 2-191)

The reaction was carried out in similar procedure to Example 27a using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 73 µL (0.64 mmol) of 2-methoxyethoxymethyl chloride to obtain 110 mg (yield: 34%) of the title compound as a white crystal.

IR spectrum ν max cm$^{-1}$ (KBr): 2926, 1645, 1472, 1375, 1280, 1137.

Mass spectrum (FAB) m/z: 789 ((M+1)$^+$, free form)

Example 57

1-(2-{(2R)-2-(3,4-Dichlorophenyl)-4-[3,5-bis(trifluoromethyl)benzoyl]morpholin-2-yl}ethyl)spiro[(2S)-2-(2-methoxymethoxy)]indane-1,4'-piperidine (Exemplary compound No. 2-192)

The reaction was carried out in similar procedure to Example 27a using 300 mg (0.43 mmol) of 1-(2-{(2R)-2-(3,4-dichlorophenyl)-4-[3,5-bis(trifluoromethyl)benzoyl]morpholin-2-yl}ethyl)spiro[(2S)-2-hydroxy]indane-1,4'-piperidine and 49 µL (0.64 mmol) of chloromethyl methyl ether to obtain 121 mg (yield: 37%) of the title compound as a white crystal.

IR spectrum ν max cm$^{-1}$ (KBr): 2928, 1646, 1472, 1375, 1280, 1139.

Mass spectrum (FAB) m/z: 745 ((M+H)$^+$, free form)

Example 58

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide hydrochloride (Exemplary compound No. 2-418 hydrochloride)

Example 58a 4-(Methylamino)butan-1-ol hydrochloride 4.00 g (0.045 mol) of 4-aminobutan-1-ol was dissolved in 10 mL of ethyl formate and the mixture was refluxed for 6 hours. After the temperature of the mixture was returned to room temperature, the solvent was distilled off under reduced pressure and the thus obtained residue was purified by silica gel column chromatography (eluting solvent: ethyl acetate/methylene chloride/methanol=5:5:1) to obtain 4.16 g (yield: 79%) of 4-hydroxybutylformamide. 4.16 g (0.036 mol) of the obtained 4-hydroxybutylformamide was dissolved in 10 mL of anhydrous tetrahydrofuran and then the mixture was stirred at 0° C. under nitrogen atmosphere. 1.35 g (0.036 mol) of lithium aluminium hydride was added to the reaction solution over 5 minutes and thereafter the mixture was refluxed. After 6 hours, the reaction mixture was cooled to 0° C. and 5.00 g of sodium sulfate 10 hydrate and 40 mL of tetrahydrofuran were slowly added thereto over 10 minutes. Thereafter, the mixture was stirred until the reaction mixture became white-turbid. The precipitated substance was removed by filtration and after 10 mL of 4N hydrochloric acid-dioxane was added thereto little by little while cooling the residue to 0° C., the solvent was distilled off to obtain 4.51 g (yield: 91%) of the title compound.

$^1$H-NMR spectrum (400 MHz, CD$_3$OD) δ ppm: 3.61 (2H, t, J=6.1 Hz), 3.02 (2H, t, 7.7 Hz), 2.70 (3H, s), 1.81-1.73 (2H, m), 1.65-1.58 (2H, m).

Example 58b

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide hydrochloride 3 g (3.95 mmol) of 1-(2-{(2R)-2-(3,4-dichlorophenyl)-4-[3,5-bis(trifluoromethyl)benzoyl]morpholin-2-yl}ethyl) spiro[(2S)-2-carboxymethoxy]indane-1,4'-piperidine, obtained in Example 27b, was dissolved in 10 mL of methylene chloride and 406 μL (4.74 mmol) of oxalyl chloride was added thereto. One drop of dimethylformamide was added to the mixture, followed by stirring at room temperature for 20 minutes. 169 μL (1.98 mmol) of oxalyl chloride was newly added thereto and the mixture was further stirred for 20 minutes. The solution in which the residue obtained by distilling off the solvent under reduced pressure was dissolved in 10 mL of methylene chloride was added dropwise to a solution of 4-(methylamino)butan-1-ol hydrochloride, obtained in Example 58a, and 1.93 mL (13.9 mmol) of triethylamine in methylene chloride (5 mL) and the mixture was stirred for 30 minutes. The reaction mixture was washed successively with water and a saturated NaCl solution and dried over anhydrous sodium sulfate. The solvent was distilled off under reduced pressure and the thus obtained residue was purified by silica gel column chromatography (eluting solvent: ethyl acetate/methylene chloride/methanol=5/5/0-1) to obtain 1.89 g (yield: 57%) of 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide.

The thus obtained 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide was dissolved in 20 mL of ethyl acetate and the mixture was extracted with 20 mL of 1N aqueous hydrochloric acid solution. After the ethyl acetate layer was dried over anhydrous sodium sulfate, the solvent was distilled off under reduced pressure. The thus obtained amorphous matter was collected by filtration by adding n-hexane to obtain 1.89 g (yield: 96%) of the title compound as a white solid.

$^1$H-NMR spectrum (400 MHz, CDCl$_3$) δ ppm: 8.20-7.14 (10H, m), 4.37-1.53 (34H, m).

IR spectrum ν max cm$^{-1}$ (KBr): 3407, 2930, 1649, 1474, 1439, 1376, 1281, 1185, 1139, 1108.

Mass spectrum (FAB) m/z: 844 ((M+H)$^+$, free form)

Elementary analysis (for C$_{41}$H$_{45}$Cl$_2$F$_6$N$_3$O$_5$ HCl H$_2$O) Calculated (%): C, 54.77; H, 5.38; Cl, 11.83; N, 4.67. Found (%): C, 54.92; H, 5.47; Cl, 11.59; N, 4.59.

Example 59

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide (Exemplary compound No. 2-418)

600 mg (0.68 mmol) of 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide hydrochloride, obtained in Example 58, was dissolved in 50 mL of ethyl acetate and the mixture was washed successively with 100 mL of a saturated aqueous sodium hydrogencarbonate solution and a saturated NaCl solution and dried over anhydrous sodium sulfate. The solvent was distilled off under reduced pressure to obtain 575 mg (yield: 100%) of the title compound as a white solid.

$^1$H-NMR spectrum (400 MHz, CDCl$_3$) δ ppm: 8.10-7.10 (10H, m) 4.70-1.20 (34H, m).

IR spectrum ν max cm$^{-1}$ (KBr): 3431, 2928, 1645, 1473, 1440, 1375, 1281, 1184, 1138, 1097, 1030, 905, 756, 707, 681.

Mass spectrum (FAB) m/z: 844 (M+H)$^+$

Elementary analysis (for C$_{41}$H$_{45}$Cl$_2$F$_6$N$_3$O$_5$ 0.5H$_2$O) Calculated (%): C, 57.68; H, 5.43; Cl, 8.31; F, 13.35; N, 4.92. Found (%): C, 57.49; H, 5.34; Cl, 8.39; F, 13.73; N, 4.85.

Example 60

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide 1/2 sulfate (Exemplary compound No. 2-418 1/2 sulfate)

100 mg (0.12 mmol) of 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2- yl)oxy]-N-(4-hydroxybutyl)-N-methylacetamide, obtained in Example 59, was dissolved in 2 mL of ethanol and 30 μL (0.12 mmol) of 4N sulfuric acid was added thereto under ice-cooling. The solvent was distilled off under reduced pressure to obtain 104 mg (yield: 98%) of the title compound as a white solid.

$^1$H-NMR spectrum (400 MHz, CDCl$_3$) δ ppm: 8.00-7.00 (10H, m), 4.40-1.40 (34H, m).

IR spectrum ν max cm$^{-1}$ (KBr): 3412, 2932, 2561, 1649, 1474, 1439, 1376, 1281, 1139, 1029, 905, 758, 681, 620.

Mass spectrum (FAB) m/z: 844 ((M+H)$^+$, free form)

Elementary analysis (for C$_{41}$H$_{45}$Cl$_2$F$_6$N$_3$O$_5$ 0.5H$_2$SO$_4$ H$_2$O) Calculated (%): C, 54.01; H, 5.31; Cl, 7.78; F, 12.50; N, 4.61; S, 1.76. Found (%): C: 53.54, H: 5.13, Cl: 7.94, F: 12.53, N: 4.51, S: 1.88.

Example 61

2-[((2S)-1'-{2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]-N-(4-hydroxybutyl)-N-methylacetamide fumarate (Exemplary compound No. 2-418 fumarate)

100 mg (0.12 mmol) of 2-[((2S)-1'-{2-[(2R)-4-[3,5-bis (trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide, obtained in Example 59, was dissolved in 1 mL of ethanol and 14 mg (0.12 mmol) of fumaric acid was added thereto. The solvent was distilled off under reduced pressure to obtain 114 mg (yield: 100%) of the title compound as a white solid.

$^1$H-NMR spectrum (400 MHz, CD$_3$OD) δ ppm: 8.20-7.30 (6H, m), 7.25-7.10 (4H, m), 6.71 (2H, s), 4.45-2.80 (24H, m), 2.70-1.40 (10H, m).

IR spectrum ν max cm$^{-1}$ (KBr): 3407, 2932, 2561, 1710, 1649, 1474, 1439, 1376, 1281, 1185, 1139, 1029, 983, 905, 757, 681, 648.

Mass spectrum (FAB) m/z: 844 ((M+H)$^+$, free form)

Elementary analysis (for C$_{41}$H$_{45}$Cl$_2$F$_6$N$_3$O$_5$ C$_4$H$_4$O$_4$ H$_2$O) Calculated (%): C, 55.22; H, 5.25; Cl, 7.24; F, 11.65; N, 4.29. Found (%): C, 55.17; H, 5.14; Cl, 7.42; F, 11.56; N, 4.17.

Example 62

2-[((2S)-1'-{2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]-N-(4-hydroxybutyl)-N-methylacetamide L-(+)- tartrate (Exemplary compound No. 2-418 L-(+)- tartrate)

100 mg (0.12 mmol) of 2-[((2S)-1'-{2-[(2R)-4-[3,5-bis (trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide, obtained in Example 59, was dissolved in 1 mL of ethanol and 18 mg (0.12 mmol) of L-(+)-tartaric acid was added thereto. The solvent was distilled off under reduced pressure to obtain 118 mg (yield: 100%) of the title compound as a white solid.

$^1$H-NMR spectrum (400 MHz, CD$_3$OD) δ ppm: 8.20-7.10 (10H, m), 4.50-1.40 (36H, m).

IR spectrum ν max cm$^{-1}$ (KBr): 3321, 2932, 2560, 1734, 1648, 1438, 1376, 1281, 1137, 905, 681.

Mass spectrum (FAB) m/z: 844 ((M+H)$^+$, free form)

Elementary analysis (for C$_{41}$H$_{45}$Cl$_2$F$_6$N$_3$O$_5$ C$_4$H$_6$O$_6$ H$_2$O) Calculated (%): C, 53.36; H, 5.27; Cl, 7.00; F, 11.25; N, 4.15. Found (%): C, 53.29; H, 5.14; Cl, 7.36; F, 11.04; N, 4.03.

Example 63

2-[((2s)-1'-{2-[(2R)-4-[3,5-bis(Trifluoromethyl)ben- zoyl]-2-(3,4-dichlorophenyl)morpholin-2-yl]ethyl}- 2,3-dihydrospiro[indene-1,4'-piperidin]-2-yl)oxy]-N- (4-hydroxybutyl)-N-methylacetamide maleate (Exemplary compound No. 2-418 maleate)

200 mg (0.24 mmol) of 2-[((2S)-1'-{2-[(2R)-4-[3,5-bis (trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide, obtained in Example 59, was dissolved in 2 mL of ethanol and 27 mg (0.24 mmol) of maleic acid was added thereto. The solvent was distilled off under reduced pressure to obtain 227 mg (yield: 100%) of the title compound as a white solid.

$^1$H-NMR spectrum (400 MHz, CD$_3$OD) δ ppm: 8.20-7.40 (6H, m), 7.25-7.10 (4H, m), 6.26 (2H, s), 4.45-2.80 (24H, m), 2.65-1.40 (10H, m).

IR spectrum ν max cm$^{-1}$ (KBr): 3424, 2932, 2574, 1648, 1582, 1476, 1376, 1281, 1186, 1138, 1029, 905, 865, 757, 707, 681.

Mass spectrum (FAB) m/z: 844 ((M+H)$^+$, free form)

Elementary analysis (for C$_{41}$H$_{45}$Cl$_2$F$_6$N$_3$O$_5$ C$_4$H$_4$O$_4$ H$_2$O) Calculated (%): C, 55.22; H, 5.25; Cl, 7.24; F, 11.65; N, 4.29. Found (%): C, 54.94; H, 5.06; Cl, 7.38; F, 11.53; N, 4.19.

Example 64

2-[((2S)-1'-{2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]-N-(3-hydroxypropyl)-N-methylacetamide hydrochloride (Exemplary compound No. 2-417 hydrochloride)

Example 64a 3-(Methylamino)propan-1-ol hydrochloride

The reaction was carried out in similar procedure to Example 58a using 2 g (0.027 mol) of 4-aminopropan-1-ol to obtain 2.77 g (yield: 83%) of the title compound.

$^1$H-NMR spectrum (500 MHz, CD$_3$OD) δ ppm: 3.70 (2H, t, 5.9 Hz), 3.12 (2H, t, 7.1 Hz), 2.70 (3H, s), 1.91-1.85 (2H, m).

Example 64b

2-[((2S)-1'-{2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]-N-(3-hydroxypropyl)-N-methylacetamide hydrochloride The reaction was carried out in similar procedure to Example 58b using 2.86 g (3.76 mmol) of 1-(2-{(2R)-2-(3, 4-dichlorophenyl)-4-[3,5-bis(trifluoromethyl)benzoyl]morpholin-2-yl}ethyl)spiro[(2S)-2-carboxymethoxy]indane-1, 4'-piperidine, obtained in Example 27b, and 3-(methylamino)propan-1-ol hydrochloride, obtained in Example 64a, to obtain 1.62 g (yield: 52%) of 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-(3-hydroxypropyl)-N-methylacetamide.

1 g (1.2 mmol) of the thus obtained 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-(3-hydroxypropyl)-N-methylacetamide was treated similarly to Example 58b to obtain 956 mg (yield: 92%) of the title compound as a white solid.

$^1$H-NMR spectrum (400 MHz, CDCl$_3$) δ ppm: 8.10-7.12 (10H, m), 4.45-1.64 (32H, m).

IR spectrum ν max cm$^{-1}$ (KBr): 3384, 2927, 1649, 1474, 1439, 1376, 1282, 1185, 1139, 1109.

Mass spectrum (FAB) m/z: 830 ((M+H)$^+$, free form)

Elementary analysis (for C$_{40}$H$_{43}$Cl$_2$F$_6$N$_3$O$_5$ HCl 2H$_2$O) Calculated (%): C, 53.19; H, 5.36; Cl, 11.78; N, 4.65. Found (%): C, 52.54; H, 5.04; Cl, 11.27; N, 4.43.

Example 65

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-[2-(2-hydroxyethoxy)ethyl]-N-methylacetamide hydrochloride (Exemplary compound No. 2-422 hydrochloride)

Example 65a

2-[2-(Methylamino)ethoxy]ethanol hydrochloride

The reaction was carried out in similar procedure to Example 58a using 2 g (0.019 mol) of 2-(2-aminoethoxy)ethanol to obtain 1.99 g (yield: 67%) of the title compound.

$^1$H-NMR spectrum (500 MHz, CD$_3$OD) δ ppm: 3.75-3.70 (4H, m), 3.60 (2H, t, J=4.4), 3.22 (2H, t, J=4.9 Hz), 2.73 (3H, s).

Example 65b

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-[2-(2-hydroxyethoxy)ethyl]-N-methylacetamide hydrochloride The reaction was carried out in similar procedure to Example 58b using 100 mg (0.136 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, obtained in Example 27b, and 106 mg (0.678 mmol) of 2-[2-(methylamino)ethoxy]ethanol hydrochloride, obtained in Example 65a, to obtain 68.2 mg (yield: 58%) of 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-[2-(2-hydroxyethoxy)ethyl]-N-methylacetamide.

68.2 mg (0.079 mmol) of the obtained 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-[2-(2-hydroxyethoxy)ethyl]-N-methylacetamide was dissolved in 5 mL of methylene chloride and 0.2 mL of 4N hydrochloric acid-dioxane solution was added dropwise thereto. The solvent was distilled off under reduced pressure and the thus obtained amorphous matter was collected by filtration by adding n-hexane to obtain 63.6 mg (yield: 89%) of the title compound as a white solid.

$^1$H-NMR spectrum (400 MHz, CD$_3$OD) δ ppm: 8.07-7.14 (10H, m), 4.46-2.16 (34H, m).

IR spectrum ν max cm$^{-1}$ (KBr): 3384, 2927, 1650, 1474, 1439, 1376, 1282, 1185, 1137.

Mass spectrum (FAB) m/z: 860 ((M+H)$^+$, free form)

Example 66

3-(1-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxyacetyl]piperidin-4-yl}propan-1-ol hydrochloride (Exemplary compound No. 2-583 hydrochloride)

Example 66a

3-Piperidin-4-ylpropan-1-ol hydrochloride 1.00 g (7.29 mmol) of 4-pyridinepropanol was dissolved in 3N aqueous hydrochloric acid solution and 206 mg of platinum oxide was added thereto, followed by stirring of the mixture at room temperature under a hydrogen atmosphere at an ordinary pressure for 12 hours. The reaction mixture was filtered with Celite and the filtrate was distilled off under reduced pressure. The thus obtained residue was reprecipitated from methanol-ether to obtain 1.31 g (yield: quantitative) of the title compound as a white solid.

$^1$H-NMR spectrum (400 MHz, CD$_3$OD) δ ppm: 6.45 (2H, t, J=6.5 Hz), 3.42-3.33 (2H, m), 2.96 (3H, brt, J=12.5 Hz), 1.96 (2H, brd, J=13.7 Hz), 1.68-1.50 (3H, m), 1.44-1.30 (4H, m).

IR spectrum ν max cm$^{-1}$ (KBr): 3440, 2945, 2851, 2802, 2687, 2625, 2493, 1585, 1453, 1391, 1102, 1042, 978, 956, 592, 514.

Mass spectrum (FAB) m/z: 143 (M$^+$, free form)

Example 66b 3-(1-{[((2S)-1'-(2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxyacetyl]piperidin-4-yl}propan-1-ol hydrochloride 2.02 g (2.67 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, obtained in Example 27b, and 881 μL (8.02 mmol) of N-methylmorpholine were dissolved in 40 mL of methylene chloride and 263 μL (2.94 mmol) of ethyl chloroformate was added thereto under ice-cooling with stirring, followed by stirring of the mixture for 15 minutes. 720 mg (4.01 mmol) of 3-piperidin-4-ylpropan-1-ol, obtained in Example 66b, was added to the reaction mixture under ice-cooling. After the mixture was stirred at room temperature for 1 hour, ethyl acetate was added thereto to dilute it and the mixture was washed successively with water and a saturated NaCl solution and dried over anhydrous magnesium sulfate. After filtration, the filtrate was evaporated under reduced pressure and the thus obtained residue was purified by silica gel chromatography (eluting solvent: ethyl acetate/methanol=88/12) to obtain 1.82 g of 3-(1-{[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxyacetyl]piperidin-4-yl}propan-1-ol.

The thus obtained 3-(1-{[((2S)-1'-(2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxyacetyl]piperidin-4-yl}propan-1-ol was dissolved in 40 mL of ethyl acetate and 1.00 mL of 4N hydrochloric acid-dioxane was added thereto. The solvent was distilled off under reduced pressure and 30 mL of n-hexane-ethyl acetate (1:1) was added thereto, followed by azeotropy. The thus obtained residue was reprecipitated from methylene chloride-hexane to obtain 1.98 g (yield: 77%) of the title compound as a white solid.

$^1$H-NMR spectrum (400 MHz, CD$_3$OD) δ ppm: 8.14 (1H, brs), 7.98 (2H, brs), 7.62 (1H, brs), 7.70-7.45 (2H, m), 7.27-7.10 (4H, m), 4.45-0.85 (38H, m).

IR spectrum ν max cm$^{-1}$ (KBr): 3422, 2931, 2861, 2555, 1647, 1473, 1457, 1440, 1376, 1280, 1242, 1185, 1166, 1139, 1110, 1029, 904, 758, 681.

Mass spectrum (FAB) m/z: 884 ((M+H)$^+$, free form)

Elementary analysis (for C$_{44}$H$_{50}$Cl$_3$F$_6$N$_3$O$_5$ 0.5H$_2$O) Calculated (%): C, 56.81; H, 5.53; Cl, 11.43; F, 12.25; N, 4.52. Found (%): C, 56.78; H, 5.80; Cl, 11.37; F, 12.22; N, 4.36.

Example 67

2-(4-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperazin-1-yl)ethanol hydrochloride (Exemplary compound No. 2-614 hydrochloride)

120 mg (0.158 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, obtained in Example 27b, was dissolved in 5 mL of methylene chloride and 27 μL (0.316 mmol) of oxalyl chloride was added thereto. One drop of dimethylformamide was added to the mixture, followed by stirring at room temperature for 1 hour. The residue obtained by distilling off the solvent under reduced pressure was dissolved in 5 mL of methylene chloride. 1-(2-Hydroxyethyl)piperazine was added dropwise to the mixture, followed by stirring for 30 minutes. The mixture was washed successively with water and a saturated NaCl solution and dried over anhydrous sodium sulfate. The solvent was distilled off under reduced pressure and the thus obtained residue was purified by silica gel column chromatography (eluting solvent: ethyl acetate/methylene chloride/methanol=5/5/0-2) to obtain 60 mg (yield: 44%) of 2-(4-{[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperazin-1-yl)ethanol.

The obtained 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide was dissolved in 5 mL of methylene chloride and 0.2 mL of 4N hydrochloric acid-dioxane solution was added dropwise thereto. The solvent was distilled off under reduced pressure and the obtained amorphous matter was collected by filtration by adding n-hexane to obtain 50 mg (yield: 80%) of the title compound as a white solid.

$^1$H-NMR spectrum (400 MHz, CDCl$_3$) δ ppm: 8.28-7.95 (3H, m), 7.70-7.15 (7H, m), 4.65-1.66 (35H, m).

IR spectrum ν max cm$^{-1}$ (KBr): 3342, 2927, 2578, 1649, 1473, 1439, 1376, 1282, 1139.

Mass spectrum (FAB) m/z: 871 ((M+H)$^+$, free form)

Elementary analysis (for C$_{42}$H$_{46}$Cl$_2$F$_6$N$_4$O$_5$ 2HCl H$_2$O) Calculated (%): C, 52.40; H, 5.24; N, 5.82. Found (%): C, 52.54; H, 5.04; N, 5.43.

Example 68

3-((2R)-1-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}pyrrolidin-2-yl)propan-1-ol hydrochloride (Exemplary compound No. 2-574 hydrochloride)

Example 68a

Benzyl (2R)-2-(hydroxymethyl)pyrrolidine-1-carboxylate 2 g (0.0198 mol) of (2R)-pyrrolidin-2-ylmethanol was dissolved in 20 mL of ethyl acetate, 20 mL of water was added thereto, and the mixture was stirred. 3.3 g (0.30 mol) of sodium hydrogencarbonate was added to the mixture, followed by stirring of the mixture for 5 minutes. 4.24 mL (0.03 mol) of benzyl chloroformate was added dropwise to the mixture, followed by stirring for 5 hours. After the ethyl acetate layer was dried over anhydrous sodium sulfate, the solvent was distilled off under reduced pressure to quantitatively obtain the title compound.

$^1$H-NMR spectrum (500 MHz, CDCl$_3$) δ ppm: 7.55-7.28 (5H, m), 5.16 (2H, s), 4.12-3.90 (1H, br), 3.83-3.33 (4H, m), 2.19-1.51 (4H, m).

Example 68b

Benzyl (2R)-2-formylpyrrolidine-1-carboxylate 1 g (4.25 mmol) of benzyl (2R)-2-(hydroxymethyl)pyrrolidine-1-carboxylate, obtained in Example 68a, was dissolved in 15 mL of methylene chloride and the mixture was stirred under ice-cooling. 1.98 g (4.68 mmol) of Dess-Martin periodinane was added to the mixture, followed by stirring for 2 hours. After a saturated aqueous sodium hydrogencarbonate solution and an aqueous sodium thiosulfate solution (2 eq.) were added to the mixture and the mixture was stirred for 30 minutes, the mixture was extracted with methylene chloride three times. After the methylene chloride layer was dried over anhydrous sodium sulfate, the solvent was distilled off under reduced pressure to obtain a crude product of the title compound.

Example 68c

Benzyl (2R)-2-(3-ethoxy-3-oxoprop-1-enyl)pyrrolidine-1-carboxylate

929 μL (4.68 mmol) of triethyl phosphonoacetate was dissolved in 15 mL of tetrahydrofuran and 3.19 mL of a solution of 1.6M n-butyl lithium in hexane was added dropwise thereto over 5 minutes while stirring at −50° C. under a nitrogen atmosphere, followed by stirring of the mixture for 20 minutes. 10 mL of a solution of benzyl (2R)-2-formylpyrrolidine-1-carboxylic acid in tetrahydrofuran, obtained in Example 68b, was added dropwise to the reaction mixture over 5 minutes and the temperature of the mixture was raised to room temperature, followed by stirring for 8 hours. Water was added to the reaction mixture and the mixture was extracted with ethyl acetate three times. After the ethyl acetate layer was dried over anhydrous sodium sulfate, the solvent was distilled off under reduced pressure. The thus obtained residue was purified by silica gel column chromatography (eluting solvent: ethyl acetate/hexane=1/5) to obtain 1.13 g (yield: 88%) of the title compound in the form of mixture of (E) and (Z) forms.

Example 68d

Benzyl (2R)-2-[(1E)-3-hydroxyprop-1-enyl]pyrrolidine-1-carboxylate 283 mg (0.933 mmol) of benzyl (2R)-2-(3-ethoxy-3-oxoprop-1-enyl)pyrrolidine-1-carboxylate, obtained in Example 68c, was dissolved in 5 mL of tetrahydrofuran and 1.85 mL (1.87 mmol) of a solution of 1.01M diisobutyl aluminium hydride in toluene was added dropwise thereto over 5 minutes while stirring at −78° C. under a nitrogen atmosphere. After the mixture was stirred for 1 hour, the cooling bath was removed and the mixture was quenched by slowly adding water drop by drop. Water and ethyl acetate were added thereto and an extraction operation was carried out. After the ethyl acetate layer was dried over anhydrous sodium sulfate, the solvent was distilled off under reduced pressure. The thus obtained residue was purified by silica gel column chromatography (eluting solvent: ethyl acetate/hexane=1/1) to obtain 135 mg (yield: 55%) of the title compound.

(E) Form $^1$H-NMR spectrum (400 MHz, CDCl$_3$) δ ppm: 7.49-7.25 (5H, m), 5.80-5.55 (2H, m), 5.26-5.00 (2H, m), 4.50-4.30 (1H, m), 4.19-3.88 (2H, m), 3.52-3.34 (2H, m), 2.11-1.67 (4H, m).

(Z) Form $^1$H-NMR spectrum (400 MHz, CDCl$_3$) δ ppm: 7.64-7.25 (5H, m), 5.89-5.82 (1H, m), 5.39 (2H, t, J=10.5 Hz), 5.16-5.08 (2H, dd, J=32.0, 12.5 Hz), 4.86 (1H, m), 4.53-4.48 (1H, dd, J=12.3, 8.8 Hz), 3.94-3.90 (1H, m), 3.59-3.30 (2H, m), 2.14-1.52 (4H, m).

Example 68e

3-[(2R)-Pyrrolidin-2-yl]propan-1-ol hydrochloride

Benzyl (2R)-2-[(1E)-3-hydroxyprop-1-enyl]pyrrolidine-1-carboxylate, obtained in Example 68d, was dissolved in 5 mL of ethanol and 50 mg of 10% palladium-carbon was added thereto, followed by vigorous stirring of the mixture under a hydrogen atmosphere. After 1 hour and 30 minutes, the palladium-carbon was removed by filtration and 0.5 mL of 4N hydrochloric acid/dioxane solution was added dropwise to the residue. The solvent was distilled off under reduced pressure to obtain the title compound as a colourless oil.

$^1$H-NMR spectrum (500 MHz, CD$_3$OD) δ ppm: 3.61 (2H, t), 3.44-3.51 (1H, m), 2.27-2.21 (35H, m), 2.12-1.99 (2H, m), 1.84-1.76 (2H, m), 1.69-1.60 (3H, m).

Example 68f 3-((2R)-1-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}pyrrolidin-2-yl)propan-1-ol hydrochloride The reaction was carried out in similar procedure to Example 58b using 200 mg (0.263 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, obtained in Example 27b, and 3-[(2R)-pyrrolidin-2-yl]propan-1-ol hydrochloride, obtained in Example 68e, to obtain 102 mg (yield: 44%) of 3-((2R)-1-{[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin)-2-yl)oxy]acetyl}pyrrolidin-2-yl)propan-1-ol.

1 g (1.2 mmol) of the obtained 2-[((2S)-1'-(2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-(3-hydroxypropyl)-N-methylacetamide was treated similarly to Example 58b to obtain 98 mg (yield: 93%) of the title compound as a white solid.

$^1$H-NMR spectrum (400 MHz, CDCl$_3$) δ ppm: 8.15-7.14 (10H, m), 4.36-1.35 (36H, m).

IR spectrum ν max cm$^{-1}$ (KBr): 3401, 2931, 2559, 1646, 1281, 1185, 1139.

Mass spectrum (FAB) m/z: 870 ((M+H)$^+$, free form)

Elementary analysis (for C$_{43}$H$_{47}$Cl$_2$F$_6$N$_3$O$_5$ HCl) Calculated (%): C, 55.44; H, 5.27; N, 4.51. Found (%): C, 55.17; H, 5.43; N, 4.47.

Example 69

2-(1-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-yl)ethanol hydrochloride
(Exemplary compound No. 2-582 hydrochloride)

200 mg (0.26 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, obtained in Example 27b, was dissolved in 4 mL of methylene chloride and 46 μL (0.53 mmol) of oxalyl chloride was added thereto under ice-cooling. One drop of dimethylformamide was added to the mixture, followed by stirring at room temperature for 30 minutes. The solvent was distilled off under reduced pressure and the thus obtained residue was dissolved in 4 mL of methylene chloride. 68 mg (0.53 mmol) of 4-piperidine ethanol and 110 μL (0.79 mmol) of triethylamine were added to the solution under ice-cooling. After the mixture was stirred at room temperature for 2 hours, it was washed successively with water and a saturated NaCl solution and dried over anhydrous sodium sulfate. The solvent was distilled off under reduced pressure and the thus obtained residue was purified by thin layer chromatography (eluting solvent: methylene chloride/methanol=10/1).

The thus obtained 2-(1-{[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-yl)ethanol was dissolved in 20 mL of ethyl acetate and the mixture was washed successively with 50 mL of 1N hydrochloric acid and a saturated NaCl solution and dried over anhydrous sodium sulfate. The solvent was distilled off under reduced pressure and the obtained residue was washed with hexane to obtain 129 mg (yield: 54%) of the title compound as a white solid.

¹H-NMR spectrum (400 MHz, CDCl₃) δ ppm: 12.05 (1H, brs), 8.20-7.90 (3H, m), 7.70-7.10 (7H, m), 4.50-2.90 (23H, m), 2.80-2.10 (7H, m), 1.90-1.00 (6H, m).
IR spectrum ν max cm⁻¹ (KBr): 3414, 2926, 2560, 1648, 1473, 1440, 1375, 1281, 1139, 1029, 985, 905, 757, 681.
Mass spectrum (FAB) m/z: 870 ((M+H)⁺, free form)
Elementary analysis (for $C_{43}H_{48}Cl_3F_6N_3O_5$ 1.5H₂O) Calculated (%): C, 55.28; H, 5.50; Cl, 11.38; F, 12.20; N, 4.50. Found (%): C, 55.20; H, 5.53; Cl, 11.24; F, 12.53; N, 4.33.

Example 70

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methoxyacetamide hydrochloride (Exemplary compound No. 2-460 hydrochloride)

Example 70a 4-(Methoxyamino)butan-1-ol 1.10 g (7.19 mmol) of 4-bromo-1-butanol was dissolved in 20 mL of ethanol and 4.59 g (28.8 mmol) of O-methylhydroxylamine hydrochloride and 6.02 mL (43.1 mmol) of triethylamine were added thereto, followed by stirring of the mixture at 70° C. for 2 hours. Ethyl acetate was added to the reaction mixture, the precipitate was removed by filtration and the solvent was distilled off under reduced pressure. The residue was purified by silica gel chromatography (eluting solvent: ethyl acetate/methanol=100/0-50/50) to obtain 52 mg (yield: 6%) of the title compound as a pale yellow oil.
¹H-NMR spectrum (400 MHz, CD₃OD) δ ppm: 3.72 (3H, s), 3.58 (2H, t, J=6.1 Hz), 3.11 (2H, t, J=7.2 Hz), 1.76-1.56 (4H, m).
IR spectrum ν max cm⁻¹ (liquid film): 3390, 2946, 2726, 1637, 1465, 1445, 1035.
Mass spectrum (EI) m/z: 119 (M⁺)

Example 70b

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methoxyacetamide hydrochloride The reaction was carried out in similar procedure to Example 69 using 200 mg (0.26 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, 46 μL (0.53 mmol) of oxalyl chloride, 47 mg (0.40 mmol) of 4-(methoxyamino)butan-1-ol, obtained in Example 70a, and 110 μL (0.79 mmol) of triethylamine to obtain 86 mg (yield: 36%) of the title compound as a white solid.
¹H-NMR spectrum (400 MHz, CDCl₃) δ ppm: 12.11 (1H, brs), 8.10-7.90 (3H, m), 7.70-7.10 (7H, m), 4.50-2.90 (23H, m), 2.85-2.10 (5H, m), 1.80-1.50 (6H, m).
IR spectrum ν max cm⁻¹ (KBr): 3394, 2936, 2555, 1649, 1473, 1440, 1376, 1281, 1138, 1029, 905, 758, 681.
Mass spectrum (FAB) m/z: 860 ((M+H)⁺, free form)
Elementary analysis (for $C_{41}H_{46}Cl_3F_6N_3O_6$ H₂O) Calculated (%): C, 53.81; H, 5.29; Cl, 11.62; F, 12.46; N, 4.59. Found (%): C, 53.82; H, 5.22; Cl, 11.31; F, 12.40; N, 4.59.

Example 71

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(5-hydroxypentyl)-N-methylacetamide hydrochloride (Exemplary compound No. 2-419 hydrochloride)

Example 71a

5-Hydroxypentylformamide 2.06 g (20.0 mmol) of 5-amino-1-pentanol was dissolved in 5 mL of ethyl formate and the mixture was stirred at 90° C. for 4 hours. The solvent was distilled off under reduced pressure and the obtained residue was purified by silica gel chromatography (eluting solvent: ethyl acetate/methanol=100/0-70/30) to obtain 1.90 g (yield: 73%) of the title compound as a pale yellow-oil.
¹H-NMR spectrum (400 MHz, CDCl₃) δ ppm: 8.14 (1H, s), 5.69 (1H, brs), 3.68-3.60 (2H, m), 3.35-3.26 (2H, m), 1.64-1.36 (6H, m).
Mass spectrum (EI) m/z: 131 (M⁺)

Example 71b 5-(Methylamino)pentan-1-ol 1.90 g (14.5 mmol) of 5-hydroxypentylformamide, obtained in Example 71a, was dissolved in 20 mL of tetrahydrofuran, and 17.4 mL (17.4 mmol) of 1M solution of lithium aluminium hydride in tetrahydrofuran was added dropwise to the solution under ice-cooling, followed with stirring of the mixture at 90° C. for 2 hours. Thereafter, 28 g (87 mmol) of sodium sulfate 10 hydrates and 20 mL of diethyl ether were added to the reaction mixture under ice-cooling and the mixture was stirred at room temperature for 18 hours. After the reaction mixture was filtered with Celite, the solvent was distilled off under reduced pressure and the obtained residue was purified by silica gel chromatography (eluting solvent: dichloromethane/methanol/ammonia water=95/5/0-80/19/1) to obtain 1.36 g (yield: 80%) of the title compound as a pale yellow oil.
¹H-NMR spectrum (400 MHz, CD₃OD) δ ppm: 3.54 (2H, t, J=6.7 Hz), 2.56-2.50 (2H, m), 2.35 (3H, s), 1.58-1.32 (6H, m).
IR spectrum ν max cm⁻¹ (liquid film): 3377, 3306, 2936, 2862, 1646, 1537, 1477, 1387, 1313, 1073, 1055.
Mass spectrum (EI) m/z: 117 (M⁺)

Example 71c

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(5-hydroxypentyl)-N-methylacetamide hydrochloride The reaction was carried out in similar procedure to Example 69 using 110 mg (0.15 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, 25 μL (0.29 mmol) of oxalyl chloride, 51 mg (0.43 mmol) of 5-(methylamino)pentan-1-ol, obtained in Example 71b, and 91 μL (0.65 mmol) of triethylamine to obtain 29 mg (yield: 22%) of the title compound as a white solid.

¹H-NMR spectrum (400 MHz, CDCl₃) δ ppm: 12.06 (1H, brs), 8.10-7.90 (3H, m), 7.70-7.10 (7H, m), 4.40-2.60 (29H, m), 2.50-2.10 (3H, m), 1.80-1.20 (4H, m).
IR spectrum ν max cm⁻¹ (KBr): 3409, 2931, 2561, 1649, 1474, 1439, 1376, 1281, 1185, 1139, 1029, 905, 757, 681.
Mass spectrum (FAB) m/z: 858 ((M+H)⁺, free form)

Example 72

4-[{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}(methyl)amino]butanoic acid hydrochloride (Exemplary compound No. 2-495 hydrochloride)

Example 72a

Ethyl 4-(methylamino)butanoate hydrochloride 2.00 g (13.0 mmol) of 4-(methylamino)butanoic acid hydrochloride was dissolved in 40 mL of ethanol and 69 μL (1.30 mmol) of concentrated sulfuric acid was added thereto, followed by stirring of the mixture at 90° C. for 1 hour. The solvent was distilled off under reduced pressure, followed by azeotropy with toluene. 3.02 g of the obtained residue was used for the subsequent reaction as such.
¹H-NMR spectrum (400 MHz, CD₃OD) δ ppm: 4.14 (2H, q, J=7.2 Hz), 3.03 (2H, t, J=7.6 Hz), 2.69 (3H, s), 2.47 (2H, t, J=7.0 Hz), 1.99-1.90 (2H, m), 1.25 (3H, t, J=7.2 Hz).

Example 72b

Ethyl 4-[{[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]acetyl}(methyl)amino]butanoate hydrochloride The reaction was carried out in similar procedure to Example 69 using 200 mg (0.26 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, 46 μL (0.53 mmol) of oxalyl chloride, 96 mg (0.53 mmol) of ethyl 4-(methylamino)butanoate hydrochloride, obtained in Example 72a, and 184 μL (1.32 mmol) of triethylamine to obtain 165 mg (yield: 68%) of the title compound as a white solid.

Example 72c

4-[{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}(methyl)amino]butanoic acid hydrochloride 120 mg (0.13 mmol) of ethyl 4-[{[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]acetyl}(methyl)amino]butanoate hydrochloride, obtained in Example 72b, was dissolved in 1.5 mL of tetrahydrofuran and 1.5 mL of methanol, and 0.39 mL (0.39 mmol) of 1N aqueous sodium hydroxide solution was added thereto under ice-cooling, followed by stirring of the mixture at room temperature for 18 hours. 20 mL of 1N hydrochloric acid was added to the reaction mixture under ice-cooling and the mixture was extracted with ethyl acetate. The extract was washed successively with water and a saturated NaCl solution and dried over anhydrous sodium sulfate. The solvent was distilled off under reduced pressure and the obtained residue was purified by thin layer chromatography (eluting solvent: methylene chloride/methanol=10/1). The obtained purified product was dissolved in 20 mL of ethyl acetate, the mixture was washed successively with 50 mL of 1N hydrochloric acid and a saturated NaCl solution and dried over anhydrous sodium sulfate, and the solvent was distilled off under reduced pressure. The obtained residue was washed with hexane to obtain 59 mg (yield: 51%) of the title compound as a white solid.
¹H-NMR spectrum (400 MHz, CDCl₃) δ ppm: 11.82 (1H, brs), 8.10-7.85 (3H, m), 7.75-7.10 (7H, m), 4.40-1.50 (32H, m).
IR spectrum ν max cm⁻¹ (KBr): 2930, 2576, 1731, 1650, 1474, 1439, 1376, 1282, 1029, 905, 756, 681.
Mass spectrum (FAB) m/z: 858 ((M+H)⁺, free form)
Elementary analysis (for $C_{41}H_{44}Cl_3F_6N_3O_6 \cdot 2H_2O$) Calculated (%): C, 52.88; H, 5.20; Cl, 11.42; F, 12.24; N, 4.51. Found (%): C, 52.94; H, 4.97; Cl, 10.93; F, 12.66; N, 4.33.

Example 73

(1-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-yl)methanol hydrochloride (Exemplary compound No. 2-581 hydrochloride)

The reaction was carried out in similar procedure to Example 69 using 200 mg (0.26 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, 46 μL (0.53 mmol) of oxalyl chloride, 61 mg (0.53 mmol) of 4-piperidinemethanol and 110 μL (0.79 mmol) of triethylamine to obtain 76 mg (yield: 32%) of the title compound as a white solid.
¹H-NMR spectrum (400 MHz, CDCl₃) δ ppm: 12.00 (1H, brs), 8.15-7.90 (3H, m), 7.70-7.10 (7H, m), 4.50-2.90 (23H, m), 2.80-2.10 (7H, m), 1.90-1.10 (4H, m).
IR spectrum ν max cm⁻¹ (KBr): 3400, 2926, 2562, 1648, 1473, 1441, 1376, 1281, 1139, 1029, 905, 758, 681.
Mass spectrum (FAB) m/z: 856 ((M+H)⁺, free form)
Elementary analysis (for $C_{42}H_{46}Cl_3F_6N_3O_5 \cdot 1.5H_2O$) Calculated (%): C, 54.82; H, 5.37; Cl, 11.56; F, 12.39; N, 4.57. Found (%): C, 54.64; H, 5.17; Cl, 11.48; F, 12.82; N, 4.30.

Example 74

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(6-hydroxyhexyl)-N-methylacetamide hydrochloride (Exemplary compound No. 2-421 hydrochloride)

Example 74a

6-Hydroxyhexylformamide

The reaction was carried out in similar procedure to Example 71a using 1.50 g (12.8 mmol) of 6-amino-1-hexanol and 3 mL of ethyl formate to obtain 1.34 g (yield: 72%) of the title compound as a white solid.

¹H-NMR spectrum (400 MHz, CD₃OD) δ ppm: 8.01 (1H, s), 3.54 (2H, t, J=6.6 Hz), 3.21 (2H, t, J=6.8 Hz), 1.60-1.30 (8H, m).
IR spectrum ν max cm⁻¹ (KBr): 3376, 3311, 3040, 2936, 2857, 1655, 1526, 1464, 1385, 1242, 1063, 1049.
Mass spectrum (EI) m/z: 144 (M–H)⁺

Example 74b 6-(Methylamino)hexan-1-ol

The reaction was carried out in similar procedure to Example 71b using 1.34 g (9.23 mmol) of 6-hydroxyhexylformamide, obtained in Example 74a, and 11.1 mL (11.1 mmol) of a solution of 1 mol/l lithium aluminium hydride in tetrahydrofuran to obtain 0.89 g (yield: 74%) of the title compound as a pale yellow oil.
¹H-NMR spectrum (400 MHz, CD₃OD) δ ppm: 3.53 (2H, t, J=6.7 Hz), 2.56-2.50 (2H, m), 2.35 (3H, s), 1.58-1.30 (8H, m).
IR spectrum ν max cm⁻¹ (liquid film): 3299, 2932, 2858, 1650, 1539, 1475, 1379, 1059.
Mass spectrum (EI) m/z: 131 (M⁺)

Example 74c

2-[((2S)-1'-{2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]-N-(6-hydroxyhexyl)-N-methylacetamide hydrochloride The reaction was carried out in similar procedure to Example 69 using 110 mg (0.15 mmol) of 1-(2-{(2R)-2-(3, 4-dichlorophenyl)-4-[3,5-bis(trifluoromethyl)benzoyl]morpholin-2-yl}ethyl)spiro[(2S)-2-carboxymethoxy]indane-1, 4'-piperidine, 25 μL (0.29 mmol) of oxalyl chloride, 57 mg (0.43 mmol) of 6-(methylamino)hexan-1-ol, obtained in Example 74b, and 91 μL (0.65 mmol) of triethylamine to obtain 54 mg (yield: 33%) of the title compound as a white solid.
¹H-NMR spectrum (400 MHz, CDCl₃) δ ppm: 12.05 (1H, brs), 8.15-7.90 (3H, m), 7.70-7.10 (7H, m), 4.40-2.60 (29H, m), 2.50-2.10 (3H, m), 1.80-1.20 (6H, m).
IR spectrum ν max cm⁻¹ (KBr): 3418, 2931, 2559, 1649, 1474, 1439, 1376, 1281, 1185, 1139, 1029, 905, 758, 681.
Mass spectrum (FAB) m/z: 872 ((M+H)⁺, free form)

Example 75

2-[(1-{[((2S)-1'-(2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]acetyl}piperidin-4-yl)oxy]ethanol hydrochloride (Exemplary compound No. 2-586 hydrochloride)

Example 75a

Tert-butyl 4-(2-{[tert-butyl(dimethyl)silyl] oxy}ethoxy)piperidine-1-carboxylate 5.00 g (24.8 mmol) of tert-butyl 4-hydroxy-1-piperidine carboxylate was dissolved in 100 mL of dimethylformamide and 1.08 g (24.8 mmol) of sodium hydride (55% or more, oily) was added thereto under ice-cooling, followed by stirring of the mixture at room temperature for 4 hours. Thereafter, 20 mL of a solution of 6.54 g (27.3 mmol) of (2-bromoethoxy)-tert-butyldimethylsilane in dimethylformamide was added dropwise to the reaction mixture under ice-cooling and the mixture was stirred at room temperature for 2 days. Water was added to the reaction mixture under ice-cooling and the mixture was extracted with ethyl acetate, followed by washing successively with water and a saturated NaCl solution and drying over anhydrous sodium sulfate. The solvent was distilled off under reduced pressure and the obtained residue was purified by silica gel chromatography (eluting solvent: hexane/ethyl acetate=100/0-90/10) to obtain 1.65 g (yield: 18%) of the title compound as a colourless oil.
¹H-NMR spectrum (500 MHz, CDCl₃) δ ppm: 3.80-3.68 (4H, m), 3.56-3.46 (3H, m), 3.14-3.04 (2H, m), 1.86-1.76 (2H, m), 1.58-1.46 (2H, m), 1.45 (9H, s), 0.90 (9H, s), 0.07 (6H, s).
IR spectrum ν max cm⁻¹ (liquid film): 3475, 2953, 2931, 2859, 1699, 1422, 1366, 1253, 1237, 1175, 1111, 836, 777.
Mass spectrum (FAB) m/z: 360 (M+H)⁺

Example 75b

Tert-butyl 4-(2-hydroxyethoxy)piperidine-1-carboxylate 1.65 g (4.59 mmol) of tert-butyl 4-(2-{[tert-butyl(dimethyl)silyl]oxy}ethoxy)piperidine-1-carboxylate, obtained in Example 75a, was dissolved in 20 mL of tetrahydrofuran and 6.88 mL (6.88 mmol) of a solution of 1M tetrabutylammonium fluoride in tetrahydrofuran was added thereto under ice-cooling, followed by stirring of the mixture at room temperature for 2 hours. Water was added to the reaction mixture and the mixture was extracted with ethyl acetate, followed by washing successively with water and a saturated NaCl solution and drying over anhydrous sodium sulfate. The solvent was distilled off under reduced pressure and the obtained residue was purified by silica gel chromatography (eluting solvent: hexane/ethyl acetate=90/10-30/70) to obtain 0.94 g (yield: 84%) of the title compound as a colourless oil.
¹H-NMR spectrum (500 MHz, CDCl₃) δ ppm: 3.84-3.68 (4H, m), 3.58 (2H, t, J=4.6 Hz), 3.54-3.46 (1H, m), 3.14-3.02 (2H, m), 2.01 (1H, t, J=6.1 Hz), 1.90-1.80 (2H, m), 1.58-1.40 (11H, m).
IR spectrum ν max cm⁻¹ (liquid film): 3458, 2933, 2867, 1695, 1426, 1367, 1276, 1240, 1173, 1141, 1114, 1067.
Mass spectrum (FAB) m/z: 246 (M+H)⁺

Example 75c 2-(Piperidin-4-yloxy)ethanol 0.94 g (3.83 mmol) of tert-butyl 4-(2-hydroxyethoxy) piperidine-1-carboxylate, obtained in Example 75b, was dissolved in 12 mL of dichloromethane and 6 mL of trifluoroacetic acid was added thereto under ice-cooling, followed by stirring of the mixture at room temperature for 2 hours. The solvent was distilled off under reduced pressure, followed by azeotropy with toluene. The obtained residue was purified by silica gel chromatography (silica gel: Chromatrex NH, 100-200 mesh, eluting solvent: dichloromethane/methanol=100/0-90/10) to obtain 564 mg (yield: 100%) of the title compound as a white solid.
¹H-NMR spectrum (500 MHz, CD₃OD) δ ppm: 3.65 (2H, t, J=4.9 Hz), 3.55 (2H, t, J=4.9 Hz), 3.54-3.46 (1H, m), 3.12-3.04 (2H, m), 2.72-2.64 (2H, m), 1.98-1.90 (2H, m), 1.58-1.50 (2H, m).

IR spectrum ν max cm⁻¹ (liquid film): 3290, 2936, 2860, 1690, 1452, 1423, 1201, 1119, 1070.

Mass spectrum (FAB) m/z: 146 (M+H)⁺

Example 75d

2-[(1-{[((2S)-1'-{2-[(2R)-4-[3,5-bis(Trifluoromethyl)benzoyl]-2-(3,4-dichlorophenyl)morpholin-2-yl]ethyl}-2,3dihydrospiro[indene-1,4'-piperidin]-2-yl)oxy]acetyl}piperidin-4-yl)oxy]ethanol hydrochloride The reaction was carried out in similar procedure to Example 66b using 150 mg (0.20 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, 21 μL (0.22 mmol) of ethyl chloroformate, 65 μL (0.59 mmol) of N-methylmorpholine and 43 mg (0.30 mmol) of 2-(piperidin-4-yloxy)ethanol, obtained in Example 75c, to obtain 116 mg (yield: 64%) of the title compound as a white solid.

¹H-NMR spectrum (400 MHz, CDCl₃) δ ppm: 12.11 (1H, brs), 8.15-7.90 (3H, m), 7.70-7.10 (7H, m), 4.40-2.90 (25H, m), 2.80-2.60 (2H, m), 2.50-2.10 (3H, m), 1.95-1.55 (6H, m).

IR spectrum ν max cm⁻¹ (KBr): 3394, 2929, 2555, 1649, 1473, 1440, 1375, 1282, 1185, 1138, 1108, 1029, 905, 758, 681.

Mass spectrum (FAB) m/z: 886 ((M+H)⁺, free form)

Elementary analysis (for C₄₃H₄₈Cl₃F₆N₃O₆ 0.5H₂O) Calculated (%): C, 55.40; H, 5.30; Cl, 11.41; F, 12.23; N, 4.51. Found (%): C, 55.06; H, 5.30; Cl, 11.22; F, 12.27; N, 4.35.

Example 76

N-[(1-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-yl)-2-hydroxyacetamide hydrochloride (Exemplary compound No. 2-590 hydrochloride)

Example 76a 2-(Benzyloxy)-N-(1-benzylpiperidin-4-yl)acetamide 2.00 g (12.0 mmol) of benzyloxyacetic acid was dissolved in 40 mL of dichloromethane and 2.77 g (14.4 mmol) of 1-ethyl-3-(3-dimethylaminopropyl)carbodiimide hydrochloride, 2.21 g (14.4 mmol) of 1-hydroxybenzotriazole 1 hydrate, 2.52 mL (18.1 mmol) of triethylamine and 2.52 g (13.2 mmol) of 4-amino-1-benzylpiperidine were added thereto under ice-cooling, followed by stirring of the mixture at room temperature for 18 hours. Dichloromethane was added to the reaction mixture and the mixture was washed successively with a saturated aqueous sodium hydrogencarbonate solution, water and a saturated NaCl solution and dried over anhydrous sodium sulfate. The solvent was distilled off under reduced pressure and the obtained residue was purified by silica gel chromatography (eluting solvent: ethyl acetate/methanol=100/0-90/10) to obtain 2.82 g (yield: 69%) of the title compound as a white solid.

¹H-NMR spectrum (500 MHz, CDCl₃) δ ppm: 7.40-7.22 (10H, m), 6.46 (1H, d, J=7.3 Hz), 4.56 (2H, s), 3.96 (2H, s), 3.90-3.80 (1H, m), 3.49 (2H, s), 2.84-2.76 (2H, m), 2.18-2.08 (2H, m), 1.95-1.85 (2H, m), 1.53-1.43 (2H, m).

IR spectrum ν max cm⁻¹ (KBr): 3309, 3025, 2931, 2795, 1643, 1549, 1495, 1451, 1337, 1283, 1105, 988, 736, 700, 652.

Mass spectrum (FAB) m/z: 339 (M+H)⁺

Example 76b

2-Hydroxy-N-piperidin-4-ylacetamide 2.82 g (8.33 mmol) of 2-(benzyloxy)-N-(1-benzylpiperidin-4-yl)acetamide, obtained in Example 76a, was dissolved in 60 mL of ethanol and 0.60 g of 10% palladium-carbon (moisture content: 51.7%) was added thereto under a nitrogen atmosphere, followed by stirring of the mixture at 50° C. for 4 hours under a hydrogen atmosphere. After the reaction mixture was filtered with Celite, the solvent was distilled off under reduced pressure to obtain 1.26 g (yield: 96%) of the title compound as a pale yellow solid.

¹H-NMR spectrum (500 MHz, CD₃OD) δ ppm: 3.94 (2H, s), 3.86-3.78 (1H, m), 3.08-3.00 (2H, m), 2.68-2.60 (2H, m), 1.88-1.80 (2H, m), 1.50-1.40 (2H, m).

IR spectrum ν max cm⁻¹ (KBr): 3323, 3248, 2942, 2894, 1659, 1538, 1452, 1431, 1364, 1330, 1084, 1010, 437.

Mass spectrum (FAB) m/z: 159 (M+H)⁺

Example 76c

N-(1-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-yl)-2-hydroxyacetamide hydrochloride The reaction was carried out in similar procedure to Example 66b using 150 mg (0.20 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, 21 μL (0.22 mmol) of ethyl chloroformate, 65 μL (0.59 mmol) of N-methylmorpholine and 37 mg (0.24 mmol) of 2-hydroxy-N-piperidin-4-ylacetamide, obtained in Example 76b, to obtain 89 mg (yield: 48%) of the title compound as a white solid.

¹H-NMR spectrum (400 MHz, CDCl₃) δ ppm: 11.94 (1H, brs), 8.15-7.90 (3H, m), 7.75-7.10 (7H, m), 6.63-6.53 (1H, m) 4.50-1.20 (34H, m).

IR spectrum ν max cm⁻¹ (KBr): 3340, 2928, 1650, 1529, 1473, 1440, 1375, 1282, 1185, 1139, 1029, 905, 758, 681.

Mass spectrum (FAB) m/z: 899 ((M+H)⁺, free form)

Elementary analysis (for C₄₃H₄₇Cl₃F₆N₄O₆ H₂O) Calculated (%): C, 54.12; H, 5.18; Cl, 11.15; F, 11.95; N, 5.87. Found (%): C, 53.81; H, 5.22; Cl, 10.72; F, 11.60; N, 5.50.

Example 77) 2-[(1-{[((2S)-1'-(2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-yl)methoxy]ethanol hydrochloride (Exemplary compound No. 2-591 hydrochloride)

Example 77a

Benzyl 4-[(2-{[tert-butyl(dimethyl)silyl]oxy}ethoxy)methyl]piperidine-1-carboxylate The reaction was carried out in the similar procedure to Example 75a using 5.00 g (20.1 mmol) of benzyl 4-(hydroxymethyl)piperidine-1-carboxylate, 0.88 g (20.1 mmol)

of sodium hydride (55% or more, oily) and 5.28 g (22.1 mmol) of (2-bromoethoxy)-tert-butyldimethylsilane to obtain 237 mg (yield: 3%) of the title compound as a brown oil.

¹H-NMR spectrum (500 MHz, CDCl₃) δ ppm: 7.40-7.28 (5H, m), 5.12 (2H, s), 4.28-4.10 (2H, m), 3.74 (2H, t, J=5.4 Hz), 3.49 (2H, t, J=5.4 Hz), 3.31 (2H, d, J=5.9 Hz), 2.86-2.70 (2H, m), 1.82-1.68 (3H, m), 1.24-1.10 (2H, m), 0.89 (9H, s), 0.06 (6H, s).

IR spectrum ν max cm⁻¹ (liquid film): 3477, 2952, 2929, 2858, 1704, 1472, 1432, 1362, 1276, 1251, 1220, 1142, 1106, 941, 836, 778, 697.

Mass spectrum (FAB) m/z: 408 (M+H)⁺

Example 77b

Benzyl 4-[(2-hydroxyethoxy)methyl]piperidine-1-carboxylate

The reaction was carried out in similar procedure to Example 75b using 237 mg (0.58 mmol) of benzyl 4-[(2-{[tert-butyl(dimethyl)silyl]oxy}ethoxy)methyl]piperidine-1-carboxylate obtained in Example 77a and 0.87 mL (0.87 mmol) of a solution of 1M tetrabutylammonium fluoride in tetrahydrofuran to obtain 133 mg (yield: 78%) of the title compound as a brown oil.

¹H-NMR spectrum (500 MHz, CDCl₃) δ ppm: 7.40-7.28 (5H, m), 5.13 (2H, s), 4.28-4.10 (2H, m), 3.76-3.70 (2H, m), 3.56-3.50 (2H, m), 3.33 (2H, d, J=6.3 Hz), 2.86-2.70 (2H, m), 1.89 (1H, t, J=6.1 Hz), 1.84-1.70 (3H, m), 1.26-1.10 (2H, m).

IR spectrum ν max cm⁻¹ (liquid film): 3453, 2923, 2861, 1699, 1473, 1434, 1364, 1276, 1249, 1221, 1151, 1126, 1073, 765, 699.

Mass spectrum (FAB) m/z: 294 (M+H)⁺

Example 77c 2-(Piperidin-4-ylmethoxy)ethanol 133 mg (0.45 mmol) of benzyl 4-[(2-hydroxyethoxy)methyl)piperidine-1-carboxylate, obtained in Example 77b, was dissolved in 2 mL of ethanol and 20 mg of 10% palladium-carbon (moisture content: 51.7%) was added thereto under a nitrogen atmosphere, followed by stirring of the mixture at room temperature under a hydrogen atmosphere for 2 hours. After the reaction mixture was filtered with Celite, the solvent was distilled off under reduced pressure to obtain 70 mg (yield: 97%) of the title compound as a colourless oil.

¹H-NMR spectrum (500 MHz, CD₃OD) δ ppm: 3.65 (2H, t, J=4.9 Hz), 3.49 (2H, t, J=4.9 Hz), 3.31 (2H, d, J=6.3 Hz), 3.18-3.00 (2H, m), 2.64-2.56 (2H, m), 1.80-1.70 (3H, m), 1.26-1.14 (2H, m).

IR spectrum ν max cm⁻¹ (liquid film): 3296, 2920, 2856, 1598, 1449, 1359, 1319, 1126, 1074, 846.

Mass spectrum (EI) m/z: 159 (M⁺)

Example 77d

2-[(1-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-yl)methoxy]ethanol hydrochloride The reaction was carried out in similar procedure to Example 66b using 239 mg (0.32 mmol) of 1-(2-{(2R)-2-(3,4-dichlorophenyl)-4-[3,5-bis(trifluoromethyl)benzoyl]morpholin-2-yl}ethyl)spiro[(2S)-2-carboxymethoxy]indane-1,4'-piperidine, 33 μL (0.35 mmol) of ethyl chloroformate, 52 μL (0.47 mmol) of N-methylmorpholine and 60 mg (0.39 mmol) of 2-(piperidin-4-ylmethoxy)ethanol, obtained in Example 77c, to obtain 206 mg (yield: 70%) of the title compound as a white solid.

¹H-NMR spectrum (400 MHz, CDCl₃) δ ppm: 12.06 (1H, brs), 8.15-7.90 (3H, m), 7.70-7.10 (7H, m), 4.50-1.50 (36H, m), 1.30-1.10 (2H, m).

IR spectrum ν max cm⁻¹ (KBr): 3410, 2926, 2864, 1648, 1473, 1440, 1375, 1281, 1185, 1137, 1029, 905, 758, 681.

Mass spectrum (FAB) m/z: 900 ((M+H)⁺, free form)

Elementary analysis (for C₄₄H₅₀Cl₃F₆N₃O₆ H₂O) Calculated (%): C, 55.32; H, 5.49; Cl, 11.13; F, 11.93; N, 4.40. Found (%): C, 55.70; H, 5.51; Cl, 10.72; F, 11.84; N, 4.31.

The reactions were carried out in similar procedure to Example 58b, 66b or 69 to synthesize the following compounds.

Example 78

1-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-one hydrochloride
(Exemplary compound No. 2-579 hydrochloride)

¹H-NMR spectrum (400 MHz, CDCl₃) δ ppm: 8.16-7.95 (3H, m), 7.70-7.15 (7H, m), 4.46-1.67 (31H, m).

IR spectrum ν max cm⁻¹ (KBr): 3414, 2926, 2553, 1719, 1651, 1282, 1138.

Mass spectrum (FAB) m/z: 840 ((M+H)⁺, free form)

Elementary analysis (for C₄₁H₄₁Cl₂F₆N₃O₅ HCl H₂O) Calculated (%): C, 55.01; H, 4.95; N, 4.69. Found (%): C, 55.08; H, 5.28; N, 4.28.

Example 79

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-ethyl-N-(2-hydroxyethyl)acetamide hydrochloride (Exemplary compound No. 2-424 hydrochloride)

¹H-NMR spectrum (400 MHz, CDCl₃) δ ppm: 8.15-7.95 (3H, m), 7.67-7.15 (7H, m), 4.48-1.21 (32H, m).

IR spectrum ν max cm⁻¹ (KBr): 3362, 2931, 2561, 1648, 1474, 1438, 1376, 1281, 1139.

Mass spectrum (FAB) m/z: 830 ((M+H)⁺, free form)

Elementary analysis (for C₄₀H₄₃Cl₂F₆N₃O₅ HCl) Calculated (%): C, 55.40; H, 5.11; N, 4.85. Found (%): C, 56.01; H, 5.67; N, 4.39.

Example 80

2-[((2S)-1'-{2-[(2R)-2-(3,4-Dichlorophenyl)-4-(3,4,5-trimethoxybenzoyl)morpholin-2-yl]ethyl}-2,3-dihydrospiro[indene-1,4'-piperidin]-2-yl)oxy]-N-[2-(2-hydroxyethoxy)ethyl]-N-methylacetamide hydrochloride (Exemplary compound No. 1-422 hydrochloride)

¹H-NMR spectrum (400 MHz, CDCl₃) δ ppm: 7.70-7.14 (7H, m), 6.74 (2H, br), 4.45-2.15 (43H, m).

IR spectrum ν max cm⁻¹ (KBr): 3410, 2935, 2567, 1646, 1583, 1464, 1427, 1330, 1239, 1125.
Mass spectrum (FAB) m/z: 814 ((M+H)⁺, free form)

Example 81

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-ethyl-N-(4-hydroxybutyl)acetamide hydrochloride (Exemplary compound No. 2-426 hydrochloride)

¹H-NMR spectrum (400 MHz, CDCl₃) δ ppm: 8.15-7.95 (3H, m), 7.68-7.14 (7H, m), 4.40-1.42 (36H, m).
IR spectrum ν max cm⁻¹ (KBr): 3395, 2932, 2558, 1647, 1473, 1438, 1376, 1281, 1139.
Mass spectrum (FAB) m/z: 858 ((M+H)⁺, free form)

Example 82

2-[((2S)-1'-{2-[(2R)-2-(3,4-Dichlorophenyl)-4-(3,4,5-trimethoxybenzoyl)morpholin-2-yl]ethyl}-2,3-dihydrospiro[indene-1,4'-piperidin]-2-yl)oxy]-N-(4-hydroxybutyl)-N-methylacetamide hydrochloride (Exemplary compound No. 1-418 hydrochloride)

¹H-NMR spectrum (400 MHz, CDCl₃) δ ppm: 7.75-7.14 (7H, m), 6.71 (2H, br), 4.53-1.48 (43H, m).
IR spectrum ν max cm⁻¹ (KBr): 3399, 2934, 2562, 1647, 1583, 1463, 1426, 1330, 1238, 1125.
Mass spectrum (FAB) m/z: 798 ((M+H)⁺, free form)

Example 83

1-{[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-ol hydrochloride (Exemplary compound No. 2-580 hydrochloride)

¹H-NMR spectrum (400 MHz, CDCl₃) δ ppm: 8.16-7.92 (3H, m), 7.71-7.13 (7H, m), 4.44-1.45 (31H, m).
IR spectrum ν max cm⁻¹ (KBr): 3397, 2927, 2563, 1648, 1473, 1440, 1375, 1282, 1139.
Mass spectrum (FAB) m/z: 842 ((M+H)⁺, free form)
Elementary analysis (for $C_{41}H_{43}Cl_2F_6N_3O_5$ HCl) Calculated (%): C, 54.89; H, 5.17; N, 4.68. Found (%): C, 54.91; H, 5.37; N, 4.43.

Example 84

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(3-methoxypropyl)-N-methylacetamide hydrochloride (Exemplary compound No. 2-466 hydrochloride)

¹H-NMR spectrum (400 MHz, CDCl₃) δ ppm: 8.14-7.90 (3H, m), 7.71-7.12 (7H, m), 4.45-1.55 (35H, m).
IR spectrum ν max cm⁻¹ (KBr): 2927, 1650, 1474, 1439, 1376, 1281, 1138.
Mass spectrum (FAB) m/z: 844 ((M+H)⁺, free form)
Elementary analysis (for $C_{41}H_{45}Cl_2F_6N_3O_5$ HCl) Calculated (%): C, 55.88; H, 5.26; N, 4.77. Found (%): C, 55.56; H, 5.57; N, 4.54.

Example 85

N-(1-{2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-yl)acetamide hydrochloride (Exemplary compound No. 2-589 hydrochloride)

¹H-NMR spectrum (400 MHz, CDCl₃) δ ppm: 8.12-7.91 (3H, m), 7.70-7.14 (7H, m), 6.48-6.27 (1H, bs), 4.20-1.23 (34H, m).
IR spectrum ν max cm⁻¹ (KBr): 2928, 1649, 1473, 1439, 1375, 1281, 1139.
Mass spectrum (FAB) m/z: 883 (M+H)⁺, free form)
Elementary analysis (for $C_{43}H_{46}Cl_2F_6N_4O_5$ HCl 3H₂O) Calculated (%): C, 53.01; H, 5.48; N, 5.75. Found (%): C: 52.94, H: 5.53, N: 5.53.

Example 86

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(2-methoxyethyl)-N-methylacetamide hydrochloride (Exemplary compound No. 2-465 hydrochloride)

¹H-NMR spectrum (400 MHz, CDCl₃) δ ppm: 8.15-7.92 (3H, m), 7.72-7.11 (7H, m), 4.42-1.60 (33H, m).
IR spectrum ν max cm⁻¹ (KBr): 2928, 1650, 1439, 1376, 1281, 1138.
Mass spectrum (FAB) m/z: 830 (M+H)⁺, free form)
Elementary analysis (for $C_{40}H_{43}Cl_2F_6N_3O_5$ HCl) Calculated (%): C, 55.40; H, 5.11; N, 4.85. Found (%): C, 56.11; H, 5.79; N, 4.38.

Example 87

(2S)-2-[2-(4-Acetylpiperazin-1-yl)-2-oxoethoxy]-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]hydrochloride (Exemplary compound No. 2-613 hydrochloride)

¹H-NMR spectrum (400 MHz, CDCl₃) δ ppm: 8.17-7.91 (3H, m), 7.72-7.12 (7H, m), 4.48-1.94 (33H, m), 1.76-1.59 (1H, m).
IR spectrum ν max cm⁻¹ (KBr): 2926, 1650, 1472, 1438, 1282, 1138.
Mass spectrum (FAB) m/z: 869 (M+H)⁺, free form)
Elementary analysis (for $C_{42}H_{44}Cl_2F_6N_4O_5$ HCl 3H₂O) Calculated (%): C, 52.54; H, 5.35; N, 5.85. Found (%): C, 53.00; H, 5.35; N, 5.50.

Example 88

2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N,N-bis(2-methoxyethyl)acetamide hydrochloride ¹H-NMR spectrum (400 MHz, CDCl₃) δ ppm: 8.16-7.91 (3H, m), 7.66 (1H, br), 7.58-7.14 (6H, m), 4.42-1.60 (37H, m).

IR spectrum ν max cm⁻¹ (KBr): 2928, 1650, 1473, 1438, 1375, 1282, 1186, 1138.
Mass spectrum (FAB) m/z: 874 (M+H)⁺, free form)
Elementary analysis (for $C_{42}H_{47}Cl_2F_6N_3O_6$ HCl) Calculated (%): C, 55.36; H, 5.31; N, 4.61. Found (%): C, 55.08; H, 5.76; N, 4.28.

Example 89

2-[((2S)-1'-{2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]-N-(3-hydroxypropoxy)-N-methylacetamide (Exemplary compound No. 2-550)

¹H-NMR spectrum (400 MHz, CDCl₃) δ ppm: 8.06-7.13 (10H, m), 4.79-1.74 (32H, m).
IR spectrum ν max cm⁻¹ (KBr): 3438, 2926, 1646, 1473, 1440, 1375, 1281, 1184, 1139.
Mass spectrum (FAB) m/z: 846 (M+H)⁺, free form)

Example 90

2-[((2S)-1'-{2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]-N-(3-hydroxypropyl)acetamide hydrochloride (Exemplary compound No. 2-410 hydrochloride)

¹H-NMR spectrum (400 MHz, CDCl₃) δ ppm: 8.21-7.93 (3H, m), 7.70-7.16 (7H, m), 4.58-1.56 (29H, m).
IR spectrum ν max cm⁻¹ (KBr): 3404, 2928, 1649, 1535, 1474, 1439, 1376, 1281, 1139.
Mass spectrum (FAB) m/z: 816 (M+H)⁺, free form)
Elementary analysis (for $C_{39}H_{41}Cl_2F_6N_3O_5$ HCl) Calculated (%): C, 54.91; H, 4.96; N, 4.93. Found (%): C, 56.56; H, 6.03; N, 4.30.

Example 91

2-[((2S)-1'-{2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]-N-(4-hydroxy-4-methylpentyl)-N-methylacetamide hydrochloride (Exemplary compound No. 2-416 hydrochloride)

¹H-NMR spectrum (400 MHz, CD₃OD) δ ppm: 8.13 (1H, brs), 7.98 (2H, brs), 7.81 (1H, brs), 7.70-7.45 (2H, m), 7.28-7.10 (4H, m), 4.45-0.85 (38H, m).
IR spectrum ν max cm⁻¹ (KBr): 3407, 2965, 2930, 1649, 1473, 1458, 1440, 1376, 1281, 1185, 1165, 1139, 681, 624.
Mass spectrum (FAB) m/z: 872 ((M+H)⁺, free form)
Elementary analysis (for $C_{43}H_{49}Cl_2F_6N_3O_5$ HCl) Calculated (%): C, 56.80; H, 5.54; N, 4.62. Found (%): C, 57.38; H, 6.16; N, 4.29.

Example 92

3-(1-{[((2S)-1'-{2-[(2R)-2-(3,4-Dichlorophenyl)-4-(3,4,5-trimethoxybenzoyl)morpholin-2-yl]ethyl}-2,3-dihydrospiro[indene-1,4'-piperidin]-2-yl)oxy] acetyl}piperidin-4-yl)propan-1-ol hydrochloride (Exemplary compound No. 1-587 hydrochloride)

¹H-NMR spectrum (400 MHz, CDCl₃) δ ppm: 7.95-7.10 (7H, m), 6.62-6.60 (2H, m), 4.50-0.85 (47H, m).

IR spectrum ν max cm⁻¹ (KBr): 3400, 2931, 2856, 1644, 1583, 1463, 1427, 1377, 1330, 1269, 1236, 1125, 1028, 1005, 761.
Mass spectrum (FAB) m/z: 838 ((M+H)⁺, free form)
Elementary analysis (for $C_{45}H_{57}Cl_2N_3O_8$ HCl H₂O) Calculated (%): C, 60.50; H, 5.77; Cl, 11.91; N, 4.70. Found (%): C, 60.48; H, 6.72; Cl, 11.85; N, 4.55.

Example 93

N-[4-(Acetylamino)butyl]-2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-methylacetamide hydrochloride (Exemplary compound No. 2-563 hydrochloride)

¹H-NMR spectrum (400 MHz, CDCl₃) δ ppm: 12.07 (1H, brs), 8.15-7.90 (3H, m), 7.75-7.10 (7H, m), 5.90-5.50 (1H, m), 4.45-1.40 (37H, m).
IR spectrum ν max cm⁻¹ (KBr): 3284, 2930, 2558, 1651, 1546, 1475, 1439, 1375, 1282, 1185, 1138, 1109, 1029, 905, 758, 707, 681.
Mass spectrum (FAB) m/z: 885 ((M+H)⁺, free form)
Elementary analysis (for $C_{43}H_{48}Cl_3F_6N_3O_6$ H₂O) Calculated (%): C, 54.93; H, 5.47; Cl, 11.31; F, 12.12; N, 5.96. Found (%): C, 54.84; H, 5.56; Cl, 11.03; F, 12.12; N, 5.81.

Example 94

2-[((2S)-1'-{2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]-N-hydroxy-N-(4-hydroxybutyl)acetamide hydrochloride (Exemplary compound No. 2-453 hydrochloride)

IR spectrum ν max cm⁻¹ (KBr): 3414, 2931, 2683, 2578, 1650, 1474, 1439, 1376, 1281, 1186, 1140, 1029, 905, 758, 681.
Mass spectrum (FAB) m/z: 846 ((M+H)⁺, free form)

Example 95

2-[((2S)-1'-{2-[(2R)-4-[3,5-bis(Trifluoromethyl) benzoyl]-2-(3,4-dichlorophenyl)morpholin-2-yl] ethyl}-2,3-dihydrospiro[indene-1,4'-piperidin]-2-yl) oxy]-N-methyl-N-{4-[(methylsulfonyl)amino] butyl}acetamide hydrochloride (Exemplary compound No. 2-569 hydrochloride)

¹H-NMR spectrum (400 MHz, CDCl₃) δ ppm: 11.96 (1H, brs), 8.15-7.90 (3H, m), 7.75-7.10 (7H, m), 5.20-4.80 (1H, m), 4.40-1.45 (37H, m).
IR spectrum ν max cm⁻¹ (KBr): 3429, 2930, 2561, 1649, 1474, 1439, 1376, 1321, 1282, 1185, 1142, 1108, 1029, 976, 905, 758, 681.
Mass spectrum (FAB) m/z: 921 ((M+H)⁺, free form)
Elementary analysis (for $C_{43}H_{48}Cl_3F_6N_3O_6$ H₂O) Calculated (%): C, 51.67; H, 5.27; Cl, 10.89; F, 11.68; N, 5.74; S, 3.28. Found (%): C, 51.44; H, 5.40; Cl, 10.51; F, 11.21; N, 5.61; S, 3.18.

| Example No. | Exemplary compound No. | Configuration in R³ | Salt | Form | MS (FAB) m/z: ((M + H) +, free form) |
|---|---|---|---|---|---|
| 96 | 2-467 | | Monohydrochloride | White solid | 858 |
| 97 | 2-574 | (S) | Monohydrochloride | White solid | 870 |
| 98 | 2-411 | | Monohydrochloride | White solid | 830 |
| 99 | 2-438 | | Monohydrochloride | White solid | 858 |
| 100 | 2-612 | | Monohydrochloride | White solid | 841 |
| 101 | 2-588 | | Monohydrochloride | White solid | 841 |
| 102 | 2-500 | | Monohydrochloride | White solid | 830 |
| 103 | 2-597 | | Monohydrochloride | White solid | 869 |
| 104 | 2-494 | | Monohydrochloride | White solid | 844 |
| 105 | 2-592 | | Monohydrochloride | White solid | 870 |
| 106 | 2-404 | | Monohydrochloride | White solid | 788 |
| 107 | 2-594 | | Monohydrochloride | White solid | 898 |
| 108 | 2-523 | | Monohydrochloride | White solid | 857 |
| 109 | 2-557 | | Dihydrochloride | White solid | 871 |
| 110 | 2-530 | | Monohydrochloride | White solid | 887 |
| 111 | 2-544 | | Monohydrochloride | White solid | 856 |
| 112 | 2-508 | | Monohydrochloride | White solid | 858 |
| 113 | 2-420 | | Monohydrochloride | White solid | 858 |
| 114 | 2-577 | (S) | Monohydrochloride | White solid | 884 |
| 115 | 2-481 | | Monohydrochloride | White solid | 839 |
| 116 | 2-447 | | Monohydrochloride | White solid | 870 |
| 117 | 2-577 | (R) | Monohydrochloride | White solid | 884 |

REFERENCE EXAMPLE

Reference Example 1

1-{2-[(2R)-2-(3,4-Dichlorophenyl)-4-[3,5-bis(trifluoromethyl)benzoyl]morpholin-2-yl]ethyl}spiro[(2S)-2-hydroxy]indane-1,4'-piperidine]

Reference Example 1a

2-{(2R)-2-(3,4-Dichlorophenyl)-4-[3,5-bis(trifluoromethyl)benzoyl]morpholin-2-yl}ethanol methanesulfonate 5.60 g (20.3 mmol) of 2-[(2R)-2-(3,4-dichlorophenyl) morpholin-2-yl]ethanol (specification of U.S. Pat. No. 6,159,967, EXAMPLE 51(d)) was dissolved in methylene chloride (60 mL) and 2.83 mL (24.3 mmol) of triethylamine was added thereto. 5.60 g (20.3 mmol) of 3,5-bis(trifluoromethyl)benzoyl chloride and 248 mg (2.03 mmol) of 4-dimethylaminopyridine were added to the mixture under ice-cooling and the mixture was stirred at room temperature for 2 hours under a nitrogen atmosphere. Water was added to the reaction mixture and the methylene chloride layer was washed with water and a saturated NaCl solution and dried over anhydrous magnesium sulfate. After filtration, the solvent was distilled off under reduced pressure and the residue was purified by silica gel column chromatography (eluting solvent: hexane/ethyl acetate=1/1) to obtain 5.68 g (yield: 54%) of 2-{(2R)-2-(3,4-dichlorophenyl)-4-[3,5-bis (trifluoromethyl)benzoyl]morpholin-2-yl}ethanol.

5.68 g (11 mmol) of the obtained alcohol form was dissolved in methylene chloride (60 mL) and 2.3 mL (16.5 mmol) of triethylamine was added thereto under a nitrogen atmosphere. 1.02 ml (13.2 mmol) of methanesulfonyl chloride was added to the mixture under ice-cooling and the mixture was stirred at room temperature for 30 minutes under a nitrogen atmosphere. Water was added to the reaction mixture and the methylene chloride layer was washed with water and a saturated NaCl solution and dried over anhydrous magnesium sulfate. After filtration, the solvent was distilled off under reduced pressure and the residue was purified by silica gel column chromatography (eluting solvent: hexane/ethyl acetate=3/2) to obtain 6.09 g (yield: 93%) of the title compound.

$^1$H-NMR spectrum (400 MHz, CDCl$_3$) δ ppm: 8.05-7.71 (3H, m), 7.70-7.29 (3H, m), 4.56-4.19 (2H, m), 4.08-3.23 (6H, m), 2.95 (3H, s), 2.52-2.16 (2H, m).

Mass spectrum (FAB$^+$) m/z: 594 ((M+H)$^+$)

Reference Example 1b

1-{2-[(2R)-2-(3,4-Dichlorophenyl)-4-[3,5-bis(trifluoromethyl)benzoyl]morpholin-2-yl]ethyl}spiro[(2S)-2-hydroxy]indane-1,4'-piperidine]

126 mg (212 mmol) of 2-{(2R)-2-(3,4-dichlorophenyl)-4-[3,5-bis(trifluoromethyl)benzoyl]morpholin-2-yl}ethanol methanesulfonate, obtained in Reference Example 1a, was dissolved in 1300 mL of dimethylacetamide and 26.7 g (318 mmol) of sodium hydrogencarbonate, 52.8 g (318 mmol) of potassium iodide and 43.1 g (212 mmol) of spiro[(2S)-2-hydroxy]indane-1,4'-piperidine] were added thereto, followed by stirring of the mixture at 80° C. for 8 hours. Water was added to the reaction mixture and the mixture was extracted twice with ethyl acetate. The ethyl acetate layer was combined and the mixture was washed with water and a saturated NaCl solution and dried over anhydrous sodium sulfate. After filtration, the solvent was distilled off under reduced pressure and the residue was purified by silica gel chromatography (eluting solvent: ethyl acetate/methanol=100/1) to obtain 129 g (yield: 87%) of the title compound as a white amorphous solid.

$^1$H-NMR spectrum (500 MHz, CD$_3$OD) δ ppm: 8.35-8.20 (1H, m), 8.06-7.99 (2H, m), 7.81-7.28 (3H, m), 7.24-7.04 (4H, m), 4.54-4.40 (1H, m), 4.29-3.04 (8H, m), 2.72-2.37 (3H, m), 2.30-1.58 (9H, m).

IR spectrum ν max cm$^{-1}$ (KBr): 3448, 2923, 1645, 1473, 1375, 1280, 1139.

Mass spectrum (FAB) m/z: 701 ((M+H)$^+$) Elementary analysis (for C$_{34}$H$_{32}$Cl$_2$F$_6$N$_2$O$_3$ 1/2H$_2$O) Calculated: C, 57.47; H, 4.68; Cl, 9.98; F, 16.04; N, 3.94. Found: C, 57.76; H, 4.63; Cl, 9.54; F, 15.78; N, 3.86. Optical rotation: $[α]_D^{20}$=+37.20 (c=1.00, methanol)

PREPARATION EXAMPLES

Preparation Example 1

Powder

A powder can be obtained by mixing 5 g of the compound of Example 1, 895 g of lactose and 100 g of corn starch in a blender.

Preparation Example 2

Granules 5 g of the compound of Example 3, 865 g of lactose and 100 g of lowly substituted hydroxypropyl cellulose are mixed followed by the addition of 300 g of 10% aqueous hydroxypropyl cellulose solution and kneading. The thus kneaded product is then extruded and granulated using a granulating machine followed by drying to obtain granules.

Preparation Example 3

Tablets 5 g of the compound of Example 5, 90 g of lactose, 34 g of corn starch, 20 g of crystalline cellulose and 1 g of magnesium stearate are mixed in a blender, followed by forming into tablets with a tablet press to obtain tablets.

Preparation Example 4

Inhalation Liquid 1

A liquid is prepared so as to contain 10% (w/w) of the compound of Example 6, 0.04% (w/w) of benzalkonium chloride, 0.40% (w/w) of phenethyl alcohol and 89.56% (w/w) of purified water.

Preparation Example 5

Inhalation Liquid 2

A liquid is prepared so as to contain 10% (w/w) of the compound of Example 31, 0.04% (w/w) of benzalkonium chloride, 10% (w/w) of polyethylene glycol, 30% (w/w) of propylene glycol and 49.96% (w/w) of purified water.

Preparation Example 6

Inhalation Powder

A powder was prepared so as to contain 40% (w/w) of the compound of Example 32 and 60% (w/w) of lactose.

Preparation Example 7

Aerosol

An aerosol is prepared so as to contain 10% (w/w) of the compound of Example 33, 0.5% (w/w) of lecithin, 34.5% (w/w) of chlorofluorocarbon 11 and 55% (w/w) of chlorofluorocarbon 12.

TEST EXAMPLES

Test Example 1

$NK_1$ Receptor Binding Test (In Vitro)

<Preparation of Crude Pulmonary Membrane Specimen>

A pulmonary membrane specimen was prepared from the lungs of a Hartley male guinea pig. Namely, the animal was exsanguinated from the abdominal aorta under chloroform anesthesia followed by promptly excising the pulmonary and respiratory tract tissue.

The excised lungs were perfused with buffer α (50 mM Tris-HCl buffer, pH 7.4) and then sliced into thin sections followed by homogenizing using a Polytron in buffer β (buffer α containing 120 mM sodium chloride and 5 mM potassium chloride).

Tissue masses were removed from the homogenate by filtering through a Nylon mesh (50 μm) followed by centrifugation (30,000×g, 30 minutes, 4° C.).

The resulting pellet was then re-suspended in ice-cooled buffer γ (buffer α containing 10 mM EDTA and 300 mM potassium chloride) followed by allowing to stand undisturbed at 4° C. for 60 minutes and then washing twice with centrifugation (30,000×g, 15 minutes, 4° C.).

The crude pulmonary membrane specimen was stored at −80° C. until the time of use.

<Receptor Binding Test>

250 μL of crude pulmonary membrane specimen liquid was added to 250 μL of a mixture of test substance and [$^3$H]-Substance P (final concentration: 1 nM) (containing 50 mM Tris-HCl, pH 7.4, 6 mM manganese chloride, 800 μg/mL of BSA, 8 μg/mL of chymostatin, 8 μg/mL of leupeptin, 80 μg/mL of bacitracin and 20 μg/mL of phosphoramidone) followed by incubating at room temperature for 30 minutes.

Following the reaction, the membrane component was recovered on a GF/B glass fiber filter (Whatman) using an automatic filtration system (Brandel).

Furthermore, the glass filter was used after pretreating for about 4 hours with 0.1% polyethylene imine solution to suppress non-specific binding to a low level.

The filter used to recover the membrane component was transferred to a mini plastic vial containing 4 mL of Picoflow followed by measurement of radioactivity with a liquid scintillation counter (Beckman, LSC3500).

Test Example 2

$NK_2$ Receptor Binding Test (In Vitro)

<Preparation of Crude Ileum Membrane Specimen>

A crude membrane specimen was prepared from the ileum of a Hartley male guinea pig. Namely, the animal was exsanguinated from the abdominal aorta under chloroform anesthesia followed by promptly excising the ileum.

The excised ileum was removed of lumen contents, secretions and epithelium by rubbing with a slide glass, and after slicing into thin sections in buffer α (50 mM Tris-HCl buffer, pH 7.4), the thin sections were homogenized using Polytron in buffer β (buffer α containing 120 mM sodium chloride and 5 mM potassium chloride).

Tissue masses were removed from the homogenate by filtering through a Nylon mesh (50 μm) followed by centrifugal separation (30,000×g, 30 minutes, 4° C.).

The resulting pellet was then re-suspended in ice-cooled buffer γ (buffer α containing 10 mM EDTA and 300 mM potassium chloride) followed by allowing to stand undisturbed at 4° C. for 60 minutes and then washing twice with centrifugation (30,000×g, 15 minutes, 4° C.).

The crude membrane specimen was stored at −80° C. until the time of use.

<Receptor Binding Test>

250 µL of the crude ileum membrane specimen liquid was added to 250 µL of a mixture of test substance and [$^3$H]-SR-48968 (Amersham, final concentration: 1 nM) (containing 50 mM Tris-HCl, pH 7.4, 6 mM manganese chloride, 800 µg/mL of BSA, 8 µg/mL of chymostatin, 8 µg/mL of leupeptin, 80 µg/mL of bacitracin and 20 µg/mL of phosphoramidone) followed by incubating at room temperature for 30 minutes.

Following the reaction, the membrane component was recovered on a GF/B glass fiber filter (Whatman) using an automatic filtration system (Brandel).

Furthermore, the glass filter was used after pretreating for about 4 hours with 0.1% polyethylene imine solution to suppress non-specific binding to a low level.

The filter used to recover the membrane component was transferred to a mini plastic vial containing 4 mL of Picoflow followed by measurement of radioactivity with a liquid scintillation counter (Beckman, LSC3500).

Test Example 3

Inhibitory Action on Increased Vascular Permeability (In Vivo, Oral Administration)

Inhibitory action on increased vascular permeability can be investigated by using the amount of escaped dye as an indicator of the inhibitory action on increased vascular permeability induced by the NK$_1$ receptor agent, Substance P (SP), using normal guinea pigs (body weights: about 400 g, Hartley male guinea pigs). Dye (Evans blue: 40 mg/kg i.v.) was administered into a femoral vein of the guinea pigs under pentobarbital anesthesia (30 mg/kg, i.p.) followed immediately by intravenous injection of SP (1 µg/kg) to induce an increase in vascular permeability. 15 minutes later, the guinea pigs are sacrificed under chloroform anesthesia and the amount of dye that escapes at the site of the primary bronchus is measured according to the method of Harada (J. Pharm. Pharmacol. 23, 218 (1971)). The test substance is suspended in a 0.5% tragacanth suspension and administered orally 1 hour prior to challenge by SP.

Inhibitory action can be assessed by using the amount of escaped dye in guinea pigs administered the test substance as an indicator.

Test Example 4

Inhibitory Action on Airway Contraction (In Vivo, Oral Administration)

Inhibitory action on airway contraction can be investigated by using airway internal pressure as an indicator of the inhibitory effects of a test substance on airway contraction induced by the NK$_2$ receptor agent, neurokinin A (NKA), using normal guinea pigs (body weights: about 500 g, Hartley male guinea pigs) in accordance with a variation of the method of Konzett-Roessler (Naunyn-Schmiedegergs Arch. Exp. Pathol. Pharmakol. 195, 71 (1940)).

Namely, after implanting a tracheal cannula in the guinea pigs under pentobarbital anesthesia (30 mg/kg, i.p.) and treating with gallamine (20 mg/kg, i.v.), positive pressure ventilation (Ugo-Basile Biological Research Apparatus, Cat. No. 7025) is rapidly carried out at 8 mL/kg and 60 times/minute. The airway internal pressure during artificial respiration is recorded with a recorder (Nihon Koden, WT-645G or WT-685G) by amplifying and sensitizing (Nihon Koden, AP-601G) via a pressure transducer (Nihon Koden, TP-200T or TP-400T) implanted to the lateral branch of the tracheal cannula. Five minutes after pretreating with atropine (1 mg/kg, i.v.) and propranolol (1 mg/kg, i.v.), NKA is administered intravenously at 4 µg/kg to induce airway contraction followed by measurement of airway internal pressure for the next 10 minutes. The test substance is prepared in the same manner as Test Example 3 and administered orally 1 hour prior to challenge by NKA.

Inhibitory action can be assessed by comparing the airway internal pressure surface area values between a test substance dose group and a non-dose group.

Test Example 5

NK$_3$ Receptor Binding Test (In Vitro)

<Preparation of Brain Crude Membrane Specimen>

A crude membrane specimen was prepared from the brain of a male Hartley guinea pig.

Namely, the Hartley male guinea pig was exsanguinated from the abdominal aorta under chloroform anesthesia, and after perfusing from the right ventricle with buffer α (50 mM Tris-HCl buffer, pH 7.4), the brain was promptly excised. The excised brain was homogenized with a Polytron (Kinematica) in buffer β (buffer α containing 120 mM sodium chloride and 5 mM potassium chloride) followed by removing tissue masses by filtering with gauze and a Nylon mesh (50 µm) and centrifuging (30,000×g, 30 minutes, 4° C.). The resulting pellet (membrane component) was then re-suspended in ice-cooled buffer γ (buffer α containing 10 mM EDTA and 300 mM potassium chloride) followed by allowing to stand undisturbed at 4° C. for 60 minutes and then washing twice with centrifugation (30,000×g, 15 minutes, 4° C.). This was then used as a crude membrane specimen by suspending in buffer α, and stored at −80° C. in the receptor binding test until the time of use.

<Receptor Binding Test>

The test tube used in the reaction was pretreated with buffer α containing 5 mg/mL of bovine serum albumin (BSA). A test substance and 150 µL of buffer α containing 400 µg/mL of BSA were added to 100 µL of buffer α containing [$^3$H]-senctide, 6 mM manganese chloride, 800 µg/mL of BSA, 8 µg/mL of chymostatin, 8 µg/mL of leupeptin, 80 µg/mL of bacitracin and 20 µg/mL of phosphoramidone followed by the addition of 250 µL of the brain crude membrane specimen (adjusted to protein concentration of 1 mg/mL) to start the reaction (at this time, the final concentration of [$^3$H]-senctide in the reaction phase is 2.5 nM).

After incubating at room temperature for 60 minutes, the membrane component was recovered on a GF/B glass fiber filter (Whatman) pretreated for 4 hours or more with 0.1% polyethylene imine using an automatic filtration system (Brandel), and then washed three times with 5 mL of ice-cooled buffer β (5 mM Tris-HCl buffer containing 400 µg/mL of BSA and 0.01% sodium dodecyl sulfate, pH 7.4).

The GF/B glass fiber filter adhered with the membrane component was transferred to a mini plastic vial containing 4 mL of Picoflow followed by measurement of radioactivity with a liquid scintillation counter (Aloka, LSC3500).

The test was carried out by adding an excess amount of senctide (final concentration: 10 µM) followed by measurement of radioactivity to determine the radioactivity attributable to non-specific binding of [$^3$H]-senctide (binding to sites other than receptors (such as the filter)).

The senctide-receptor binding inhibition rate by the test substance was determined according to the following equation.

Inhibition rate (%)=[1−(C−A)/(B−A)]×100

A: Radioactivity attributable to non-specific binding
B: Radioactivity in test carried out without adding test substance
C: Radioactivity in test in which test substance was added Test Example 6

Inhibitory Action on Increased Vascular Permeability (In Vivo, Transtracheal Administration)

A test substance was dissolved in 5% aqueous glucose solution, and a 0.5 mL/kg solution was administered transtracheally to guinea pigs (body weights: about 400 g, Hartley male guinea pigs) using an intratracheal dosing instrument (1A-1B, Penn-Century) under pentobarbital anesthesia (0.2 to 0.25 mL/body, i.p.). Immediately after drug administration, Evans blue (40 mg/2 mL/kg, i.v.) and then the NK$_1$ receptor agonist, Substance P (1 µg/2 mL/kg, i.v.) were administered via a femoral (inside) vein.

The animals were sacrificed with carbon dioxide gas 15 minutes after administration of Substance P, and about 2 cm of the primary bronchus was excised from the neck. The excised primary bronchus was immersed for about 24 hours in 4 mL of a 7:3 mixture of acetone and 0.5% Na$_2$SO$_4$ to extract the dye followed by measurement of the optical density (OD 620 nm) of the extract.

The amount of dye was converted using a calibration curve, and the amount of dye that escaped per 0.1 g of trachea was taken to represent the strength of the increase in vascular permeability followed by calculating the inhibition rate relative to a control (5% glucose transtracheal dose group).

Test Example 7

Inhibitory Action on Airway Contraction (In Vivo, Transtracheal Administration)

The inhibitory action on airway contraction by the NK$_2$ receptor agonist, neurokinin A (NKA) was investigated using airway internal pressure as an indicator in normal guinea pigs (body weights: about 500 g, Hartley male guinea pigs) using a variation of the method of Konzett-Roessler (Naunyn-Schmiedebergs Arch. Exp. Pathol. Pharmakol. 195, 71 (1940)).

A tracheal cannula and venous cannula were implanted in the guinea pigs under pentobarbital anesthesia (50 mg/mL of liquid, 0.40 to 0.50 mL/body, s.c.). In addition, an arterial cannula filled with heparin-containing physiological saline (100 U/mL) was implanted to monitor blood pressure and heart rate via an amplifier and instantaneous cardiograph. Next, after administering gallamine (20 mg/kg, i.v.) and interrupting spontaneous respiration, positive pressure ventilation (Ugo-Basile Biological Research Apparatus, Cat. No. 7025) was rapidly carried out at 10 mL/kg and 60 times/minute. The airway internal pressure during artificial respiration was detected with a pressure transducer (Nihon Koden, TP-200T or TP-400T) implanted in the lateral branch of the tracheal cannula, amplified (Nihon Koden, AP-601G) and recorded with a recorder (Nihon Koden, WT-645G or WT-685G). After the airway internal pressure, blood pressure and heart rate had stabilized, the standard tracheal contracting substance, methacholine was administered at 10 µg/kg (100 µg/mL, 0.10 mL/kg) to confirm airway response. In the case the prescribed contraction response was not obtained, methacholine was additionally administered at 12 µg/kg (120 µg/mL, 0.10 mL/kg) followed by confirmation of airway response. Five minutes after confirming airway response, NKA was administered intravenously through the intravenous cannula at 4 µg/kg to induce airway contraction followed by measuring airway internal pressure for the next 10 minutes.

The test substance was dissolved in 5% glucose, and a 0.5 mL/kg solution was administered into the airway using an intratracheal administration instrument (1A-1B, Penn-Century).

The surface value over which airway internal pressure had increased at 10 minutes after administration of NKA was taken to represent the strength of NKA-induced airway contraction, and the inhibition rate was calculated relative to a control group (5% glucose transtracheal dose group).

The airway contraction inhibition rates when preferred compounds of the present invention were administered followed 16 hours later by the administration of NKA are as shown below.

| Test Substance | Dose | Inhibition Rate (%) |
| --- | --- | --- |
| Example 6 | 10 µg/kg | 97 |
| Example 31 | 10 µg/kg | 82 |
| Example 32 | 10 µg/kg | 89 |
| Example 33 | 10 µg/kg | 93 |
| Example 58 | 10 µg/kg | 90 |
| Example 64 | 10 µg/kg | 87 |
| Example 69 | 10 µg/kg | 88 |

INDUSTRIAL APPLICABILITY

Since a compound having the general formula (I) of the present invention or pharmacologically acceptable salt thereof demonstrates antagonistic action on neurokinin receptors (NK$_1$, NK$_2$ and NK$_3$), has little toxicity and has superior pharmacokinetics, it is useful as a pharmaceutical, and is particularly useful as a preventive or therapeutic agent for respiratory diseases such as asthma, bronchitis and chronic obstructive lung disease; allergic diseases such as rhinitis; and/or urinary incontinence in particular.

The invention claimed is:
1. A compound represented by the general formula (I)

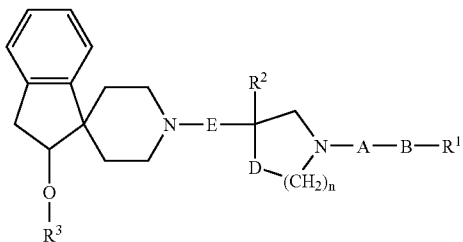

wherein,
R$^1$ and R$^2$ may be the same or different and each represents an aryl group, heteroaryl group, aryl group substituted with 1 to 3 groups selected from Substituent group α, or heteroaryl group substituted with 1 to 3 groups selected from Substituent group α;
R$^3$ represents any one of the following groups:
—CO—R$^4$,
—CO—O—R$^4$,
—CO—NH—R$^4$,
—CO—CH$_2$—N(R$^a$)R$^b$,
—(CH$_2$)$_m$—CO—R$^5$,
—(CH$_2$)$_m$—R$^5$,
—CO—NH—CO—N(R$^a$)R$^b$,
—CO—NH—SO$_2$—N(R$^a$)R$^b$,
—CO—NH—CO—(CH$_2$)$_m$—N(R$^a$)R$^b$, and
—CO—NH$_2$;
R$^4$ represents a lower alkyl group, cycloalkyl group, cycloalkyl group substituted with 1 to 3 groups selected from Substituent group α, lower alkenyl group, lower alkynyl group, halogeno lower alkyl group, hydroxy lower alkyl group, lower alkoxyalkyl group, lower aliphatic acyloxyalkyl group or lower alkoxycarbonylalkyl group;
R$^5$ represents a hydroxyl group, a group —OR$^4$, or a group —N(R$^a$)R$^b$;
R$^a$ and R$^b$ may be the same or different and each represents a hydrogen atom, hydroxyl group, lower alkoxy group, hydroxy lower alkoxy group, hydroxy lower alkoxyalkyl group, lower alkoxy lower alkoxyalkyl group, cyano lower alkyl group, cyano lower alkoxyalkyl group, carboxy lower alkyl group, carboxy lower alkoxyalkyl group, lower alkoxycarbonyl lower alkoxyalkyl group, carbamoyl lower alkyl group, carbamoyl lower alkoxyalkyl group, lower aliphatic acylamino lower alkyl group, lower aliphatic acylamino lower alkoxyalkyl group, lower alkylsulfonylamino lower alkyl group, lower alkylsulfonylamino lower alkoxyalkyl group, (N-hydroxy-N-methylcarbamoyl) lower alkyl group, (N-hydroxy-N-methylcarbamoyl) lower alkoxyalkyl group, (N-lower alkoxy-N-methylcarbamoyl) lower alkyl group, (N-lower alkoxy-N-methylcarbamoyl) lower alkoxyalkyl group or R$^4$, or together, including the nitrogen atom to which they are attached, represent a nitrogen-containing heterocyclic group or nitrogen-containing heterocyclic group substituted with 1 to 3 groups selected from Substituent group α;
m represents an integer of 1 to 6;
A represents a methylene group, carbonyl group or sulfonyl group;
B represents a single bond, C$_1$-C$_4$ alkylene group or C$_2$-C$_4$ alkenylene group;
D represents an oxygen atom or methylene group;
E represents a C$_1$-C$_4$ alkylene group or C$_2$-C$_4$ alkenylene group;
n represents an integer of 1 to 3; and,
Substituent group α represents a group of substituents consisting of halogen atoms, lower alkyl groups, hydroxy lower alkyl groups, halogeno lower alkyl groups, carboxy lower alkyl groups, lower alkoxy groups, hydroxy lower alkoxy groups, hydroxy lower alkoxyalkyl groups, lower alkoxy carbonyl groups, carboxyl groups, hydroxyl groups, lower aliphatic acyl groups, lower aliphatic acylamino groups, (N-hydroxy-N-methylcarbamoyl) lower alkyl groups, (N-lower alkoxy-N-methylcarbamoyl) lower alkyl groups, hydroxy lower aliphatic acylamino groups, amino groups, carbamoyl groups and cyano groups,
or a pharmacologically acceptable salt thereof.

2. The compound or pharmacologically acceptable salt thereof according to claim 1, wherein one of R$^a$ and R$^b$ represents a hydrogen atom, lower alkyl group, hydroxyl group or lower alkoxy group and the other represents a hydroxy lower alkyl group, hydroxy lower alkoxyalkyl group, carboxy lower alkyl group, carboxy lower alkoxyalkyl group, lower alkoxy carbonyl lower alkyl group or lower alkoxy carbonyl lower alkoxyalkyl group, or R$^a$ and R$^b$ together, including the nitrogen atom to which they are attached, form a nitrogen-containing heterocyclic group or nitrogen containing heterocyclic group substituted with 1 to 3 groups selected from Substituent group α.

3. The compound or pharmacologically acceptable salt thereof according to claim 1, wherein —N(R$^a$)R$^b$ is N-(3-hydroxypropyl)-N-methylamino, N-(4-hydroxybutyl)-N-methylamino, N-(5-hydroxypentyl)-N-methylamino, N-(6-hydroxyhexyl)-N-methylamino, N-[2-(2-hydroxyethoxy)ethyl]-N-methylamino, N-(2-hydroxyethyl)-N-methoxyamino, N-(3-carboxypropyl)-N-methylamino, 2-(3-hydroxypropyl)pyrrolidino, 4-hydroxymethylpiperidino, 4-(2-hydroxyethyl)piperidino, 4-(3-hydroxypropyl)piperidino, 4-(2-hydroxyethoxy)piperidino, 4-(hydroxyacetamido)piperidino, 4-(2-hydroxyethoxymethyl)piperidino or 4-(2-hydroxyethyl)piperazino.

4. A pharmaceutical composition containing an effective amount of a compound or pharmacologically acceptable salt thereof to claim 1, in a pharmaceutically acceptable carrier.

5. The composition according to claim 4 for pulmonary administration.

6. A method for treating asthma, bronchitis and/or chronic obstructive lung disease in a mammal in need thereof which comprises administering an effective amount of a compound or pharmacologically acceptable salt thereof according to claim 1 to said mammal.

7. The method according to claim 6, wherein a compound having the general formula (I) or pharmacologically acceptable salt thereof is administered by pulmonary administration.

8. The method according to claim 6, wherein the mammal is a human.

9. The compound or pharmacologically acceptable salt thereof according to claim 1, wherein
R$^1$ is an aryl group or an aryl group substituted with 1 to 3 groups selected from substituent group α,
R$^2$ is an aryl group substituted with 1 to 3 groups selected from substituent group α,
A is a methylene group or carbonyl group,
B is a single bond or C$_1$-C$_4$ alkylene group, D is an oxygen atom or a methylene group and E is a $C_1$-$C_4$ alkylene group and wherein one of $R^a$ and $R^b$ represents a hydrogen atom, lower alkyl group, hydroxyl group or lower alkoxy group and the other represents a hydroxy lower alkyl group, hydroxy lower alkoxyalkyl group, carboxy lower alkyl group, carboxy lower alkoxyalkyl group, lower alkoxy carbonyl lower alkyl group or lower alkoxy carbonyl lower alkoxyalkyl group, or $R^a$ and $R^b$ together, including the nitrogen atom to which they are attached, form a nitrogen-containing heterocyclic group or nitrogen-containing heterocyclic group substituted with 1 to 3 groups selected from Substituent group α.

10. The compound or pharmacologically acceptable salt thereof according to claim 9, wherein $R^1$ is phenyl or phenyl substituted with 1 to 3 groups selected from substituent group α, $R^2$ is a phenyl group substituted with 1 or 2 halogen atoms and wherein —N($R^a$)$R^b$ is N-(3-hydroxypropyl)-N-methylamino, N-(4-hydroxybutyl)-N-methylamino, N-(5-hydroxypentyl)-N-methylamino, N-(6-hydroxyhexyl)-N-methylamino, N-[2-(2-hydroxyethoxy)ethyl]-N-methylamino, N-(2-hydroxyethyl)-N-methoxyamino, N-(3-carboxypropyl)-N-methylamino, 2-(3-hydroxypropyl)pyrrolidino, 4-hydroxymethylpiperidino, 4-(2-hydroxyethyl)piperidino, 4-(3-hydroxypropyl)piperidino, 4-(2-hydroxyethoxy)piperidino, 4-(hydroxyacetamido)piperidino, 4-(2-hydroxyethoxymethyl)piperidino or 4-(2-hydroxyethyl)piperazino.

11. The compound or pharmacologically acceptable salt thereof according to claim 10, wherein $R^1$ is phenyl; or phenyl substituted with 1 to 3 groups selected from the group consisting of halogeno lower alkyl groups, lower alkoxy groups and hydroxyl groups and $R^3$ is —($CH_2$)$_m$—CO—$R^5$.

12. The compound or pharmacologically acceptable salt thereof according to claim 11, wherein $R^1$ is phenyl substituted with 1 to 3 groups selected from the group consisting of halogeno lower alkyl groups and lower alkoxy groups, $R^2$ is 3,4-difluorophenyl or 3,4-dichlorophenyl, $R^3$ is —$CH_2$—CO—N($R^a$)$R^b$, $R^5$ represents a group —N($R^a$)$R^b$, A is a carbonyl group, B is a single bond, and E is ethylene or trimethylene.

13. The compound or pharmacologically acceptable salt thereof according to claim 12, wherein $R^1$ is 3,5-bis(trifluoromethyl)phenyl or 3,4,5-trimethoxyphenyl n is 1 or 2 and $R^3$ is —$CH_2$—CO—N($CH_3$)—($CH_2$)$_4$—OH.

14. The compound according to claim 1, designated 1-(2-{(2R)-2-(3,4dichlorophenyl)-4-[3,5-bis(trifluoromethyl)benzoyl]morpholin-2-yl}ethyl)spiro((2S)-2-{[(morpholin-1-yl)acetyl]oxy})indane-1,4'-piperidine.

15. The pharmacologically acceptable salt of the compound according to claim 1, wherein said compound is designated 1-(2-{(2R)-2-(3,4-dichlorophenyl)-4-[3,5-bis(trifluoromethyl)benzoyl]morpholin-2-yl}ethyl)spiro((2S)-2{[(morpholin-1-yl)acetyl]oxy})indane-1,4'-piperidine.

16. The compound according to claim 1, designated 1-(2-{(2R)-2-(3,4-dichlorophenyl)-4-[3,5-bis(trifluoromethyl)benzoyl]morpholin-2-yl}ethyl)spiro((2S)-2-{2-[bis(2-hydroxyethyl)amino]-2-oxoethoxy})indane-1,4'-piperidine.

17. The pharmacologically acceptable salt of the compound according to claim 1, wherein said compound is designated 1-(2-{(2R)-2-(3,4-dichlorophenyl)-4-[3,5-bis(trifluoromethyl)benzoyl]morpholin-2-yl}ethyl)spiro((2S)-2-{2-[bis(2-hydroxyethyl)amino]-2-oxoethoxy})indane-1,4'-piperidine.

18. The compound according to claim 1, designated 1-(2-{(2R)-2-(3,4-dichlorophenyl)-4-[3,5-bis(trifluoromethyl)benzoyl]morpholin-2-yl}ethyl)spiro((2S)-2-{[N-(2-hydroxyethyl)-N-methylamino]-2-oxoethoxy})indane-1,4'-piperidine.

19. The pharmacologically acceptable salt of the compound according to claim 1, wherein said compound is designated 1-(2-{(2R)-2-(3,4-dichlorophenyl)-4-[3,5-bis(trifluoromethyl)benzoyl]morpholin-2-yl}ethyl)spiro((2S)-2-{[N-(2-hydroxyethyl)-N-methylamino]-2-oxoethoxy})indane-1,4'-piperidine.

20. The compound according to claim 1, designated 1-(2-{(2R)-2-(3,4-dichlorophenyl)-4-[3,5-bis(trifluoromethyl)benzoyl]morpholin-2-yl}ethyl)spiro((2S)-2-{2-[N-(2-hydroxyethyl)amino]-2-oxoethoxy})indane-1,4'-piperidine.

21. The pharmacologically acceptable salt of the compound according to claim 1, wherein said compound is designated 1-(2-{(2R)-2-(3,4-dichlorophenyl)-4-[3,5-bis(trifluoromethyl)benzoyl]morpholin-2-yl}ethyl)spiro((2S)-2-{2-[N-(2-hydroxyethyl)amino]-2-oxoethoxy})indane-1,4'-piperidine.

22. The compound according to claim 1, designated 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide.

23. The pharmacologically acceptable salt of the compound according to claim 1, wherein said compound is designated 2-[((2S)-1'-{2-[(2R)-4-[3,5-bis(Trifluoromethyl)benzoyl]-2-(3,4-dichlorophenyl)morpholin-2-yl]ethyl}-2,3-dihydrospiro[indene-1,4'-piperidin]-2-yl)oxy]-N-(4-hydroxybutyl)-N-methylacetamide.

24. The compound according to claim 1, designated 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-(3-hydroxypropyl)-N-methylacetamide.

25. The pharmacologically acceptable salt of the compound according to claim 1, wherein said compound is designated 2-[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]-N-(3-hydroxypropyl)-N-methylacetamicle.

26. The compound according to claim 1, designated 2-(1-{[((2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-yl)ethanol.

27. The pharmacologically acceptable salt of the compound according to claim 1, wherein said compound is designated 2-(1-{[((2S)-1'-{2[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl)oxy]acetyl}piperidin-4-yl)ethanol.

28. The compound or pharmacologically acceptable salt thereof according to claim 1, wherein $R^3$ is —CO—$R^4$.

29. The compound or pharmacologically acceptable salt thereof according to claim 1, wherein $R^3$ is —CO—O—$R^4$.

30. The compound or pharmacologically acceptable salt thereof according to claim 1, wherein $R^3$ is —CO—NH—$R^4$.

31. The compound or pharmacologically acceptable salt thereof according to claim 1, wherein $R^3$ is —CO—CH$_2$—N($R^a$)$R^b$.

32. The compound or pharmacologically acceptable salt thereof according to claim 1, wherein $R^3$ is —(CH$_2$)$_m$—CO—$R^5$.

33. The compound or pharmacologically acceptable salt thereof according to claim 1, wherein $R^3$ is —(CH$_2$)$_m$—$R^5$.

34. The compound or pharmacologically acceptable salt thereof according to claim 1, wherein $R^3$ is —CO—NH—CO—N($R^a$)$R^b$.

35. The compound or pharmacologically acceptable salt thereof according to claim 1, wherein $R^3$ is —CO—NH—SO$_2$—N($R^a$)$R^b$.

36. The compound or pharmacologically acceptable salt thereof according to claim 1, wherein $R^3$ is —CO—NH—CO—(CH$_2$)$_m$—N($R^a$)$R^b$.

37. The compound or pharmacologically acceptable salt thereof according to claim 1, wherein $R^3$ is —CO—NH$_2$.

* * * * *